(12) United States Patent
Saliman et al.

(10) Patent No.: US 11,355,247 B2
(45) Date of Patent: Jun. 7, 2022

(54) SYSTEMS AND METHODS FOR DETERMINING A WELLNESS SCORE, AN IMPROVEMENT SCORE, AND/OR AN EFFECTIVENESS SCORE WITH REGARD TO A MEDICAL CONDITION AND/OR TREATMENT

(71) Applicant: OutcomeMD, Inc., Los Angeles, CA (US)

(72) Inventors: Justin Saliman, Los Angeles, CA (US); Leonard Coster, Portland, OR (US); Albert Frates, Portland, OR (US); Floyd Noel, Boise, ID (US); Doug Grim, Portland, OR (US); Jason Hurst, Portland, OR (US); Crystal Rutland, Portland, OR (US); Liam McGranahan, Portland, OR (US)

(73) Assignee: OUTCOMEMD, INC., Los Angeles, CA (US)

( * ) Notice: Subject to any disclaimer, the term of this patent is extended or adjusted under 35 U.S.C. 154(b) by 647 days.

(21) Appl. No.: 15/427,962

(22) Filed: Feb. 8, 2017

(65) Prior Publication Data

US 2017/0228517 A1   Aug. 10, 2017

Related U.S. Application Data

(60) Provisional application No. 62/376,829, filed on Aug. 18, 2016, provisional application No. 62/308,107, (Continued)

(51) Int. Cl.
*G16H 50/30* (2018.01)
*G16H 10/60* (2018.01)
*G16H 10/20* (2018.01)

(52) U.S. Cl.
CPC ............. *G16H 50/30* (2018.01); *G16H 10/20* (2018.01); *G16H 10/60* (2018.01)

(58) Field of Classification Search
None
See application file for complete search history.

(56) References Cited

U.S. PATENT DOCUMENTS 5,642,731 A   7/1997   Kehr
5,660,176 A   8/1997   Iliff
(Continued)

FOREIGN PATENT DOCUMENTS

| CN | 1547721 A | 11/2004 |
| KR | 20130126041 A | 11/2013 |
| WO | 2012174304 A1 | 12/2012 |

OTHER PUBLICATIONS

"Code Technology | How it works", Code Technology, accessed Jun. 3, 2016, from WaybackMachine: https://web.archive.org/web/20160820204549/https://www.codetechnology.com/outcome-platform/, 6 pages.
(Continued)

*Primary Examiner* — Christopher L Gilligan
*Assistant Examiner* — Karen A Hranek
(74) *Attorney, Agent, or Firm* — Resonance IP Law, PC

(57) ABSTRACT

A medical questionnaire may be provided to a patient and responses to the medical questionnaire may be scored using a scoring procedure associated with the medical questionnaire. The scored responses may then be used to determine a wellness score for the patient. At times, the medical questionnaire may be treatment, diagnosis, and/or symptom specific and the wellness scores determined from the responses thereto may be used to determine a wellness score regarding the patient's wellness with regard to the treatment, diagnosis, and/or symptom. The wellness score may be provided to the patient, a treatment provider, a treatment (Continued)

facility, and/or a treatment administrator. At times a first and second wellness score may be determined and a difference therebetween may be used to determine an improvement score.

34 Claims, 61 Drawing Sheets

Related U.S. Application Data filed on Mar. 14, 2016, provisional application No. 62/292,766, filed on Feb. 8, 2016.

(56) References Cited

U.S. PATENT DOCUMENTS

| | | | |
|---|---|---|---|
| 6,177,940 B1 | 1/2001 | Bond et al. | |
| 6,454,705 B1 | 9/2002 | Cosentino et al. | |
| 6,581,038 B1 | 6/2003 | Mahran | |
| 7,801,741 B2 | 9/2010 | Fracek, Jr. et al. | |
| 7,805,385 B2 | 9/2010 | Steck et al. | |
| 7,873,525 B1 | 1/2011 | Kraus | |
| 7,996,245 B2 | 8/2011 | Gejdos et al. | |
| 8,380,531 B2 | 2/2013 | Paty et al. | |
| 8,392,215 B2 | 3/2013 | Tawil | |
| 8,489,418 B2 | 7/2013 | Gustafson et al. | |
| 8,583,450 B2 | 11/2013 | Baker et al. | |
| 8,781,859 B2 | 7/2014 | Manning et al. | |
| 9,129,054 B2 | 9/2015 | Nawana et al. | |
| 9,483,618 B2 | 11/2016 | Brincat et al. | |
| 2003/0083556 A1 | 5/2003 | Cosentino et al. | |
| 2005/0015309 A1 | 1/2005 | Fracek, Jr. et al. | |
| 2006/0161456 A1 | 7/2006 | Baker et al. | |
| 2006/0206013 A1 | 9/2006 | Rothman et al. | |
| 2006/0241972 A1* | 10/2006 | Lang | G06Q 30/0203 705/2 |
| 2008/0114617 A1* | 5/2008 | Heniford | G06Q 50/22 705/2 |
| 2008/0188733 A1 | 8/2008 | Al-Ali et al. | |
| 2009/0030945 A1* | 1/2009 | Miller | G06F 19/00 |
| 2009/0216556 A1 | 8/2009 | Martin et al. | |
| 2009/0259488 A1 | 10/2009 | Gounares et al. | |
| 2010/0023346 A1* | 1/2010 | Paty | G06Q 10/00 705/2 |
| 2010/0131434 A1 | 5/2010 | Magent et al. | |
| 2010/0235185 A1 | 9/2010 | Firminger et al. | |
| 2011/0093481 A1* | 4/2011 | Hussam | G06Q 10/06 707/756 |
| 2011/0125518 A1 | 5/2011 | Dhoble | |
| 2011/0231786 A1 | 9/2011 | Kenney et al. | |
| 2011/0246242 A1 | 10/2011 | Gejdos et al. | |
| 2012/0116180 A1* | 5/2012 | Rothman | G06Q 50/22 600/300 |
| 2012/0158433 A1* | 6/2012 | Schmieding | G16H 40/67 705/3 |
| 2013/0046557 A1 | 2/2013 | Mirza | |
| 2013/0054260 A1 | 2/2013 | Evans | |
| 2013/0144645 A1 | 6/2013 | Bjorner et al. | |
| 2013/0157244 A1 | 6/2013 | Eger et al. | |
| 2013/0159010 A1 | 6/2013 | Paty et al. | |
| 2013/0197926 A1 | 8/2013 | Gustafson et al. | |
| 2013/0304504 A1* | 11/2013 | Powell | G16H 20/90 705/3 |
| 2014/0052462 A1* | 2/2014 | Bond | G16H 10/20 705/2 |
| 2014/0052475 A1 | 2/2014 | Madan et al. | |
| 2014/0114674 A1 | 4/2014 | Krughoff et al. | |
| 2014/0136237 A1* | 5/2014 | Anderson | G16H 10/60 705/3 |
| 2014/0257836 A1* | 9/2014 | Walker | G06F 19/3456 705/2 |
| 2014/0330578 A1 | 11/2014 | Pincus | |
| 2014/0378500 A1 | 12/2014 | Cohen et al. | |
| 2015/0106123 A1* | 4/2015 | Amarasingham | G16H 50/30 705/3 |
| 2015/0213220 A1* | 7/2015 | Courville | G16H 50/30 705/2 |
| 2015/0223747 A1* | 8/2015 | Adelman | G06Q 10/06 424/94.2 |
| 2015/0254431 A1* | 9/2015 | Gaertner | G16H 15/00 705/2 |
| 2015/0286787 A1* | 10/2015 | Chen | G16H 10/20 705/2 |
| 2015/0356701 A1 | 12/2015 | Gandy et al. | |
| 2016/0125158 A1 | 5/2016 | Erdmann et al. | |
| 2016/0147951 A1* | 5/2016 | Francois | G16H 20/30 705/3 |
| 2016/0147953 A1 | 5/2016 | Menon et al. | |
| 2016/0210442 A1* | 7/2016 | Ethington | G16H 10/20 |
| 2016/0246943 A1 | 8/2016 | Lake et al. | |
| 2016/0256060 A1* | 9/2016 | Katra | G16H 50/30 |
| 2016/0283676 A1* | 9/2016 | Lyon | G06Q 10/10 |
| 2018/0330800 A1* | 11/2018 | Bogue | G16H 50/20 |

OTHER PUBLICATIONS

"Guidance for Industry Patient-Reported Outcome Measures: Use in Medical Product Development to Support Labeling Claims", Clinical/Medical (Dec. 2009), U.S. Departmnent of Health and Human Services Food and Drug Administration, 43 pages.

"Patient Reported Outcomes", Code Technology, accessed Jun. 3, 2016, from WaybackMachine: https://web.archive.org/web/20160820161935/https://www.codetechnology.com/patient-reported-outcomes/, 7 pages.

"PRO Tools Resource Center", Code Technology, accessed Jun. 3, 2016, from WaybackMachine: https://web.archive.org/web/20160820134429/https://www.codetechnology.com/resource-center/, 6 pages.

Clough-Gorr; et al., "The SAKK cancer-specific geriatric assessment (C-SGA): a pilot study of a brief tool for clinical decision-making in older cancer patients", BMC Medical Informatics and Decision Making (2013), 13:93, 11 pages.

Deshpande; et al., "Patient-reported outcomes: A new era in clinical research", Perspectives in Clinical Research (Oct.-Dec. 2011), 2(4):137-144.

Green, MD; et al., "Development and Evaluation of the Kansas City Cardiomyopathy Questionnaire: A New Health Status Measure for Heart Failure", Journal of American College of Cardiology (2000), 35(5):1245-55.

Keswani; et al., "What Quality Metrics Is My Hospital Being Evaluated on and What Are the Consequences?", The Journal of Arthroplasty (2016), 31:1139-1143.

Lee, "Comments, Compliments and Complaints the Use of Patient Feedback in the Management of Hospitals in the National Health Service in England", King's College London, thesis, downloaded Jul. 20, 2016, 282 pages.

Nixon; et al., "Interpreting change from patient reported outcome (PRO) endpoints: patient global ratings of concept versus patient global ratings of change, a case study among osteoporosis patients", Health and Quality of Life Outcomes (2016), 14:25, 12 pages.

Finnegan, "Patient outcomes: the view from France", Science Business, Nov. 29, 2016, retrieved from: https://sciencebusiness.net/healthy-measures/news/patient-outcomes-view-france#, 4 pages.

Gurria; et al., "Putting People at the Centre of Health Care", Huffington Post, The Wold Post, Jan. 2017, retrieved from: https://www.huffingtonpost.com/oecd/putting-people-at-the-cen_b_14247824.html, 6 pages.

Olson; et al., "How Hospitals Are Using Patient-Reported Outcomes to Improve Care", Harvard Business Review, Oct. 23, 2017, retrieved from: https://hbr.org/2017/10/how-hospitals-are-using-patient-reported-ou...improve-care?utm_source=twitter&utm_medium=social&utm_campaign=hbr, 7 pages.

International Search Report and Written Opinion dated Apr. 28, 2017, from the International Searching Authority, for International Patent Application No. PCT/US17,17027 (filed Feb. 8, 2017), 26 pages.

(56) References Cited

OTHER PUBLICATIONS

International Search Report and Written Opinion dated Oct. 24, 2017, from the International Searching Authority, for International Patent Application No. PCT/US17/46170 (filed Aug. 9, 2017), 10 pages.

* cited by examiner

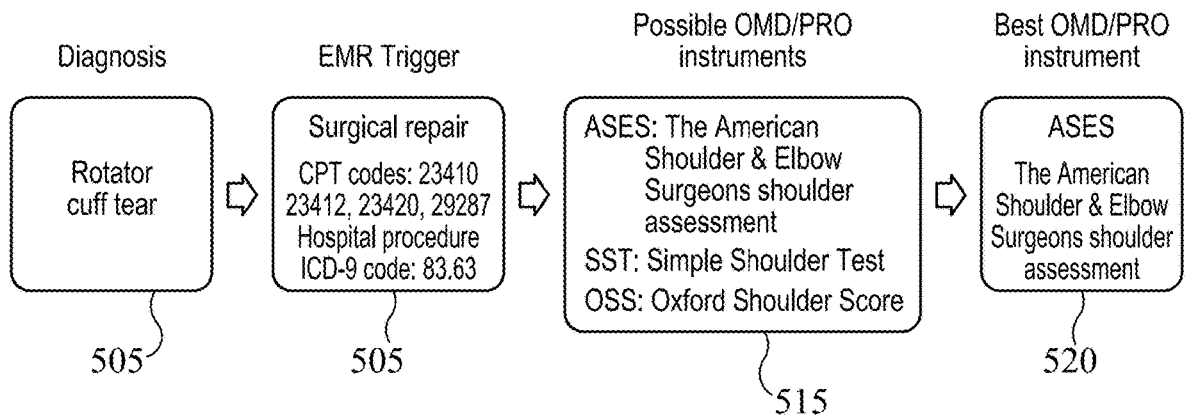
FIG. 5
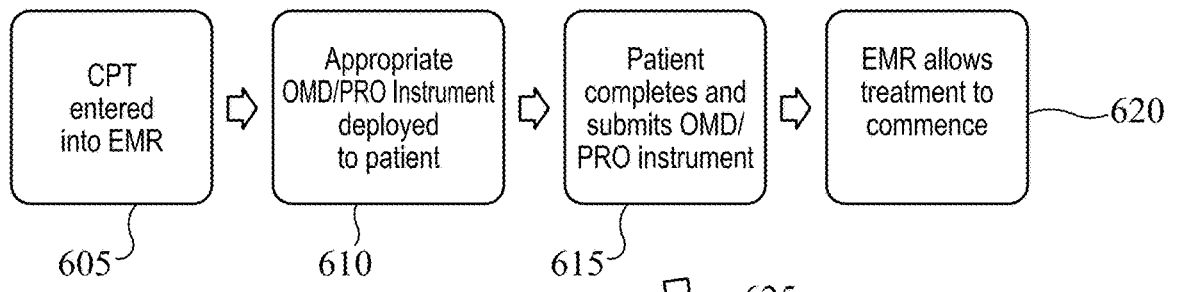
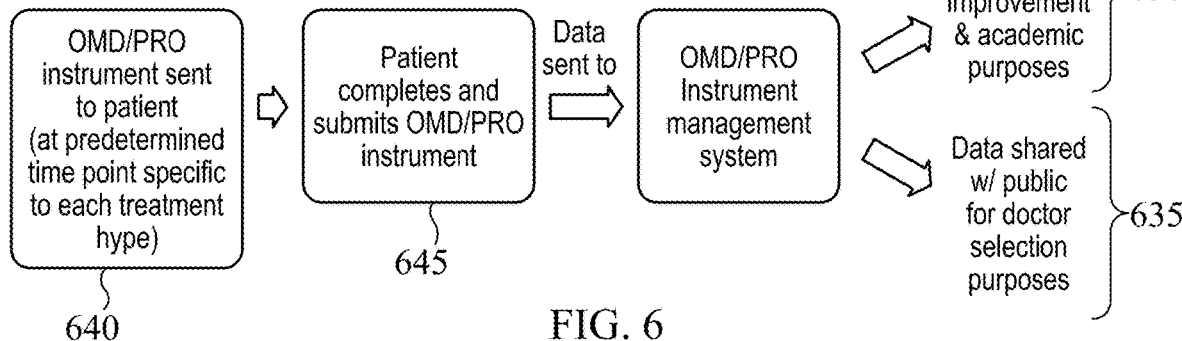
FIG. 6

1200

```
┌─────────────────────────────────────────────────┐
│ Access a pre-treatment wellness score database │
│ to retrieve a pre-treatment wellness score for  │
│ a medical condition of a patient                │
│ 1205                                            │
└─────────────────────────────────────────────────┘
                      ▼
┌─────────────────────────────────────────────────┐
│ Facilitate provision of an OMD to the patient   │
│ following treatment by a treatment provider     │
│ 1210                                            │
└─────────────────────────────────────────────────┘
                      ▼
┌─────────────────────────────────────────────────┐
│ Receive responses to the OMD from the patient   │
│ 1215                                            │
└─────────────────────────────────────────────────┘
                      ▼
┌─────────────────────────────────────────────────┐
│ Accessing a scoring-metrics database to         │
│ retrieve a scoring metric indexed to the        │
│ medical questionnaire                           │
│ 1220                                            │
└─────────────────────────────────────────────────┘
                      ▼
┌─────────────────────────────────────────────────┐
│ Evaluating the received responses using the     │
│ retrieved scoring metric                        │
│ 1225                                            │
└─────────────────────────────────────────────────┘
                      ▼
┌─────────────────────────────────────────────────┐
│ Determining a post-treatment wellness score     │
│ for the medical condition based on the          │
│ evaluation                                      │
│ 1230                                            │
└─────────────────────────────────────────────────┘
                      ▼
┌─────────────────────────────────────────────────┐
│ Determining an improvement score for the        │
│ patient's medical condition                     │
│ 1235                                            │
└─────────────────────────────────────────────────┘
                      ▼
┌─────────────────────────────────────────────────┐
│ Determine an effectiveness score for the        │
│ treatment provider, treatment, and/or           │
│ treatment facility                              │
│ 1240                                            │
└─────────────────────────────────────────────────┘
                      ▼
┌─────────────────────────────────────────────────┐
│ Storing the effectiveness score(s)              │
│ 1245                                            │
└─────────────────────────────────────────────────┘
                      ▼
┌─────────────────────────────────────────────────┐
│ Providing the effectiveness score(s) to a       │
│ treatment provider, treatment facility,         │
│ treatment administrator, and/or patient         │
│ 1250                                            │
└─────────────────────────────────────────────────┘
```

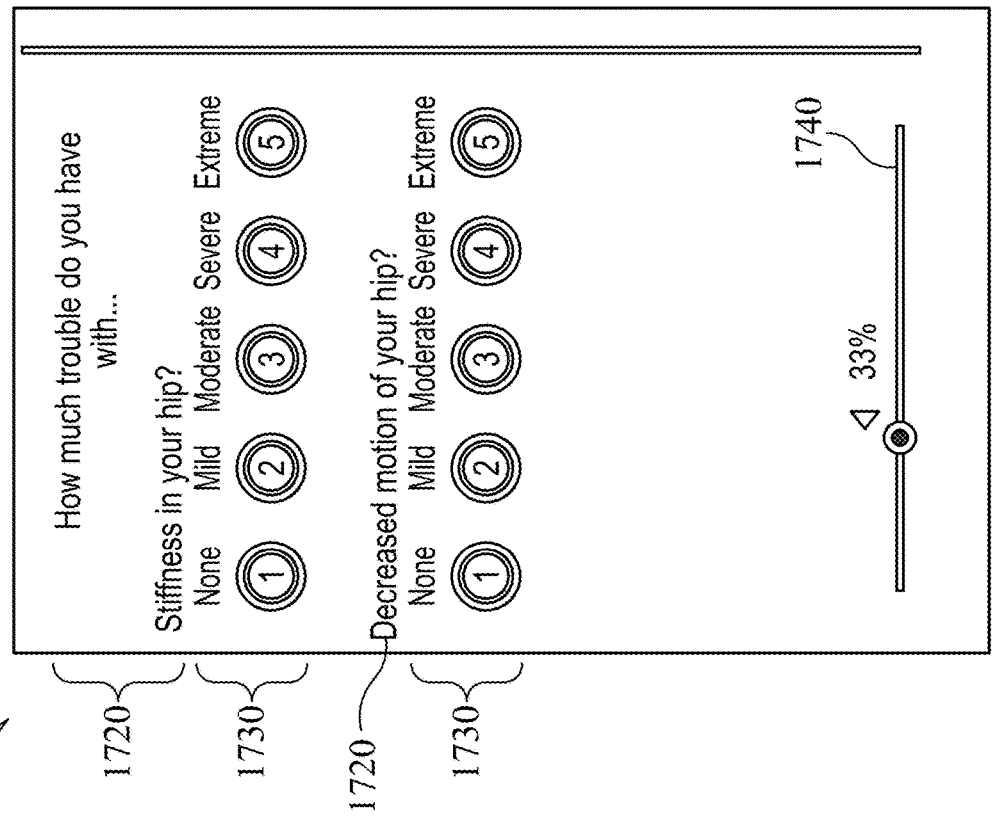

Question Sources

The questions that you answered have been used in the medical literature to define outcome after similar procedures

Similar Use Paper:
Lundstrom M et al.. Cataract surgery and quality of life in patients with age related macular degeneration. Br J Ophthalmol. 2002;86;1330-5.

Similar Use Paper:
Day AC et al. Randomised, single - masked non-inferiority trial of femtosecond laser-assisted versus manual phacoemusisification cataract surgery for adults with visually significant cataract: the FACT trial protocol. BMJ Open. 2015;5:e010381.

SYMPTOM TRACKER

Existing Patient

Searchable patient
identifier: ___Smith___

2311
{
Abigail Smith
Allison Smith
Amy Smith
Curtis Smith
Fred Smith
Karen Smith
Lionel Smith
Matt Smith
Mellissa Smith
Tamara Smith
Wendy Smith
}

FIG. 23B

Enter New Patient

2308
{
First name:
Last name:
Date of Birth
Social Security Number
Cell Phone Number:
Email:
}

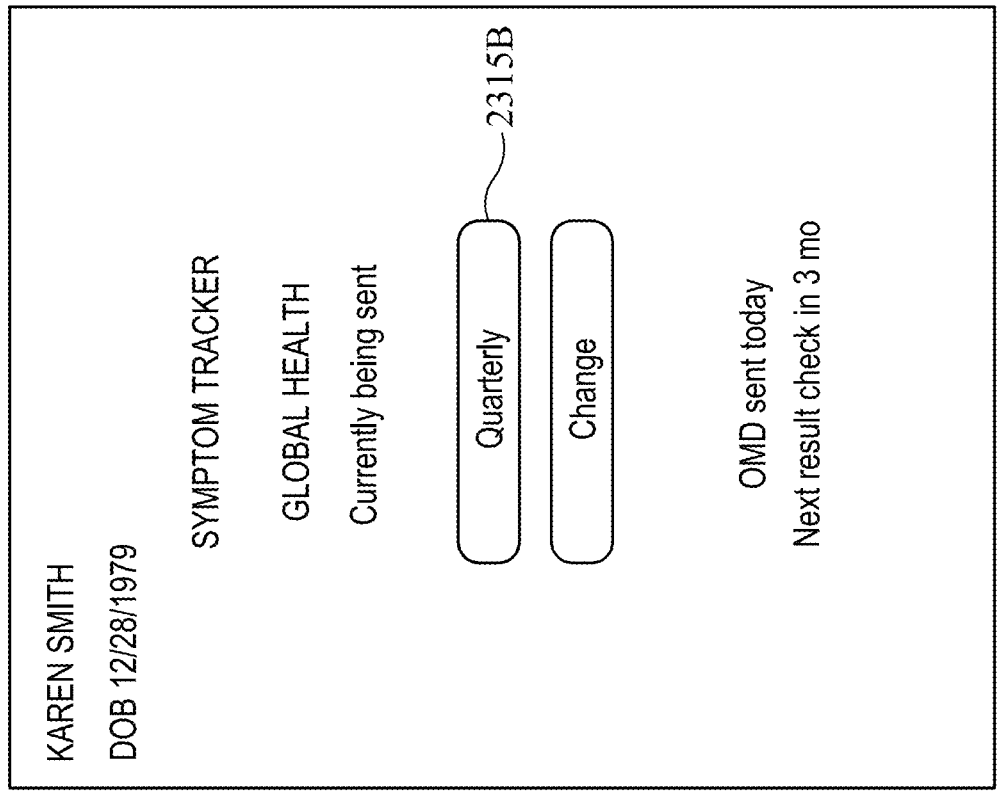

2307

KAREN SMITH   SYMPTOM TRACKER
DOB 12/28/1979

DIAGNOSIS        [ Anxiety ]

DISEASE SPECIFIC TREATMENT

[ Treatment B ]      OMD SENT

FIG. 23G

SYSTEMS AND METHODS FOR DETERMINING A WELLNESS SCORE, AN IMPROVEMENT SCORE, AND/OR AN EFFECTIVENESS SCORE WITH REGARD TO A MEDICAL CONDITION AND/OR TREATMENT

RELATED APPLICATIONS

The present application is a NON-PROVISIONAL of, and claims priority to, U.S. Provisional Patent Application No. 62/292,766, filed on 8 Feb. 2016 entitled "METHODS AND APPARATUSES FOR IMPROVING MEDICAL TREATMENT USING PATIENT-AVAILABLE PATIENT REPORTED OUTCOMES," U.S. Provisional Patent Application No. 62/308,107, filed on 14 Mar. 2016 and entitled "METHODS AND APPARATUSES FOR IMPROVING MEDICAL TREATMENT USING PATIENT-AVAILABLE PATIENT REPORTED OUTCOMES," and U.S. Provisional Patent Application No. 62/376,829, filed on 18 Aug. 2016, entitled "SYSTEMS AND METHODS FOR DETERMINING QUALITATIVE HEALTH TREATMENT OUTCOMES AND USES THEREOF" all of which are incorporated, in their respective entireties, herein.

FIELD OF THE INVENTION

The present invention relates to medical information technology. More specifically, the present invention relates to systems and methods for determining a wellness score, an improvement score, and/or an effectiveness score with regard to a medical condition and/or treatment.

BACKGROUND

Current medical and healthcare systems lack universal outcome measures. As a consequence, healthcare providers and patients are often uncertain of which treatments are effective, and healthcare providers cannot be judged by their true effectiveness at treating patients. This inability to universally measure medical treatment effectiveness, combined with the widespread availability of subjective online reviews of providers, has resulted in physicians focusing on patient catering rather than patient care.[1] Clinicians over utilize healthcare resources and over prescribe tests and medications to make patients happy because their business models are dependent on receiving good subjective reviews from patients rather than delivering good end results. This phenomenon has been associated with increased overall US healthcare costs, and increased mortality.[2]

[1] Porter M, Teisberg E, Redefining Heath Care: Creating Value-Based Competition on Results, *Harvard Business Review Press*, Boston Mass., 2006.
[2] Fenton, J J et. al. The Cost of Satisfaction: A National Study of Patient Satisfaction, Healthcare Utilization, Expenditures, and Mortality. *Archives of Internal Medicine* 2012; 172(5):405-411.

SUMMARY OF THE INVENTION

Systems and methods for determining a wellness score, an improvement score, and/or an effectiveness score with regard to a medical condition and/or medical treatment are herein provided. In one embodiment a medical questionnaire may be provided to a patient via, for example, a patient's personal electronic device (e.g., smart phone or tablet computer). The medical questionnaire may be, for example, a medical symptom questionnaire, a disease-specific medical symptom questionnaire, a global medical symptom questionnaire, and a patient reported outcome questionnaire.

The medical questionnaire may be associated with a scoring procedure for scoring responses to the medical questionnaire. Both the scoring procedure and an identifier of the medical questionnaire may be stored in a scoring-procedure database so that the identifier of the medical questionnaire may being used to retrieve the scoring procedure from the scoring-procedure database.

In some instances, the medical questionnaire is provided to each of a plurality of patients, responses to the medical questionnaire are received from at least some of the plurality of patients, and a wellness score is determined for at least some of the plurality of patients. Then, a disease-specific registry of information, a diagnosis-specific registry of information, a treatment-specific registry of information, a patient-specific registry of information, and/or a treatment-provider-specific registry of information may be created using, for example, the responses to the medical questionnaire received from at least some of the plurality of patients and/or the wellness scores determined for the at least some of the patients. The disease-specific registry of information, diagnosis-specific registry of information, treatment-specific registry of information, patient-specific registry of information, and/or treatment-provider-specific registry of information may then be stored in a database. In some instances, this storage may involve removing some, or all, patient identifying information from the received responses to the medical questionnaire and the determined wellness scores prior to creation of the least one disease-specific registry of information, diagnosis-specific registry of information, treatment-specific registry of information, patient-specific registry of information, and treatment-provider-specific registry of information so that no patient-identifying information is stored in the least one of one disease-specific registry of information, diagnosis-specific registry of information, treatment-specific registry of information, patient-specific registry of information, and/or treatment-provider-specific registry of information.

In one embodiment, it may be determined whether the wellness score falls below a minimum threshold and, if so, a notification that indicates the wellness score is below the minimum threshold may be generated and provision of the notification to a treatment provider may be facilitated via, for example, communication of the notification to a personal electronic device operated by the treatment provider (e.g., smart phone or pager). In some instances, the treatment provider may be able to select the manner (e.g., SMS text message or email) in which he or she wishes to be notified. In some cases, the notification may include contact information of the patient and/or a link to the patient's personal electronic device and/or contact information (e.g., phone number or email address) so that when, for example, the notification is received on a smart phone, the treatment provider may use the information from the notification to directly call, email, or otherwise contact, the patient. In some embodiments, the treatment provider may be provided with a dashboard or other interface by which he or she may enter preferences for the threshold, how he or she wishes to be contacted with the notification, and what he or she wishes to be included in the notification. In some instances, the interface and/or dashboard may also provide options for the treatment provider to set up preferences for other treatment providers he or she may be associated with and/or may establish global policies for thresholds and/or notifications. In some cases, this interface may be managed by a treatment administrator who sets thresholds and/or notification policies according to rules and/or policies of a treatment facility and/or institution via, for example, establishment of best practices for providing care to patients.

On some occasions, it may be determined whether the wellness score falls below a first minimum threshold and, upon determining that the wellness score does fall below the first minimum threshold, determining whether the wellness score falls below a second minimum threshold. When the wellness score does fall below the second minimum threshold, a notification that indicates the wellness score is below the second minimum threshold may be generated. Provision of the notification to a treatment provider may then be facilitated. In some circumstances, the first threshold may be established for a more senior treatment provider (e.g., doctor or surgeon) and the second threshold may be established for a less senior treatment provider (e.g., nurse or administrator).

On some occasions, a subsequent provision of the medical questionnaire to the patient may be facilitated at, for example, a pre-determined time and/or upon occurrence of an event (e.g., scheduling of a treatment) and a subsequent set of responses to the medical questionnaire from the patient may be received. The scoring procedure may then be retrieved from the scoring-procedure database using the identifier of the medical questionnaire and a subsequent wellness score may be determined by applying the scoring procedure to the subsequent set of responses. The subsequent wellness score may then be provided to the patient.

On some occasions, an improvement score for the patient may be determined using the wellness score and the subsequent wellness score and/or a difference in the wellness score and the subsequent wellness score. Provision of the improvement score to the patient, a treatment provider, treatment administrator, and/or treatment facility may then be facilitated. At times, it may be determined whether the improvement score falls below a minimum threshold and, if so, a notification that indicates the improvement score is below the minimum threshold may be generated and provision of the notification to a treatment provider may be facilitated. In some cases, the notification may include contact information of the patient and/or a link to the patient's personal electronic device and/or contact information (e.g., phone number or email address) so that when, for example, the notification is received on a smart phone, the treatment provider may use the information from the notification to directly call, email, or otherwise contact, the patient.

In some embodiments, an indication of a scheduling of the treatment for the patient may be received prior to facilitating the provision of the medical questionnaire to the patient. The scheduling of the treatment may act as a trigger for the administration of a questionnaire to a patient and, in response to the scheduling, a questionnaire database storing a plurality of medical questionnaires or other OMDs may then be accessed. In most instances, each medical questionnaire stored in the questionnaire database is indexed with a treatment identifier, such as a CPT code. The medical questionnaire that is indexed with an identifier of the scheduled treatment for provision to the patient may then be selected for provision to the patient and provision of the selected medical questionnaire to the patient may be facilitated.

In some embodiments, accessing an electronic medical record of the patient may be accessed and information about the patient from the accessed electronic medical record may be extracted and correlated, for example, the wellness score, the received set of responses, a diagnosis of the patient, a treatment provided to the patient, and/or the medical questionnaire.

In one embodiment, an additional, or subsequent, medical questionnaire may be provided to the patient upon, for example, an expiration of a predetermined time period measured from, for example, a time at which the patient received a treatment and/or a time at which the set of responses was received from the patient, facilitating an additional provision of the medical questionnaire to the patient. An additional set of responses to the medical questionnaire may be received from the patient and an additional wellness score may be determined by applying the scoring procedure to the additional set of responses. The additional wellness score may then be provided to the patient. In some cases, the additional medical questionnaire is the same as the initially provided questionnaire but, this need not always be the case. For example, the initial medical questionnaire may include a first set of questions and the additional medical questionnaire may include a second set of questions. In another example, the initial medical questionnaire may include a first set of questions and the additional medical questionnaire may include the first set of questions and a second set of questions. A change between the initial questionnaire and the additional medical questionnaire may be triggered by, for example, a change in the patient's health or medical condition and/or a change in the medical literature underlying use of the initial medical questionnaire.

In some instances, the provision of the medical questionnaire to the patient at a plurality of time points (e.g., daily, weekly, monthly, quarterly, biannually, yearly, etc.) may be repeatedly facilitated so as to monitor the patient's wellness over time (e.g., weeks, months, years, decades). On occasion, a predicted and/or projected wellness score may be determined for the patient. The projected wellness score may be based on, for example, historical information from the patient's EMR, information from other patients with one or more similar characteristics to the patient, information from other patients with one or more similar diagnoses to the patient, and/or information from other patients who have undergone one or more treatments similar to the patient.

In some embodiments, a medical questionnaire may be selected for provision to the patient responsively a received indication of at least one of a diagnosis and a treatment associated with the patient. Then, a set of responses to the medical questionnaire may be received from the patient. Next, the scoring procedure for the medical questionnaire may be retrieved from the scoring-procedure database using the identifier of the medical questionnaire. A wellness score for the patient may then be determined by applying the scoring procedure to the set of responses. Provision of the wellness score to the patient a treatment provider for the patient, and/or a treatment administrator may then be facilitated. At times, the wellness score may be provided to the patient automatically (e.g., without an action from a treatment provider, doctor, nurse, researcher, clinician or treatment facility administrator).

In some instances, the wellness score is a raw wellness score provided on a scale determined by the scoring procedure that is, for example, not a base ten scale (i.e., not 0-10 or 0-100). In these instances, the raw wellness score may be adjusted to be on a normalized (e.g., base ten), scale thereby generating an adjusted wellness score. In some cases, when, for example, a plurality of wellness scores are provided to a patient this adjustment may involve normalizing all of the wellness scores so that they are provided on the same scale and facilitating provision of the wellness score to the patient may include facilitating provision of the adjusted wellness score to the patient. In this way, different wellness scores that are determined for the patient via a plurality of OMDs may be more easily compared and understood, especially when they relate to the same, or a similar treatment.

In some instances, a determined wellness score may be stored in, for example, a score database maintained by a server and/or a data storage device provided by the patient's personal electronic device. On some occasions, the storage process may involve removing any and/or all patient-identifying information from the wellness score. This may be accomplished by, for example, associating a key or a binary string with, for example, the patient, the set of responses, and/or the wellness score so that it may be later retrieved without entry of patient-identifying information into a query.

In some embodiments, the wellness score may be communicated to a treatment facility computer system for storage in an electronic medical record (EMR) database in communication with the treatment facility computer system. Storage in the EMR may include associating the wellness score with the patient and/or an anonymous identifier for the patient. At times, patient-identifying information associated with the wellness score may be removed from the wellness score prior to communication of the wellness score to the treatment facility computer system.

In some cases, facilitating provision of the wellness score to the patient may include determining whether the medical questionnaire, a diagnosis, a treatment the patient is scheduled to undergo and/or has undergone pertains to the medical questionnaire, and/or a disease or medical condition of the patient is associated with alternate terminology for a name of the respective medical questionnaire, treatment, disease or medical condition. Exemplary alternate terminology includes terms that would be easily understood by those not trained in the medical arts (e.g., not doctors or nurses). For example, alternate terminology for a diagnosis of a spiral fracture of the ulna may include "a broken arm" and alternate terminology for a "bronchogenic carcinoma" diagnosis may be "lung cancer."

The alternate terminology may be provided to the patient along with the wellness score and/or the questionnaire responsively to a determination that the medical questionnaire is associated with alternate terminology. Providing the alternate terminology may have the effect of assisting the patient with understanding what the wellness score relates to so that he or she may have greater incite into their treatment and/or a diagnosis and/or recovery therefrom.

In some embodiments, a plurality of medical questionnaires may be provided to a patient at the same time. For example, a global health medical questionnaire and a disease-specific medical questionnaire or two different types of disease-specific medical questionnaires for the same disease and/or different diseases may be provided to the patient. In these embodiments, a first and second medical questionnaire may be provided to the patient and the second medical questionnaire may be different from the first medical questionnaire. Both the first and second medical questionnaires are associated with a first and second scoring procedure, respectively for scoring the respective responses to the first and second medical questionnaires. The first and second scoring procedures may be associated with a respective first and second identifier of the medical questionnaire and may be stored in a scoring-procedure database. The first and second identifiers of the respective first and second medical questionnaires may be used to retrieve the respective first and second scoring procedures from the scoring-procedure database.

In this embodiment, the set of responses may include responses to the first medical questionnaire and the second medical questionnaire and each of the responses in the set of responses responsive the first questionnaire grouped into a first set of responses. Then, the first scoring procedure may be retrieved from the scoring-procedure database using the identifier of the first medical questionnaire and a first wellness score may be determined by applying the first scoring procedure to the first set of responses. Next, each of the responses in the set of responses responsive the second questionnaire may be grouped into a second set of responses. The second scoring procedure may be retrieved from the scoring-procedure database using the identifier of the second medical questionnaire and a second wellness score may be determined by applying the second scoring procedure to the second set of responses. Then, provision of the first and second wellness scores to the patient via, for example, a display provided by his or her personal electronic device, may be facilitated. In some cases, a response included in the set of responses may be grouped into both the first set of responses and the second set of responses as me be the case when, for example, the first and second medical questionnaires share a common question.

In some instances, facilitating provision of the wellness score to the patient may include providing the patient with a numerical wellness score and depicting a location for the numerical wellness score within a graphically represented wellness score progress chart (e.g., a bar chart, a graph, a pie chart, etc.) wherein a location of the numerical wellness score on the graphically represented wellness score progress chart is associated with a magnitude of the numerical wellness score. In some instances, the graphically represented wellness score progress chart may include a minimum and/or maximum wellness score such that a relative distance between the location of the numerical wellness score and the location of the maximum numerical wellness score indicates how close the numerical wellness score is to a maximum wellness score, which may be an indication of overall wellness or how the patient is doing, or how much the patient can expect his or her wellness to improve.

In a still further embodiment, a post-treatment provision of a medical questionnaire to a patient may be facilitated (via, for example, communication of the medical questionnaire to the patient's personal electronic device and/or activation of the medical questionnaire already stored on the patient's personal electronic device) after the patient receives a treatment for a medical condition. The medical questionnaire may be associated with a scoring procedure and the scoring procedure and an identifier of the medical questionnaire may be stored in a scoring-procedure database. The identifier of the medical questionnaire may be used to retrieve the scoring procedure from the scoring-procedure database.

A post-treatment set of responses to the medical questionnaire may be received from the patient and the scoring procedure for the medical questionnaire may be retrieved from the scoring-procedure database using the identifier of the medical questionnaire. Then, a post-treatment wellness score for the medical condition may be determined by applying the scoring procedure to the post-treatment set of responses and provision of the post-treatment wellness score to the patient may be facilitated. On some occasions, provision of the medical questionnaire to the patient at a plurality of time points after the patient receives the treatment may be repeatedly facilitated at a plurality of time points.

In another embodiment, provision of a medical questionnaire to each of a plurality of patients may be facilitated. The medical questionnaire may be associated with a scoring procedure for scoring the medical questionnaire and the scoring procedure and an identifier of the medical questionnaire may be stored in a scoring-procedure database. The identifier of the medical questionnaire may be used to retrieve the scoring procedure from the scoring-procedure database. Then, a set of responses to the medical questionnaire may be received from the patient and the scoring procedure may be retrieved from the scoring-procedure database using the identifier of the medical questionnaire. A wellness score for the medical condition may then be determined by applying the scoring procedure to the set of responses and provision of the wellness score to the patient may be facilitated. Then, at least one of the received sets of responses may be mapped to the determined wellness score to create a medical-condition-specific registry of information.

On some occasions, one or more patient characteristics for at least some of the patients of the plurality of patients may be received and the creation of the medical-condition-specific registry may further include mapping the received patient characteristics to the medical condition. At times, the patient characteristics may be provided by the patient's EMR and/or the treatment provider and may not be received as a response to the OMD. At times, provision of the medical questionnaire to the patient at a plurality of time points after the patient receives the treatment may be repeatedly facilitated.

In some instances, an electronic medical record of each patient may be accessed and, for at least some of the patients, one or more patient characteristics may be extracted from the electronic medical record of the respective patient and the creation of the medical-condition-specific registry may further include mapping the extracted one or more patient characteristics to the medical condition and/or a wellness score.

BRIEF DESCRIPTION OF THE DRAWINGS

The present invention is illustrated by way of example, and not limitation, in the figures of the accompanying drawings in which:

FIGS. 5 and 6 provide flowcharts of an exemplary processes for selecting an OMD to provide to a patient, providing the OMD to the patient, and receiving a response thereto, in accordance with some embodiments of the present invention;

FIG. 12 provides a flowchart of an exemplary process for determining an effectiveness score for treatment provider, treatment, and/or treatment facility, in accordance with some embodiments of the present invention;

FIGS. 17A-17H show exemplary interfaces provided by a patient's wellness account, in accordance with some embodiments of the present invention;

FIGS. 21A-21E depict screen shots from provided by a patient's wellness to a patient who has undergone eye surgery in accordance with some embodiments of the present invention;

FIGS. 23A-23G provide screen shots of exemplary interfaces provided to a treatment provider and/or treatment administrator for associated one or more OMDs with a patient's wellness account and facilitating provision of the OMD to the patient in accordance with some embodiments of the present invention;

Figure 1A:
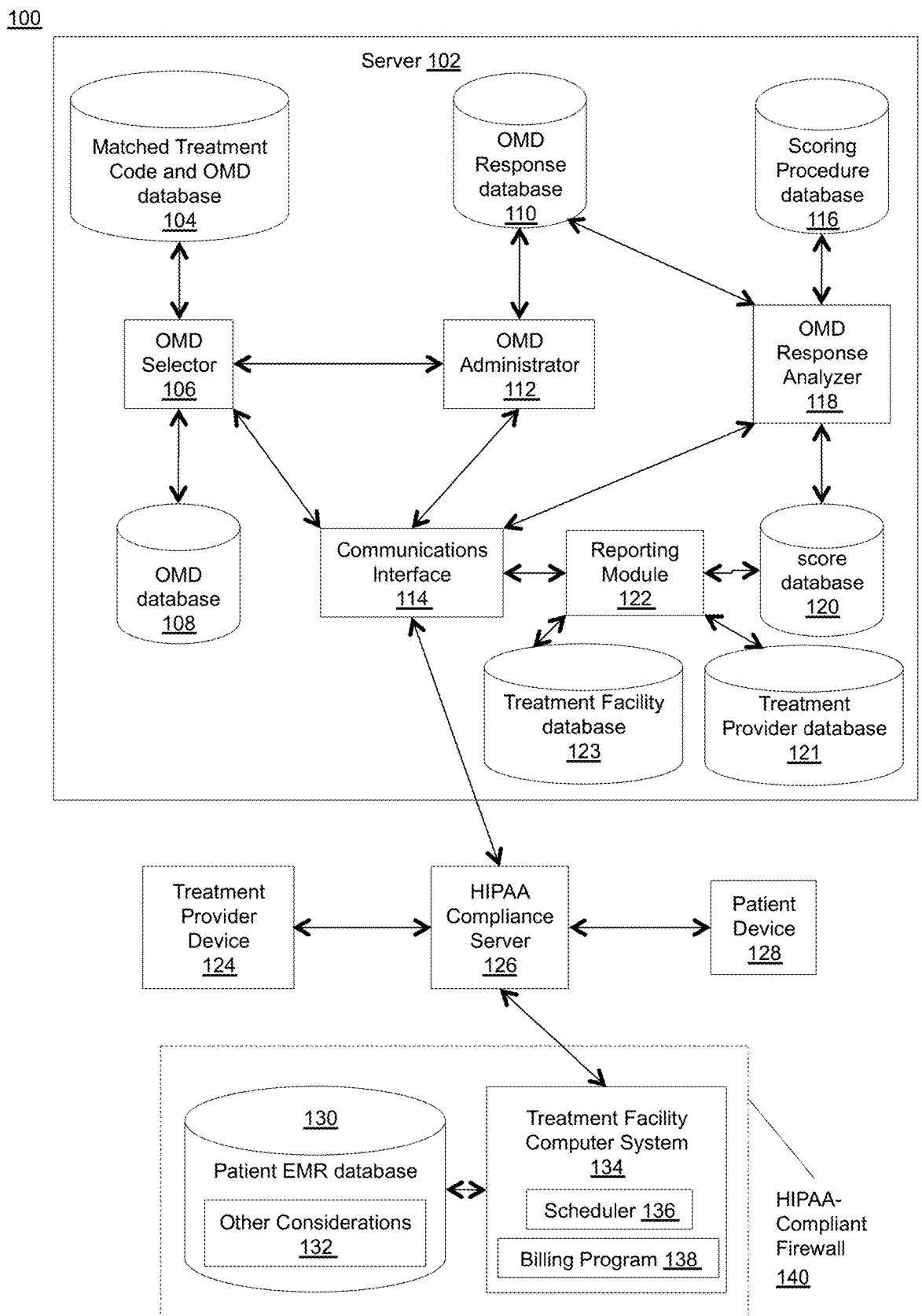
FIG. 1A is a block diagram of an exemplary system, in accordance with some embodiments of the present invention.

Throughout the drawings, the same reference numerals and characters, unless otherwise stated, are used to denote like features, elements, components, or portions of the illustrated embodiments. Moreover, while the subject invention will now be described in detail with reference to the drawings, the description is done in connection with the illustrative embodiments. It is intended that changes and modifications can be made to the described embodiments without departing from the true scope and spirit of the subject invention as defined by the appended claims.

WRITTEN DESCRIPTION

The present invention uses medical treatment and/or diagnosis outcome data reported via one or more outcome measurement devices (OMDs) to better understand, for example, the effectiveness of treatments for a medical condition and various factors that may affect the effectiveness of the treatments, recovery from a treatment, and/or improvement in the medical condition. Outcome data may be, for example, responses to patient reported outcome (PRO) instruments, responses to questionnaires, laboratory data, physical function tests, and/or responses to other OMDs.

Since the outcome data may be made publicly available, the present invention provides patients with an opportunity to select their treating clinicians based on the specific treatment outcomes from patients with similar medical conditions who have received similar treatments. The public availability of the outcomes, along with the fact that the data can be gathered without interaction with the clinician, may result in outcome data that is substantially unbiased by, for example, clinicians, medical device manufacturers, pharmaceutical companies, and/or others in the medical/healthcare industry reporting their own results and outcomes. Clinicians may be able to access the outcome data and, for example, improve their practice of medicine and/or publish their analysis of the outcome data in the medical literature to advance medical science. Since outcome data obtained in this manner is likely to be unbiased, the literature may be more likely to be trusted by other clinicians who are, for example, looking to improve the effectiveness with which they provide treatments, hence advancing medical science and improving healthcare delivery at the same time.

Outcome data can also be used by, for example, treatment providers, hospital centers, and insurance providers for quality assurance and quality improvement purposes. Use of the outcome data may enable hospitals and other treatment facilities to better discern which clinicians fall short of delivering a satisfactory level of care, and better defend their decisions to terminate clinicians who under-perform. Outcome data of this nature may also help patients better understand their medical condition, treatment results, and/or recovery over time, by providing them a pre-treatment baseline, and showing them their recovery over time and compared to other patients with similar treatments, thereby improving, for example, patients overall expectations for their treatment and understanding of their recovery.

As used herein, the term "treatment" is broadly defined to cover medical interventions to address physical and/or mental health issues and may be responsive to a particular diagnosis or combination of diagnoses a patient may receive. The term "treatment" may also encompass diagnostic tests and a monitored lack of treatment as may be provided with a placebo and/or wait-and-see type of approach. In some instances, a treatment may address a cosmetic issue, as may be the case with elective plastic surgery or certain dermatological procedures. The term treatment may further incorporate alternative medical treatments, such as acupuncture that have recognized merit within the medical literature. A treatment is typically performed by a healthcare professional, also referred to herein as a treatment provider, in a healthcare administration facility, also referred to herein as a treatment facility. Exemplary treatment providers include healthcare professionals, healthcare providers, doctors, nurse practitioners, physician's assistants, pharmacists, dentists, orthodontists, chiropractors and nurses. In some instances, a particular treatment provider may represent a group or team of healthcare professionals as may be the case with a lead surgeon and a team of doctors and nurses who support the lead surgeon during a surgical procedure or a group of doctors who work together to address a complex medical diagnosis such as cancer or cardiac disease. Exemplary treatment facilities include hospitals, clinics and independent doctors' offices.

In the past, it has been difficult to collect patient reported outcomes from patients. There are many reasons for this including, but not limited to, cumbersome presentation of questionnaires (e.g., PRO instruments) to the patients, inefficient mechanisms by which the patient responds to the questionnaires, and the lack of motivation for the patient to provide information about his or her diagnosis, treatment, and/or recovery. The present invention provides a solution to these problems by providing easy to use mechanisms for the delivery of questionnaires to the patient (via a patient wellness account) and questionnaires that are easy to understand and respond to. Furthermore, the present invention provides a motivation for the patient to provide information regarding his or her diagnosis, treatment, and/or recovery in the form of wellness and/or improvement scores that provide the individual patient with valuable incite into his or her own recovery and health or wellness. Often times, these wellness and/or improvement scores are calculated in over a very short time period (e.g., seconds or minutes) and provided to the patient very quickly following his or her provision of information thereby providing nearly immediate feedback to the user regarding his or her wellness. Thus, the patient is motivated to provide the information because he or she can track his or her own wellness as they progress through, for example, a treatment recovery process or manage a disease/diagnosis. For example, one problem is that it's been difficult to collect PRO data from patients; you've managed to make this information immediately useful to patients (tracking their own progress) and also made it more likely that patient's will provide longitudinal PRO information. Therefore I would include at least one set of claims that directly speaks to these features:

Turning now to the figures, FIG. 1A provides a block diagram of an exemplary system 100 that may be used to execute one or more of the processes described herein. At a high level, system 100 includes a server 102, a patient device 128, a treatment provider device 124, and a treatment facility computer system 134, all directly or indirectly communicatively coupled to one another via Health Insurance Portability and Accountability Act (HIPAA) compliance server 126. Patient device 128 may be any device (e.g., a smartphone, a laptop computer, a tablet computer, a desktop computer, etc.) that enables communication between a patient and other components of system 100. Similarly, treatment provider device 124 may be any device (e.g., a smartphone, a tablet computer, a laptop computer, a desktop computer, etc.) that enables communication between a treatment provider and other components of system 100. In some cases, treatment provider device 124 may also be a device that is enabled to perform a specific healthcare treatment and/or diagnostic task. For example, treatment provider device 124 may be a network-connected treadmill or a network-connected ultrasound machine. For simplicity, only one treatment provider device 124 is depicted, while it is understood that in practice there may be a plurality of treatment provider devices, one or more for each treatment provider. Similarly, while only one patient device 128 is depicted, it is understood that in practice there may be a plurality of patient devices, one or more for each patient. It should also be understood that while the databases depicted in FIGS. 1A and 1B and discussed throughout may be a series of one or more databases that may, in some instances, be geographically disparate.

Treatment facility computer system 134 may be a computer system that is located in, and/or communicatively coupled to, a treatment facility (i.e., a computer/server that is located in a doctor's office or treatment facility). Due to HIPAA regulations, treatment facility computer system 134 and its associated patient electronic medical record (EMR) database 130 may be protected by HIPAA-compliant firewall 140. As is understood in the art, an EMR (as stored in EMR database 130) may include notes prepared by a treatment provider regarding the health of a patient, results of medical tests performed on a patient, treatments administered on a patient, etc. Further due to HIPAA regulations, medical records from treatment facility computer system 134 may be communicated to treatment provider device 124, patient device 128 and server 102 via HIPAA compliance server 126. It is understood that other data (i.e., not patient-specific data) may be transmitted between treatment provider device 124, patient device 128, sever 102 and facility computer system 134 via a conventional communication network (e.g., the Internet, a wired network, a wireless network, a private network, a public network, routers, switches, etc.), which has not been depicted in FIG. 1A. Further, it is understood that treatment provider device 124, patient device 128, server 102 and facility computer system 134 may be communicatively coupled to HIPAA compliance server 126 via a similar communication network (although components 124, 128, 102 and 134 have been depicted as being directly coupled to HIPAA compliance server 126 for simplicity of illustration).

In one embodiment, HIPAA compliance server 126 may replace any patient identifying information (e.g., patient name, social security number, birthdate, address, etc.) in medical records with, for example, a binary string to form anonymized medical records containing no patient identifying information (e.g., patient name, social security number, birthdate, address, etc.). More generally, HIPAA compliance server 126 may replace any patient identifying information in medical data (e.g., EMR, questionnaire responses provided by a patient, wellness scores computed for a patient, etc.) with a binary string to form anonymized medical data. Such anonymized medical data may be stored at HIPAA compliance server 126, in various databases operated by server 102 (e.g., OMD response database 110, score database 120, etc.), cloud-based storage (e.g., Amazon Web services, Google Cloud platform or Microsoft Azure) (not depicted), etc. In the event the anonymized medical data is intercepted by a malicious individual (e.g., a hacker), patient privacy will still be preserved since the malicious individual will not be able to associate the anonymized medical data with any specific patient.

A mapping between respective binary strings and respective patient identifying information may be securely stored (e.g., stored in an encrypted manner) at HIPAA compliance server 126 (or other location). Such mapping may enable an electronic device (e.g., server 102, treatment provider device 124, and/or patient device 128) to access medical data associated with a specific patient. The steps for an electronic device to access the medical data of a patient may proceed as follows. First, the electronic device may be authenticated by HIPAA compliance server (e.g., the electronic device is required to provide the proper credentials, such as a login identifier and password). Following successful authentication, the electronic device may request medical data concerning an exemplary patient, John Doe. HIPAA compliance server 126 may map the patient name of "John Doe" to "patient 001010" via the mapping and/or indexing, and the medical data of patient 001010 may be retrieved from a database which stores the anonymized medical data (e.g., HIPAA compliance server 126, OMD response database 110, score database 120, etc.). HIPAA compliance server 126 (or software providing the functionality of HIPAA compliance server 126) may be provided by a third party data service (e.g., TrueVault of Redwood City, Calif. and/or Redox of Madison, Wis.). In the discussion below, server 102, treatment provider device 124, patient device 128 and treatment facility computer system 134 may be described to directly communicate various information (e.g., patient medical records) with one another for ease of discussion, but it is understood that in such communication, HIPAA compliance server 126 may perform the anonymization and mapping processes described above in order to ensure the communication complies with HIPAA regulations.

While server 102, treatment provider device 124 and patient device 128 have been depicted as being located outside of HIPAA-compliant firewall 140, this is not necessarily so. In another embodiment, one or more of server 102, treatment provider device 124 and patient device 128 may be located within HIPAA-compliant firewall 140. If server 102, treatment provider device 124, patient device 128 and treatment facility computer system 134 are all located within HIPAA compliant firewall 140, HIPAA compliance server 126 may not be necessary, as medical data would not need to be anonymized within HIPAA compliant firewall 140.

In one embodiment, the process flow for system 100 may proceed as follows. Upon receiving a request from, for example, a treatment provider, hospital administrator, and/or patient to schedule a treatment, scheduler 136 may request server 102 to administer an outcome measurement device (OMD) to and/or on that patient (or more generally may request server 102 to initiate a process which eventually results in an OMD being administered to and/or on that patient). In some cases, the request to administer the OMD may be triggered via the entry of a treatment code (e.g., a Current Procedural Terminology (CPT) code) or a treatment/diagnostic test name into the patient's EMR (as stored in patient EMR database 130), a treatment facility's billing software (e.g., billing program 138) and/or a treatment facility's scheduling software (e.g., scheduler 136). In some instances, when a treatment/diagnostic test name or other related information (other than a treatment/diagnostic code) is received, server 102 may interpret (using, for example, natural language analysis) the treatment/diagnostic test name so that it matches one or more treatment codes. In such cases, OMD selector 106 may determine one or more OMDs that match the treatment code via matched treatment code and OMD database 104. More generally, matched treatment code and OMD database 104 may also include matches between treatment names and OMDs, as well as diagnostic codes and OMDs.

Next, OMD selector 106 may retrieve the one or more determined OMDs from OMD database 108. The retrieved OMDs may be provided to OMD administrator 112, which may administer the OMDs to the patient via, for example, patient device 128. In the instance that the retrieved OMDs are patient reported outcome (PRO) instruments, the PRO instruments may be provided to patient device 128. Completed OMDs (also called OMD responses) may be transmitted from patient device 128 and stored in OMD response database 110. More specifically, OMD responses may be stored in OMD response database 110 in an anonymized fashion. For example, OMD responses may be indexed in OMD response database 110 by a binary string, or other anonymous identifier, rather than by a patient name. Similarly to the discussion above, if an OMD response for a specific patient is desired, HIPAA compliance server 126 may map the patient name to a binary string, and the OMD response associated with that binary string may be retrieved from OMD response database 110. For simplicity of discussion, the remainder of the description will merely state that an OMD response of a patient is retrieved from OMD response database 110, but it is understood that any such retrieval may require the assistance of HIPAA compliance server 126.

Once the OMD has been completed, the treatment may be scheduled for the patient. In other words, the completion of the OMD may be a precondition for the scheduling of the treatment. Upon the patient receiving the treatment, billing program 138 may notify server 102 that the patient has received a treatment for his/her medical condition. In response to such notification, a subsequent post-treatment OMD may be administered on the patient by OMD administrator 112. In many cases, the post-treatment OMD may be identical to the pre-treatment OMD, but in some instances, the two OMDs may vary (e.g., in response to unforeseen complications during the treatment, a post-treatment OMD which is different from the pre-treatment OMD may be chosen). The response to the post-treatment OMD may similarly be stored in OMD response database 110.

OMD response analyzer 118 may analyze the OMD responses stored in OMD response database 110 to generate one or more scores (e.g., a wellness score, an improvement score, a treatment effectiveness score, a treatment provider effectiveness score, a treatment facility effectiveness score, etc.). Such scores are described in more detail below with regard to FIG. 1B. Such analysis may rely upon scoring procedures stored in scoring procedure database 116. Such scoring may also rely upon other considerations and/or esoteric factors 132 stored at patient EMR database 130. In most circumstances, what may be referred to herein as "other considerations" are factors that may directly, or closely, relate to and/or have an impact on, a medical condition, diagnosis, and/or treatment. For example, it is known that smoking has an impact on a person's cardiovascular health. Thus, whether a person smokes may be an "other consideration" for a patient's treatment related to cardiovascular health. This relationship between cardiovascular health and smoking may be indexed or otherwise stored in other consideration database 132. An esoteric factor is one that is less directly related to a medical condition, diagnosis, and/or treatment but may still have an impact thereon. For example, a vegetarian diet may have an impact on a person's cardiovascular health yet this impact may be less well understood when compared with the impact of smoking on the same patient's cardiovascular health. As such, a person's status as a vegetarian may be considered an "esoteric factor."

The scores that are generated by OMD response analyzer 118 may be stored at score database 120. More specifically, scores may be stored in score database 120 in an anonymized fashion so as to, for example, comply with HIPAA regulations or other data security requirements/preferences. For instance, wellness scores associated with a patient may be indexed by a binary string in score database 120 rather than by a patient name. Similarly to the discussion above, if a wellness score for a specific patient is desired, the patient name may be mapped to a binary string by HIPAA compliance server 126, and the wellness score associated with the binary string may be retrieved from score database 120. For simplicity of discussion, the remainder of the description will merely state that a wellness score for a patient is retrieved from score database 120, but it is understood that any such retrieval may require the assistance of HIPAA compliance server 126. In some embodiments, score database 120 may store pre-treatment wellness scores and/or post treatment wellness scores. In some instances, score database 120 may also store one or more of a disease-specific registry of information, a diagnosis-specific registry of information, a treatment-specific registry of information, a patient-specific registry of information, and a treatment-provider-specific registry of information.

Finally, reporting module 122 may report the scores to one or more of treatment provider device 124, patient device 128 and treatment facility computer system 134. In addition to being communicatively coupled to score database 120, reporting module 122 may be communicatively coupled to treatment provider database 121 and treatment facility database 123. Treatment provider database 121 may store a collection of treatment provider names, indexed by one or more of the location of the treatment provider, the specialty (or specialties) of the treatment provider, service(s) provided by the treatment provider, a treatment facility the treatment provider is associated with, etc. Treatment provider database 121, in conjunction with score database 120, may allow reporting module 122 to provide a patient with a collection of treatment providers associated with one or more particular treatments located within a certain geographical area. Further, the treatment providers may be tagged with their respective treatment provider effectiveness scores (described below in FIG. 1B). Similarly, treatment facility database 123 may store a collection of treatment facility names (e.g., hospital names), indexed by one or more of the location of the treatment facility, service (or services) provided by the treatment facility, etc. Treatment facility database 123 in conjunction with score database 120 may allow reporting module 122 to provide a patient with a collection of treatment facilities associated with one or more particular treatments located within a certain geographical area. Further, the treatment facilities may be tagged with their respective treatment facility effectiveness scores (described below in FIG. 1B). While not described in detail, it is understood that any communication to and from server 102 may involve the use of a communication interface 114 (e.g., an Ethernet card) of server 102.

In addition to the request for a treatment, there are other events that may prompt an OMD to be administered to a patient. In one example, the scheduling of an initial appointment (e.g., a consultation) for a patient to discuss a medical condition with a healthcare professional may prompt an OMD to be administered to the patient. Administering an OMD to the patient prior to this initial appointment may be useful for establishing a baseline state of health for the patient, but the selection of the OMD may have some complexity, as no treatment code, treatment name or diagnostic code may yet be available when the initial appointment is scheduled. In many instances, all that the patient will provide is a brief description of the symptoms he/she may be experiencing (e.g., shortness of breath, fever, etc.) In one embodiment, such symptoms may be provided to OMD selector 106, which attempts to match the symptoms with one or more treatment codes, treatment names or diagnostic codes.

Such matching by OMD selector 106 may be performed using a learning machine. For instance, matches between, for example, symptoms and treatment codes; symptom and treatment names; and/or symptoms and diagnostic codes) may be provided by a healthcare professional when treating patients, and such matches may be used to train a model that can then be used to determine treatment codes, treatment names or diagnostic codes based on, for example, a patient's symptoms and/or treatment provider notes. Upon determining a treatment code, treatment name, or a diagnostic code, OMD selector 106 may select one or more OMDs based on matches provided in matched treatment code and OMD database 104 (as described above). It is anticipated that the determination of a treatment code, treatment name or diagnostic code by OMD selector 106 may be, in some instances, an imperfect process, so a healthcare provider, or other expert, may be asked to make any necessary adjustments to the treatment code, treatment name and/or diagnostic code determination, before OMD selector 106 selects the one or more OMDs.

As another example, the billing for a medical appointment during which a patient discusses a medical condition with a healthcare professional may prompt an OMD to be administered to the patient. More specifically, billing program 138 may notify server 102 when a bill (or invoice) is generated. If the billing for the appointment occurs after the appointment has concluded, the bill may be associated with a diagnostic code (which may be determined by the healthcare professional during the medical appointment). OMD selector 106 may use the diagnostic code to locate one or more appropriate OMDs for the patient with the assistance of matched treatment code and OMD database 104.

In the examples provided above, it was assumed that an OMD is administered to a patient via patient device 128. In other instances, a medical professional may be required to administer the OMD to the patient. For example, server 102 may notify treatment provider device 124 that one or more OMDs should be administered as part of, for example, a medical examination of a patient. In one example, if a patient has recently undergone cardiothoracic surgery, OMD administrator 112 may provide one or more OMDs to treatment provider device 124 (e.g., the Intrathoracic Gas Volume Test, Total Lung Capacity Test, Vital Capacity Test, 6 Minute Walk Test, Aortic Insufficiency Test, Mitral Regurgitation Test and/or Aortic Valve Area Test) that could, or should, be administered to the patient during an exam and/or provide one or more mechanisms to treatment provider device 124 (e.g., fillable forms) for the treatment provider to enter the OMD responses.

Figure 1B:
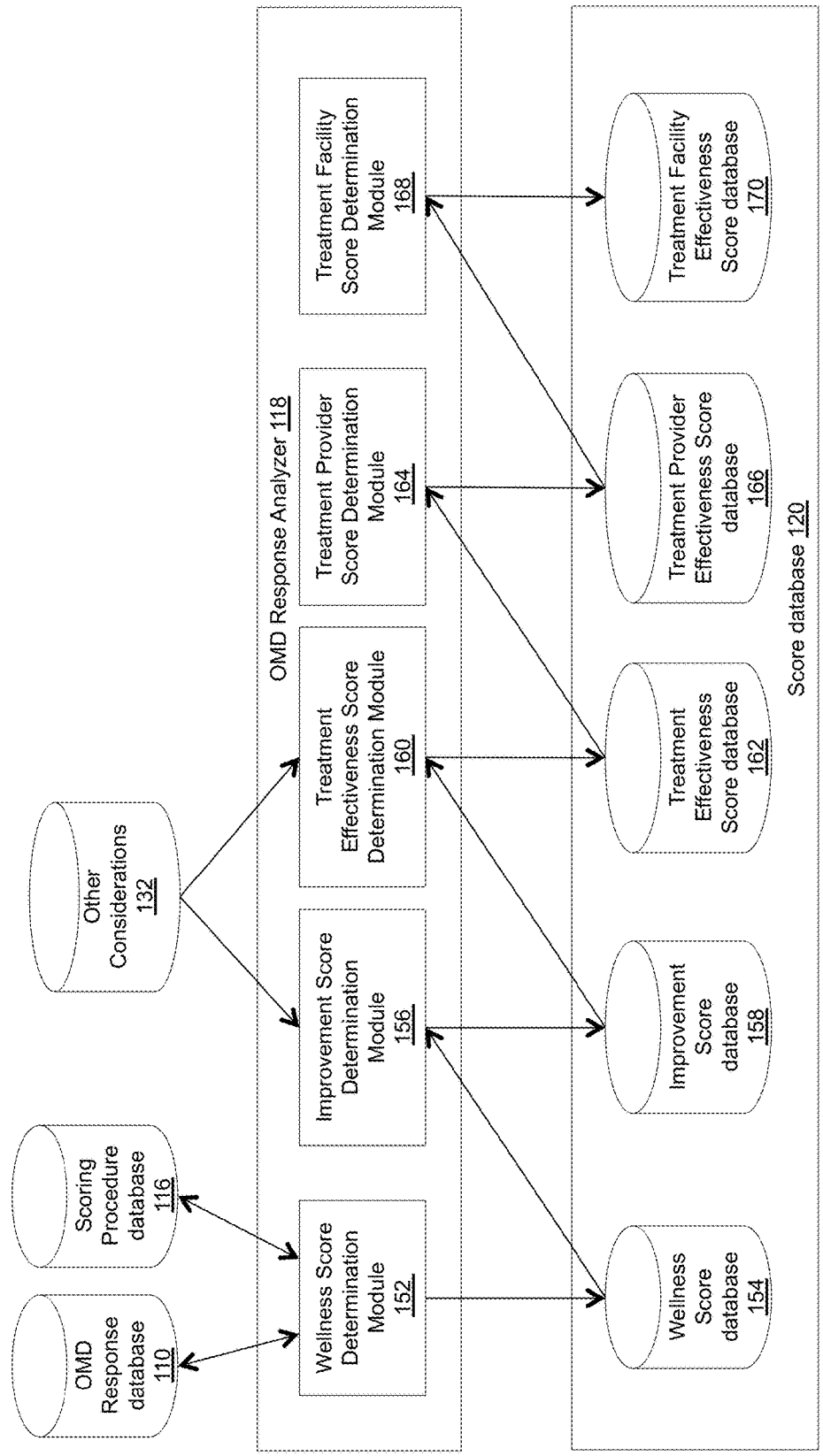
FIG. 1B depicts an outcome measurement device (OMD) response analyzer and score database, in accordance with some embodiments of the present invention.

FIG. 1B depicts one embodiment of a system 150 that supports the operation of OMD response analyzer 118 and score database 120 (and some associated components). OMD response analyzer 118 may comprise wellness score determination module 152. In one embodiment, wellness score determination module 152 retrieves responses to OMD instrument from OMD response database 110, and further may retrieve a scoring procedure associated with the OMD responses from scoring procedure database 116. The scoring procedures may be indexed by an identifier of an OMD for which responses have been received, making for easy retrieval of a corresponding scoring procedure. Various scoring procedures may be employed to score a completed OMD, and in one embodiment, the generated score may be known as a "wellness score". In some cases, a "wellness score" may serve to indicate how severe a patient's symptoms are. In these cases, a low wellness/symptom severity score may indicate that a patient's symptoms are relatively more severe than a higher wellness/symptom severity score such that an increasing wellness/symptom severity score indicates an improvement (i.e., decrease in severity) in the symptoms.

In the case where an OMD is a questionnaire (or PRO instrument), a certain weighing may be used to score or evaluate the patient's responses. For example, certain responses that are more objective in nature (e.g., heart rate, blood glucose level, etc.), may receive greater weights (and hence have a greater influence on the wellness score) than certain responses that are more subjective in nature (e.g., degree of pain, mood, etc.). The reverse scenario, of course, could be true in which subjective responses receive a greater weight than objective responses. Scores generated by wellness score determination module 152 may be stored in wellness score database 154. The wellness scores may be indexed in various fashions, for ease of retrieval. In one embodiment, wellness scores may be indexed according to one or more of a patient identifier (e.g., binary string to protect patient privacy), medical condition, treatment provider, treatment facility, time at which OMD was completed, etc.

Improvement score determination module 156 may retrieve two wellness scores for a patient (i.e., a first score calculated for an OMD completed at a first time point and a second score calculated for an OMD completed at a second time point) from wellness score database 154. Improvement score determination module 156 may calculate the difference between the first and second score, and such difference may be known as an improvement score. More generally, the improvement score may be called a health progression score, as the patient's health may decline instead of improve. The improvement score may be stored in improvement score database 158. In one refinement, a relative improvement score may be calculated as the improvement score (i.e., the difference described above) normalized by a maximum improvement score, which may be calculated based on, for example, other considerations 132 stored in a patient's EMR. The maximum improvement score may take into consideration other factors such as the state of a patient prior to a medical treatment (e.g., if patient was in fairly good health, the maximum improvement score might be lower than if the patient was in poor health), and/or the age of a patient (e.g., younger patients might have a higher maximum improvement score than older patients), etc. An improvement score (or a relative improvement score) may be stored in improvement score database 158. The improvement scores may be indexed in various fashions, for ease of retrieval. In one embodiment, improvement scores may be indexed according to one or more of a patient identifier (e.g., binary string to protect patient privacy), medical condition, treatment provider, treatment facility, and time duration over which improvement score was measured, etc.

Treatment effectiveness score determination module 160 may calculate a treatment effectiveness score for a particular treatment based on an improvement score (or a relative improvement score) that, for example, measures the changes in a patient's health from prior to the treatment to after the treatment or at various points (e.g., weeks, months, etc.) after the treatment. In a simplistic embodiment, the treatment effectiveness score may be set equal to an improvement score. In other words, if the patient's condition improves a lot, the treatment may be determined as very effective; if the patient's condition does not improve, the treatment may be determined as not effective; if the patient's condition gets worse, the treatment may be determined as not effective; and so on.

In an embodiment, the treatment effectiveness score may be set equal to a relative improvement score. Such implementation might rate a certain treatment as highly effective, even if a patient's condition were to only improve by a small amount. For example, if patients suffering from a medical condition typically only live three to six months with a conventional treatment (leading to a low maximum improvement score), but a new treatment allows a patient to live nine months, the new treatment would receive a high treatment effectiveness score, despite the fact that the patient died after nine months.

In another embodiment, "other considerations" (as stored as element 132 in patient EMR database 130) may be taken into account when calculating the treatment effectiveness score. For example, if a patient's EMR indicates that the patient has received two medical treatments, and a relative improvement score is calculated based on a first wellness score measured prior to the first medical treatment and a second wellness score measured after the second medical treatment, it would not be clear whether the improvement was due to the first medical treatment, the second medical treatment, or both the first and second medical treatment. In such instance, treatment effectiveness score determination module 160 may generate an output of "undetermined".

As another example, if a patient's EMR notes, or if the patient's OMD response(s) indicate, that a patient has experienced an injury (e.g., sprained ankle) following a treatment (e.g., knee surgery), an improvement score (or more generally, a medical progression score) which measures the patient's progress from before the treatment to after the subsequent injury would not be used to calculate any treatment effectiveness score. After all, the knee surgery could have been successful, allowing a patient to resume normal daily activities, and the subsequent sprained ankle could be the reason for a patient's current state of poor health.

As another example, if a patient's EMR notes, or if the patient's OMD response(s) indicate, that a patient has not complied with pre-treatment and/or post-treatment instructions, an improvement score (or more generally, a medical progression score) which measures the patient's progress from before a treatment to after the treatment may not be used to calculate any treatment effectiveness score because the patient's failure to comply with instructions may be a direct cause of a delayed, or otherwise not successful recovery. For example, if the treatment being evaluated is one that requires wound recovery (from, for example, a surgical incision), the failure of a wound of a particular patient to heal could have been due to the patient's non-compliance with post-treatment instructions (e.g., failure to apply an antibiotic cream over the wound every other day), and not the treatment provider's lack of skill at performing a surgical procedure.

Any treatment effectiveness scores may be stored in treatment effectiveness score database 162. The treatment effectiveness scores may be indexed in various fashions, for ease of retrieval. In one embodiment, treatment effectiveness scores may be indexed according to one or more of a patient identifier (e.g., binary string to protect patient privacy), medical condition, treatment name, treatment provider, treatment facility, etc.

Treatment provider score determination module 164 may determine a treatment provider score for a treatment provider based on a collection of treatment effectiveness scores (e.g., treatment effectiveness scores aggregated for a group of patients treated by the treatment provider). In a simplistic embodiment, the treatment provider score may be determined as an average of the treatment effectiveness scores. In a preferred embodiment, the treatment provider score may be determined as a weighted average of the treatment effectiveness scores, where, for example, the more recent treatment effectiveness scores may be given higher weight. The treatment provider effectiveness scores may be stored in treatment provider effectiveness score database 166. The treatment provider effectiveness scores may be indexed in various fashions, for ease of retrieval. In one embodiment, treatment provider effectiveness scores may be indexed according to one or more of a medical condition, treatment name, treatment provider, treatment facility, etc. Treatment provider effectiveness score database 166 may be used in a doctor finder application (described below) in which treatment providers in the proximity of patient's location may be displayed along with their respective treatment provider scores.

Treatment facility score determination module 168 may determine a treatment facility effectiveness score for a treatment facility based on a collection of treatment provider effectiveness scores (e.g., treatment provider effectiveness scores aggregated for a group of treatment providers who work at the treatment facility). In a simplistic embodiment, the treatment facility score may be determined as an average of treatment provider effectiveness scores for treatment providers affiliated with the treatment facility. In one embodiment, the treatment facility score may be determined as a weighted average of the treatment provider effectiveness scores, with weights proportional to the number of patients treated by each treatment provider. The treatment facility effectiveness scores may be stored in treatment facility effectiveness score database 170. The treatment facility effectiveness scores may be indexed in various fashions, for ease of retrieval. In one embodiment, treatment facility effectiveness scores may be indexed according to one or more of a medical condition, treatment name, treatment facility, etc. Treatment facility effectiveness score database 170 may be used in a treatment facility finder application in which treatment facilities in the proximity of a patient's location may be displayed along with their respective treatment facility effectiveness scores.

Figure 2:
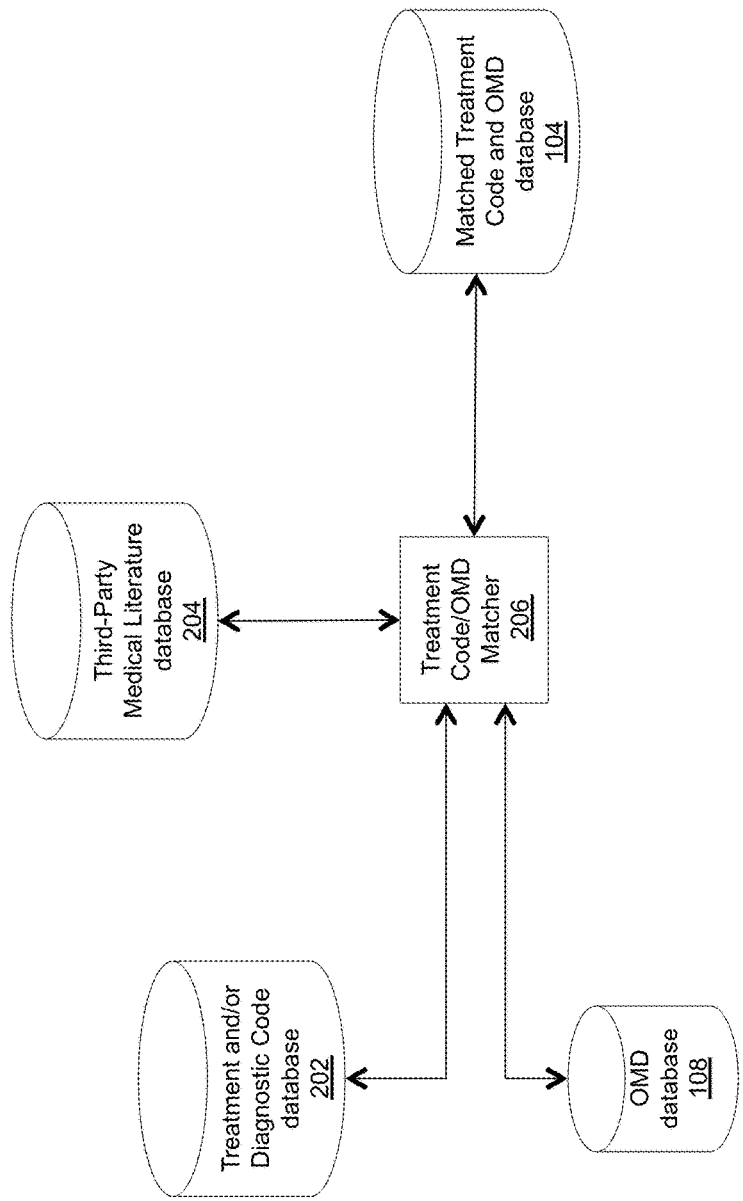
FIG. 2 depicts a system diagram of components that are used to generate a matched treatment code and OMD database, in accordance with some embodiments of the present invention.

FIG. 2 depicts system diagram 200 of components that may be used to generate a matched treatment code and OMD database. In one embodiment, treatment and/or diagnostic code database 202 may provide a number of standardized treatment and diagnostic codes to the treatment code/OMD matcher 206. Exemplary treatment and diagnostic code databases 202 include a database operated by a third party (i.e., not a patient or provider), such as a health insurance company or industry group, or a database operated by a healthcare provider (e.g., a doctor) and/or a treatment facility (e.g., a clinic or hospital).

The treatment and/or diagnostic codes provided by treatment and/or diagnostic code database 202 may be standardized codes, such as Current Procedural Terminology (CPT) codes, hospital procedure codes, and/or diagnostic codes. In some instances, the codes may not be standardized (i.e., may be specific to a particular treatment provider or treatment facility) and, in these instances, the codes may be translated into a standard code like a CPT code by, for example, treatment code/OMD matcher 206. As disclosed herein, the treatment and/or diagnostic codes may be referred to as CPT codes, but those of skill in the art will recognize that any coding naming convention may be used in lieu of CPT codes.

Third-party medical literature database 204 may be any database that stores medical literature, including, but not limited to, a database operated by a subscription service, a library, and/or a publisher that provides medical literature. Third-party medical literature database 204 may provide medical literature to the treatment code/OMD matcher 206. The medical literature provided by third-party medical literature database 204 might include scientifically rigorous literature related to the medical arts and sciences, as well as literature peripheral to the medical arts and sciences. In most cases, the medical literature provided by third-party medical literature database 204 is vetted and/or accredited by one or more recognized medical authorities. The medical literature may be in any language and, in instances where a base language is preferred (e.g., English), a translation mechanism (not shown) configured to translate the medical literature into the base language may be included in system 200.

Medical literature is generally understood by those of skill in the art as literature of scientific nature that is peer reviewed. Sources of medical literature include, but are not limited to, the *Journal of the American Medical Association*, the *Journal of the American College of Cardiology*, and the *New England Journal of Medicine*. Medical literature may also include information published by the *National Institutes of Health's Patient-Reported Outcomes Measurement Information System (NIH PROMIS)*. NIH PROMIS provides compiled sets of questions that may be included in, for example, patient-reported outcome (PRO) instruments based on peer groups for specific medical or treatment specialties who agree on the proper questions to include in a particular set of questions designed to measure an outcome. These groups of questions may, or may not be specifically validated in peer-reviewed medical literature. In many instances, third-party medical literature database 204 will be continuously maintained and updated so that it provides the most up-to-date medical literature and continuously evolves over time to capture advances in the medical field and patient care.

As described above, OMD database 108 may store a plurality of OMDs. The OMDs may be any treatment- or outcome-monitoring device (or vehicle) for monitoring a patient's outcome from a treatment or procedure, including the lack of a treatment (e.g., where the treatment is not taking any affirmative action as may be the case with a "wait and see" type of approach). In some instances, OMDs may be vetted by the medical establishment (in, for example, the medical literature or by a particular treatment provider or treatment facility) and/or via clinical trials as effective tools for measuring a treatment outcome or a patient's rate of recovery from a particular medical treatment or procedure.

OMDs are typically designed to gather information from a patient with regard to a particular medical condition he or she may have and/or a treatment the patient has received. An OMD may be designed to gather treatment outcome data over a short (e.g., hours or days), medium (e.g., weeks or months), and/or long (e.g., months or years) period of time. Additionally, or alternatively, an OMD may be designed to gather information regarding a patient's condition prior to a patient receiving a treatment or procedure so as to, for example, establish a baseline degree of wellness for the patient. In most instances, OMDs are tailored to specific treatments and/or diagnoses and their use may be advised/directed by one or more articles of medical literature.

As mentioned above, one example of an OMD is a patient reported outcome ("PRO") instrument. PRO instruments may include a questionnaire and other documentation that supports the use and/or rationale of the questionnaire. Exemplary PROs include the Kidney Disease Quality of Life Instrument, the National Eye Institute Visual Functioning Questionnaire, the Epilepsy Surgery Inventory, the Adult Asthma Quality of Life Questionnaire (AQLQ), the Migraine Specific Quality of Life Questionnaire (MSQOL), the Ankylosing Spondylitis Quality of Life Questionnaire (ASQOL), and the Seattle Angina Questionnaire, to name a few. In the past, PRO instruments have been used to obtain patient reported treatment outcomes within the specific circumstances of an academic medical study.

OMDs may also include, for example, bio-chemical tests (e.g., blood tests, biopsies, etc.) and objective measures of patient performance as may be provided by, for example, a lung capacity test, an oximeter, or an EKG machine. In some circumstances, a plurality of OMDs may be used to, for example, gather different types of data regarding a patient's condition prior to, or following, the patient receiving a treatment, or an array of treatments. For example, when obtaining treatment outcome information regarding cardiothoracic surgery, relevant OMDs may include a Intrathoracic Gas Volume test, a Total Lung Capacity test, a Vital Capacity test, a 6 Minute Walk Test, an Aortic insufficiency test, a Mitral regurgitation test, and/or an Aortic valve area test, as well as a number of PRO instruments.

Treatment code/OMD matcher 206 may be communicatively coupled to treatment and/or diagnostic code source 202, third-party medical literature source 204, OMD data source 108, and matched treatment code and OMD database 104. Treatment code/OMD matcher 206 may be configured to match medical literature provided by third-party medical literature source 204 with one or more treatment and/or diagnostic codes provided by treatment and/or diagnostic code source 202. Treatment code/OMD matcher 206 may further be configured to match one or more OMDs with relevant medical literature and/or treatment/diagnostic codes. A data structure that stores matched, or indexed, OMDs and treatment/diagnostic codes, such as matched treatment code and OMD data structure 104 may then be built, populated, and/or updated.

In some embodiments, a particular treatment and/or diagnostic code may be associated with information, an OMD, and/or one or more sets of instructions that may be executed upon the occurrence of one or more events described herein via, for example, one or more of processes 300-900 and 1600-2200. This association may be stored in, for example, matched treatment code and OMD database 104, OMD database 108, treatment and/or diagnostic code database 202, for use by, for example, OMD selector 106 and/or treatment code/OMD matcher 206.

In some cases, treatment and/or diagnostic codes may be related to one another as may be the case when a treatment and/or diagnostic code shares common characteristics with another treatment and/or diagnostic code. When treatment and/or diagnostic codes share common characteristics, they may be grouped together. The grouping information may be stored in, for example, matched treatment code and OMD database 104, OMD database 108, treatment and/or diagnostic code database 202, for use by, for example, OMD selector 106 and/or treatment code/OMD matcher 206.

In some embodiments, treatment and/or diagnostic codes may also be grouped together to link multiple steps of a treatment together as may be desired for a treatment that requires multiple steps (e.g., a multi-step surgery or chemotherapy treatment) or for a treatment that has multiple facets (e.g., a surgery that has facets of pre-operation preparation, anesthesia, performance of the surgery, an implanted device, etc.). At times, a treatment may also be associated with other treatments as may be required to revise or redo a treatment, such as a revision of a knee replacement surgery or a repeat of a chemotherapy regimen to treat cancer.

Treatment and/or diagnostic codes that are linked together may be associated with the same, or similar, OMDs and/or scoring procedures for analyzing responses to respective OMDs. In some instances, when a particular piece of medical literature associates a particular treatment and/or diagnosis with an OMD for determining a level of effectiveness for the treatment/diagnosis, other treatment and/or diagnostic codes that are in a group with the particular treatment/diagnosis may also be associated with this OMD. In this way, OMDs may be associated with treatment and/or diagnostic codes even when the medical literature relating to a particular OMD does not provide for such an explicit association. For example, treatment codes associated with various aspects and/or types of eye/retinal surgery may share common characteristics that may be assessed via the same OMD (e.g., the National Eye Institute Visual Function Questionnaire PRO instrument). Thus, some, or all, treatment and/or diagnostic codes associated with eye or retinal surgery may be associated with a common OMD in the form of the National Eye Institute Visual Function Questionnaire PRO instrument whether or not a specific piece of medical literature mentions such an association is appropriate/required.

On some occasions, treatment and/or diagnostic codes may also be linked to relatively general or all-purpose types of OMDs, or questions to be inserted into and/or added to an OMD or questionnaire. For example, one or more treatment and/or diagnostic codes (whether in a group or not) may be associated with a treatment/diagnostic code specific OMD as well as one or more general OMDs, such as a general quality of life questionnaire that includes, for example, questions regarding a patient's general health (e.g., level of pain, mobility, and so on) or an OMD related to a blood pressure reading or a patient's weight.

The one or more treatment and/or diagnostic codes and/or OMDs may be associated with, for example, alternate terminology (e.g., a medical specialty, medical subspecialty, and/or procedure type) that may be used to refer to the treatment and/or diagnostic code, an OMD, and/or an aspect thereof. For example, a CPT treatment code of 67101, which is associated with a "repair of retinal detachment by diathermy" treatment, may be associated with one or more clinician descriptors like "enucleation of eye," or patient descriptors like "repair of detached retina," and/or other terms like "eye," "optical," "ocular," "eye surgery," "vision," "ophthalmology," etc. This terminology may be used to, for example, search for a treatment and/or diagnostic code and/or OMD that matches a natural language entry into, for example, a surgical scheduler, such as scheduler 136 and/or EMR. This terminology may also be used to communicate with patients, who are more familiar with terms like "eye surgery" than terms like "repair of retinal detachment by diathermy," regarding their treatment and/or recovery, and/or completion of an OMD. In some instances, this terminology may be used to populate forms for communication to a particular patient, a health insurance provider of the patient, and/or a treatment provider of the patient.

In some embodiments, an OMD may be associated with one or more characteristics such as an abbreviated name and/or documents, such as scoring procedures for the OMD, a list of questions for a questionnaire associated with the OMD, a license or copyright for the OMD, and/or medical literature related to the OMD. When an OMD is associated with medical literature, the OMD may be linked to the relevant piece (or pieces) of medical literature so as to facilitate provision of the relevant medical literature to, for example, a treatment administrator, treatment provider, and/or patient. On some occasions, the OMD may also be linked with relevant patient characteristics such as age, gender, race, and so on.

In some instances, an OMD may be linked with a set or rules for scoring/interpreting responses to an OMD, which may be referred to herein as a "scoring procedure" and, in some cases, one or more subsets of rules for scoring the OMD. Subsets of rules for a scoring procedure, which may be referred to herein as "a sub-scoring procedure" may be defined by, for example, patient characteristics (e.g., age, race, gender) or other factors/considerations. In some cases, these scoring procedures may also be associated with threshold values (on a scale of, for example, 1-100 or A-F) for scores that may define various stages of recovery. In some instances, these preferred values are provided to patient as a minimum wellness descriptor, or minimum wellness score, a 50% wellness score, and a full wellness descriptor, or full wellness score. Examples of a minimum well score and a maximum wellness score for knee function are provided by interface 1813 as discussed below with regard to FIG. 18N. A full wellness score may also be referred to as a maximum wellness score. These threshold values for a particular patient may be adjusted based on, for example, a subset of rules that are appropriate for the patient or other considerations (e.g., comorbidities, patient- or doctor-specific goals, etc.). Information about other considerations may be stored in, for example, other considerations element 132. Examples of patient-facing interfaces that provide various wellness scores are provided by interfaces 1800-1813 of FIGS. 18A-18N.

Figure 3:
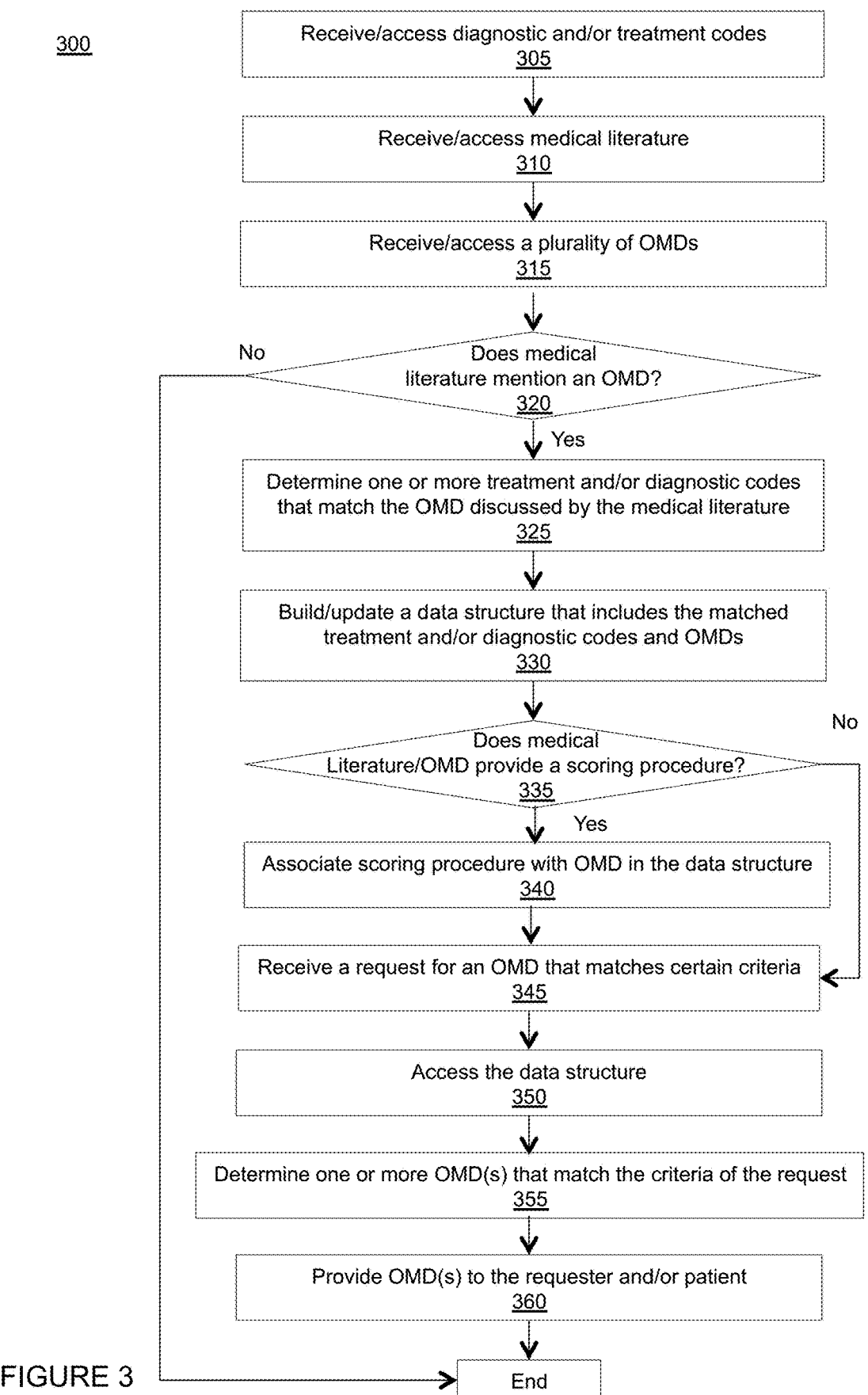
FIG. 3 provides a flowchart of an exemplary process for matching a treatment code and/or a diagnostic code with an OMD, in accordance with some embodiments of the present invention.

FIG. 3 provides a flow chart of an exemplary process 300 for matching a treatment and/or diagnostic code with an OMD. Process 300 may be executed by, for example, treatment code/OMD matcher 206. In step 305, treatment request information, treatment codes, and/or diagnostic codes may be received by, for example, treatment code/OMD matcher 206 from, for example, treatment and/or diagnostic code database 202. In instances where the received codes are not standard or recognized codes (e.g., not CPT codes), they may be translated into a recognized code using, for example, natural language analysis and/or machine learning and/or alternate terminology associated with one or more of the known treatment codes. In step 310, the medical literature may be received and/or accessed via, for example, third-party medical literature database 204. In step 315, a plurality of OMDs may be received and/or accessed via, for example, OMD database 108.

In step 320, a determination may be made as to whether a particular article of medical literature included within the received/accessed medical literature mentions one or more OMDs. When the particular article of medical literature does not mention an OMD, process 300 may end. Step 320 may be performed by, for example, employing an individual to read the medical literature and manually associate a particular article of medical literature with one or more OMDs and/or characteristics. Additionally, or alternatively, step 320 may be performed by one or more automated processes including, but not limited to, keyword searching, a semantic language analysis, and/or a natural language analysis. In some embodiments, step 320 may include one or more quality review processes, such as review of the medical literature and/or determinations regarding the medical literature's discussion of OMDs and other medical issues by skilled professionals. Exemplary skilled professionals include, but are not limited to, doctors, nurses, treatment facility administrators, and academics or researchers skilled in one or more medical fields.

Next, in step 325, one or more treatment and/or diagnostic codes that match the OMD discussed in the particular article of medical literature analyzed in step 320 may be determined. In some embodiments, execution of step 325 may include association of various terms or phrases that relate to the OMD. In some embodiments, execution of step 325 may include determining whether one or more treatment and/or diagnostic codes that share common characteristics with the treatment and/or diagnostic code mentioned in the medical literature (but are not specifically mentioned in the medical literature) should also be associated with the OMD. In some instances, these treatment and/or diagnostic codes that share common characteristics with the treatment and/or diagnostic code mentioned in the medical literature may be grouped with the treatment and/or diagnostic code mentioned in the medical literature.

Then, in step 330, a data structure that indicates how the OMD(s) discussed by a particular article of medical literature are matched, or otherwise associated with, treatment and/or diagnostic codes may be built, modified, or updated. One example of the data structure that may be built, modified, or updated in step 330 is matched treatment/diagnostic code and OMD data structure 104.

In step 355, it may be determined whether or not the OMD (when, for example, the OMD is a PRO instrument) is associated with a scoring procedure or sub-scoring procedure and/or whether the medical literature mentions a scoring procedure and/or sub-scoring procedure that should be used with the OMD and, if so, the scoring procedure and/or sub-scoring procedure may be associated with the OMD in the data structure built and/or updated in step 330 (step 340). Additionally, or alternatively the scoring procedure and/or sub-scoring procedure may be associated with the OMD and/or medical literature in a different data structure, such as scoring procedure database 116.

When the OMD is not associated with a scoring procedure (step 335), or when step 340 has been completed, a request for an OMD may be received by, for example, OMD selector 106 (step 345). The request may be received from, for example, a treatment provider via, for example, treatment facility computer system 134 and/or treatment provider device 124. The request may also be received from a patient via, for example, patient device 128. In some instances, a request for an OMD may be automatically triggered upon receipt of a request to schedule a treatment at, for example, treatment facility computer system 134 and/or treatment provider device 124. In other instances, a request for an OMD may be received as part of a scheduled OMD patient follow-up program, wherein a patient is scheduled to receive one or more OMDs over a period of time so as to, for example, obtain information regarding the patient's condition with regard to the treatment (or otherwise) over time. For example, a patient who undergoes knee replacement surgery may be set up with a patient follow-up program so that the patient receives an OMD immediately following surgery, two weeks after surgery, four weeks after surgery, six months after surgery, and so on. Requests for OMDs that match the schedule may then be received at step 345. In some embodiments, a request for an OMD may be triggered when a billing or accounting entity associated with the treatment provider requests pre-approval of payment from an insurance company for a treatment prior to the treatment being performed.

When a request for an OMD is received, the data structure built and/or updated in step 330 may be accessed (step 350) so that one or more OMD(s) that match one or more criteria (e.g., a treatment code, diagnostic code, interval of time since the treatment was performed on patient, etc.) of the request may be determined or selected (step 355). The determined or selected one or more OMD(s) may then be provided to the requester and/or patient (step 360). In some embodiments, execution of step 355 may include determining a scoring procedure that is associated with the one or more determined OMDs. In these embodiments, execution of step 360 may also include providing the scoring procedure to the requester. In instances where a plurality of OMDs are determined to match the request, execution of steps 355 and/or 360 may include determining a preferred OMD out of the plurality of OMDs, or a combination of preferred OMDs. In some instances, this determination may include consideration of one of more preferences of, for example, a treatment provider or treatment facility and/or analysis of a particular patient's medical condition as may be provided by the patient's EMR. In this way, a requester may not have to determine which is the best OMD for a particular set of circumstances or treatment code. Following step 360, process 300 may end.

Below is one example of how process 300 may be executed. Initially, a diagnostic and/or treatment code for a transcatheter aortic valve treatment which is associated with the American Medical Association (AMA) CPT code of 33361-33366 may be received (step 305). The medical literature and/or OMDs may be accessed to determine whether there is medical literature and/or OMDs that mentions a diagnosis or treatment associated with the transcatheter aortic valve treatment (steps 310 and 315).

A determination may then be made that one or more PRO instruments or other OMDs are mentioned in the medical literature with regard to transcatheter aortic valves treatments (step 320). For example, a PRO instrument associated with a transcatheter aortic valve treatment and/or an underlying disease state or diagnosis may be found in the medical literature along with one or more papers (i.e., articles of medical literature) that validate use of the PRO instrument and/or the OMD found in the search (step 325). An example of a paper that explains how a transcatheter aortic valve is used in patients is Reynolds M R, et al., "Health-Related Quality Of Life After Transcatheter Aortic Valve Replacement in Inoperable Patients with Severe Aortic Stenosis", *Circulation*. 2011 Nov. 1; 124(18): 1964-72, and an example of a validating paper for a PRO instrument used in connection with a transcatheter aortic valve is "Development and Evaluation of the Kansas City Cardiomyopathy Questionnaire: A New Health Status Measure for Heart Failure", *Journal of the American College of Cardiology*, Vol. 35, No. 5, 2000. The validating paper may also explain how the PRO instrument should be used and/or how responses to the PRO instrument should be evaluated to determine, for example, an effectiveness of the medical treatment. Thus, the validating paper may provide a scoring procedure and/or sub-scoring procedure for the OMD.

A data structure may then be built and/or updated to associate the PRO, a disease state or diagnosis being treated with the transcatheter aortic valve replacement treatment, and/or the medical literature found to be associated with transcatheter aortic valve replacement treatments (step 330). In some instances, the questions or other information from the PRO instrument may also be added to the data structure. More specifically, in this example the Kansas City Cardiomyopathy Questionnaire, CPT codes 33361-33366, the actual PRO questions of the PRO instrument found in the medical literature, and/or a schedule for administering the PRO instrument may all be added to the data structure.

Then, when a patient is scheduled for transcatheter aortic valve replacement with prosthetic valve via percutaneous femoral artery approach treatment (AMA CPT 33361), a request for an OMD (step 345) may be received in response to the scheduling of the transcatheter aortic valve replacement treatment. The data structure may be accessed (step 350) in order to determine one or more OMDs that match the scheduled treatment (i.e., Kansas City Cardiomyopathy Questionnaire) (step 355). Then, the Kansas City Cardiomyopathy Questionnaire may be sent to a requester (e.g., whoever scheduled the treatment) and/or the patient automatically without any further input from, for example, a treatment provider, treatment facility, or patient (step 360).

Figure 4:
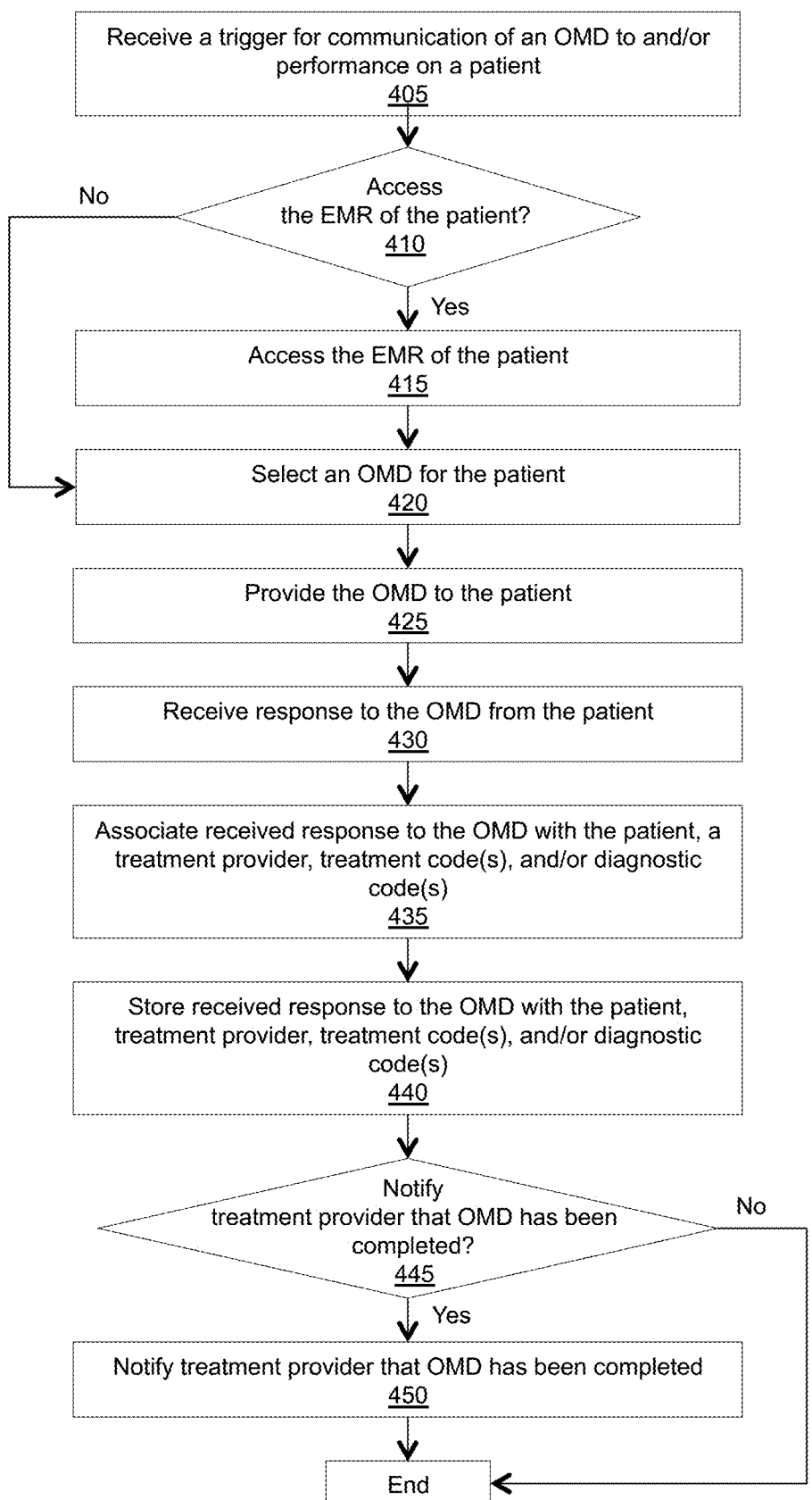
FIG. 4 provides a flowchart of an exemplary process for selecting an OMD to provide to and/or perform on a patient, providing the OMD to the patient, and receiving a response thereto, in accordance with some embodiments of the present invention.

FIG. 4 provides a flowchart 400 of an exemplary process for selecting an OMD to provide to and/or perform on a patient, providing the OMD to the patient, and receiving a response thereto. Process 400 may be executed by, for example, any of the systems, system components, and/or combination of components, included therein.

In step 405, a trigger for communication of an OMD to and/or performance on a patient may be received. In some embodiments, the trigger may be a request to schedule a treatment for a patient and may be received by, for example, scheduler 136 of treatment facility computer system 134. In other embodiments, the trigger may be an explicit request by, for example, a treatment provider and/or patient to communicate an OMD to the patient.

Often times, the trigger is associated with and/or includes a treatment code, or codes, such as a CPT code. In some embodiments, execution of step 405 may involve the entering of a treatment code into the EMR of the patient. In other embodiments, execution of step 405 may require the manual entry of a treatment into a scheduler 136 or billing program 138. At times, manually entered treatments may not include a treatment and/or diagnostic code. For example, a treatment facility may schedule a patient for a treatment or the accounting department of a treatment facility may bill a client for a treatment without entering a treatment or diagnostic code into the patient's EMR. The scheduling and/or billing information may then be analyzed to determine which, if any, treatment and/or diagnostic codes are appropriate. This determination may be performed using, for example, natural language analysis and/or machine learning and/or alternate terminology that may be associated with information treatment codes and/or diagnostic codes and/or information entered into an EMR, a scheduler, and/or an accounting system. In some instances, the scheduling and/or billing information may be analyzed and a preliminary determination of the appropriate treatment and/or diagnostic codes for the information may be determined. Optionally, a skilled professional (e.g., nurse or healthcare administrator) may then review the preliminary determination and make any necessary adjustments to the treatment and/or diagnostic code determination. Then, one or more OMDs may be matched to the determined and/or adjusted treatment and/or diagnostic codes.

In step 410, a determination may be made as to whether the EMR of the patient should be accessed. If so, the EMR may be accessed (in step 415) in order to, for example, obtain information regarding the medical history of the patient, prior treatment codes associated with the patient, prior treatment providers associated with the patient, and/or a treatment provider associated with the received request to schedule the patient for the treatment. Otherwise, the process continues to step 420.

The treatment code (or another information associated with the trigger received in step 405) may then be used to select one or more OMDs to be communicated to the patient (step 420). In circumstances where process 400 includes step 415, information included within the patient's EMR may also be used to select the OMD to be communicated to the patient. In many instances, the selected OMD will be a PRO, or medical, questionnaire to be completed by the patient. In some embodiments, the OMD selected for communication to the patient is a pre-treatment, or pre-operation, OMD. Execution of step 420 may include OMD selector 106 consulting matched treatment code and OMD database 104 to determine an OMD that matches one or more treatment codes associated with the trigger received in step 405, and OMD selector 106 retrieving the determined OMD from OMD database 108.

In some embodiments, execution of step 420 may include consulting medical literature directly. For example, once a treatment code is received or understood from information received, a source of medical literature, such as third-party medical literature database 204, may be searched to find one or more OMDs that match, or are grouped with, a treatment code and/or a diagnostic code that is associated with the treatment code. In some instances, when multiple OMDs are associated with a particular treatment and/or diagnostic code, the process for selecting the OMD to be provided to the patient may include determining which is the best OMD to communicate to the patient based on, for example, the patient's EMR, treatment provider preference, and/or treatment facility preference.

Next, in step 425, the OMD may be provided to the patient. The OMD may be provided to the patient via any appropriate means including, but not limited to, providing a fillable form to the patient and/or communicating the OMD to a treatment provider device, such as treatment provider device 124 or a computerized device, such as patient device 128. In some instances, the fillable form may be provided in a hard copy format (i.e., printed on paper).

Responses to the OMD may then be received from the patient (step 430). In some circumstances, these responses may be the results of one or more tests or other physical examinations performed on the patient as suggested and/or required by the selected OMD. In other circumstances, the responses may be one or more answers to a questionnaire (e.g., a PRO or medical questionnaire).

In step 435, the received responses may be associated with, for example, the patient, and/or one or more of a treatment provider, treatment code, and/or diagnostic code mentioned in, for example, the trigger and/or the patient's EMR. These associations may be stored in, for example, a data storage device such as OMD response database 110 (step 440). In some instances, OMD administrator 112 may perform some or all of step 435.

In step 445, a determination may be made as to whether the treatment provider should be notified that the OMD has been completed. If so, the treatment provider is notified that the OMD has been completed (step 450). Otherwise, the process ends. In some embodiments, receipt of this notification may be required in advance of commencement of the treatment to be scheduled and/or performed. For example, if a patient is scheduling a surgical procedure, the treatment provider may require the patient to complete the OMD in advance of the patient receiving the surgical procedure.

FIG. 5 provides an example of how process 400 may be executed. In the example of FIG. 5, a diagnosis of a rotator cuff tear is made (step 505) and the trigger that is received in step 405 is an entry of a surgical repair for a rotator cuff tear with CPT codes of 23410, 23412, 23420, and 29287 and a hospital procedure ICD-9 code of 83.63 (step 510) into, for example, a scheduler like scheduler 136. It is then determined, using a process similar to that of step 420, that possible OMDs (indicated in FIG. 5 as PRO instruments) appropriate for these CPT codes are the American Shoulder and Elbow Surgeons Shoulder Assessment (ASES), the Simple Shoulder Test (SST), and the Oxford Shoulder Score (OSS) (step 515). The best OMD for the treatment code may then be selected as the ASES based on, for example, the patient's EMR, treatment provider preference, most recently used OMD in the medical literature, and/or treatment facility preference (step 520).

FIG. 6 provides another example of how process 400 may be executed. Initially, before a treatment is performed, a treatment code (shown as a CPT code in the figure) is entered into a patient's EMR (step 605) and the appropriate OMD/PRO instrument is deployed to the patient (step 610). The patient then completes the OMD/PRO instrument and submits his/her responses to the treatment provider and/or treatment facility (step 615) and the EMR allows the treatment to commence (step 620). The information supplied by the patient in step 615 is communicated to an OMD/PRO instrument management system (step 625). The OMD/PRO instrument management system may be similar to server 102. The OMD/PRO instrument management system may then communicate the received information to the treatment facility computer system 134 for quality assessment, quality improvement, and/or academic purposes (step 630). The OMD/PRO instrument management system may also communicate the received information with the public via, for example, patient device 128, so that members of the public may, for example, make an informed selection of a treatment provider/doctor (step 635).

FIG. 6 also provides for post-treatment OMDs/PRO instruments, whereby a post-treatment OMD/PRO instrument is sent to a patient following a treatment at, for example, a predetermined time that may be specific to, for example, each treatment type (step 640). Patient responses to the post-treatment OMDs/PRO instrument may then be submitted to the PRO management system (step 645) and steps 630 and/or 635 may be repeated with the post-treatment OMD/PRO information and/or a combination of the pre-treatment and post treatment OMD/PRO information (as, for example, an improvement score and/or effectiveness score as will be discussed below).

Figure 7:
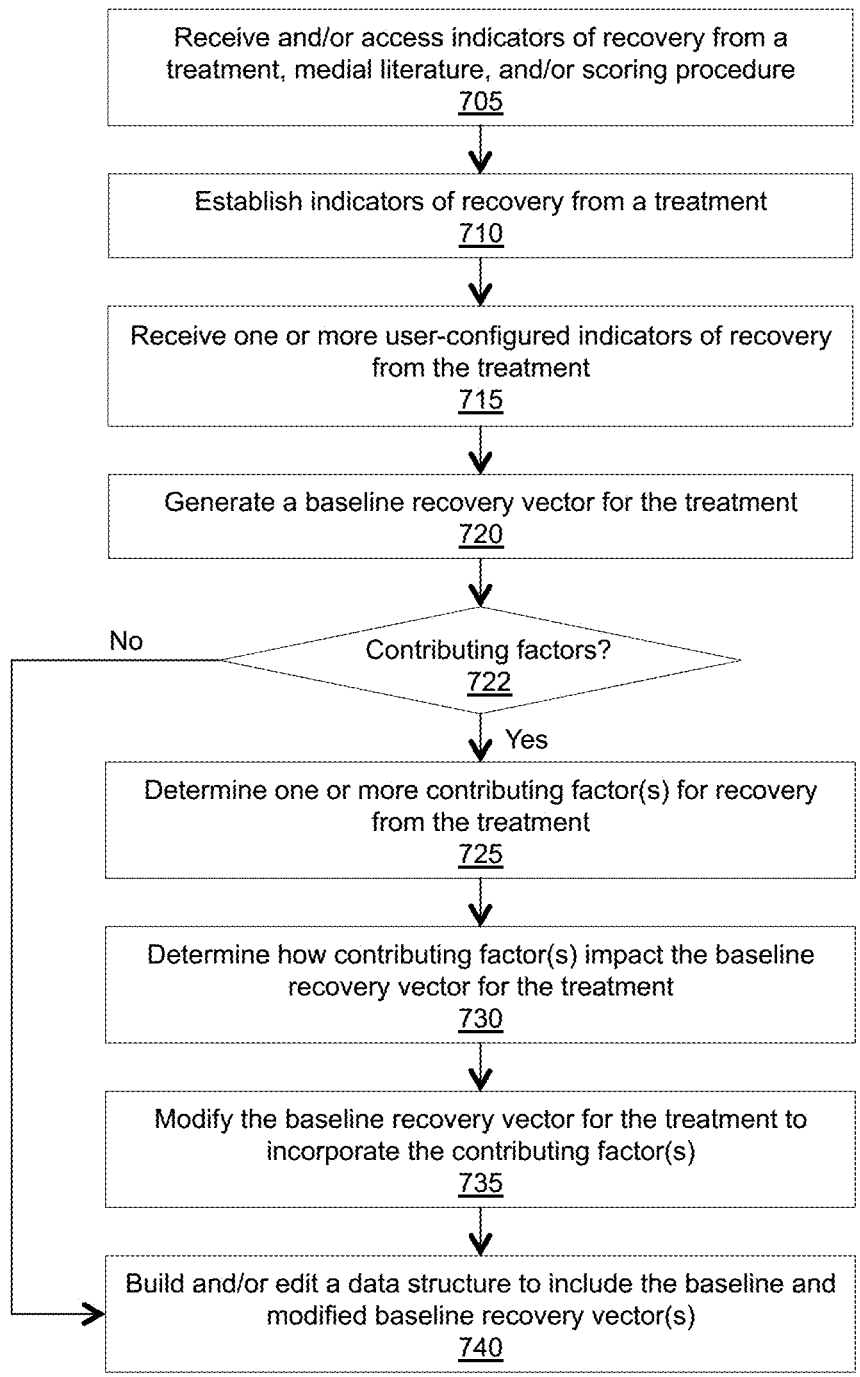
FIG. 7 provides a flowchart of an exemplary process for determining a baseline recovery vector and/or a modified recovery vector and building a data structure including same, in accordance with some embodiments of the present invention.

FIG. 7 provides a flowchart of a process 700 for determining a baseline recovery vector and/or a modified recovery vector and building a data structure including same. The recovery vector and/or modified recovery vector may, in some embodiments, be used to determine an improvement score, wellness score, effectiveness score, all of which will be discussed below.

Process 700 may be executed by, for example, any of the systems or any component, or combination of components, thereof disclosed herein. In FIG. 7, baseline is used to indicate a "typical measured value" (i.e., measurements aggregated/averaged over a large pool of patients). To avoid any potential confusion, it is noted that in FIGS. 15A-C, baseline is used to indicate a "pre-treatment data point" (i.e., a baseline measurement before a treatment, used as a reference point for a measurement after a treatment).

In step 705, the indicators of recovery from a treatment may be received or accessed. Additionally or alternatively, in step 705, medical literature and/or a scoring procedure for a treatment may be accessed and/or received. Step 705 may be similar to, for example, step 310. When, for example, indicators of recovery from a treatment are not directly received in step 705, the medical literature may be analyzed to determine indicators of recovery from a variety of treatments (step 710). In some embodiments, execution of step 710 may include analyzing the medical literature to determine what types of OMDs are appropriate for a particular treatment or diagnosis and may also be used to determine expected or preferred treatment outcomes (e.g., ranges of values for diagnostic tests performed on a patient or ranges of values for responses by the patient to a PRO instrument/questionnaire) at various stages in a process of recovering from a treatment. For example, if the medical literature pertains to hip replacement treatments, the medical literature may be analyzed to determine expected indicators of recovery (i.e., milestones) for the treatment such as pain management, mobility, rate of infection, etc. in the recovery from a hip replacement and when these milestones should be met. In some instances, execution of step 710 includes determining one or more treatment and/or diagnostic codes that are relevant to a particular article of medical literature and/or an indicator of recovery from a treatment discussed therein.

In step 715, one or more user-configured indicators of recovery from a treatment or treatments may be received from, for example, a treatment provider, treatment facility, treatment administrator, and/or patient. Exemplary user-configured indicators of recovery include, but are not limited to, tests to be performed to gauge a level of recovery, ranges of scores on tests that indicate a level of recovery, preferred OMDs to be used to measure treatment outcomes, preferred timing for the delivery of OMDs to a patient, preferred timing for the execution of a test on a patient, and so on.

Then, in step 720, a baseline recovery vector for the particular treatment may be generated using, for example, the medical literature, received indicators of recovery, and/or user-configured indicators of recovery. The baseline recovery vector may serve to indicate, for example, an expected rate of recovery from a treatment, milestones to be achieved when recovering from a treatment, ranges of values for OMD responses relating to the treatment, indicators of improvement in the recovery from a treatment, target values for indicators of improvement in the recovery from a treatment, and so on. In one embodiment, a baseline recovery vector may be determined on a numerical (e.g., 0-100) scale, while in another embodiment recovery may be determined based on milestones in a treatment recovery process. The baseline recovery vector may establish a trajectory of milestones (indicator) for treatment recovery over time. In some instances, the baseline recovery vector may be used to determine, for example, values relating to a minimum wellness descriptor, or minimum wellness score, a 50% wellness score, and a full wellness descriptor or maximum wellness score. Interface 1813 of FIG. 18N, as discussed below, provides an example of a minimum and maximum wellness score for knee function. The baseline recovery vector may also incorporate various non-linear factors in recovery from a treatment. For example, a baseline recovery vector for complex back surgery may incorporate the relatively slow rate of recovery from potential nerve damage caused by the surgery and the relatively faster rate of recovery for mobility from the same surgery.

Optionally, when a treatment has contributing factors (step 722) one or more contributing factors for the treatment and/or an underlying diagnosis may be determined (step 725). On occasions when a treatment has no contributing factors (step 722), process 700 may proceed directly from step 720 to step 740. Exemplary contributing factors include, but are not limited to, weight, age, gender, pre-existing conditions, and comorbidities. Information regarding contributing factors may be stored in, for example, a database like other considerations database 132 and/or scoring procedure database 116

Then, in step 730, it may be determined how the one or more contributing factors for the treatment and/or an underlying diagnosis may impact the baseline recovery from the treatment. A particular treatment may have more than one contributing factor and the determination of step 730 may incorporate determinations of relationships between one more contributing factor and recovery.

The baseline recovery vector generated in step 720 may then be modified to incorporate the one or more contributing factors (step 735). Modification of the baseline recovery vector may include, for example, increasing or decreasing the expected rate of recovery from the treatment, adding or subtracting milestones from a recovery trajectory, modifying a range of values for OMDs relating to the treatment, adding or subtracting indicators of improvement in the recovery from a treatment, adjusting target values for indicators of improvement in the recovery from a treatment, and so on. In many instances, steps 722, 725, 730, and/or 735 may be performed via accessing and/or analyzing the medical literature received in step 705.

In step 740, a data structure including baseline and/or modified recovery vector(s) may be built, edited, and/or updated to include the baseline recovery vector and/or modified baseline recovery vector generated in, for example, steps 720 and/or 735.

In some instances, one or more steps of process 700 may be executed on an as-needed basis. In other instances, one or more steps of process 700 may be executed at a preferred time so that the data structure built/edited in step 740 may be accessed by one or more components to, for example, execute a wellness protocol for a patient, determine an improvement score, determine a wellness score, determine an effectiveness score as discussed below. In some embodiments, the baseline recovery vector and/or modified baseline recovery vector may be stored in, for example, score database 120, scoring procedure database 116.

Figure 8:
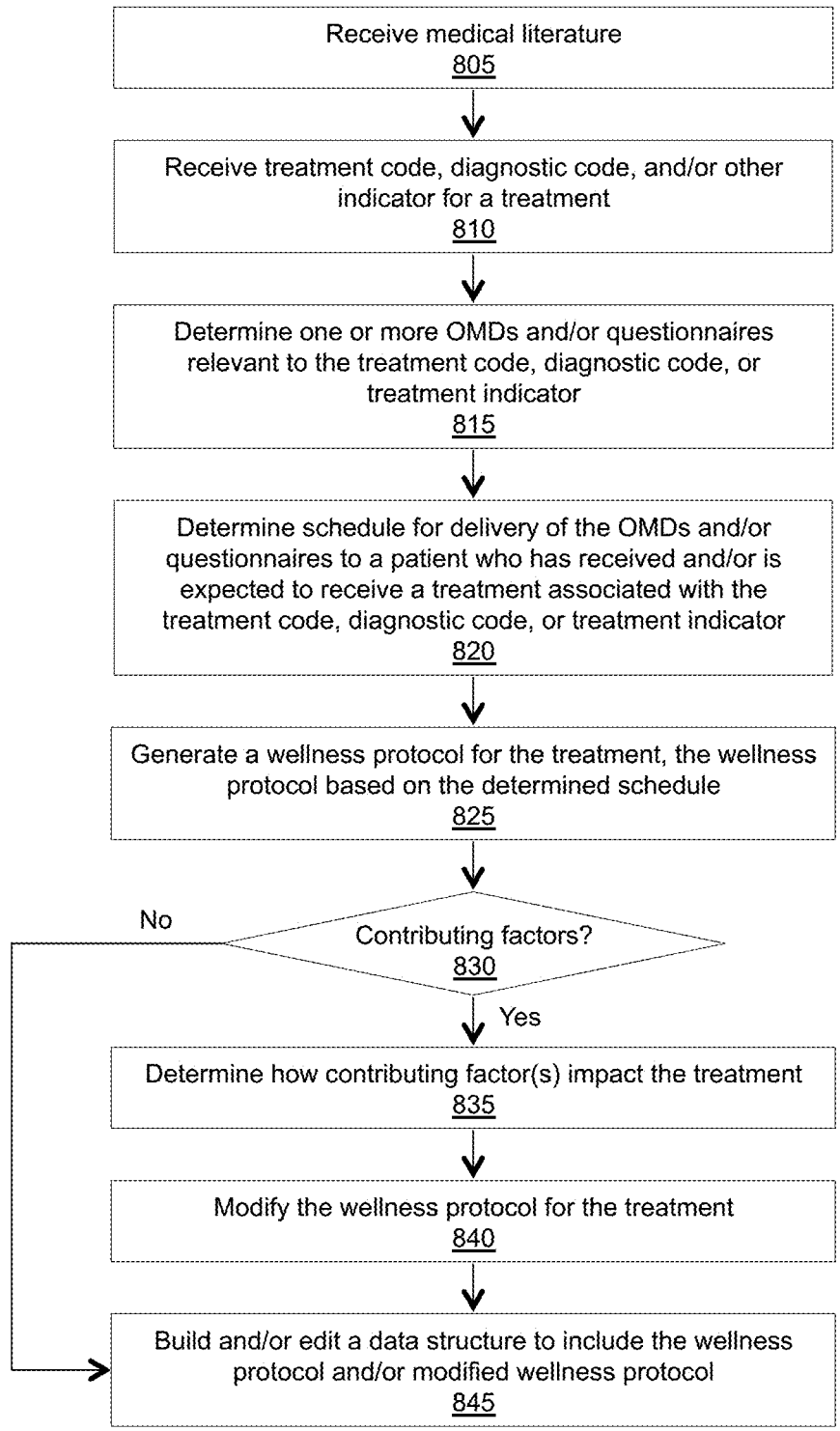
FIG. 8 provides a flowchart of an exemplary process for generating and/or modifying a wellness protocol for one or more treatments, in accordance with some embodiments of the present invention.

FIG. 8 provides a flowchart of a process 800 for generating and/or modifying a wellness protocol for one or more treatments. Process 800 may be executed by, for example, any of the systems or any component, or combination of components, thereof disclosed herein.

In step 805, the medical literature may be received. Execution of step 805 may resemble execution of, for example, steps 310 and/or 705. A treatment code, diagnostic code, and/or other indicator for a treatment may also be received (step 810). Exemplary other indicators for a treatment include the scheduling of a treatment in a treatment provider's scheduling program or entry of a treatment into a treatment provider's billing or accounting program. Next, one or more OMDs and/or questionnaires relevant to the treatment code, diagnostic code, or treatment indicator may be determined (step 815). Execution of step 815 may involve execution of one or more steps of process 300 and/or 400.

In step 820, a schedule for delivery of the OMDs and/or questionnaires to a patient, or group of patients, who has/have undergone, or who is/are expected to undergo, a treatment associated with the treatment code, diagnostic code, or treatment indicator may be determined. In some embodiments, step 820 may also include determining when, or how, to access a patient's EMR to check for different types of information such as test results or other measurements that may be included in the patient's EMR. For example, the schedule may determine that a patient's EMR should be checked at various intervals pre- and/or post-treatment in order to determine lab results or other information in order to, for example, track recovery from the treatment.

In step 825, a wellness protocol for a treatment associated with the treatment code, diagnostic code, or treatment indicator may be generated based on the determined schedule. The wellness protocol may establish, for example, which types of OMDs are to be delivered to a patient, when the OMDs are to be delivered to a patient, when a patient's EMR should be accessed to retrieve test results, when a patient and/or treatment provider should be reminded to administer and/or complete an OMD, feedback mechanisms for a patient, treatment provider, and/or treatment facility associated with the treatment, and so on.

In some embodiments, generation of a wellness protocol (step 825) may include incorporating one or more scoring protocols associated with the OMDs incorporated into the wellness protocol. Additionally, or alternatively, step 825 may also incorporating one or more baseline recovery vectors and/or modified recovery vectors into the wellness protocol.

Optionally, it may be determined whether there are any factors that contribute to the treatment and/or recovery for a patient (step 830). Exemplary contributing factors include, but are not limited to, weight, age, gender, pre-existing conditions, medications, and comorbidities. When there are contributing factors, it may be determined how the one or more contributing factors for the treatment and/or an underlying diagnosis may impact recovery from the treatment (step 835). The wellness protocol may then be modified to incorporate the one or more contributing factors (step 840). Modification of the wellness protocol may include, for example, increasing or decreasing a number of OMDs scheduled for delivery to a patient, changing an OMD to be delivered to a patient, modifying when the OMDs are delivered to a patient, and so on. In many instances, steps 830 and/or 835 may be performed via accessing and/or analyzing the medical literature received in step 805.

In step 845, a data structure including wellness protocol and/or modified wellness protocol may be built, edited, and/or updated to include the wellness protocol and/or modified wellness protocol generated in, for example, step 825 and/or modified in step 840. Step 845 may be executed when there are no contributing factors (i.e., following the NO branch of step 830).

In some instances, one or more steps of process 800 may be executed on an as-needed basis (e.g., in response to a request for a wellness protocol for a particular patient). In other instances, one or more steps of process 800 may be executed at a preferred time so that the data structure built/edited in step 845 may be accessed by one or more components to, for example, design and/or execute a wellness protocol for a group of patient and/or recipients of a treatment.

Figure 9A:
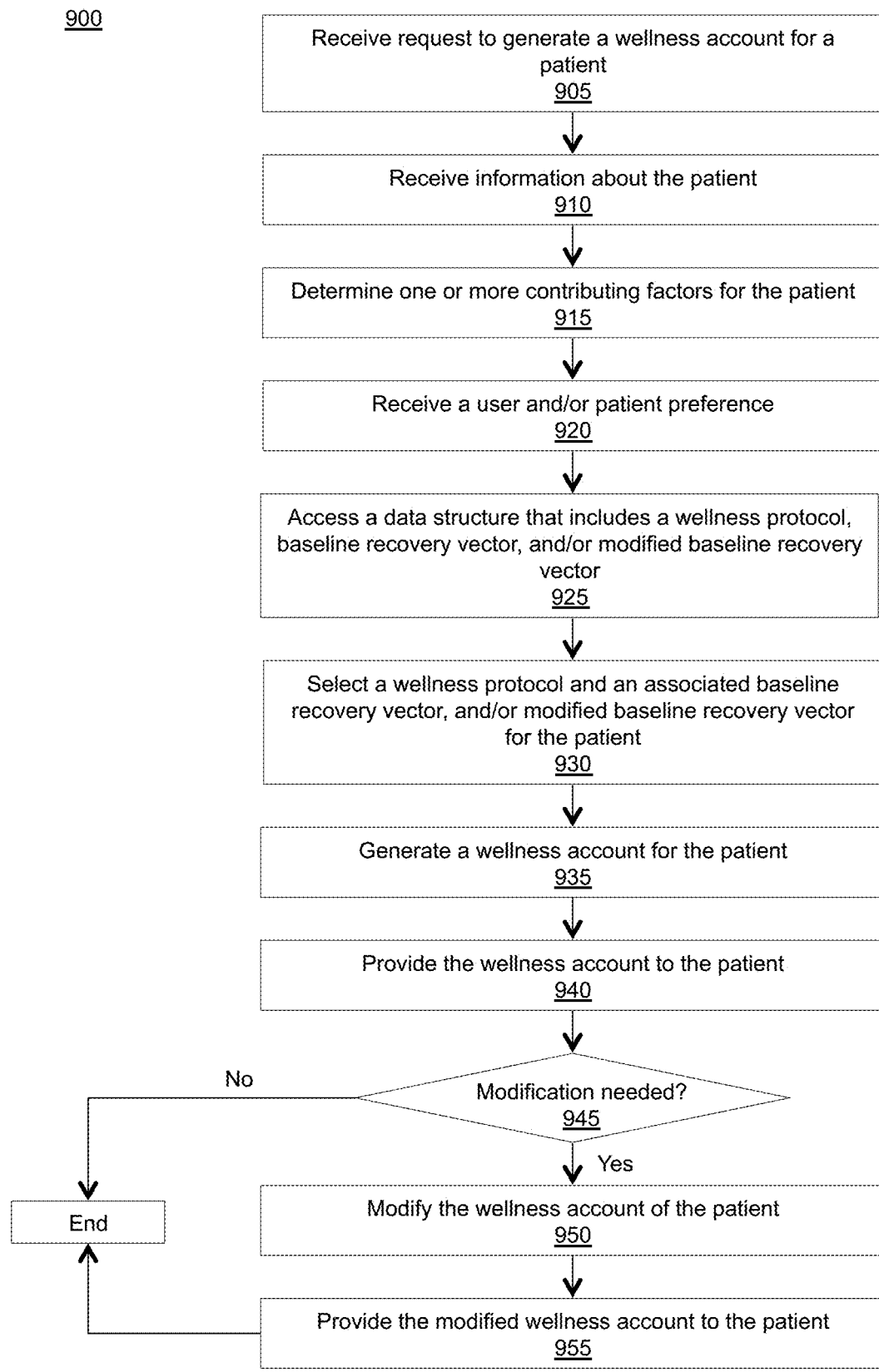
FIG. 9A provides a flowchart that illustrates an exemplary process for generating and/or modifying a wellness protocol for one or more treatments, in accordance with some embodiments of the present invention.

FIG. 9A provides a flow chart of a process 900 for generating and/or modifying a wellness protocol for one or more treatments. Process 900 may be executed by, for example, any of the systems or any component, or combination of components, thereof disclosed herein.

In step 905, a request to generate a wellness account for a patient may be received. The request may be received from, for example, the patient, a treatment provider for the patient, a caregiver of the patient (e.g., spouse or nurse), and/or a treatment facility. In some instances, requests to generate a wellness account for a patient may be a component to scheduling a treatment and/or recovering from a treatment. For example, when a patient is scheduled for a surgery, part of the scheduling process may include requesting (automatically or otherwise) generation of a wellness account for a patient. The request may be received by, for example, reporting module 122 and may be received from, for example, patient device 128, treatment provider device 124, and/or treatment facility computer system 134. Often times, the request will include information about one or more treatments and/or diagnosis relevant to the patient.

In step 910, information about the patient may be received. Information received in step 910 may include information regarding the health of the patient and any factors contributing to the health of the patient, treatment performance, or treatment recovery. Information about the patient may be received from, for example, the patient's EMR, the patient, the requester of step 905, a treatment provider, and/or a treatment facility. Information about the patient may include, for example, age, gender, comorbidities, whether or not the patient smokes, and so on. In step 915, one or more factors that may contribute to the wellness and/or recovery from a treatment may be determined based on, for example, the information received in step 910 and/or the request.

Optionally, in step 920, a user and/or patient preference may be received. Exemplary users are the requester of step 905, a treatment provider, and/or a treatment facility. Exemplary patient and/or user preferences include preferred aspects of the patient's wellness to monitor via the wellness account, preferred treatment outcomes, preferred aspects of the wellness account (e.g., whether reminders to interact with the wellness account should be provided to the patient, preferred manners of interacting with the wellness account, etc.), and so on. At times the user and/or patient preference received in step 920 may relate to a scoring procedure and/or modification of a baseline recovery vector to be applied when scoring responses to OMDs responses received from the patient and/or included in the patient's EMR. For example, a professional athlete may have different recovery goals than a 75-year old man when recovering from knee surgery and these varying recovery goals may be received at step 920 for inclusion in the patient's wellness account and/or a manner of scoring OMD responses received in connection with the patient's wellness account.

Optionally, in step 925, a data structure that includes one or more pre-generated wellness protocols, baseline recovery vectors, and/or modified baseline recovery vectors may be accessed and a wellness protocol and an associated baseline recovery vector and/or modified baseline recovery vector may be selected for the patient using, for example, the information received and/or the determination of steps 905-920 (step 930). Exemplary data structures accessed in step 925 are the data structures built or modified in via execution of processes 700 and/or 800.

In step 935, a wellness account for the patient may be generated. When steps 925 and 930 are executed, generation of the wellness account in step 935 may include the assembly of the wellness protocol and associated baseline recovery vector(s) and/or modified baseline recovery vector(s) selected in step 930 into a wellness account for the patient. When steps 925 and 930 are not executed, step 935 may be executed by assembling information received and/or the determination of steps 905-920 into a wellness account for the patient. In step 940, the wellness account may be provided to the patient. Typically, the wellness account will be provided to the patient via the patient's device, such as patient device 128. In most cases, the wellness account will be provided to the patient with a login requirement or other security protocol so as to keep the information of the patient's wellness account private and secure.

Optionally, in step 945, it may be determined whether a modification to the patient's wellness account is necessary or preferred. When no modification to the patient wellness account is necessary or preferred, process 900 may end. Modifications to the patient's account may be necessary or preferred when, for example, the patient's health or wellness changes (e.g., weight gain, medication change, smoking cessation, etc.), when a wellness protocol and an associated, baseline recovery vector, and/or modified baseline recovery vector associated with the patient's wellness account is changed or modified, when a treatment for the patient changes (e.g., change in medication or therapy regimen), a new patient or treatment provider preference, and so on. When modification to the patient wellness account is necessary or preferred, the wellness account may be modified to accommodate whatever prompted the determination that modification to the patient wellness account is necessary or preferred (step 950). At times, step 950 may be performed in response to information received at step 945 (e.g., a notification that the wellness account should be modified). In some instances, step 950 may be performed using information accessed about the patient from, for example, the patient's EMR and/or treatment provider. In some instances, modification of the patient's wellness account may be triggered by a change to the patient's EMR or a treatment provider protocol. For example, if a treatment provider protocol changes to incorporate a new medication or device into the treatment of a particular condition, the patient's wellness account may be automatically modified to reflect it. Likewise, if a change to a patient's EMR is made (e.g., a new allergy or event (e.g., a cardiac event or a broken bone)) the patient's wellness account may be automatically modified to reflect same. In some instances, execution of step 950 may include re-executing steps 915, 925, and/or 930 and/or prompting the patient to enter information into the wellness account. In some embodiments, steps 945 and 950 may be executed at a time considerably later than completion of step 940. For instance, a patient's wellness account may be modified over the course of days, months, years, and/or decades to keep pace with the patient's changing medical condition over his or her lifespan. Following step 950, the modified wellness account may be provided to the patient (step 955) in a manner similar to that described with regard to step 940 and process 900 may end.

Figure 9B:
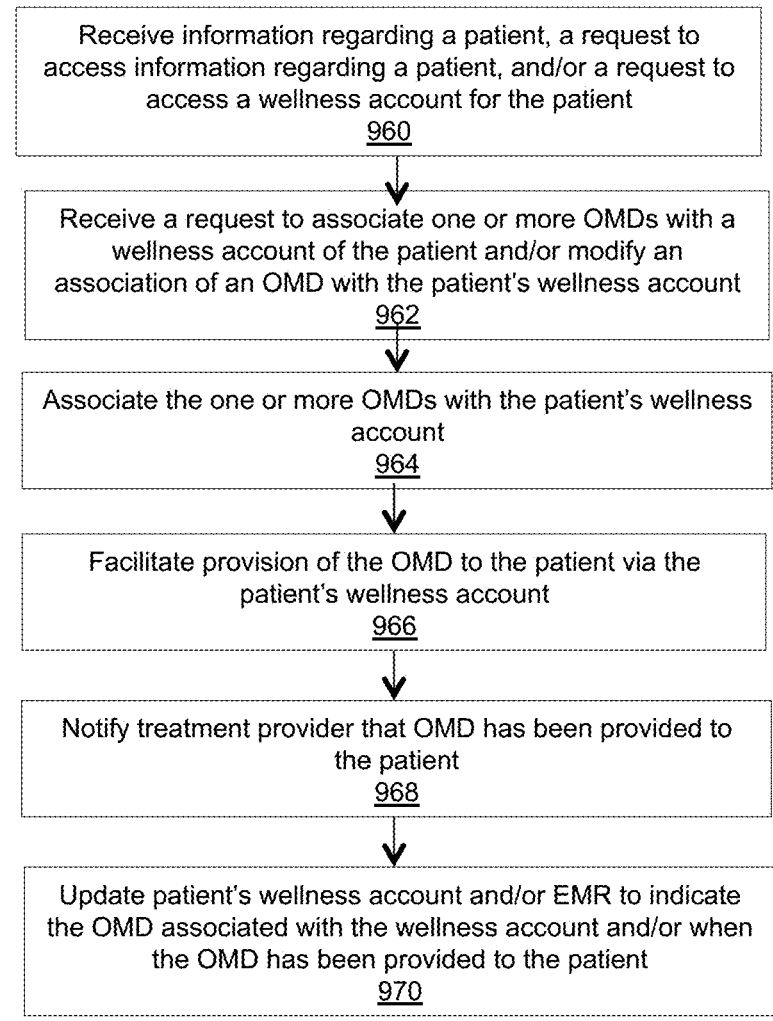
FIG. 9B provides a flowchart that illustrates an exemplary process for associating an OMD with a patient's wellness account, in accordance with some embodiments of the present invention.

FIG. 9B provides a flowchart that illustrates an exemplary process 901 for associating an OMD with a patient's wellness account and determining a wellness score using a set of responses to the OMD. Process 901 may be executed by, for example, system 100 and/or any component or combination of components disclosed herein.

Initially, information (e.g., name, date of birth, address, social security number, phone number, email address, etc.) regarding a new (e.g., new to the treatment provider and/or treatment facility) patient, a request to access information regarding an existing patient, and/or a request to access a wellness account of an existing patient may be received (step 960). In some instances, the information regarding a new patient received in step 960 may be used to establish and/or generate a wellness account for the patient and/or preferences (e.g., language, mode of communication with the patient, etc.) for the wellness account. In some instances, the received request may be a search query. In many cases, information regarding a new patient may be received from a treatment provider and/or a person (e.g., nurse or administrative assistant) working with the treatment provider via an interface like new patient data entry interface 2301 of FIG. 23A, which provides a list 2308 of new patient data entry fields for the new patient's first name, last name, date of birth, social security number, cell phone number, and email address. Of course, list 2308 not exclusive of new patient data that may be entered. For example, list 2308 may include options to enter more/fewer and/or different types of new patient data (e.g., care giver phone number, age, etc.). Information regarding a search for an existing patient may be received via a patient search interface like patient search interface 2302 of FIG. 23B. In the case of interface 2301, a request for information regarding a patient with the last name of Smith has been received (step 960).

Figure 23C:
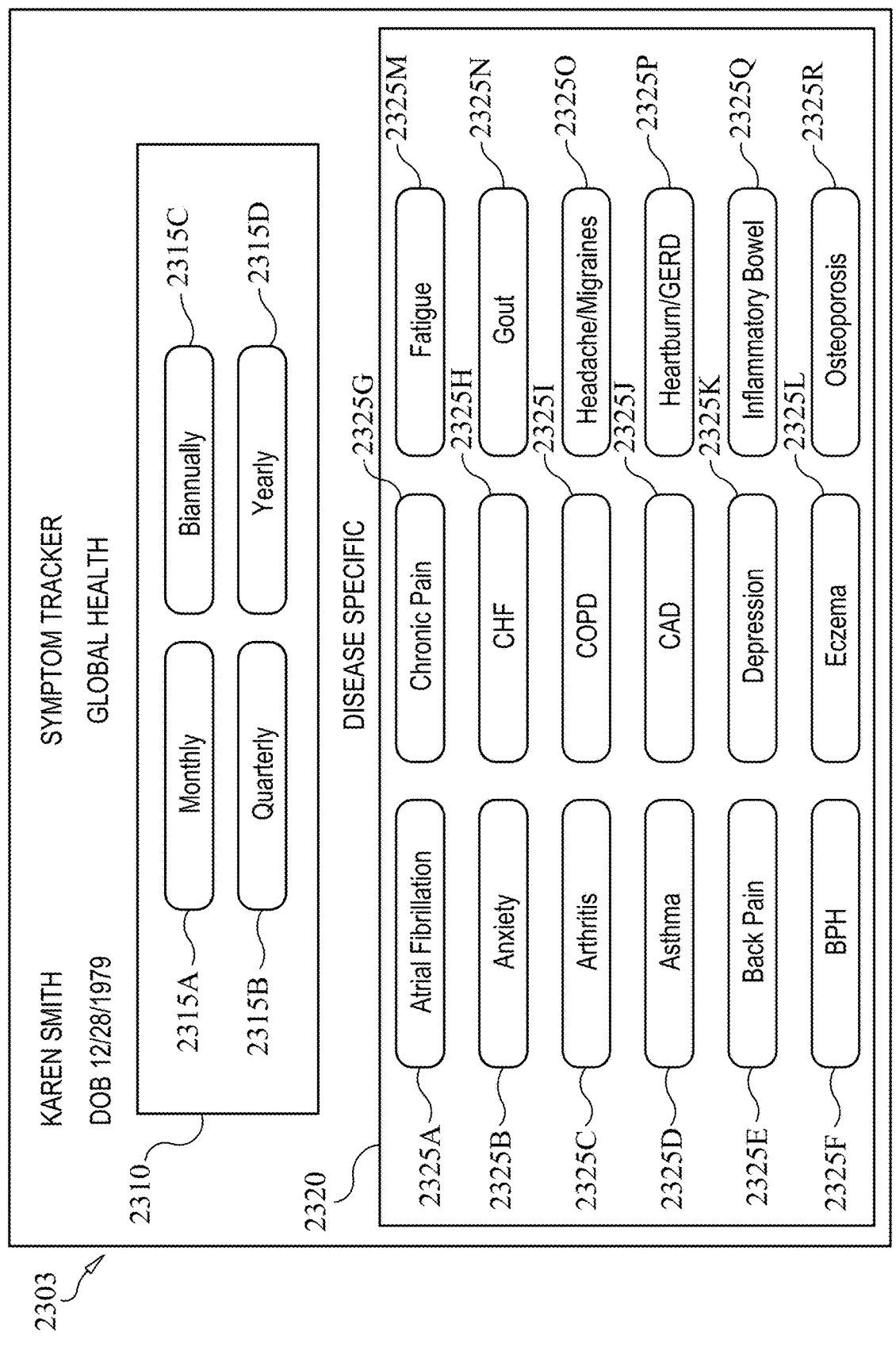

Then, in step 962, a request to associate one or more OMDs with the patient's wellness account and/or a request to modify an association of an OMD with a patient's wellness account may be received via, for example, an interface like interface 2303 of FIG. 23C. In the example of interface 2303, the patient wellness account is for a patient named Karen Smith who has a birthdate of Dec. 28, 1979. Interface 2303 provides an array 2310 of scheduling buttons: monthly scheduling button 2315A, quarterly scheduling button 2315B, biannually scheduling button 2315C, and yearly scheduling button 2315D for the monthly, quarterly, biannually, and yearly scheduling of the provision of a global health OMD, a disease-specific OMD, or other questionnaire, to the patient.

Interface 2303 also provides and an array 2320 of exemplary disease specific buttons 2325A-2325R. Each of the disease specific buttons 2325A-2325R is associated with one or more diseases, symptoms, or medical conditions as well as one or more disease/symptom/medical condition specific OMDs to be provided to a patient. Selection of one or more of disease specific buttons 2325A-2325R facilitates association of the disease/symptom/medical condition with the patient (via, for example, saving the association in the patient's EMR) and association of the OMD(s) associated with the selected disease specific buttons 2325A-2325R with the patient's wellness account so that the respective OMD(s) may be provided to the patient at an appropriate time and, in some instances, repeatedly provided to the patient at following expiration of a pre-determined time period (e.g., day, week, month, year, etc.) that may be established via selection of, for example, monthly scheduling button 2315A, quarterly scheduling button 2315B, biannually scheduling button 2315C, and yearly scheduling button 2315D.

In the example of interface 2303, array 2320 provides exemplary disease specific buttons for atrial fibrillation 2325A, anxiety 2325B, arthritis 2325C, asthma 2325D, back pain 2325E, benign prostatic hyperplasia ("BPH") 2325F, chronic pain 2325G, congestive heart failure ("CHF") 2325H, chronic obstructive pulmonary disease ("COPD") 2325I, coronary artery disease ("CAD") 2325J, depression 2325K, eczema 2325L, fatigue 2325M, gout 2325N, headache/migraines 2325O, heartburn/gastroesophageal reflux disease ("GERD") 2325P, inflammatory bowel 2325Q, and osteoporosis 2325R. Array 2320 may provide any appropriate number of disease specific buttons and, in some instances; the disease specific buttons provided by array 2320 may be tailored for a particular doctor or treatment provider preference. For example, if the treatment provider is a cardiologist, then array 2320 may display disease specific buttons that represent diseases that are common to the heart. Likewise, if the treatment provider is a pediatrician, then array 2320 may display disease specific buttons that represent diseases that are common to the children. In other instances, the disease specific buttons provided by array 2320 may be tailored for a patient, patient characteristic, or treatment the patient has undergone. For example, if the patient is a 75-year-old male, then array 2320 may display disease specific buttons that represent diseases that are common to 75-year-old males. In another example, if the patient has undergone a heart transplant, then array 2320 may display disease specific buttons that represent diseases/conditions that are common to heart transplant recipients. In some embodiments, step 962 may be executed upon receiving a selection of one or more disease specific buttons 2325A-2325R.

Next, in step 964, one or more OMDs may be associated with the patient's wellness account responsively to the request received in step 962. For example, FIG. 23D shows an exemplary global health OMD management interface 2304, which provides the treatment provider with information regarding how often (in this case quarterly) the global health OMD is provided to the patient as well as a message regarding when the global health OMD has been sent, when the next global health OMD will be sent, and an option to modify the scheduling of provision of the global health OMD to the patient. Quarterly provision of the global health OMD to the patient (in this case, Karen Smith) may be responsive to selection of quarterly scheduling button 2315B on interface 2303, as shown on interface 2304 of FIG. 23D.

Figure 23E:

In some embodiments, selection of one or more disease specific buttons 2325A-2325R (step 962) may initiate association of an OMD associated with the disease represented by the disease specific button to be associated with the patient's (Karen Smith's) wellness account and/or be provided to the patient (Karen Smith). FIG. 23E shows interface 2305, which the which provides a list 2340 of current disease specific trackers associated with the patient, Karen Smith. More particularly, list 2340 shows current disease specific trackers for anxiety 2345A, depression 2355B, and eczema 2345C, which were added to Karen Smith's wellness account following selection of the anxiety disease specific button 2325B, the depression disease specific button 2325K, and the eczema disease specific button 2325L. List 2340 also provides a number of options 2350 for adding information to and/or modifying the patient's wellness account with regard to each of the selected disease specific trackers. The options 2350 may be general to all disease specific trackers and/or specific to a particular disease specific tracker. Exemplary options include 1) change dose of medication, 2) add new medication, 3) add new treatment, and 4) cancel tracking this diagnosis.

Figure 23F:
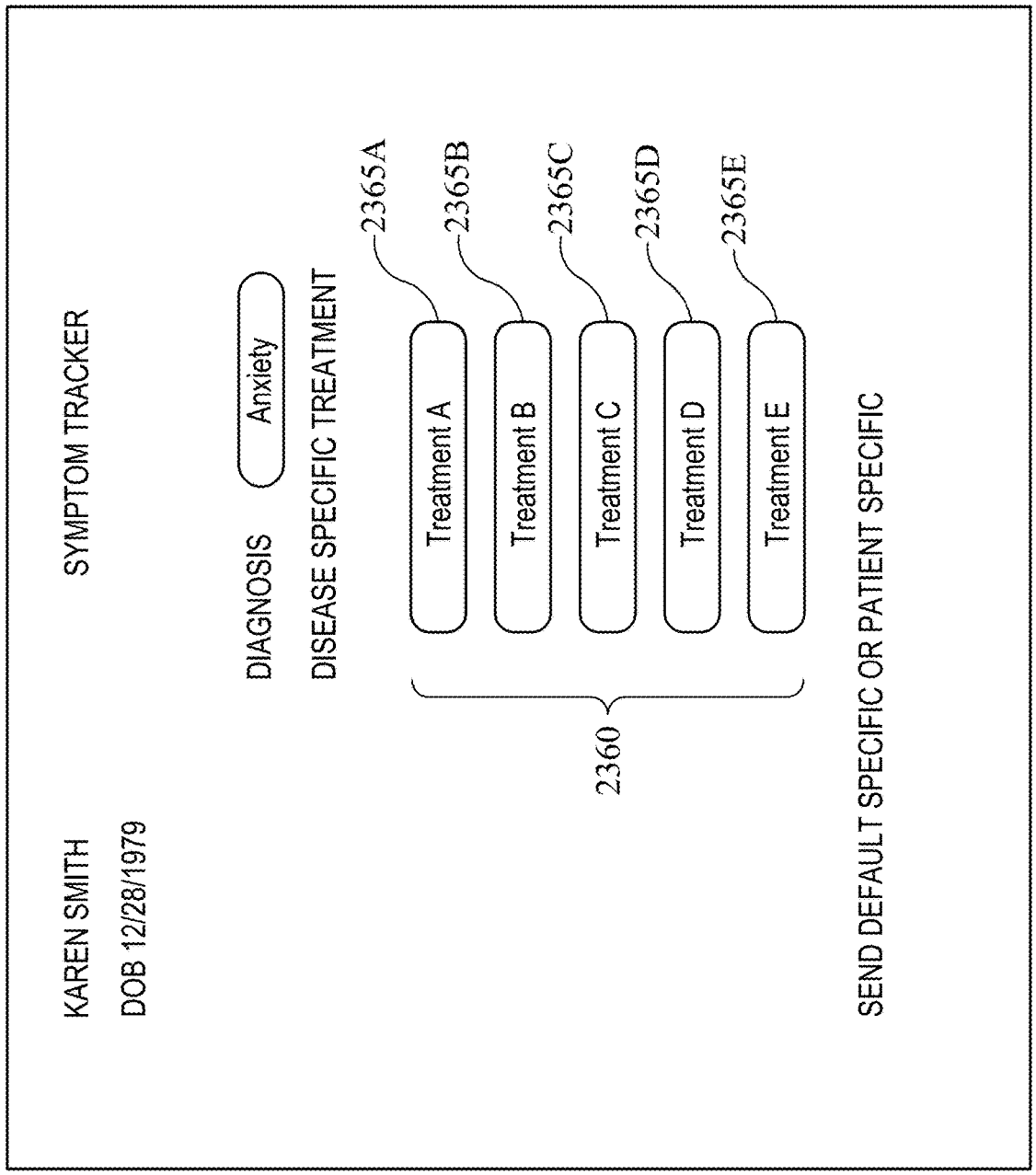

In some embodiments, a treatment provider may associate one treatments for a disease with a patient's wellness account (step 962) via an interface like disease specific treatment interface 2306 of FIG. 23F. Continuing the example of patient Karen Smith, upon selection of disease specific tracker for anxiety 2345A, interface 2360 provides a list 2360 of various treatments specific to the selected disease (i.e., anxiety). In this example, list 2360 provides treatment selection buttons for treatment A 2365A, treatment B 2365B, treatment C 2365C, treatment D 2365D, and treatment E 2365E. It will be understood by those of skill in the art that treatments listed in list 2360 may be any form of treatment (e.g., medication, physical therapy, etc.) or dosage/frequency of treatment. In most situations, the treatment selection buttons provided by list 2360 will be specific to the disease/diagnosis associated with the selected disease specific tracker but this need not always be the case.

In some instances, one or more of the treatments selected from list 2360 may be used to select an OMD provided to the patient and/or how a scoring procedure is applied to a set of responses to the OMD received from the patient. Disease specific treatment interface 2306 provides a list 2360 of various treatments specific to the selected disease.

Once information that may be used to request/select an OMD for provision to a patient is received from a treatment provider via, for example, interaction with one or more of interfaces 2301-2306, the requested/selected OMD may be associated with the patient's wellness account (step 964) and the requested/selected OMD may be provided to the patient via his or her wellness account as described herein (step 966). Once the OMD is provided to the patient, a notification of such may be provided to the treatment provider (step 968). FIG. 23 provides an exemplary notification interface 2307 that demonstrates that an OMD associated with anxiety and treatment B (the treatment from list 2360 selected by the treatment provider) has been sent to the patient, Karen Smith.

Optionally, in step 970, the patient's wellness account and/or EMR may be updated to indicate which OMD(s) are/have been associated with the patient's wellness account and/or which diagnosis and/or treatment are/have been associated with the patient's wellness account.

Figure 10A:
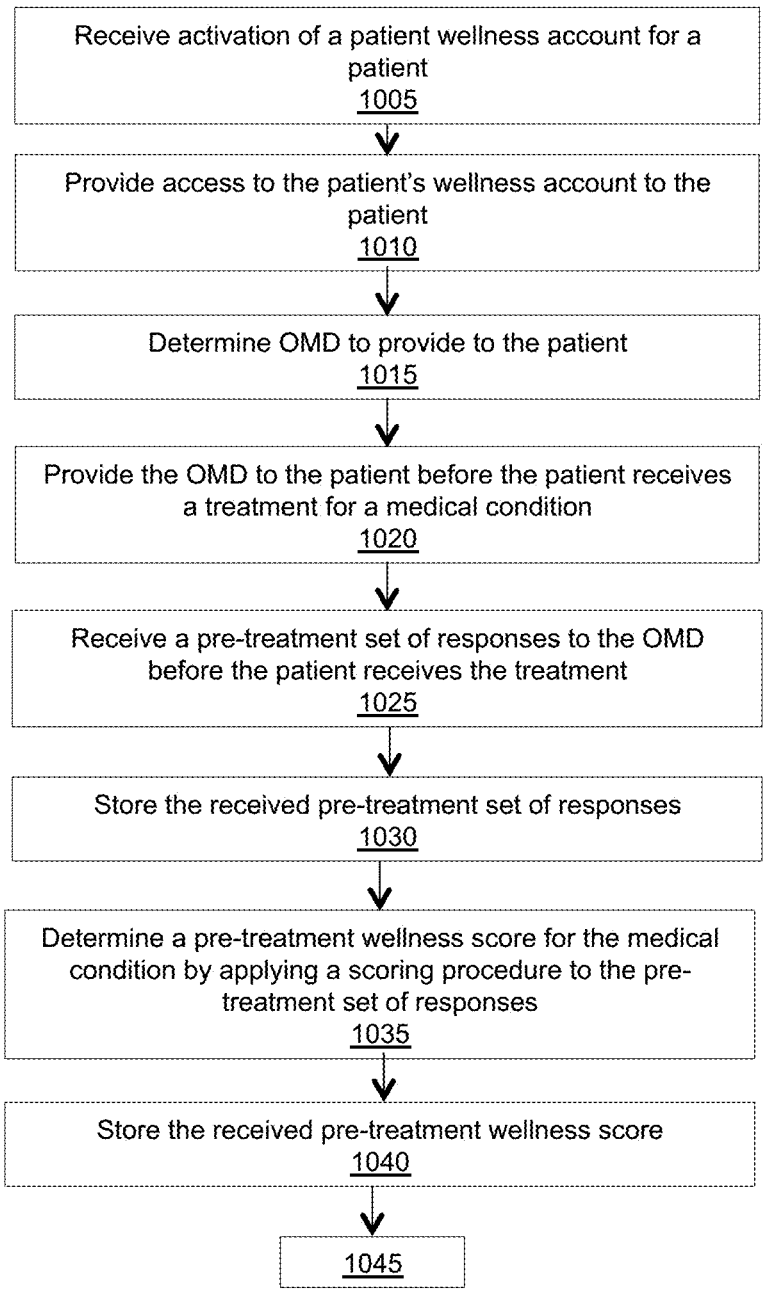
FIGS. 10A and 10B provide flowcharts of an exemplary process for providing one or more of a pre-treatment wellness score, post-treatment wellness score and an improvement score to a patient, treatment provider, treatment facility and/or treatment administrator, in accordance with some embodiments of the present invention.
Figure 10B:
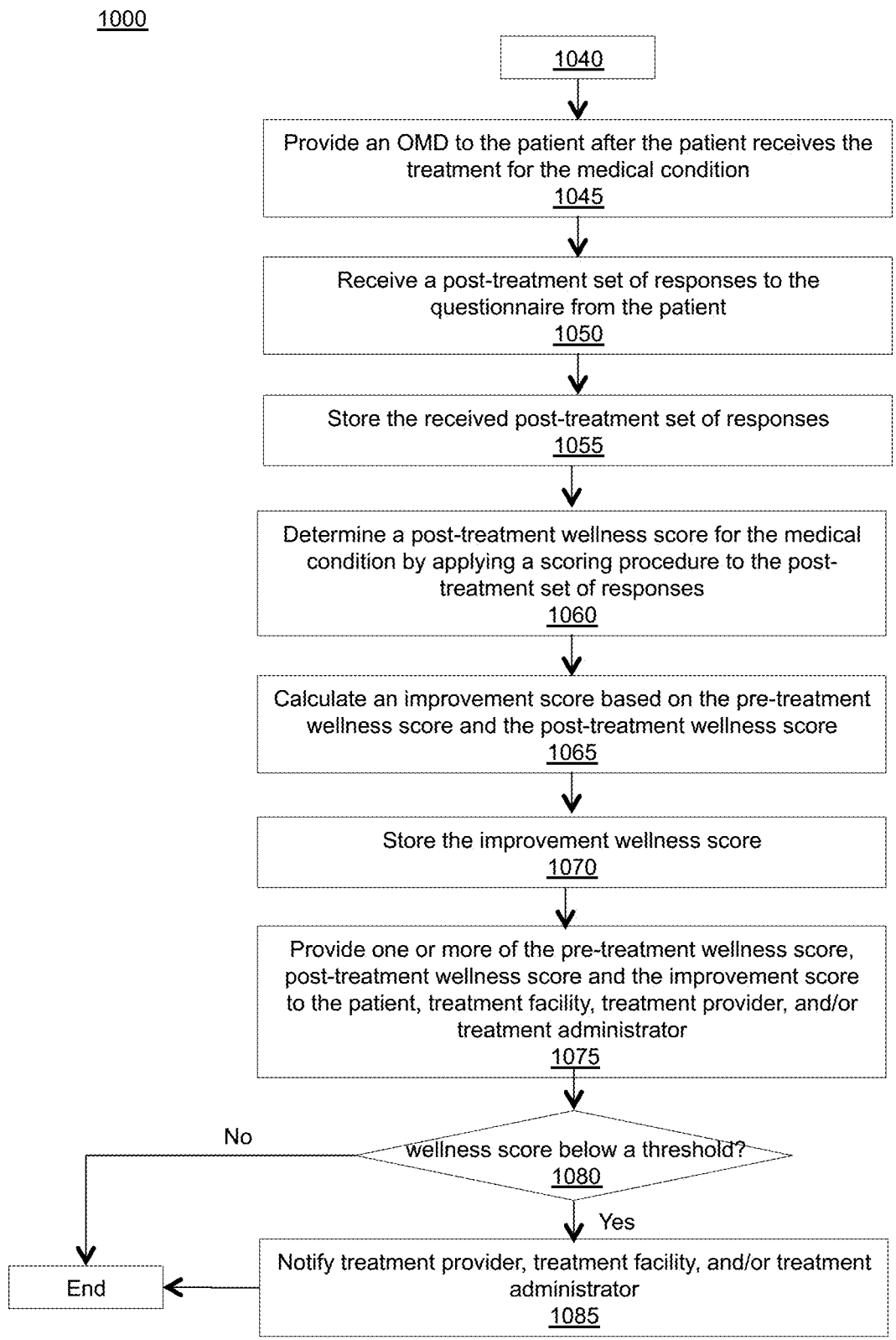

FIGS. 10A and 10B provide flowcharts that illustrate an exemplary process 1000 for providing one or more of a pre-treatment wellness score, post-treatment wellness score and an improvement score to a patient, treatment provider, treatment facility and/or treatment administrator. Process 1000 may be executed by, for example, any of the systems and/or system components disclosed herein. In some instances, execution of some or all steps of process 1000 may be referred to herein as a recovery tracker or a wellness tracker. Often times, some, or all of process 1000 may be facilitated by a software application running on the patient's device (e.g., a smart phone or tablet computer) such as, patient device 128 and the patient may interact with the software application via an interface (e.g., touchscreen or keyboard) provided by the patient device.

In some embodiments, process 1000 and/or portions of process 1000 may be executed with regard to and/or with assistance with a patient's wellness account as generated by, for example execution of processes 800 and/or 900 and described above with regard to FIGS. 8 and 9. Exemplary screenshots of interfaces that may be provided to a patient via his or her wellness account during execution of process 1000 and/or portions of process 1000 are provided by FIGS. 17A-17G and 18A-18N, which will be discussed in detail below with regard to these figures.

In some instances, a patient wellness account for the patient may be set up by, for example, a treatment provider in advance of, or following, the patient undergoing a particular treatment. In other instances, the patient may sign up for his or her patient wellness account independently of a treatment provider. Often times, the patient wellness account for the patient will include information about the patient that is relevant to the particular treatment or health condition. Optionally, in step 1005, an indication of an activation of a patient wellness account may be received. In some instances, the indication may also include patient identifying information and/or login information (e.g., username and password) that comply with one or more security protocols. In some instances, the indication received in step 1005 may be activation of an icon, such as "wellness tracker" icon 1710 provided by a user interface, such as home page interface 1700 of FIG. 17A.

Following the receipt of the patient's login information and verification of same, access to the patient's wellness account may be provided, via, for example, display of a landing page to the patient (step 1010). An exemplary landing page is provided by interface 1701 displayed in FIG. 17B. Interface 1701 may provide patient information designed to orient the patient to the patient account. For example, interface 1701 includes the patient's name (in this instance, Kate), a welcome message, the name of the patient's doctor (in this instance, Dr. Rob Hilleran), a date the treatment was administered, and an estimate of how long responding to the OMD (usually in the form of a questionnaire) may take.

Whether or not steps 1005 and/or 1010 are performed, in step 1015, one or more OMDs, typically in the form of a questionnaire, to be provided to the patient may be determined (step 1015). In one embodiment, the determination of the OMD to provide to the patient may be made via execution of some of process 300 as discussed above with regard to FIG. 3 and/or execution of steps 405-430 of process 400 as discussed above with regard to FIG. 4. In some embodiments, the OMD may be provided to the patient following a scheduling of the patient's treatment. In such case, an identifier of the scheduled treatment may be determined (e.g., a treatment identifier), and such treatment identifier may be used as a key to look up a corresponding OMD in an OMD database (in which OMDs and/or questionnaires are indexed by treatment identifiers). The OMD/questionnaire database may be part of OMD database 108 in FIG. 1.

In some environments, one or more OMDs to be provided to the patient may be determined, or otherwise set up, as part of a recovery/wellness tracker schedule when a patient wellness account is set up and/or when a treatment is scheduled or performed. For example, a schedule of OMDs may be established for a patient based on a treatment the patient will receive and/or one or more other factors that may influence a patient's recovery from the treatment. This determination may be dependent upon, for example, OMDs deemed by, for example, the medical literature, a treatment facility, a treatment provider, and/or the patient to be relevant to assessing the patient's treatment and/or recovery from treatment.

Step 1015 may be executed by, for example, OMD selector 106. In some embodiments, the OMD to be sent to the patient may be sent to the patient's device, such as patient device 128, for storage and later display to the patient. The OMD may be sent to the patient's electronic device on, for example, an as-needed basis (e.g., in response to a request from the patient's device for a OMD) and/or as a batch of OMDs that are part of a previously determined recovery/wellness tracker program for a particular treatment the patient has undergone. In one embodiment, the OMD is provided to the electronic device of the patient while the patient is not located within a treatment facility.

In one embodiment, step 1015 may include accessing an OMD database (e.g., OMD database 108) that stores a plurality of OMDs. In the database, each of the medical OMDs may be indexed with a treatment identifier. Determining which OMD to provide may include determining an identifier of the scheduled treatment, and selecting the OMD that is indexed by the identifier of the scheduled treatment.

In some instances, the OMD is at least one of a standardized PRO instrument recommended by the medical literature, a medical symptom OMD, a disease-specific medical symptom OMD, a global medical symptom OMD, and a PRO questionnaire. In some instances, the OMD uses computerized adaptive testing.

Additionally, or alternatively, the OMD selected for presentation to the patient may be dependent on where, in the treatment cycle, the patient is. For example, a first OMD may be scheduled for the initial OMD and a second OMD may be scheduled for provision to the patient following a predetermined time period (e.g., 1 week or 2 months from treatment date).

In step 1020, the determined OMD may be provided to the patient before the patient receives a treatment for a medical condition. The OMD may be in any appropriate format and may attempt to ascertain a patient's state of health (e.g., how far the patient can walk, how much pain does the patient experience, the patient's mood, etc.).

Figure 17A:
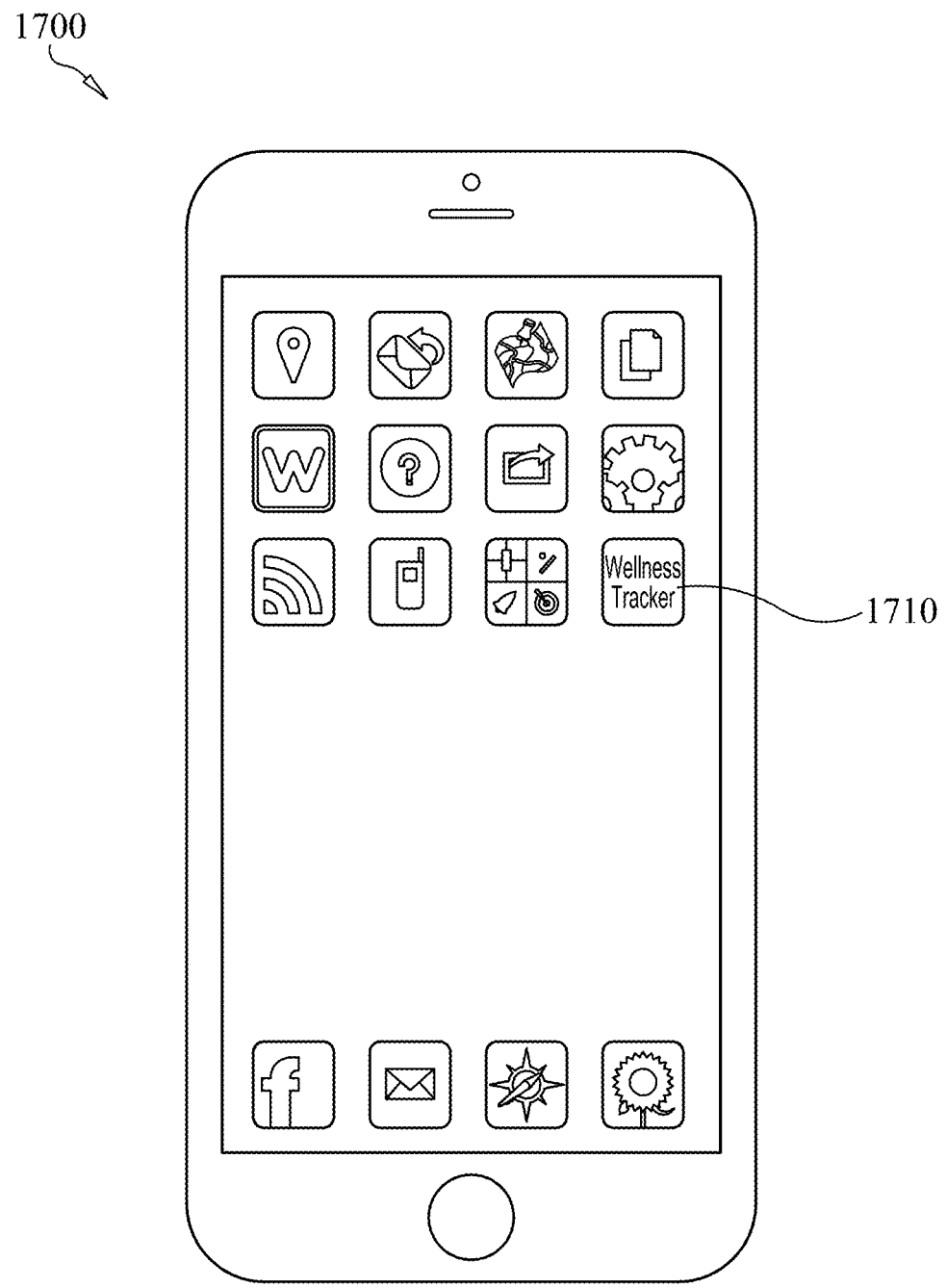
Figure 17B:
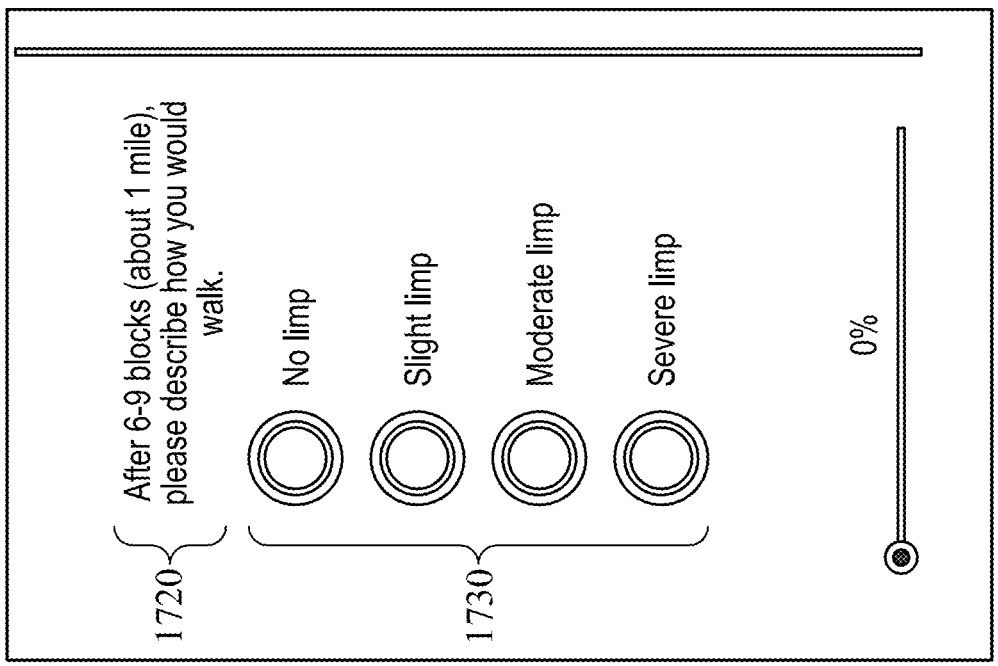
Figure 17C:
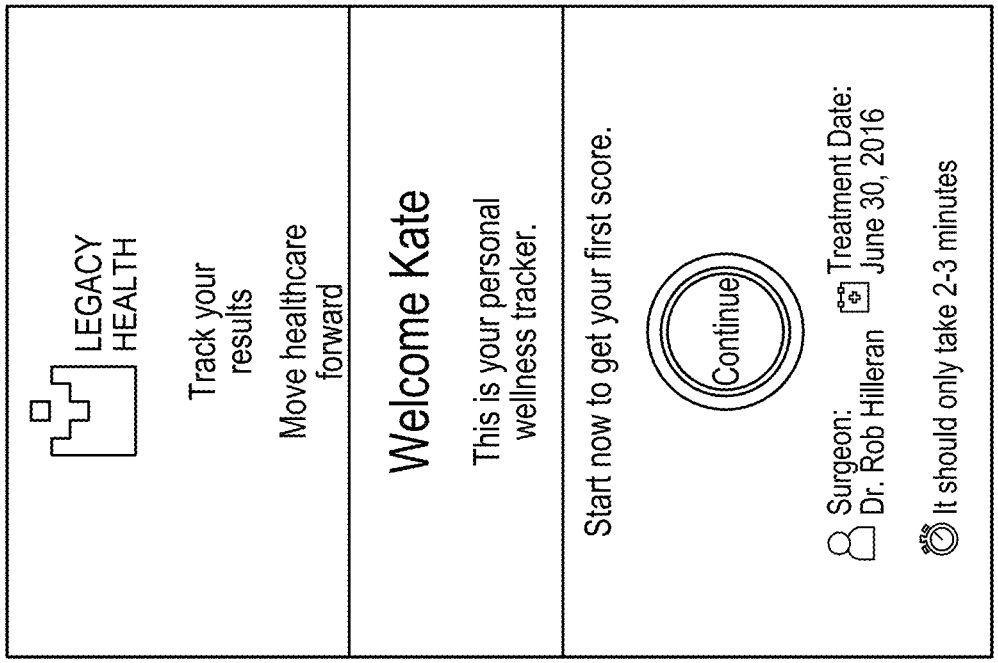

FIGS. 17C-17E show exemplary OMDs in the form of questionnaires that may be provided to the patient via interfaces 1702, 1703, and 1704, respectively when step 1020 is executed. For example, interface 1702 provides a question 1720 to the patient (who is scheduled to receive a hip replacement treatment) "after 6-9 blocks (about 1 mile) please describe how you would walk." Interface 1702 then provides a number of options/answers 1730 the patient may select to indicate his or her answer to the question. Interface 1703 asks two questions 1720 regarding "how much trouble do you have with . . . 1) "stiffness in your hip?" and 2) "decreased motion of your hip" and provides two sets of possible answers 1730, one for each question, in the form of a ranking of none (1) to extreme (5).

Interface 1704 presents an introductory paragraph 1750 that explains the questions to be completed in interface 1704 and provides directions for answering the questions. For example, the introductory paragraph 1750 of interface 1704 states: "The following questions concern your physical function. By this we mean your ability to move around and look after yourself. For each of the following activities please indicate the degree of difficulty you have experienced in the last week due to your hip." Interface 1704 then provides two questions 1720: 1) "descending stairs" and 2) "ascending stairs," and provides two sets of possible answers 1730, one for each of the questions, in the form of a ranking from none (1) to extreme (5).

Next, in step 1025, a pre-treatment set of responses to the OMD may be received before the patient receives the treatment. In one embodiment, the pre-treatment set of responses may be stored in a registry, which is specific to the medical condition (i.e., a disease-specific registry). Such disease-specific registry may compile responses from a plurality of patients who are being treated for a similar medical condition. In one embodiment, a determination may be made as to whether the pre-treatment set of responses answers all questions of the OMD. If not, a prompt may be provided to the patient, which requests all questions of the OMD to be answered. The received pre-treatment set of responses may then be stored and/or saved (step 1030). Storage of the pre-treatment set of responses may include, for example, associating the pre-treatment set of responses with the patient's wellness account. In some instances, execution of step 1030 may include communicating the pre-treatment set of responses to, for example, HIPAA compliance server 126, treatment facility computer system 134, and/or server 102 for processing and/or indexing. Storage of the pre-treatment set of responses may include, for example, indexing the pre-treatment set of responses with, for example, the patient's wellness account and/or EMR, one or more treatment providers, treatments, and/or treatment facilities.

The pre-treatment set of responses may be scored using, for example, a scoring procedure associated with the OMD provided in step 1015 in order to determine a pre-treatment wellness score for the medical condition (step 1035). Step 1035 may be executed by, for example, the patient device and/or a server like server 102. In some instances, execution of step 1035 may include retrieving a scoring procedure from scoring procedure database 116 using an identifier of the OMD. For instance, an OMD may have an associated code (e.g., 2232), and such code may be used to retrieve a scoring procedure from scoring procedure database 116. Example scoring procedures include taking an average of all the patient responses (e.g., assuming all responses are numeric), taking a weighted average of the patient responses (e.g., weighting certain responses higher than other responses), adjusting the range of patient responses (e.g., changing responses choices from 1, 2, 3 to 1, 4, 6). In some embodiments, execution of step 1035 also includes retrieval of a sub-scoring procedure that may be specific to the patient (i.e., associated with the patient's account or a co-morbidity of the patient) as may be indicated by, for example, the patient's wellness account and/or EMR.

In step 1040, the pre-treatment wellness score may be stored. Storage of the pre-treatment wellness score may include, for example, associating the pre-treatment wellness score with the patient's wellness account. In some instances, execution of step 1030 may include communicating the pre-treatment wellness score to, for example, HIPAA compliance server 126, treatment facility computer system 134, and/or server 102 for processing and/or indexing. Storage of the pre-treatment wellness score may include, for example, indexing the pre-treatment wellness score to, for example, the patient's wellness account and/or EMR, one or more treatment providers, treatments, and/or treatment facilities. After step 1040 and before step 1045, the patient may receive a treatment for his/her medical condition.

In step 1045, a second, or post-treatment OMD may be provided to the patient after the patient receives the treatment for the medical condition. In some embodiments, the OMD provided in step 1045 is identical to the OMD provided in step 1020, allowing for responses to the twice-administered OMD to be compared. In other embodiments, the OMD provided in step 1045 is not identical to the OMD provided in step 1020 when, for example, additional questions are added to the OMD (e.g., questions that are appropriate post-treatment but not pre-treatment, questions that address a change in the patient's overall health, medical condition, and/or treatment recovery, and so on). In these embodiments, the questions of, and/or information requested by, the OMD provided in step 1045 that are identical to the questions of, and/or information requested by, the OMD provided in step 1020 may be directly compared; and OMD provided in step 1045 that are not identical to the questions of, and/or information requested by, the OMD provided in step 1020 may be separately scored and/or otherwise accounted for.

In step 1050, a post-treatment set of responses to the OMD provided in step 1045 may be received from the patient. In one embodiment, the post-treatment set of responses may be stored in the disease-specific registry. Further, a determination may be made as to whether the post-treatment set of responses answers all questions of the OMD. If not, a prompt may be provided to the patient, which requests all questions of the OMD to be answered. In step 1055, the post-treatment set of responses may be stored. Storage of the post-treatment set of responses may include, for example, associating the pre-treatment set of responses with the patient's wellness account. In some instances, execution of step 1055 may include communicating the post-treatment set of responses to, for example, HIPAA compliance server 126, treatment facility computer system 134, and/or server 102 for processing and/or indexing. Storage of the post-treatment set of responses may include, for example, indexing the post-treatment set of responses to, for example, the patient's wellness account and/or EMR, one or more treatment providers, treatments, and/or treatment facilities.

In step 1060, a post-treatment wellness score for the medical condition may be determined by applying a scoring procedure, and where appropriate, a sub-scoring procedure, to the post-treatment set of responses. Such scoring procedure and sub-scoring procedure may be identical to that retrieved in step 1035 and/or retrieved in a manner similar to the execution of step 1035.

In step 1065, an improvement score may be calculated based on the pre-treatment wellness score and the post-treatment wellness score. In one embodiment, the improvement score may be calculated as the post-treatment wellness score minus the pre-treatment wellness score. More generally, the improvement score may be known as a "health progression" score, accommodating the scenarios in which the patient's condition stays the same or worsens following the treatment. Further details regarding the calculation of an improvement score is provided below with regard to FIGS. 15A-15C. The improvement score may then be stored (step 1070) in a manner similar to, for example, step 1055.

Figure 17G:
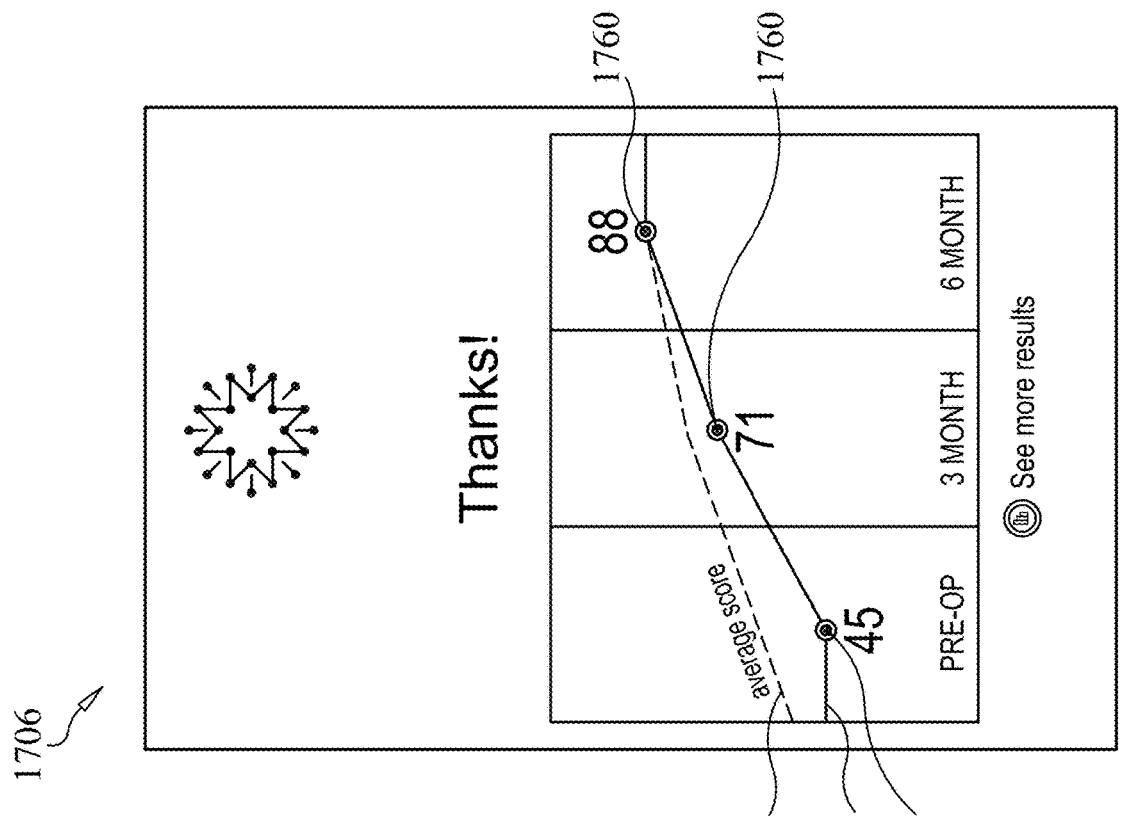

In step 1075, feedback including one or more the pre-treatment wellness score, post-treatment wellness score and the improvement score may be provided to the patient via an interface, for example, like interfaces 1705 and 1706 of FIG. 17F and FIG. 17G, respectively, which will be discussed in more detail below. The feedback may also be provided, for example, to a treatment provider, a treatment facility, and/or a treatment administrator. In one embodiment, the pre-treatment wellness score may only be provided to the patient upon the pre-treatment set of responses answering all questions of the OMD. In one embodiment, the post-treatment wellness score may only be provided to the patient upon the post-treatment set of responses answering all questions of the OMD. Hence, the pre-treatment/post-treatment wellness score can serve as an incentive for a patient to complete the OMD. In some embodiments, execution of step 1075 may include providing a patient/treatment provider/treatment facility/treatment administrator with information regarding medical literature that discusses the OMD provided to the patient.

In some instances, the storage of steps 1030, 1040, 1055, and/or 1070 may include entering the information being stored into and/or indexing the information being stored to one or more of a medical-condition-specific registry of information, a treatment-specific registry of information, a disease-specific registry of information, a medical-condition-specific registry of information, a diagnosis-specific registry of information, a treatment-facility-specific registry of information, and/or a treatment-provider-specific registry of information. In some embodiments, the storage of steps 1030, 1040, 1055, and/or 1070 may further include indexing and/or correlating information from the patient's EMR with the received responses, patient's pre-treatment wellness score, patient's post-treatment wellness score, and/or the patient's improvement score thereby creating a registry that includes patient-specific information (e.g., patients height, weight, sex, race, income, medical comorbidities, medications, etc.). In some embodiments, the information from the patient's EMR may also be included in one or more of the medical-condition-specific registry of information, treatment-specific registry of information, disease-specific registry of information, medical-condition-specific registry of information, diagnosis-specific registry of information, treatment-facility-specific registry of information, and/or treatment-provider-specific registry of information. All of these registries of information may be searched and/or queried by, for example, a treatment provider and/or patient in order to, for example, receive information regarding the performance or effectiveness of a particular treatment for treating a diagnosed medical condition for a patient with a set of characteristics or receive information regarding the effectiveness of a treatment provider at providing a particular treatment for a type of patient. Further information regarding this process is provided below with regard to FIG. 14.

In one embodiment, providing the pre-treatment wellness score, post-treatment wellness score and/or improvement score to the patient, treatment provider, a treatment facility, and/or a treatment administrator does not involve an action from a treatment provider or treatment facility administrator (e.g., doctor, nurse, researcher, clinician, etc.). In one embodiment, the pre-treatment wellness score, post-treatment wellness score and/or improvement score may be provided to the patient treatment provider, a treatment facility, and/or a treatment administrator along with an average pre-treatment wellness score, an average post-treatment wellness score and an average improvement score (where the "average" is calculated for a group of patients who are being treated for a similar medical condition as the instant patient, and who also are in the same age range, the same gender, etc. as the instant patient), allowing the patient, treatment provider, a treatment facility, and/or a treatment administrator to, for example, assess how much (or little) the patient's recovery process deviates from the typical recovery process or estimate how long it may take the patient to recover from the treatment.

In some instances, the feedback may be provided based on one or more characteristics of the patient (e.g., age, gender, profession, etc.) or a patient goal established before treatment. For example, if a patient sets the goal that he or she wants to be able to walk for one mile without knee pain following knee replacement surgery, the feedback provided to the patient may indicate how close the patient is to that goal. The additional feedback may be provided in any appropriate manner including, but not limited to, a score (e.g., 0-100 or A-F), a word (e.g., needs improvement, good, great), or an image (e.g., a linear regression graph that shows recovery from the treatment over time or a pie chart that provides feedback regarding the recovery rate of the patient when the OMD is responded to). In most cases, the feedback will be specific to the patient and responsive to the OMD responses. In some instances, the feedback may indicate next steps for the treatment recovery process and/or recommendations to assist with accelerating the pace of recovery and/or maintaining a recovery state.

In one embodiment, the pre-treatment wellness score, post-treatment wellness score, and/or improvement score may be correlated with information extracted from the electronic medial record (EMR) of the patient. For instance, if the post-treatment wellness score is below a certain threshold, the information form the EMR may be analyzed in order to find a possible cause for the low post-treatment wellness score (e.g., the patient has a low level of blood clotting factors, the patient is diabetic, etc.).

Figure 20:
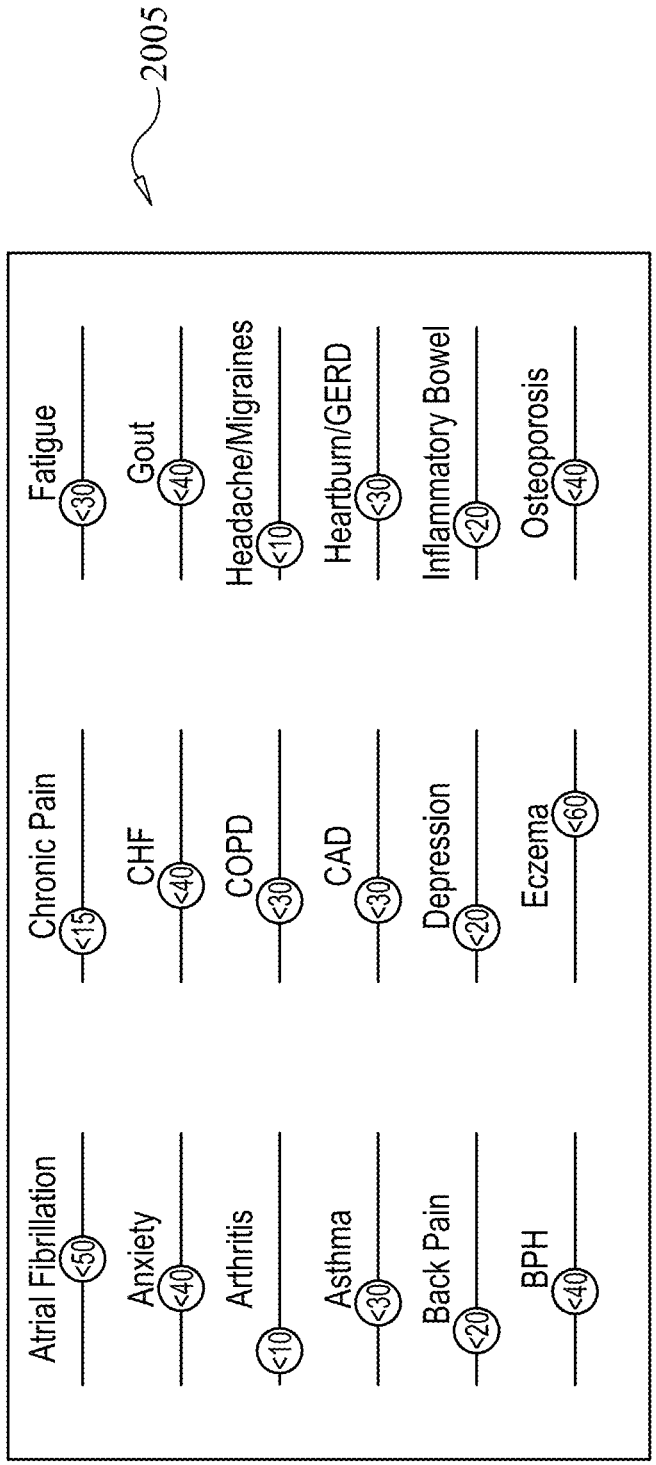
FIG. 20 is a screen shot of a care management dashboard in accordance with some embodiments of the present invention.

Optionally, in step 1080, the pre-treatment wellness score, post-treatment wellness score, and/or improvement score may be compared to a minimum threshold. If one or more of the scores are below the minimum threshold, a notification may be generated and provision of the notification to a treatment provider, treatment facility, and/or treatment facility administrator, alerting the treatment provider, treatment facility, and/or treatment facility administrator to the abnormally low one or more scores may be facilitated (step 1085). In some embodiments, a treatment provider, treatment facility, and/or treatment facility administrator may establish minimum wellness and/or improvement score thresholds for various medical conditions, treatments, and other circumstances via an interface like care management dashboard 2000 of FIG. 20. Care management dashboard 2000 is adapted for presentation to a particular treatment provider, in this case, J. D. Smith and provides a number of contact preferences (SMS text message to a phone number and/or by email to an email address) by which the treatment provider may choose how he or she is contacted when a wellness score falls below a certain threshold. Interface 2000 also provides a table 2005 of medical conditions for which a wellness score threshold may be established. In some instances, the entries in table 2005 may be specific to a particular patient (e.g., related to the patient's medical condition(s)) and in other instances, the entries in table 2005 may be more generally applicable (e.g., level of pain, mobility, etc.). More specifically, table 2005 enables Dr. Smith to set a minimum wellness and/or improvement score thresholds for the medical conditions of atrial fibrillation (<50), anxiety (<40), arthritis (<10), asthma (<30), back pain (<20), BPH (<40), chronic pain (<15), CHF (<40), COPD (<30), CAD (<30), depression (<20), eczema (<60), fatigue (<30), gout (<40), headache/migraines (>10), GERD (<30), inflammatory bowel (<20), and osteoporosis (<40). Should a wellness score for any of the patient's Dr. Smith has associated with care management dashboard 2000 fall below one of these established minimum thresholds, he or she will receive a notification indicating as such. In some embodiments, an interface like interface 2000 may be provided to another treatment provider for the patient who, for example, an assistant to the treatment provider (e.g., registered nurse, medical assistant, etc.) and, in this embodiments, one or more of the thresholds may be set higher so that the assistant is contacted when the score is below a higher number. For example, a treatment provider may set a chronic pain wellness score threshold of <15 and an assistant to the treatment provider may set a chronic pain wellness score threshold of <30 so that he or she may follow up with the patient before his or her pain gets too bad (i.e., wellness score drops to an unacceptable level).

In one embodiment, the notification may include contact information of the patient, allowing the treatment provider to immediately contact the patient. In one embodiment, the notification may be sent according to one or more preferences of, for example, treatment provider, treatment facility, and/or treatment facility administrator. In one example, if an improvement score is below 30% (when comparing, for example, a pre-treatment wellness score and a first post-treatment wellness score), a notification may be sent to a treatment facility administrator or care management department for follow up by, for example, a nurse or case manager for a treatment provider. In this same example, if an improvement score is below 10% (when comparing, for example, a pre-treatment wellness score and a first post-treatment wellness score), a notification may be sent to the treatment provider for follow up. In some embodiments, a treatment provider may be provided with an interface showing one or more notifications he or she has received.

Figure 17F:
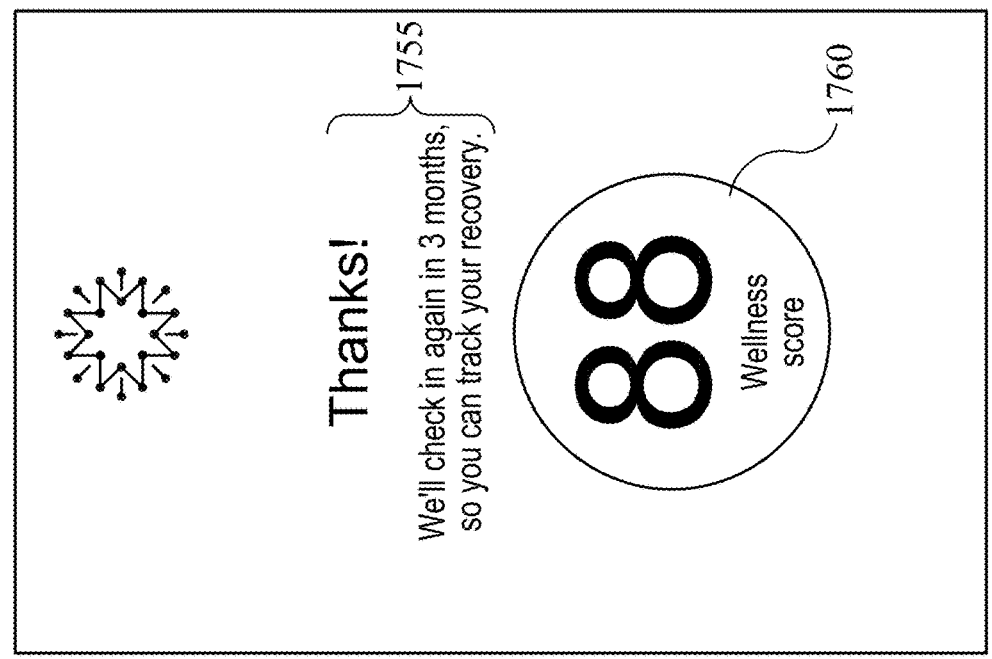

Interface 1705 of FIG. 17F provides exemplary patient feedback in the form of a numerical wellness score 1760 (in this case 88) along with a message 1755 to the patient indicating, for example, when the patient will be prompted to respond to another OMD (e.g., "We'll check in again in 3 months so you can track your recovery."). Interface 1706 of FIG. 17G provides exemplary patient feedback in the form of a graph 1770 that shows the patient's numerical wellness scores over time, including a pre-op wellness score of 45, a post-treatment wellness score of 71 three months after surgery and a post-treatment wellness score of 88 six months after surgery. In the example of FIG. 17G, the post-treatment wellness scores may also be called "recovery scores". As described above, interface 1706 may also provide a progression of average wellness scores over time in the form of graph 1775, thereby allowing the patient to assess his or her recovery process relative to the typical recovery process.

In one embodiment, further information may be collected from the patient before the treatment. For example, the information may include the patient's compliance with pre-treatment instructions prior to the treatment. In such case, a patient compliance question relating to the patient's compliance with pre-treatment instructions before the treatment may be determined. The determined patient compliance question may be provided to the patient. A response to the patient compliance question may be received from the patient. Finally, the received response may be stored with a key that is used to retrieve the received response. The key may include at least one of the treatment to be provided to the patient, a treatment provider for the patient, a treatment facility used by the patient, patient characteristics.

In another embodiment, further information may be collected from the patient following the treatment. For example, the information may include the patient's compliance with post-treatment instructions following the treatment. In such case, a patient compliance question relating to the patient's compliance with post-treatment instructions following the treatment may be determined. The determined patient compliance question may be provided to the patient. A response to the patient compliance question may be received from the patient. Finally, the received response may be stored with a key that is used to retrieve the received response. The key may include at least one of the treatment provided to the patient, a treatment provider for the patient, a treatment facility used by the patient, patient characteristics, and an outcome score of the treatment.

In one embodiment, the pre-treatment set of responses and the post-treatment set of responses may be stored in OMD response database 110 with a key that is used to retrieve at least one of the pre-treatment set of responses and the post-treatment set of responses, wherein the key includes at least one of the treatment provided to the patient, a treatment provider for the patient, a treatment facility used by the patient, patient characteristics, and an outcome score of the treatment.

In some circumstances, the OMD provided to the patient in process 1000, and/or the feedback provided to the patient may be designed so as to encourage the patient to engage with the software application providing the recovery/wellness tracker. For example, the OMD may be designed so as to be easy to understand and respond to, and the feedback to the patient may be provided in a manner easy for a patient with little medical knowledge to understand. In some instances, a patient's response to the one or more OMDs may be a requirement that must be fulfilled before a patient is permitted to receive treatment and/or treatment recovery services. For example, a patient's response to the OMDs may be a pre-condition for scheduling follow up appointments with the provider of his or her treatment.

In one embodiment, the OMD may be provided to the patient at a plurality of time points after the patient receives the treatment. More specifically, upon an expiration of a predetermined time period measured from at least one of a time at which the patient received the treatment and a time at which the post-treatment set of responses was received from the patient, an additional OMD may be provided to the patient, the additional OMD being in addition to the OMDs provided at steps 1020 and 1045. The additional post-treatment set of responses to the OMD may be received from the patient. An additional post-treatment wellness score for the medical condition may be determined by applying the scoring procedure to the additional post-treatment set of responses. Subsequently, the additional post-treatment wellness score may be provided to the patient. The "recovery score" of 88 may be an example of such an additional post-treatment wellness score.

In one embodiment, process 1000 may be performed on each of a plurality of patients. In such case, a medical-condition-specific registry of information, a treatment-specific registry of information, a treatment-facility-specific registry of information, and/or a treatment-provider-specific registry of information may be created. In the medical-condition-specific registry of information, one or more of the pre-treatment set of responses (received from one or more patients), the pre-treatment wellness scores (determined for one or more patients), the post-treatment set of responses (received from one or more patients), the post-treatment wellness scores (determined for one or more patients), and patient characteristics (e.g., patient characteristics extracted from a patient's EMR) may be mapped to the medical condition, treatment, treatment facility, and/or treatment provider as appropriate.

In some embodiments, step 1015 and/or 1045 may include determining multiple OMDs to provide to the patient. For example, if a patient is undergoing a treatment for removing a cataract from an eye, it may be determined in step 1015 that a combination of PRO questionnaires and medical symptom questionnaires are appropriate to provide to the patient. More specifically, it may be determined that the Catquest 9-SF Visual Function Test is the most appropriate PRO instrument to use when determining visual function for the patient and the NIH PROMIS Global Health Short Form 1D is the most appropriate general health questionnaire to provide to the patient so as to determine the patient's general state of health. Both of these OMDs/questionnaires may be provided to the patient in step 1020 via one or more interfaces like 17C-17E provided to the patient via his or her wellness account and/or patient device. A set of responses to the OMDs provided to the patient may be received (step 1025) and stored (step 1030).

Figure 21A:
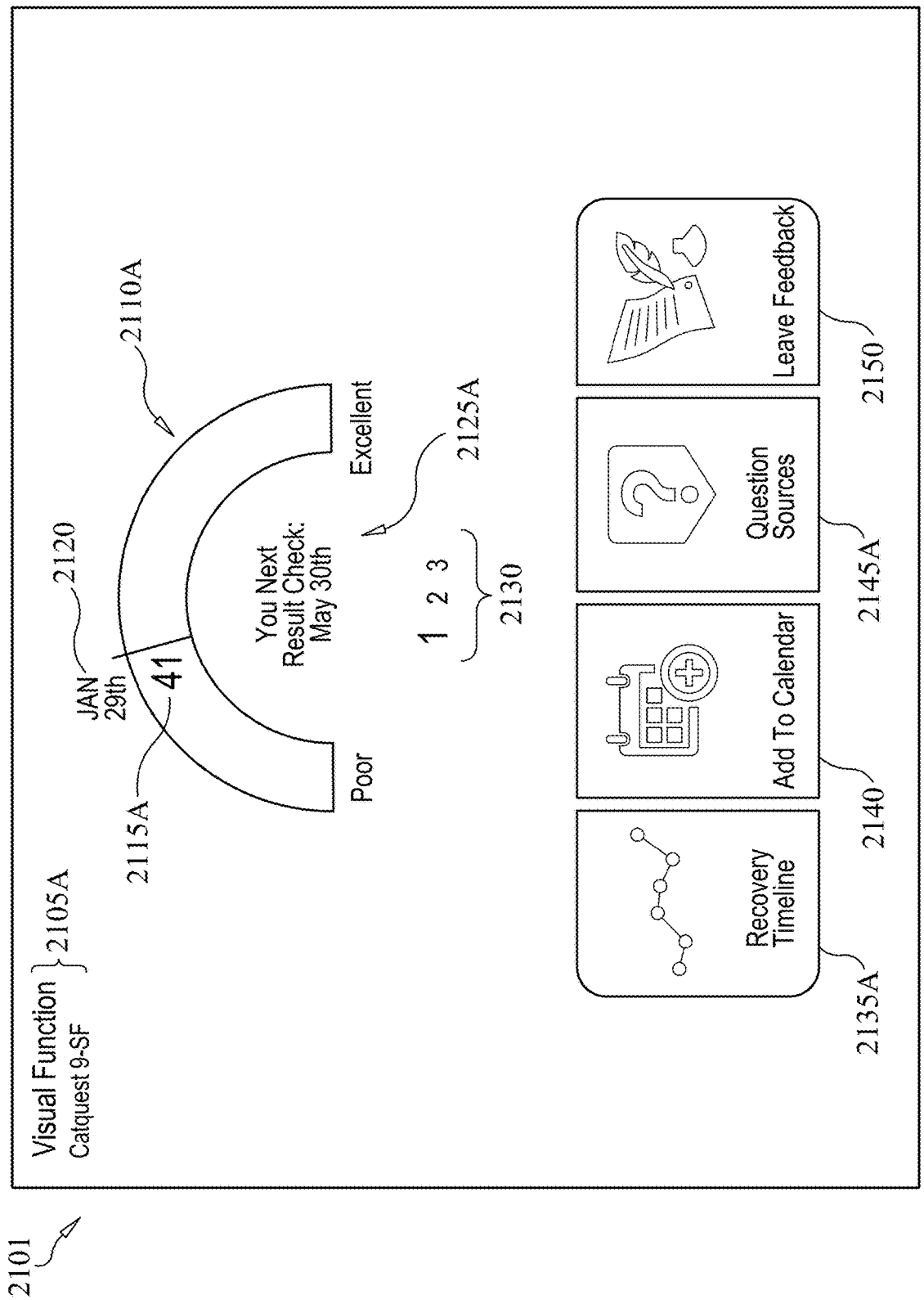

Next, a pre-treatment wellness score for the medical condition/treatment, in this case, a cataract, and the patient's general health may be determined (step 1035) by applying a scoring procedure associated with the Catquest 9-SF Visual Function Test to responses to questions from the Catquest 9-SF Visual Function Test received in step 1025 and applying a scoring procedure associated with the NIH PROMIS Global Health Short Form 1D to responses to questions from the NIH PROMIS Global Health Short Form 1D received in step 1025. Then, a pre-treatment wellness score for the patient's responses to the Catquest 9-SF Visual Function Test and the NIH PROMIS Global Health Short Form 1D may be determined (step 1035) and provided to the patient (step 1075) via an interface like visual function interface 2101 of FIG. 21A and general health wellness score interface 2102 of FIG. 21B. In some instances, provision of the wellness scores to the patient may involve adjusting the wellness score (e.g., putting on a scale of 1-100) so that it is more meaningful to the patient. In some instances, adjusting the wellness score may include normalizing the wellness score to be on a scale common to all of the wellness scores provided to the patient (i.e., a normalized scale). Additionally, or alternatively, provision of the wellness scores to the patient may involve using commonly known terms/alternate terminology to refer to what the wellness score is measuring. In the examples of visual function interface 2101, the wellness score determined by the Catquest 9-SF Visual Function Test has been provided along with a heading 2105A that states what the test/OMD measures (in this case, visual function) in non-medical alternate terms. In some instances, the information included in heading 2105A (and the other headings disclosed herein) may be added to the heading using alternate terminology associated with, for example, the medical condition of the patient, a name of the OMD administered to the patient, a treatment the patient is undergoing or has undergone, and so on.

The visual function wellness score determined by scoring the patient's responses to the Catquest 9-SF Visual Function Test has also been converted to a number on a scale from 1-100 with an adjusted score 2115A of 41, which is provided to the patient on a graphically-represented semi-circularly shaped wellness score progress chart 2110A with a minimum (i.e., poor) score on one side and a maximum (i.e., excellent) score on the other side. It will be understood by those of skill in the art that the shape/form of wellness score progress chart 2110A, as well as the other wellness score progress charts disclosed herein may be different from a semi-circle. For example, a wellness score progress chart may take the form of a pie chart, a bar chart, and/or a graph. Interface 2102A also provides a date 2120 at which the visual function wellness score was determined (in this case, January $29^{th}$) and a message 2125A regarding when the next result check will be (in this case, May $30^{th}$). Interface 2102A further provides a scrolling mechanism 2130 by which a patient may scroll through the various (in this case, 3) wellness scoring interfaces provided by his or her wellness account.

Visual function interface 2101 also includes a recovery timeline icon 2135A, an add to calendar icon 2140, a question sources icon 2145A, and leave feedback icon 2150. Selection of recovery timeline icon 2135A causes a recovery timeline interface related to visual function to be displayed, selection of add to calendar icon 2140 causes the next scheduled administration of the OMD to be added to the patient's calendar, selection of question sources icon 2145A causes a question sources interface that includes sources of medical literature related to the Catquest 9-SF Visual Function Test and/or visual function to be displayed, and selection of leave a feedback icon 2150 causes a feedback interface to be displayed.

Figure 21B:
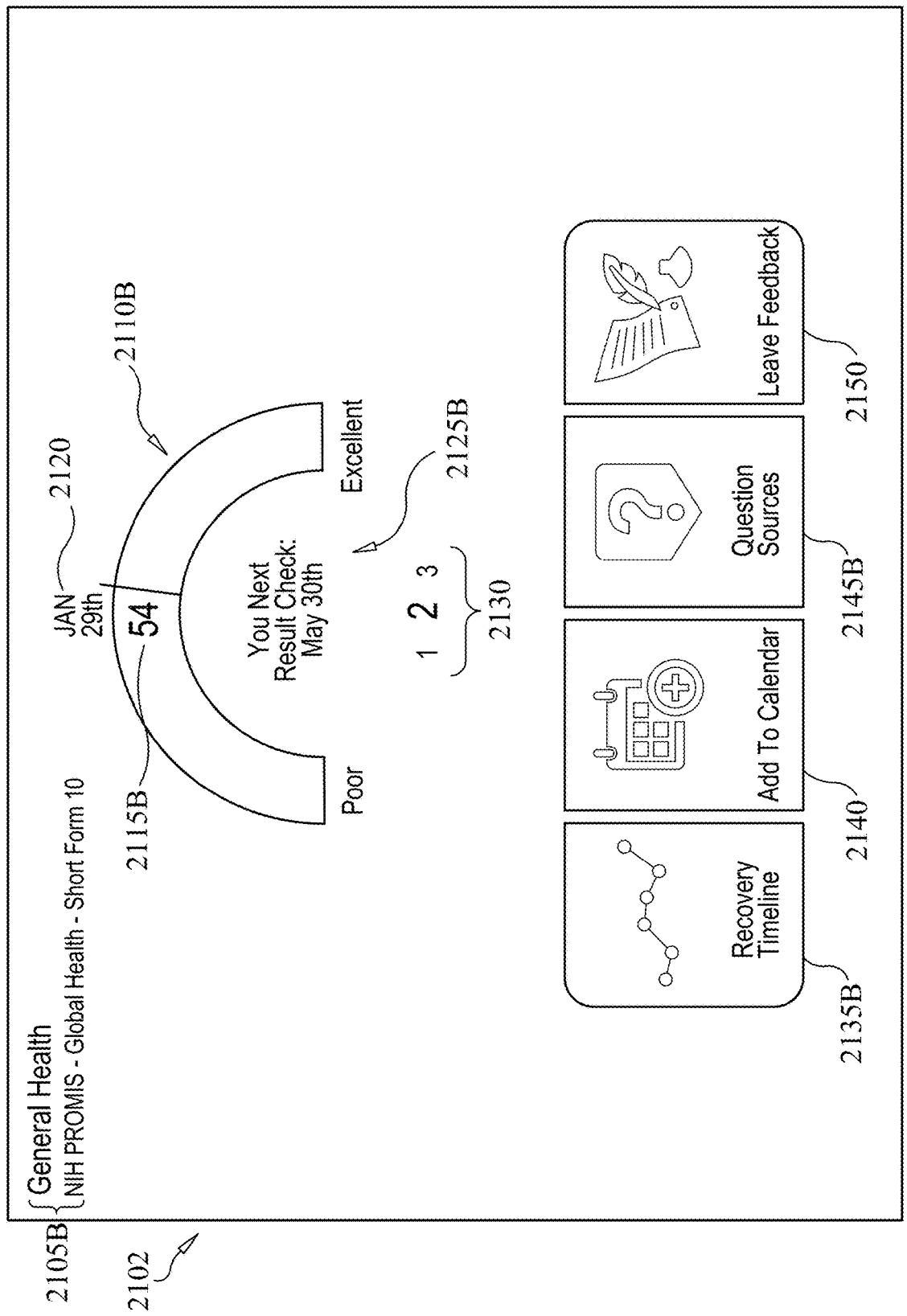

General health wellness score interface 2102 of FIG. 21B provides an adjusted general health wellness score 2115B of 54 along a graphically represented wellness score progress chart 2110B. The general health wellness score is determined by applying the scoring procedure for the NIH PROMIS Global Health Short Form 1D OMD to the responses received thereto and adjusting and/or normalizing the determined wellness score to be on a scale of 1-100. Interface 2102 includes a heading 2105B that states in non-medical language what the wellness score provided by interface 2102 relates to. The information included in heading 2105B may be added to the heading using alternate terminology associated with, for example, the medical condition of the patient, a name of the OMD administered to the patient, a treatment the patient is undergoing or has undergone, and so on. Interface 2102B also provides a date 2120 at which the general health wellness score has been determined (in this case, January $29^{th}$) and a message 2125B regarding when the next result check will be (in this case, May $30^{th}$).

General health interface 2102 also includes a recovery timeline icon 2135B, add to calendar icon 2140, a question sources icon 2145B, and leave feedback icon 2150. Selection of recovery timeline icon 2135B causes a recovery timeline interface related to the patient's general health wellness scores to be displayed and selection of question sources icon 2145B causes a question sources interface that lists sources of medical literature related to the patient's general health and the NIH PROMIS Global Health Short Form 1D OMD (i.e., the OMD used to determine the patient's general health) to be displayed.

Figure 21C:
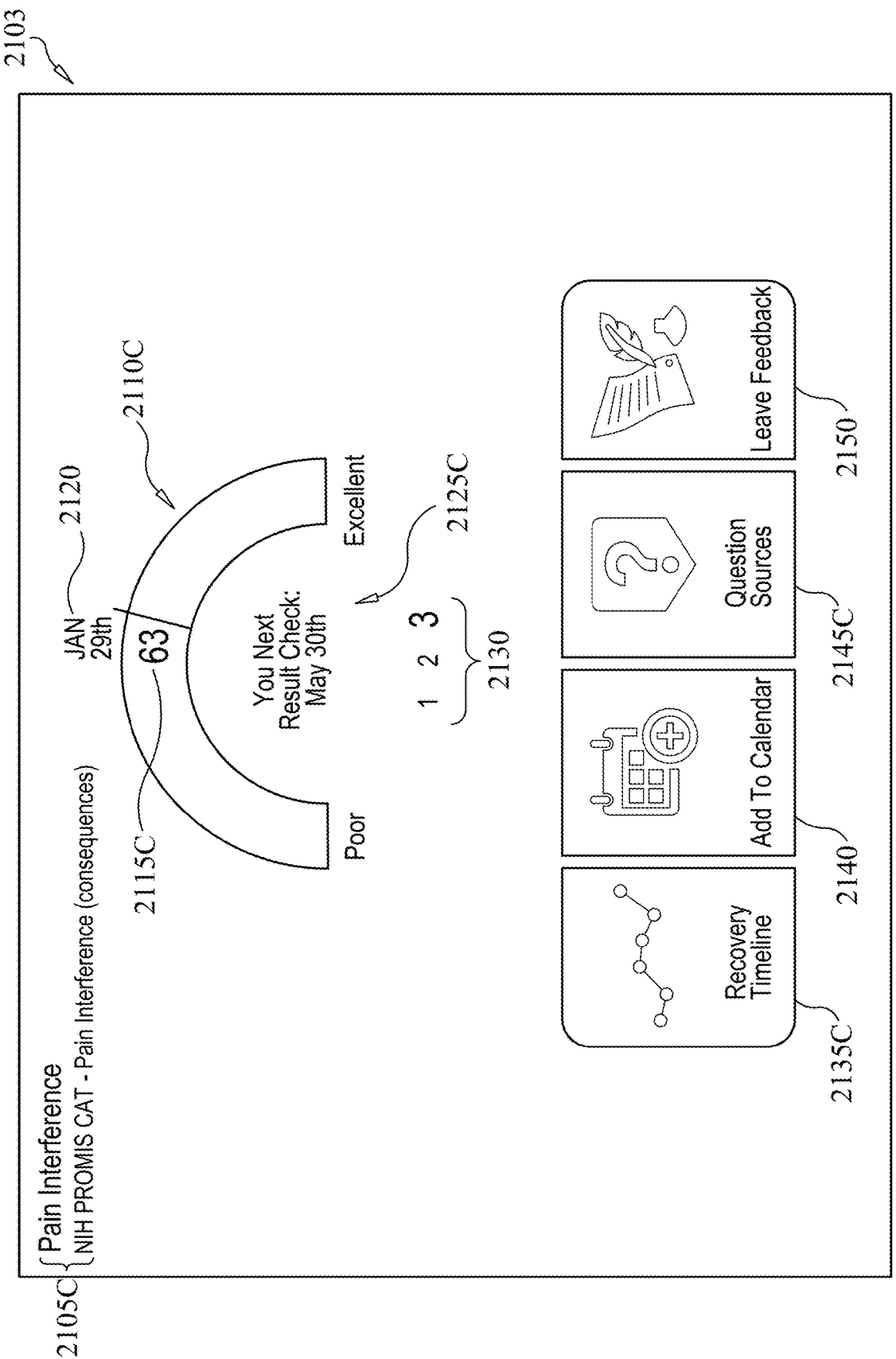

Pain interference wellness score interface 2103 of FIG. 21C provides an adjusted pain interference wellness score 2115C of 63 along a graphically represented wellness score progress chart 2110C. The pain interference wellness score is determined by applying the scoring procedure for a NIH PROMIS CAT—Pain Interference (Consequences) OMD to responses received thereto via the patient's wellness account and adjusting the determined wellness score to be on a scale of 1-100. Interface 2103 includes a heading 2105C that states in non-medical language what the wellness score provided by interface 2103 relates to (i.e., pain interference). The information included in heading 2105C may be added to the heading using alternate terminology associated with, for example, the medical condition of the patient, a name of the OMD administered to the patient, a treatment the patient is undergoing or has undergone, and so on. Interface 2102C also provides a date 2120 at which the pain interference score has been determined (in this case, January $29^{th}$) and a message 2125C regarding when the next result check will be (in this case, May $30^{th}$).

Pain interference interface 2103 also includes a recovery timeline icon 2135C, add to calendar icon 2140, a question sources icon 2145C, and leave feedback icon 2150. Selection of recovery timeline icon 2135C causes a recovery timeline interface related to the patient's pain interference wellness scores to be displayed and selection of question sources icon 2145C causes a question sources interface that lists sources of medical literature related to the patient's pain interference and the NIH PROMIS CAT—Pain Interference (Consequences) OMD to be displayed.

Figure 21D:
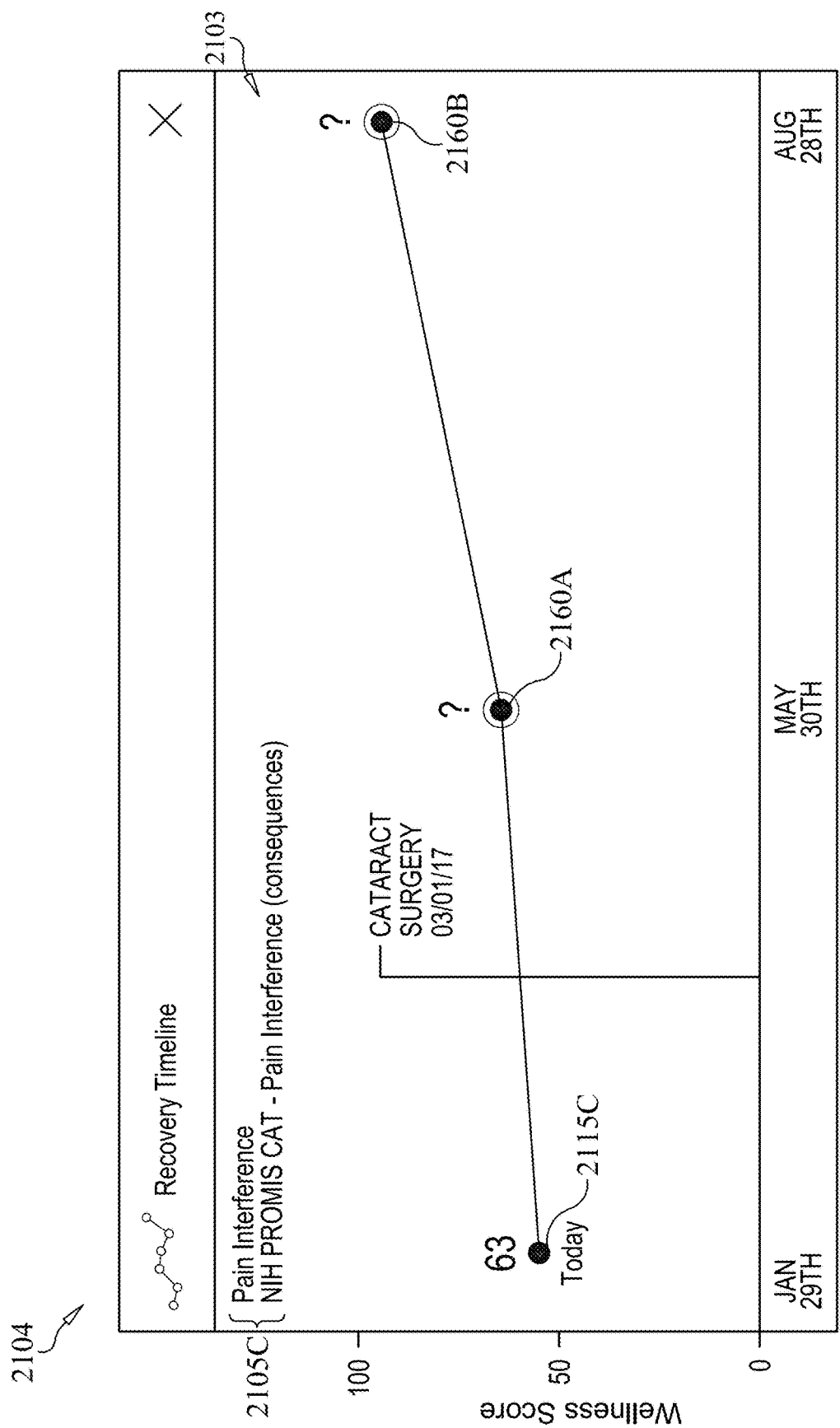

FIG. 21D provides an exemplary pain interference recovery timeline interface 2104 for pain interference wellness scores and projected/predicted pain interference wellness scores for the patient. Pain interference recovery timeline interface 2104 may be provided to the patient upon selection of recovery timeline icon 2135C and may provide heading 2105C, and a recovery timeline graph 2155 that plots wellness scores on a scale of 1-100 vs. time as measured in months. Graph 2155 provides the determined pain interference wellness score 2115C of pain interference interface 2103 (i.e., 63), a first predicted/projected pain interference wellness score 2160A, and a second predicted/projected pain interference wellness score 2160B. Predicted/projected pain interference wellness scores 2160A and 2160B may be determined via one or more processes described herein.

FIG. 21E provides an exemplary question sources interface 2106 that provides a list of exemplary sources of information 2165A and 2165B related to the OMDs provided to the patient, in this case papers that discuss cataract surgery.

Continuing with this example, at a predetermined time (e.g., 3 months after the cataract surgery), the patient may be provided with the Catquest 9-SF Visual Function Test and the NIH PROMIS Global Health Short Form 1D questionnaires (step 1045) and a post-treatment set of responses thereto may be received (step 1050) and stored (step 1055). Then, a post-treatment wellness score for the medical condition/treatment (cataract surgery) and the patient's general health may be determined (step 1065) by applying a scoring procedure associated with the Catquest 9-SF Visual Function Test to responses to questions from the Catquest 9-SF Visual Function Test received in step 1025 and applying a scoring procedure associated with the NIH PROMIS Global Health Short Form 1D to responses to questions from the NIH PROMIS Global Health Short Form 1D received in step 1050. Then, a post-treatment wellness score for the patient's visual function and general health may be determined (step 1060) and provided to the patient (step 1075). In some cases, these may be separate scores and, in other cases, the scores may be combined into a single overall post-treatment wellness score.

In another example, if a patient is undergoing a treatment for a shoulder injury, it may be determined in step 1015 that a combination of PRO questionnaires and medical symptom questionnaires are appropriate to provide to the patient. More specifically, it may be determined that the American Shoulder & Elbow Surgeons Assessment is the most appropriate PRO instrument to use for determining shoulder function for the patient, the NIH PROMIS CAT Pain Behavior questionnaire is the most appropriate questionnaire to provide to the patient to determine how the patient's behavior is effected by pain, the NIH PROMIS CAT Physical Function questionnaire is the most appropriate questionnaire to provide to the patient to determine how the patient's physical function is effected by his/her shoulder injury, and the NIH PROMIS CAT Pain Interference questionnaire is the most appropriate questionnaire to provide to the patient to determine how much the patient's pain interferes with his or her daily life. These four questionnaires may be provided to the patient in step 1020 and a set of responses thereto may be received (step 1025) and stored (step 1030).

Next, a pre-treatment wellness score for the medical condition, in this case, a shoulder injury, may be determined (step 1035) by applying a scoring procedure associated with the American Shoulder & Elbow Surgeons Assessment to responses to questions from the American Shoulder & Elbow Surgeons Assessment received in step 1025, applying a scoring procedure associated with the NIH PROMIS CAT Pain Behavior questionnaire to responses to questions from the NIH PROMIS CAT Pain Behavior questionnaire received in step 1025, applying a scoring procedure associated with the NIH PROMIS CAT Physical Function questionnaire to responses to questions from the NIH PROMIS CAT Physical Function questionnaire received in step 1025, and applying a scoring procedure associated with the NIH PROMIS CAT Pain Interference questionnaire to responses to questions from the NIH PROMIS CAT Pain Interference questionnaire received in step 1025.

Then, a pre-treatment wellness score for the patient's shoulder function, behavior due to pain, physical function, and pain interference may be determined (step 1035) and provided to the patient (step 1075). In some cases, these may be separate post-treatment wellness scores (i.e., one for each OMD) and, in other cases, the scores may be combined into a single overall pre-treatment wellness score.

Figure 22A:
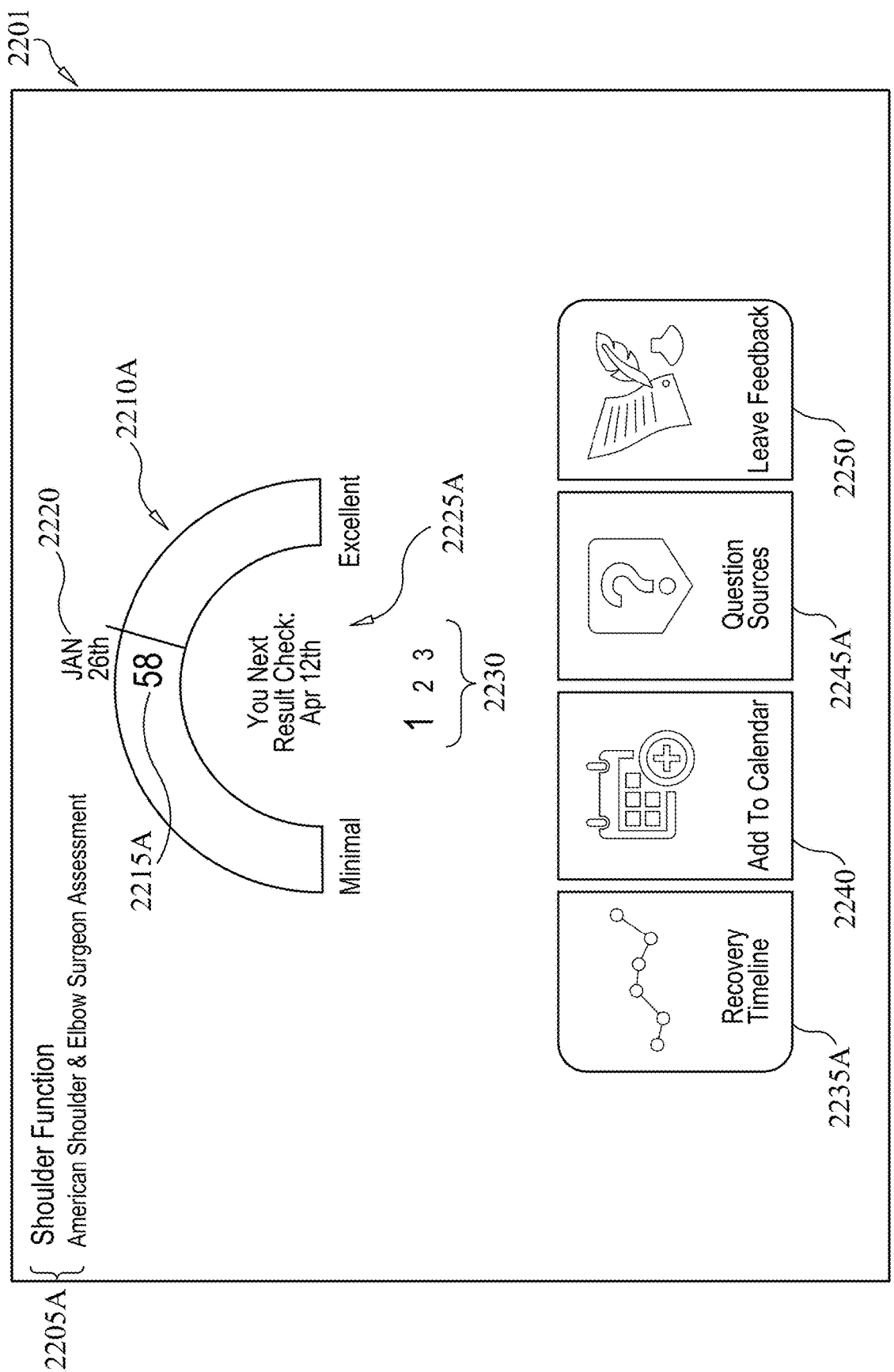
FIGS. 22A-22E depict screen shots from provided by a patient's wellness to a patient who has undergone shoulder surgery in accordance with some embodiments of the present invention.
Figure 24A:
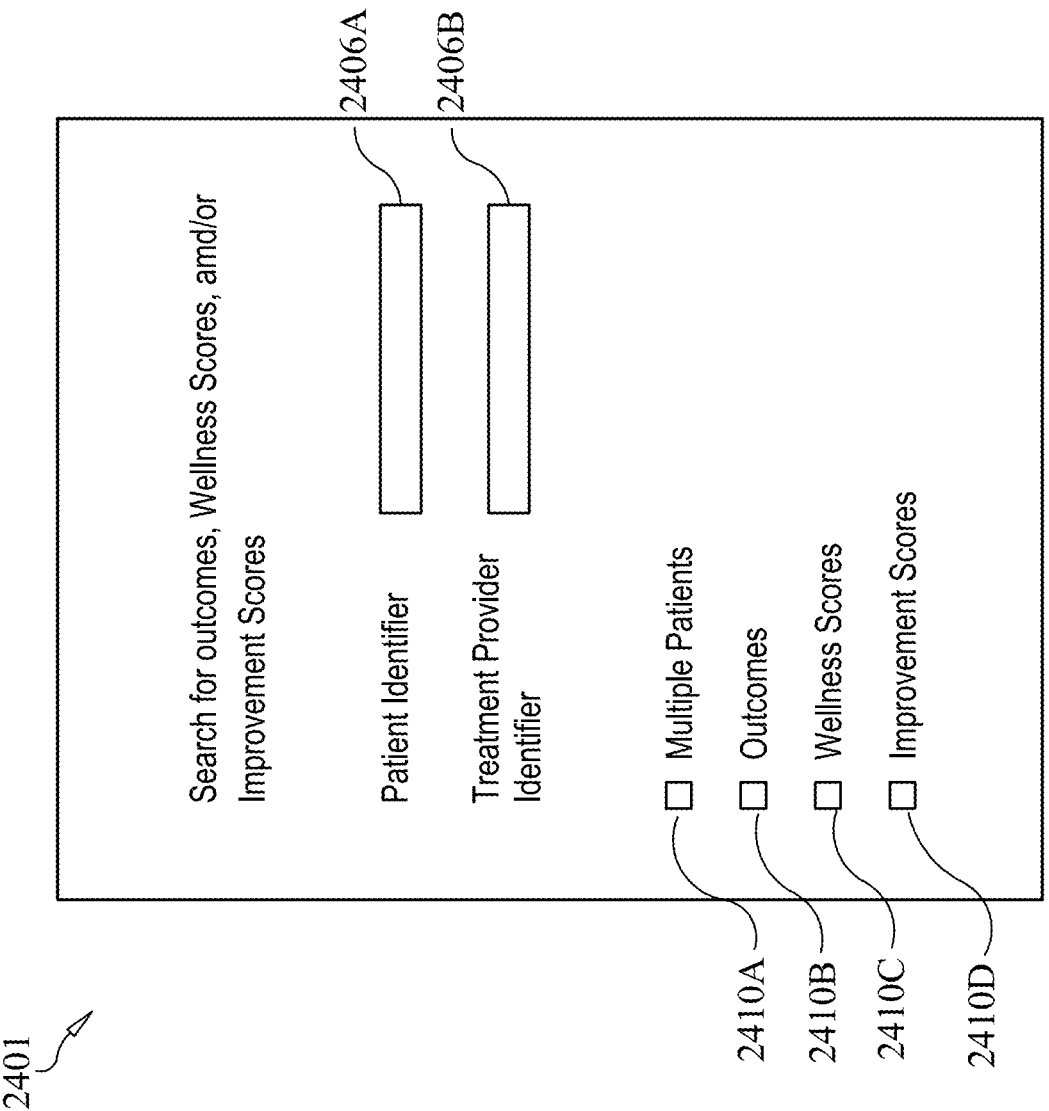
FIGS. 24A-24E provide screen shots of exemplary interfaces provided to a requester of information regarding treatment outcomes, wellness scores, and/or improvement scores in accordance with some embodiments of the present invention.
Figure 24B:
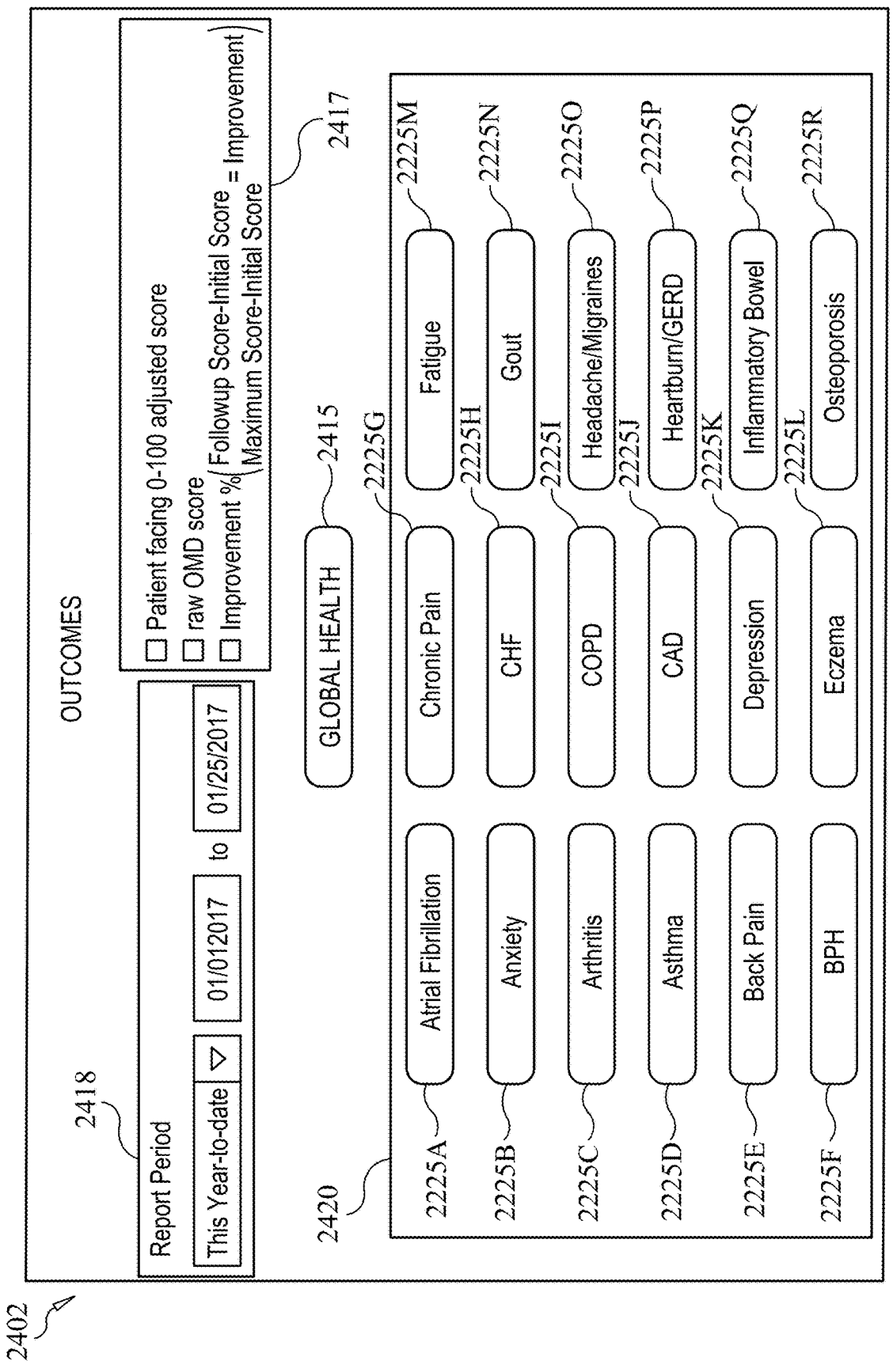
Figure 24C:
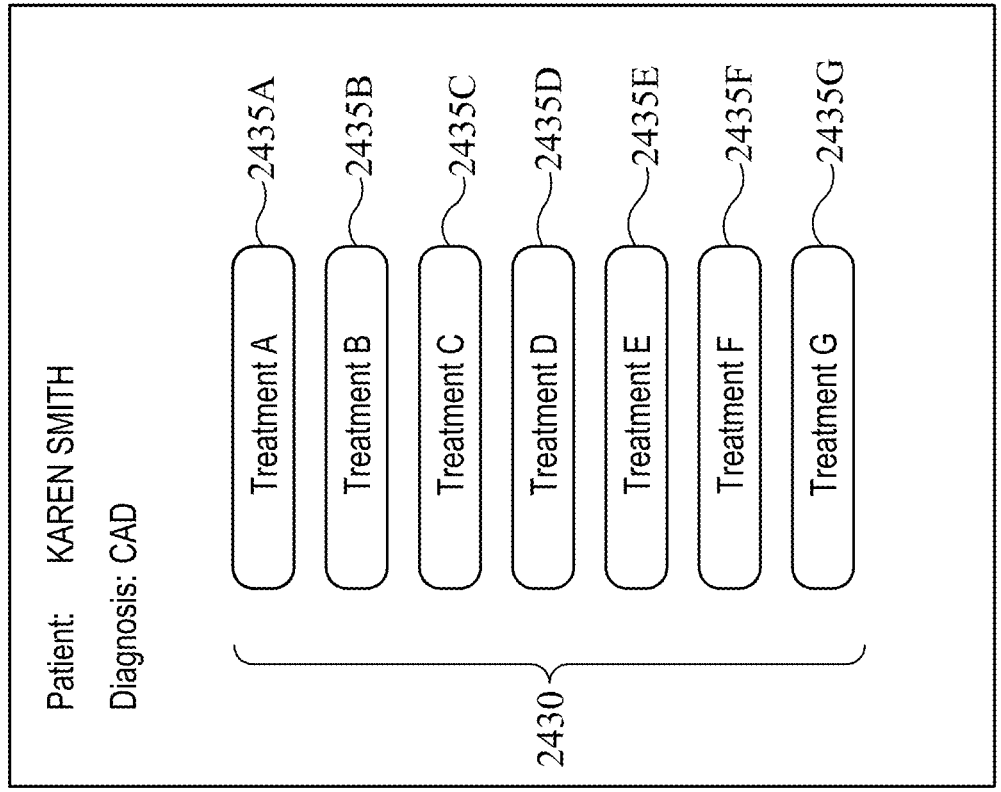
Figure 24D:
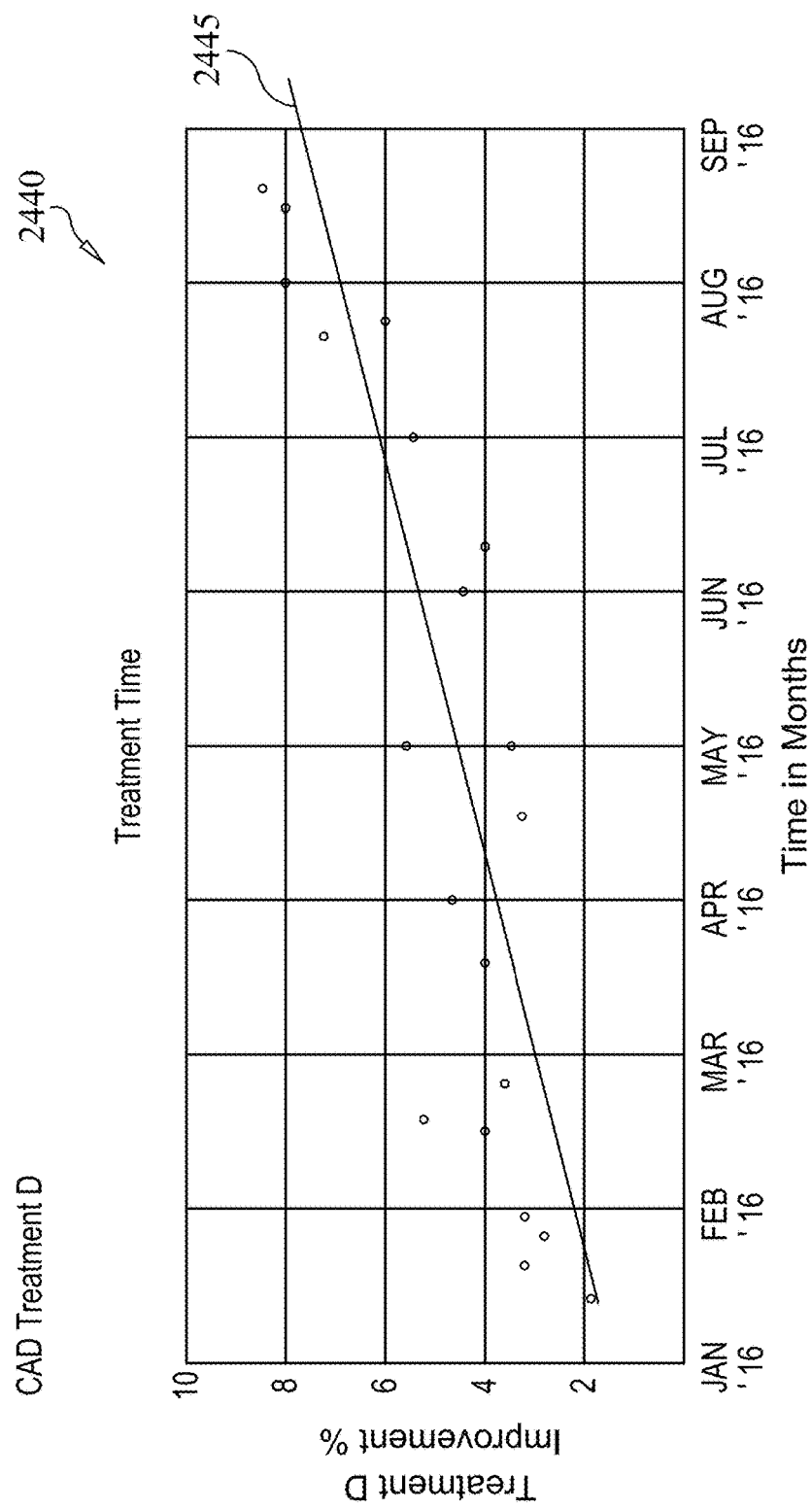

FIGS. 22A-22E provide a series of interfaces that are responsive to providing the American Shoulder & Elbow Surgeons Assessment, NIH PROMIS CAT Pain Behavior questionnaire, and NIH PROMIS CAT Pain Interference questionnaire OMDs to the patient as may occur when a treatment provider associates a shoulder-related injury diagnosis or treatment with the patient via, for example, an interface like interface 2303 and/or 2402 of FIGS. 23C and 24B, respectively. For example, FIG. 22A provides a shoulder function wellness score interface 2201 that provides a graphically represented wellness score progress chart 2210A with a shoulder function wellness score 2215A of 58, which is determined by applying a scoring procedure associated with the American Shoulder & Elbow Surgeons Assessment to the patient's responses to that questionnaire and adjusting the determined wellness score to be on an adjusted scale of 0-100. Wellness score progress chart 2210A is also associated with a date on which the wellness score was determined 2220 (i.e., January 26$^{th}$) and a message regarding when the next administration of the OMD will occur (i.e., "your next result check: April 12$^{th}$"). Shoulder function wellness score interface 2201 also provides a scrolling mechanism 2230 by which a patient may advance through various (in this case, four) interfaces associated with the patient's shoulder treatment and/or wellness account.

Shoulder function wellness score interface 2201 has a heading 2205A that includes the name of the OMD (in this case, American Shoulder & Elbow Surgeons Assessment) as well as what the OMD measures in non-technical/medical language using alternate terminology (in this case, shoulder function). A purpose of heading 2205A is to describe the wellness score provided by interface 2201 in a meaningful way to the patient. The information included in heading 2205A may be added to the heading using alternate terminology associated with, for example, the medical condition of the patient, a name of the OMD administered to the patient, a treatment the patient is undergoing or has undergone, and so on.

Shoulder function wellness score interface 2201 also includes a recovery timeline icon 2235A, an add to calendar icon 2240, a question sources icon 2245A, and a leave feedback icon 2250. Selection of recovery timeline icon 2235A causes a recovery timeline interface related to shoulder function to be displayed, selection of add to calendar icon 2240 causes the next scheduled administration of the OMD to be added to the patient's calendar, selection of question sources icon 2245A causes a question sources interface that includes sources of medical literature related to the American Shoulder & Elbow Surgeons Assessment and/or shoulder function to be displayed, and selection of leave a feedback icon 2150 causes a feedback interface to be displayed.

Figure 22B:
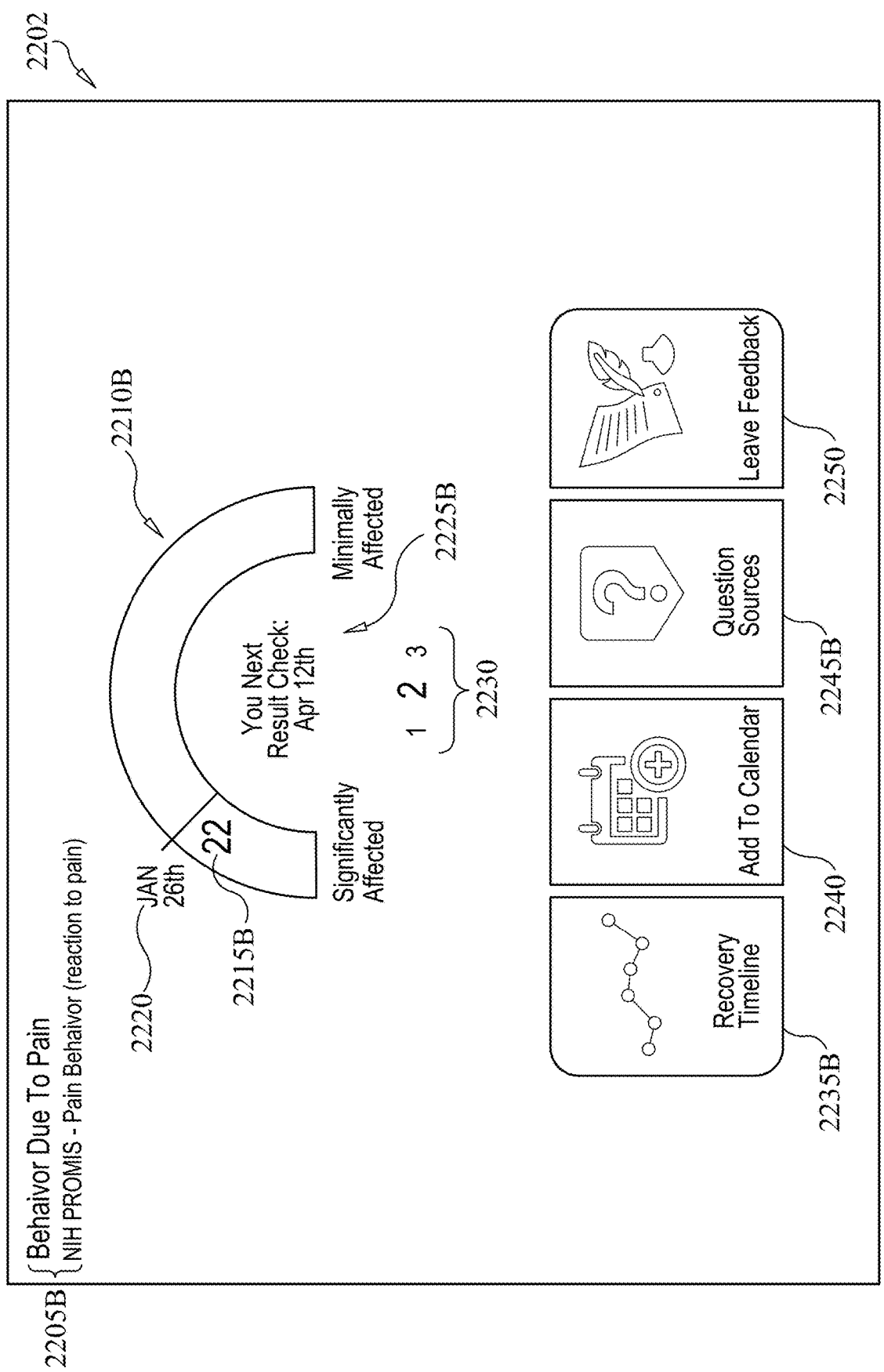

FIG. 22B provides an exemplary behavior due to pain interface 2202 that provides a graphically represented wellness score progress chart 2210B with a behavior due to pain wellness score 2215B of 22, which is determined by applying a scoring procedure associated with the NIH PROMIS CAT Pain Behavior questionnaire to the patient's responses to that questionnaire and adjusting the determined wellness score to be on an adjusted scale of 0-100. In this way both wellness scores (pain behavior and shoulder function) are provided to the patient on the same scale. Wellness score progress chart 2210B is also associated with a date on which the wellness score was determined 2220 (i.e., January 26$^{th}$) and a message regarding when the next administration of the OMD will occur (i.e., "your next result check: April 12$^{th}$"). Behavior due to pain wellness score interface 2205B also provides a scrolling mechanism 2230 by which a patient may advance through various (in this case, four) interfaces associated with the patient's shoulder treatment and/or wellness account.

Behavior due to pain wellness score interface 2202 has a heading 2205B that includes the name of the OMD (in this case, NIH PROMIS CAT Pain Behavior) as well as what the OMD measures in non-technical/medical language in alternate terminology (in this case, behavior due to pain). A purpose of heading 2205B is to describe the wellness score provided by interface 2202 in a meaningful way to the patient and to provide context for the wellness score. The information included in heading 2205B may be added to the heading using alternate terminology associated with, for example, the medical condition of the patient, a name of the OMD administered to the patient, a treatment the patient is undergoing or has undergone, and so on.

Behavior due to pain interface 2202 also includes a recovery timeline icon 2235B, add to calendar icon 2240, a question sources icon 2245B, and leave feedback icon 2250. Selection of recovery timeline icon 2235B causes a recovery timeline interface related to behavior due to pain to be displayed and selection of question sources icon 2245B causes a question sources interface that includes sources of medical literature related to the NIH PROMIS CAT Pain Behavior, pain, and/or shoulder surgery to be displayed.

Figure 22C:
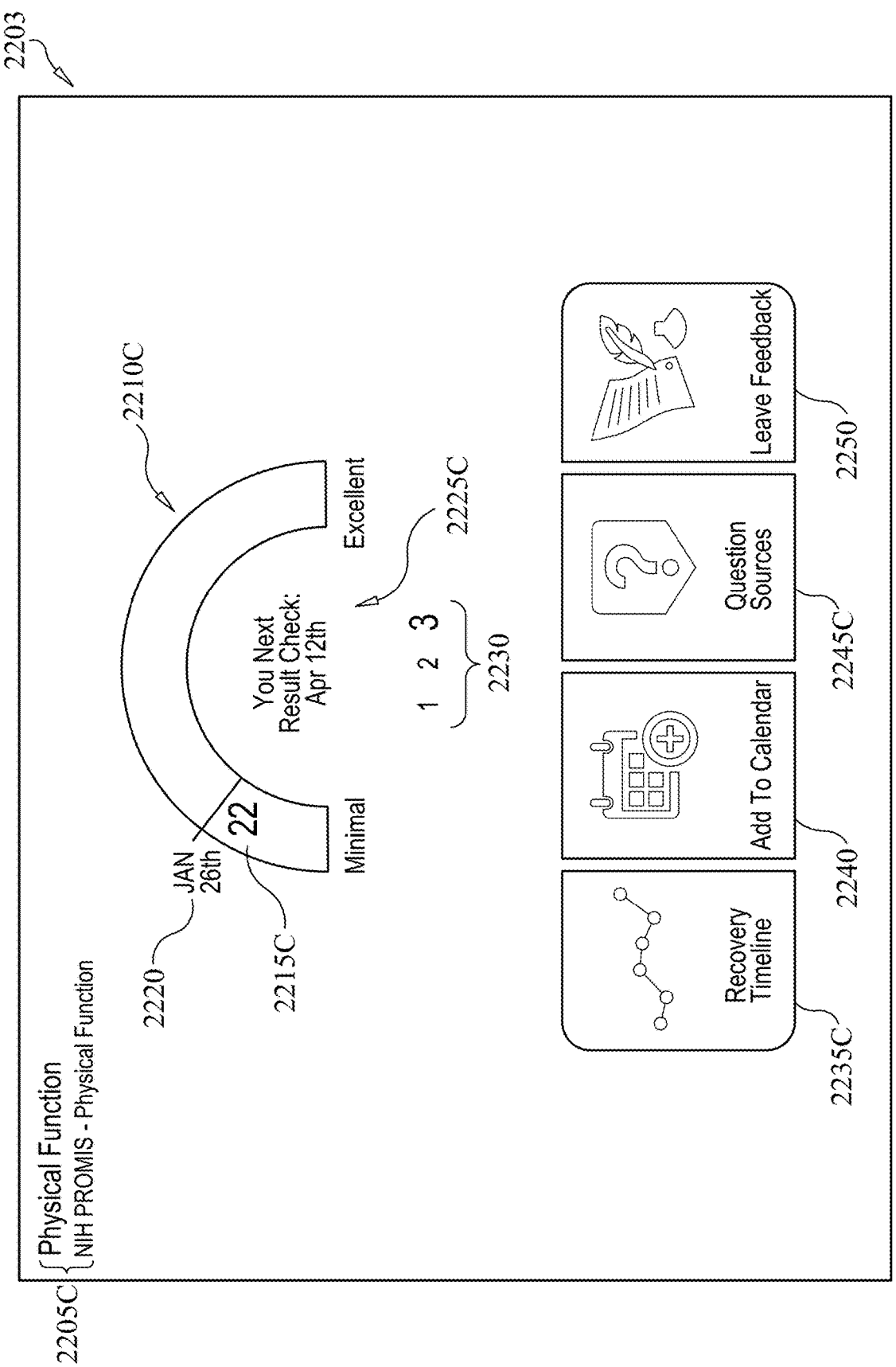

FIG. 22C provides an exemplary physical function wellness score interface 2203 that provides a graphically represented wellness score progress chart 2210C with a physical function wellness score 2215C of 22, which is determined by applying a scoring procedure associated with the NIH PROMIS CAT Physical Function questionnaire to the patient's responses to that questionnaire and adjusting the determined wellness score to be on an adjusted scale of 0-100. Wellness score progress chart 2210C is also associated with a date on which the wellness score was determined 2220 (i.e., January 26$^{th}$) and a message 2225C regarding when the next administration of the OMD will occur (i.e., "your next result check: April 12$^{th}$"). Physical function wellness score interface 2203 also provides scrolling mechanism 2230.

Physical function wellness score interface 2203 has a heading 2205C that includes the name of the OMD (in this case, NIH PROMIS CAT Physical function) as well as what the OMD measures in non-technical/medical language (in this case, physical function). A purpose of heading 2205C is to describe the wellness score provided by interface 2203 in a meaningful way to the patient and to provide context for the wellness score so they can understand his or her medical condition and/or treatment. The information included in heading 2205C may be added to the heading using alternate terminology associated with, for example, the medical condition of the patient, a name of the OMD administered to the patient, a treatment the patient is undergoing or has undergone, and so on.

Physical function interface 2203 also includes a recovery timeline icon 2235C, add to calendar icon 2240, a question sources icon 2245C, and leave feedback icon 2250. Selection of recovery timeline icon 2235C causes a recovery timeline interface related to physical function to be displayed and selection of question sources icon 2245C causes a question sources interface that includes sources of medical literature related to the NIH PROMIS CAT physical function OMD, pain, physical function, and/or shoulder surgery to be displayed.

Figure 22D:
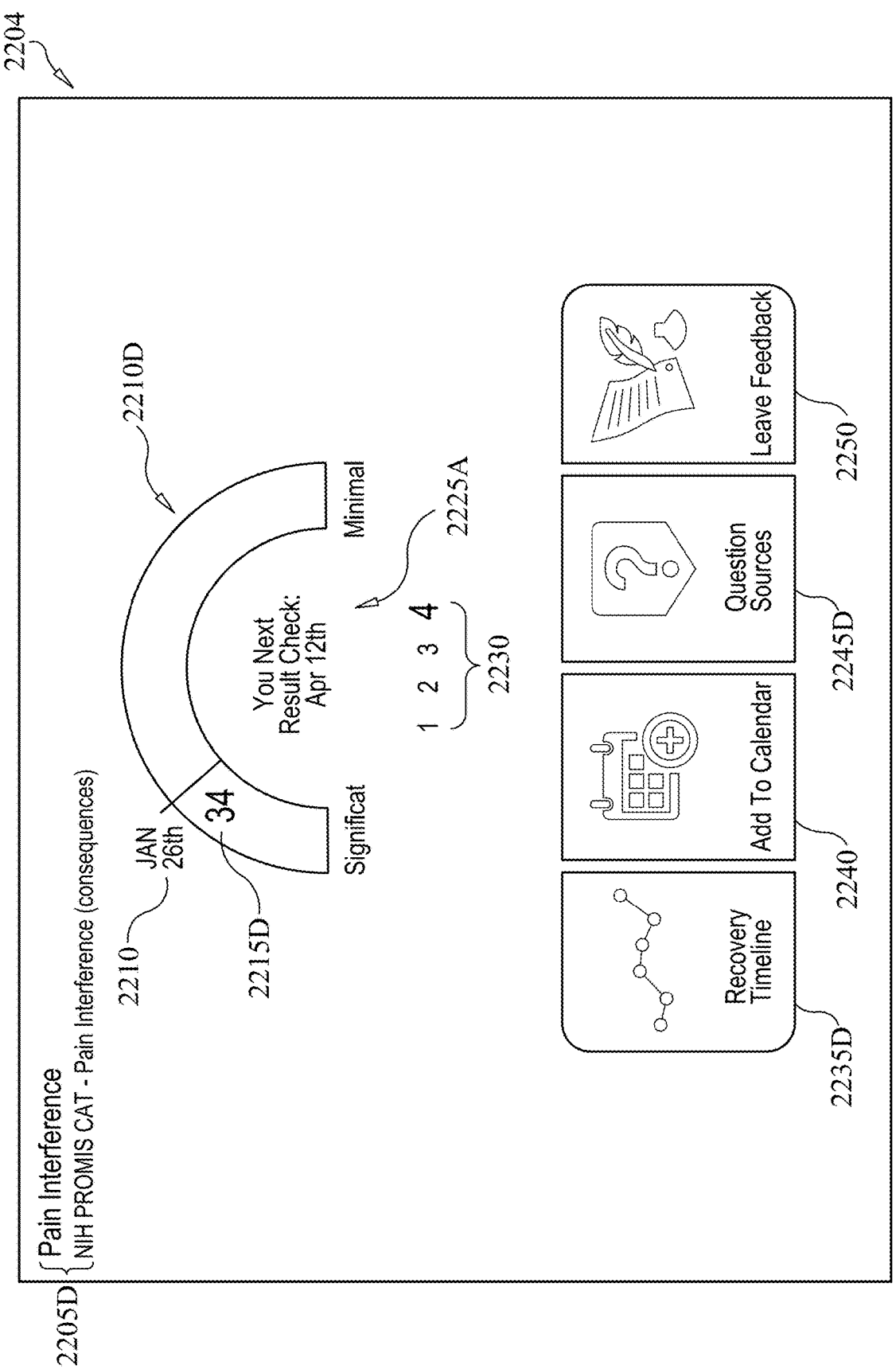

FIG. 22D provides an exemplary pain interference wellness score interface 2204 that provides a graphically represented wellness score progress chart 2210D with a pain interference wellness score 2215D of 34, which is determined by applying a scoring procedure associated with the NIH PROMIS CAT Pain Interference questionnaire to the patient's responses to that questionnaire and adjusting the determined wellness score to be on an adjusted scale of 0-100. Wellness score progress chart 2210D is also associated with a date on which the wellness score was determined 2220 (i.e., January 26$^{th}$) and a message 2225D regarding when the next administration of the OMD will occur (i.e., "your next result check: April 12$^{th}$"). Pain interference wellness score interface 2204 also provides scrolling mechanism 2230.

Pain interference wellness score interface 2204 has a heading 2205D that includes the name of the OMD (in this case, NIH PROMIS CAT Pain Interference) as well as what the OMD measures in non-technical/medical language (in this case, pain interference function). A purpose of heading 2205D is to describe the wellness score provided by interface 2204 in a meaningful way to the patient and to provide context for the wellness score so they can understand their medical condition and treatment. The information included in heading 2205D may be added to the heading using alternate terminology associated with, for example, the medical condition of the patient, a name of the OMD administered to the patient, a treatment the patient is undergoing or has undergone, and so on.

Pain interference wellness score interface 2204 also includes a recovery timeline icon 2235D, add to calendar icon 2240, a question sources icon 2245D, and leave feedback icon 2250. Selection of recovery timeline icon 2235D causes a recovery timeline interface related to pain interference to be displayed and selection of question sources icon 2245D causes a question sources interface that includes sources of medical literature related to the NIH PROMIS CAT Pain Interference OMD, pain, and/or shoulder surgery to be displayed.

Figure 22E:
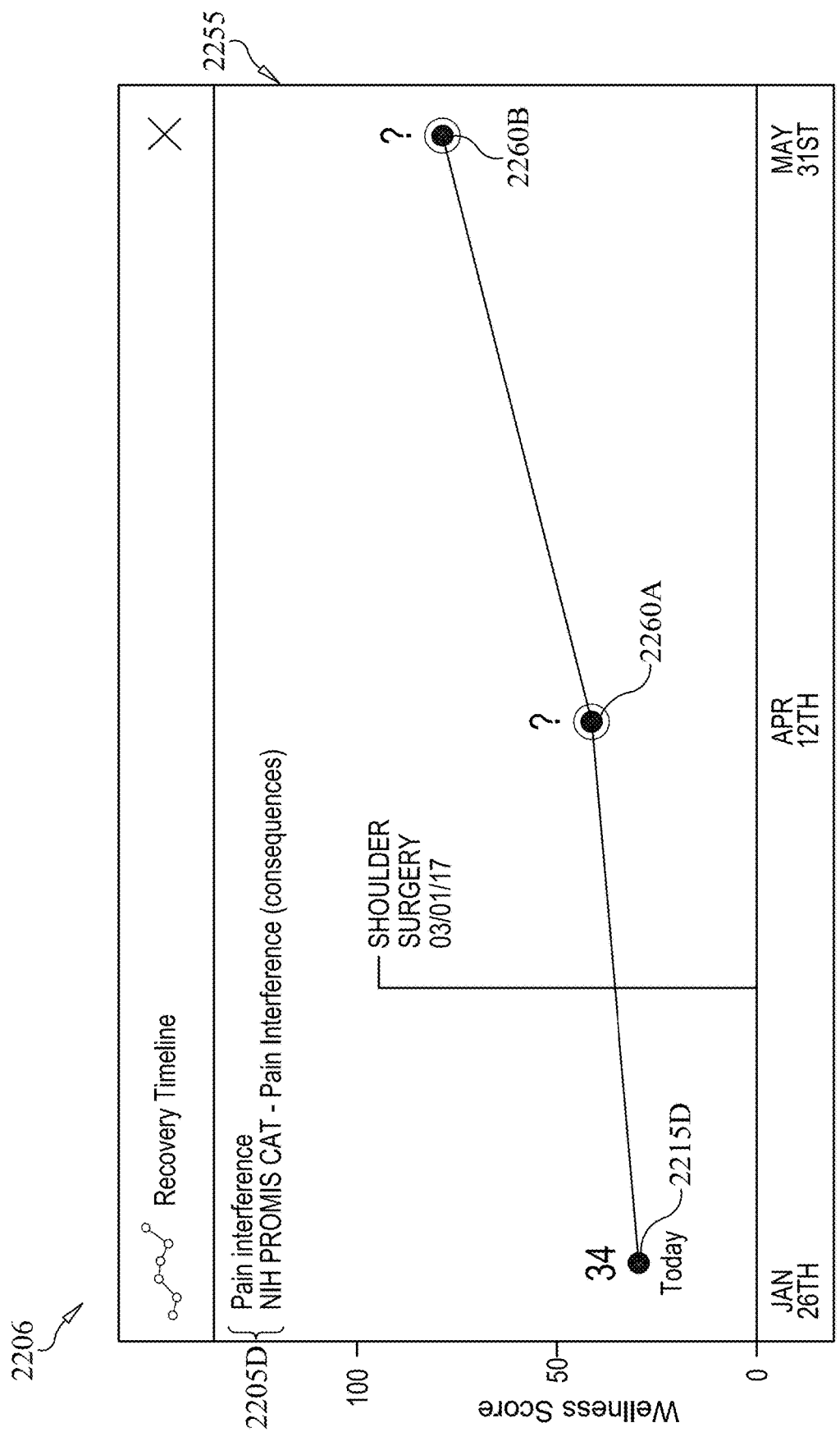

FIG. 22E provides an exemplary pain interference recovery timeline interface 2206 for pain interference wellness scores and projected/predicted pain interference wellness scores for the patient. Pain interference recovery timeline interface 2206 may be provided to the patient upon selection of recovery timeline icon 2235D and may provide heading 2205D, and a recovery timeline graph 2255 that plots wellness scores on a scale of 1-100 vs. time as measured in months. Graph 2255 provides the determined pain interference wellness score 2215D of pain interference interface 2104 (i.e., 34), a first predicted/projected pain interference wellness score 2260A, and a second predicted/projected pain interference wellness score 2260B. Predicted/projected pain interference wellness scores 2260A and 2260B may be determined via one or more processes described herein.

Continuing with this example, at a predetermined time following treatment for the shoulder injury (e.g., 3 months after shoulder surgery to fix the shoulder injury, or April 12th), the patient may be provided with the American Shoulder & Elbow Surgeons Assessment, the NIH PROMIS CAT Pain Behavior questionnaire, the NIH PROMIS CAT Physical Function questionnaire, and the NIH PROMIS CAT Pain Interference questionnaire (step 1045) and a post-treatment set of responses thereto may be received (step 1050) and stored (step 1055).

Then, a post-treatment wellness score for the medical condition/treatment (shoulder surgery) for shoulder function, behavior due to pain, physical function, and pain interference may be determined (step 1065) by applying a scoring procedure associated with the American Shoulder & Elbow Surgeons Assessment to responses to questions from the American Shoulder & Elbow Surgeons Assessment received in step 1050, applying a scoring procedure associated with the NIH PROMIS CAT Pain Behavior questionnaire to responses to questions from the NIH PROMIS CAT Pain Behavior questionnaire received in step 1050, applying a scoring procedure associated with the NIH PROMIS CAT Physical Function questionnaire to responses to questions from NIH PROMIS CAT Physical Function questionnaire received in step 1050, and applying a scoring procedure associated with the NIH PROMIS CAT Physical Function questionnaire to responses to questions from NIH PROMIS CAT Physical Function questionnaire received in step 1050.

Then, a post-treatment wellness score for the patient's shoulder function, behavior due to pain, physical function, and pain interference may be determined (step 1060) and provided to the patient (step 1075). In some cases, these may be separate scores (i.e., one for each) and, in other cases, the scores may be combined into a single overall post-treatment wellness score. Additionally, or alternatively, one or more of the post-treatment wellness scores may be combined. For example, the post-treatment wellness scores for shoulder function and physical function may be combined into a single function post-treatment wellness score and/or the post-treatment wellness scores for pain interference and pain behavior may be combined into a single pain post-treatment wellness score.

In some embodiments, providing or facilitating the provision of a wellness score (pre-treatment and/or post-treatment) and/or an improvement score to a patient (step 1075) may include transforming these scores into numbers and/or statements that are meaningful to, and/or more easily understood by, the patient. In some instances, this may involve converting a score calculated on a scale that is not readily understood to a scale that is more easily understood by most people/patient. Consider, for example, an OMD where the scoring procedure indicates that a scale for wellness scores generated therefrom is from 1-64 (with 64 being maximum wellness score). According to this scale, a wellness score of 60 (which may also be considered a raw score) is quite good. However, for people unaccustomed to scales of this type, this wellness score may be misunderstood as a 60% wellness score when, in reality, the adjusted, or percentage based, wellness score is 94%. Thus, providing a wellness score of 94 to a patient is more meaningful to him or her than the raw, unadjusted, score of 60.

Additionally, or alternatively, providing or facilitating the provision of a wellness score (pre-treatment and/or post-treatment) and/or an improvement score to a patient, treatment facility, treatment provider, and/or treatment administrator (step 1075) may include adjusting the wellness and/or improvement score(s) so that they are provided on a common scale so that, for example, results from different OMDs that may be scored using different scoring procedures and/or scales may be more easily, for example, compared, averaged, analyzed, and understood. One way to perform this adjustment is to perform a percentage calculation using the determined wellness score and/or improvement score and the maximum wellness score; all of which may be determined on a scale specific to the related OMD as follows:

Wellness Score/Maximum Wellness Score*100%  (Equation 1)

Additionally, or alternatively, providing or facilitating the provision of a wellness score (pre-treatment and/or post-treatment) and/or an improvement score and/or facilitating provision of the OMD to a patient may include using commonly understood terms for medically-related information that may be meaningful to, and/or more easily understood by, the patient instead of the medically precise terminology used to explain medical treatment and/or an OMD to fellow medical professionals. In some circumstances, providing the wellness and/or improvement scores to the patient in this manner may include, for example, using the alternate terminology associated with an OMD to which a patient has responded. For example, if a patient has undergone a repair of retinal detachment by diathermy treatment (which is associated with CPT treatment code of 67101), then references to the treatment provided to the patient in, for example, steps 1020, 1045, and 1075 may refer to "eye surgery" or "vision function" instead of "repair of retinal detachment by diathermy."

In another example, a patient undergoing rotator cuff repair surgery may be provided with the American Shoulder & Elbow Surgeons Assessment OMD in steps 1020 and/or 1045. However, when providing questions to the patient in steps 1020 and/or 1045 the treatment may be referred to as "shoulder surgery" rather than "rotator cuff repair surgery." Likewise, instead of providing an "American Shoulder & Elbow Surgeons Assessment" wellness or improvement score to the patient a "shoulder function" or "shoulder pain" wellness or improvement score may be provided to the patient in step 1075. Using terminology easily understood by the patient, instead of medically specific terminology, makes the wellness scores and/or improvement scores provided to the patient more meaningful and more easily understood. Thus, the patient may have greater incite into his or her wellness and/or treatment recovery because the medical information provided to them it is more easily understood by him or her.

Figure 17H:
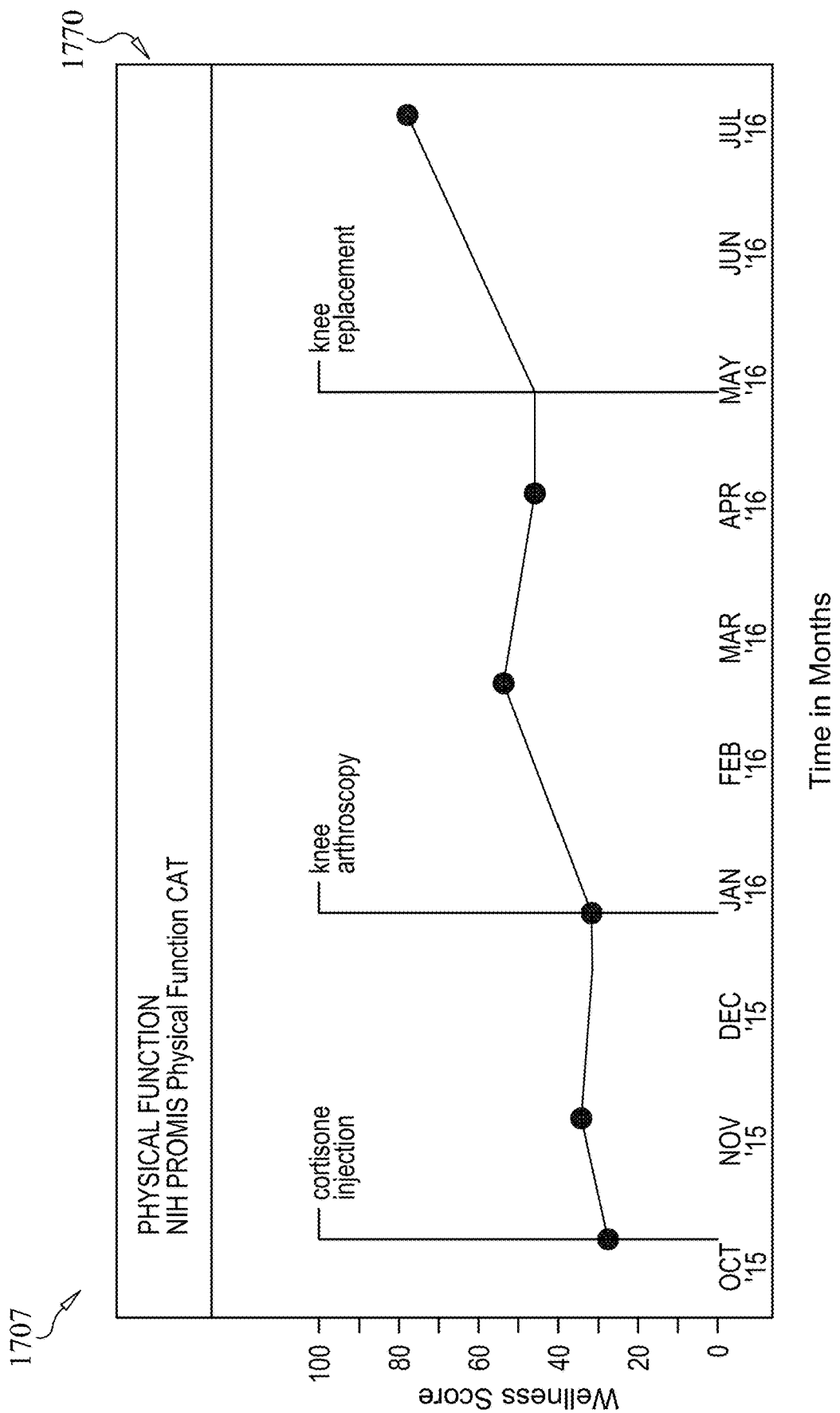

In some embodiments, a portion of process 1000 (e.g., steps 1045-1085) may be repeated over time (e.g., monthly, quarterly, etc.) to periodically determine a patient's pre-treatment and/or post-treatment wellness scores over time as, for example, one or more treatments for underlying medical condition are administered. For example, FIG. 17H provides an exemplary interface 1707 that provides a graph 1770 that shows a patient's wellness scores from October 2015 through July 2016 with regard to a knee condition for a particular patient. In the embodiment of FIG. 17H, the OMD used to determine the patient's wellness scores is the NIH PROMIS Physical Function CAT questionnaire. This questionnaire has been provided to the patient in October 2015, November 2015, January 2016, March 2016, April 2016, and July 2016 and wellness scores determined from responses thereto are plotted on graph 1770. Also shown on graph 1770 are the dates of various treatments for the knee injury. More specifically, graph 1770 shows that the patient was treated with a cortisone injection in October of 2015, a knee arthroscopy in January of 2016 and a knee replacement in May of 2016. Using this graph, the patient and/or his or her treatment provider and/or treatment facility can see how the medical condition has changed over time with the administration of the 3 treatments (i.e., cortisone injection, knee arthroscopy, and knee replacement). The patient and/or his or her treatment provider and/or treatment facility may also use historical wellness score information to make decisions regarding future treatment. For example, the patient's wellness score for physical function of his knee in October 2015 was 30. In November of 2015 it improved to 39 but then went down to 37 in January of 2016. The patient's post-knee arthroscopy wellness score taken in late February of 2016 shows that the patient's knee physical function improved after surgery to a wellness score of 50 and then declined somewhat to 45 in April of 2016. The patient then had a knee replacement in May of 2016 and his or her post-knee-replacement-surgery wellness score improved to 70.

Figure 10C:
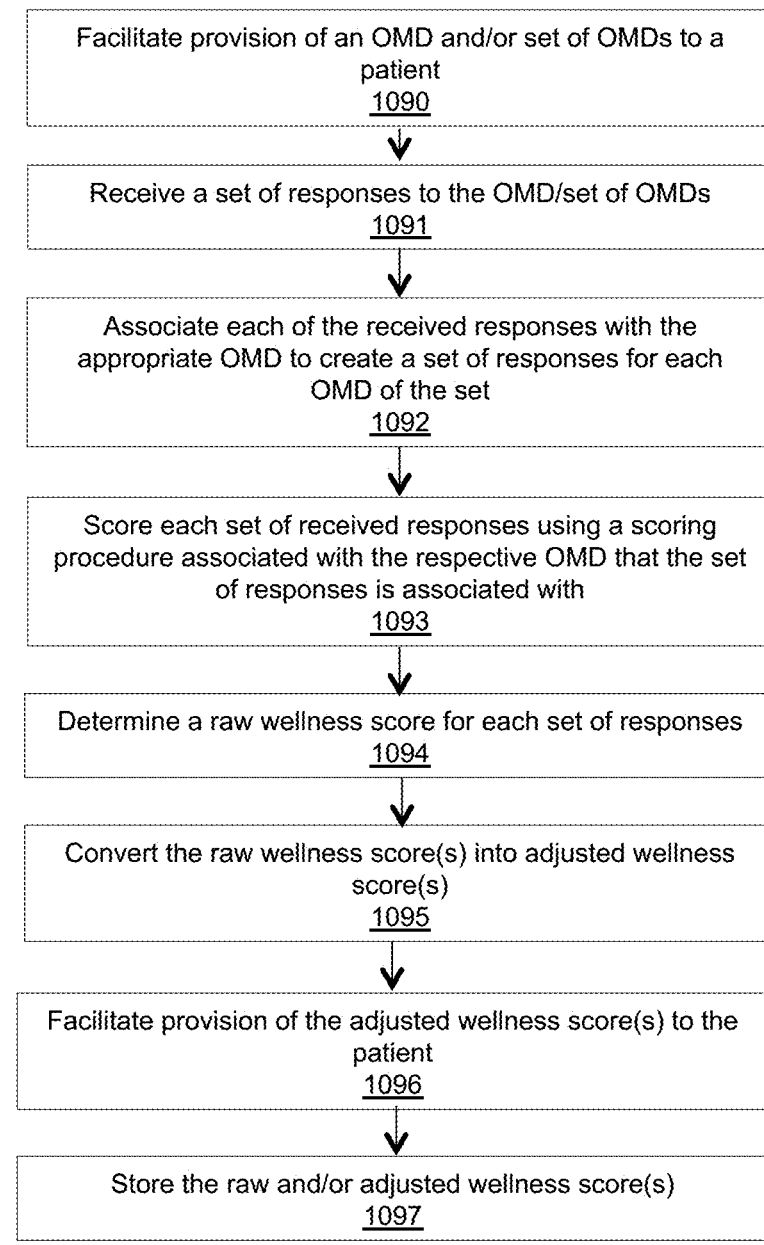
FIG. 10C provides a flowchart of an exemplary process for providing a wellness score to a patient, in accordance with some embodiments of the present invention.

FIG. 10C provides a flowchart of an exemplary process 1001 for providing a wellness score to a patient, in accordance with some embodiments of the present invention. Process 1001 may be executed by system 100, a system component and/or a combination of components thereof. In some instances, process 1001 may be executed solely by a patient's personal electronic device, such as patient device 128 and, in other instances; process 1001 may be executed via communication between the patient's personal electronic device and a server, such as server 102.

Initially, provision of an OMD and/or a set of OMDs to a patient may be facilitated (step 1090). Step 1090 may be executed via, for example, a patient wellness account running on the patient's device. In some instances, provision of the OMD and/or set of OMDs may be facilitated by communication of a hyperlink to the patient's device and selection of the link, may facilitate provision of an interface like interfaces 1702, 1702, and 1704, of FIGS. 17C-17E, respectively, to the patient and which may provide the OMD and/or set of OMDs or questions therefrom to the patient. In some circumstances, execution of step 1090 may be responsive to a patient activating his or her wellness account via, for example, selection of an icon provided by an interface like interfaces 1700 and 1701 of FIGS. 17A and 17B, respectively.

In step 1091, responses to the OMD and/or set of OMDs and/or questions provided thereof may be received via, for example, interaction with question and the response icons of an interface like interfaces 1702, 1702, and 1704, of FIGS. 17C-17E. Optionally, when a set of OMDs are provided in step 1090, each of the received responses of the set of responses may be associated with the OMD that provided the question associated with the respective response so as to create one or more sets of responses wherein each set of responses is associated with a respective one OMD (step 1092). In this way the set of responses is separated into sets that are appropriate for each OMD so that they may be appropriately scored using a scoring procedure associated with the respective OMD (step 1093).

Next, in step 1094, a raw wellness score for each set of responses may be determined using a scale established by the scoring procedure so that when a plurality of OMDs are provided to the patient, a raw wellness score for responses to each OMD is determined. Thus, when a set of OMDs is provided in step 1090, a plurality of raw wellness scores (e.g., one for each OMD) may be determined. Optionally, in step 1095, the raw score(s) may be adjusted and/or normalized to a preferred scale (e.g., 0-10 or 0-100) so that, for example, all wellness scores provided to the patient (as determined via scoring a plurality of OMDs) are provided on the same scale. The preferred scale may be selected based on scale that may be easily understood by the patient. At times, execution of step 1095 may be unnecessary when, for example, the raw score is already determined using the preferred scale (as may be the case when the scale of the scoring procedure and the preferred scale is the same). When multiple raw wellness scores are generated in step 1094, then converting the raw wellness scores into adjusted wellness scores may include normalizing the multiple raw scores to the same scale.

Then, in step 1096, provision of the adjusted wellness score(s) may be facilitated via, for example, presentation of one or more interfaces like interfaces 2101, 2102, 2103, 2104, 2201, 2202, 2202, 2203, 2204, and/or 2205 provided by FIGS. 21A-21D and 22A-22E, respectively. In some cases, the raw and/or adjusted wellness score may also be provided to a treatment provider, treatment administrator, and/or caregiver. In step 1097, the raw and/or adjusted wellness score(s) may be stored in, for example, score database 120 and/or the patient's device. In some circumstances, the raw and/or adjusted wellness score(s) may be stored in, for example, the patient's EMR and/or a registry of information such as medical-condition-specific registry of information, treatment-specific registry of information, disease-specific registry of information, medical-condition-specific registry of information, diagnosis-specific registry of information, treatment-facility-specific registry of information, and/or treatment-provider-specific registry of information.

Figure 11:
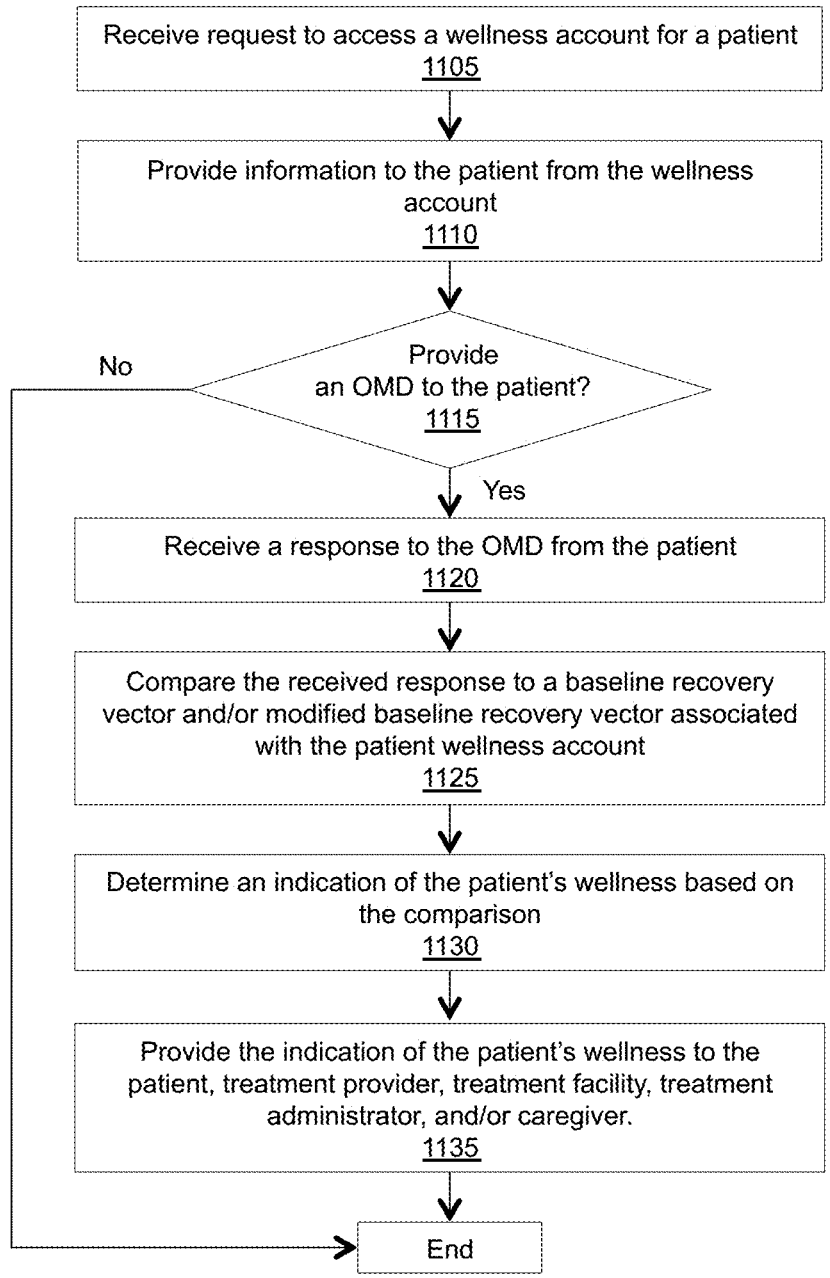
FIG. 11 provides a flowchart of a process for providing an indication of patient's wellness to the patient, in accordance with some embodiments of the present invention.

FIG. 11 provides a flowchart of a process 1100 for providing an indication of patient's wellness to the patient. Process 1100 may be executed by, for example, any of the systems, components, or combination of components thereof disclosed herein.

Optionally, in step 1105, a request to access a wellness account for a patient may be received. Exemplary requesters include patients, treatment providers, and/or caregivers for patients. The wellness account for the patient may be the wellness account generated and/or modified via execution of all, or part of, process 900 as described above. Exemplary requests to access a wellness account include, but are not limited to, opening, or starting, a software application that provides the wellness account, and signing into a software application that provides the wellness account. Often times, the request may be received via a patient device, such as patient device 128. Then, in step 1110, information from the wellness account may be provided to the patient. Exemplary information provided at step 1110 includes a welcome message, an indication of information to be entered into the patient's account, an initial wellness indicator or score, and an indication of the patient's wellness the last time he or she accessed the patient wellness account.

It may then be determined (whether or not steps 1105 and 1110 are executed) whether or not to provide the patient with an OMD (step 1115). Execution of step 1115 may involve accessing one or more wellness protocol(s) associated with the patient's wellness account and determining whether the wellness protocol requires or recommends the provision of an OMD to the patient and/or the occurrence of one or more trigger events. Execution of step 1115 may also include determining which OMD to provide to the patient and/or when to provide it. This determination may also involve accessing one or more wellness protocol(s) associated with the patient's wellness account and determining which OMD (s) the wellness protocol requires or recommends providing to the patient. When an OMD is not to be provided to the patient, process 1100 may end.

When an OMD is to be provided to the patient, a response, or set of responses, to the OMD may be received in step 1120. The response(s) may be received via, for example, an interface of the patient's device and/or the patient's EMR. The received response may then be compared to a baseline recovery vector and/or modified baseline recovery vector associated with the patient wellness account (step 1125) and an indication of the patient's wellness may be generated (step 1130) and provided to the patient (step 1135) via, for example, an interface like the interfaces provided in FIGS. 17F, 17G, and/or 18A-18N. Exemplary indications of a patient's wellness include a pre-treatment wellness score, a post-treatment wellness score, and/or an improvement score.

FIG. 12 provides a flowchart of an exemplary process 1200 for determining an effectiveness score for treatment provider, treatment, and/or treatment facility. Process 1200 may be performed by, for example, any of the systems, system components or combination of system components discussed herein.

Initially, a pre-treatment wellness score database, such as score database 120, may be accessed in order to retrieve a pre-treatment wellness score for a medical condition of a patient (step 1205). In some instances, step 1205 may include the generation of a pre-treatment wellness score via execution of, for example, process 1000. The pre-treatment wellness score may assess one or more aspects (e.g., pain, degree of mobility, average blood flow) of the medical condition of the patient prior to the patient being treated for the medical condition.

Next, an OMD (typically in the form of a questionnaire) may be provided to the patient following the patient being treated for the medical condition (step 1210). The OMD may be associated with and/or indexed with one or more scoring procedures stored in, for example, a scoring-procedures database such as scoring procedure database 116. In some instances, the OMD and/or a process for selecting the OMD provided in step 1210 may include determining a patient compliance question relating to the patient's compliance with pre-treatment instructions for preparing for the treatment and/or post-treatment instructions for recovering from the treatment. In step 1215, responses to the OMD may be received from the patient. Often times, the responses will indicate a state of the medical condition following the treatment. In some cases, the received responses may indicate a patient-perceived effectiveness of the treatment in treating the medical condition.

Upon receipt of the responses, the scoring-procedures database may be accessed to retrieve the one or more scoring procedures indexed to the OMD that has been provided to the patient (step 1220) and the received responses may be evaluated (or scored) using the retrieved one or more scoring procedures (step 1225) to determine a post-treatment wellness score for the medical condition based on the evaluation (step 1230). An improvement score for the patient's medical condition using the pre-treatment wellness score and the post-treatment wellness score may then be determined (step 1235). Exemplary processes for determining the improvement score were described above with regard to FIG. 10B. In some embodiments, when for example, an improvement score for a patient is already available (as stored in, for example, score database 120) steps 1205-1230 may not be performed and execution of step 1235 may involved accessing the improvement score database 120 to retrieve an improvement score for the patient.

Next, in step 1240, an effectiveness score for the treatment provider, treatment and/or treatment facility may be determined based on the improvement score of step 1235. The effectiveness score may serve to indicate a degree of effectiveness for the treatment provider, treatment, and/or treatment facility at providing the treatment and/or treating the medical condition. In may cases, process 1200 may be repeated with a plurality of patients so as to determine an average, or weighted, effectiveness score for a treatment provider and/or treatment facility across the plurality of patients.

In circumstances where a patient compliance question was included in the OMD provided via step 1210, determination of the effectiveness score may also include analysis of the patient's response to the patient compliance question to determine what, if any, impact the patient's compliance may have had on the improvement score determination and/or effectiveness of the treatment. For example, in some embodiments, when a relatively small portion (e.g., 6%, 10%, or 15%) of patients associated with a particular treatment provider and/or treatment facility answer that they have not complied with the pre-treatment and/or post-treatment instructions, one or more responses to the OMD received in, for example, step 1215 may be disregarded (i.e., not used) when determining the effectiveness score in step 1245. These responses may be disregarded because the patient's failure to comply may adversely affect their recovery through no fault of the treatment provider and/or treatment facility.

If, however, a number of patients who report not complying with pre-treatment and/or post-treatment instructions exceeds a threshold (e.g., 10%, 20%, or 30%) then, this failure of compliance rate may indicate that the treatment provider and/or treatment facility is not properly administering pre-treatment and/or post-treatment instructions and/or equipment for the care of the patient's medical condition, which may be an indicator of how effective the treatment provider and/or treatment facility is. Thus, when a sufficiently high number of patients indicate that that they did not comply with pre-treatment and/or post-treatment instructions the responses received in step 1215 may be included in a determination of an effectiveness score (step 1245) for the treatment provider and/or treatment facility. In most instances, when a patient indicates a lack of compliance with pre-treatment and/or post-treatment instructions, responses received in step 1215 may not be used to determine the effectiveness score of the treatment. In most cases, responses received in step 1215 may not be used to determine the effectiveness score of the treatment (step 1245) because, in many cases, it may be assumed that compliance with pre-treatment and/or post-treatment instructions is not a component of the effectiveness of the treatment itself (i.e., removed from the treatment provider and/or treatment facility).

Further details regarding how an effectiveness score may be determined (i.e., execution of step 1245) are provided below with regard to FIGS. 15A-15C.

In some instances, execution of step 1240 may include accessing the patient's EMR to retrieve information regarding the patient's medical condition (e.g., treatment outcome measurements, wellness scores, improvement scores, prior treatments, general health, other factors, etc.) and the determination of step 1240 may incorporate the retrieved information.

The determined effectiveness score may then be stored in, for example, a treatment-provider database (step 1245). Often times, storage of the effectiveness score includes indexing the effectiveness score to the treatment, the treatment provider, and/or other factors relating to the treatment, patient (demographic information, comorbidities, etc.), or medical condition. In some instances, storing the effectiveness score may also include indexing the effectiveness score with one or more of the pre-treatment wellness score, the post-treatment wellness score, the improvement score, the treatment, and the patient.

When some, or all, of process 1200 is performed a plurality of times thereby determining a plurality of effectiveness scores for the treatment provider and each of the treatment provider effectiveness scores are stored in treatment provider database 121 (or score database 120) and indexed to the treatment provider, the treatment-provider database upon, for example, receipt of a request for an effectiveness score for the treatment provider, may be accessed to retrieve the effectiveness scores for the treatment provider and the retrieved effectiveness scores may be used to determine an effectiveness score for the treatment provider based on an analysis of the retrieved improvement scores, which may also be stored in the treatment-provider database.

In some instances, process 1200 may be performed any number of times for any number of treatment providers. In some instances, process 1200 may be performed a number of times when a particular treatment provider performs the same treatment (called treatment A for the purposes of this example), thereby generating a plurality of effectiveness scores for the particular treatment provider when he or she performs treatment A. This plurality of effectiveness scores may then be processed, or otherwise analyzed, in order to calculate an aggregate, or average, effectiveness score for the particular treatment provider when performing treatment A that may be more statistically robust than a single effectiveness score determination. Additionally, or alternatively, process 1200 (or a portion thereof) may be performed for multiple treatment providers who perform treatment A. In these instances, the effectiveness scores for each treatment provider for performing treatment A may be compared. It is important to note that for this example, any number of esoteric factors and/or other considerations may be used to define the characteristics of treatment A. Each of the effectiveness scores may be stored in the treatment-provider database 121 (or score database 120) and indexed to the respective treatment provider and, optionally, to the treatment performed by the respective treatment provider and/or a treatment facility associated with the respective treatment or treatment provider. Then, for each treatment provider of the plurality, the treatment-provider database may be accessed to retrieve the effectiveness scores for the treatment provider.

When a request for an effectiveness score for at least one treatment provider associated with a treatment and/or diagnosis is received from a user, the treatment-provider database may be accessed to retrieve the requested effectiveness score, which may, in turn be provided to the user by, for example, facilitating display of the retrieved effectiveness score to the user on a display device such as patient device 128 and/or treatment provider device 124. At times, the effectiveness score may be displayed on a map as shown on interfaces 1901 and 1902 of FIGS. 19A and 19B, respectively In one embodiment, process 1200 and/or a portion thereof may be performed more than once (e.g., twice, three times, etc.) as may be the case when the OMD and/or medical questionnaire is associated with multiple scoring procedures and/or a scoring procedure and one or more sub-scoring procedures and one or more of the responses may be separately evaluated using, for example, a first and second scoring procedure. From there, a first post-treatment wellness score for the medical condition may be determined based on analysis of one or more of the responses using the first scoring procedure and a second post-treatment wellness score for the medical condition may be determined based on analysis of one or more of the responses using the second scoring procedure.

Then, first and second improvement sub-scores for the patient's medical condition may be determined using the pre-treatment wellness score and the first and second post-treatment wellness scores, respectively. The first and second improvement sub-scores may then be used to re-calculate and/or modify the effectiveness score (for the treatment provider) determined in step 1240.

At times, process 1200 may also include selecting received responses received in step 1215 that are relevant to the treatment facility and evaluating the selected responses using one or more scoring procedures. That evaluation may then be used to determine an effectiveness score for the treatment facility.

In some instances, process 1200 may be performed a plurality of times for a plurality of patients and/or treatment providers who are affiliated with a treatment facility or a plurality of treatment facilities in order to, for example, determine an effectiveness score of the treatment facility and/or facilities. In one embodiment, determining an effectiveness score of the treatment facility and/or facilities may include retrieving the effectiveness scores for the treatment for each of the treatment providers associated with a treatment facility and/or treatment facilities. The retrieved effectiveness scores may be used to determine an effectiveness score for the treatment facility/facilities, which may be stored in a score database, like score database 120. Storage of the effectiveness score may include indexing the effectiveness score to the treatment facility and/or treatment providers associated with the treatment facility.

In one embodiment, a treatment may be provided by more than one treatment provider (e.g., a surgeon and a physical therapist or a surgeon and an anesthesiologist). In this embodiment, a first set of responses that are relevant to the first treatment provider may be selected from the responses received in step 1215. The first selected set of responses may then be evaluated using one or more appropriate scoring procedures and a post-treatment wellness score for the medical condition for the first treatment provider may be determined. Then, an improvement score for the patient's medical condition as it relates to the first treatment provider may be determined using the pre-treatment wellness score and the post-treatment wellness score for the first treatment provider. This improvement score may be used to determine an effectiveness score for the first treatment provider, which may be stored in, a score database like score database 120. This storage may include including indexing the effectiveness score of the first treatment provider to the treatment and the first treatment provider.

Then, a second set of responses that are relevant to the second treatment provider may be selected from the responses received in step 1215. The second selected set of responses may then be evaluated using one or more appropriate scoring procedures and a post-treatment wellness score for the medical condition for the second treatment provider may be determined. Then, an improvement score for the patient's medical condition as it relates to the second treatment provider may be determined using the pre-treatment wellness score and the post-treatment wellness score for the second treatment provider. This improvement score may be used to determine an effectiveness score for the second treatment provider, which may be stored in the score database 120 and/or the treatment provider database. This storage may include including indexing the effectiveness score of the second treatment provider to the treatment and the second treatment provider.

In some circumstances, process 1200 may be repeated upon, for example, an expiration of a predetermined time period measured from performance of the treatment as may be determined by, for example, a schedule of a patient's wellness account in order to determine a subsequent effectiveness score for the treatment provider, which may be based on, for example, the improvement score determined in step 1235 and/or a subsequent execution of step 1235. The subsequent effectiveness score may provide insight into a treatment provider's effectiveness at performing the treatment over time.

Figure 13A:
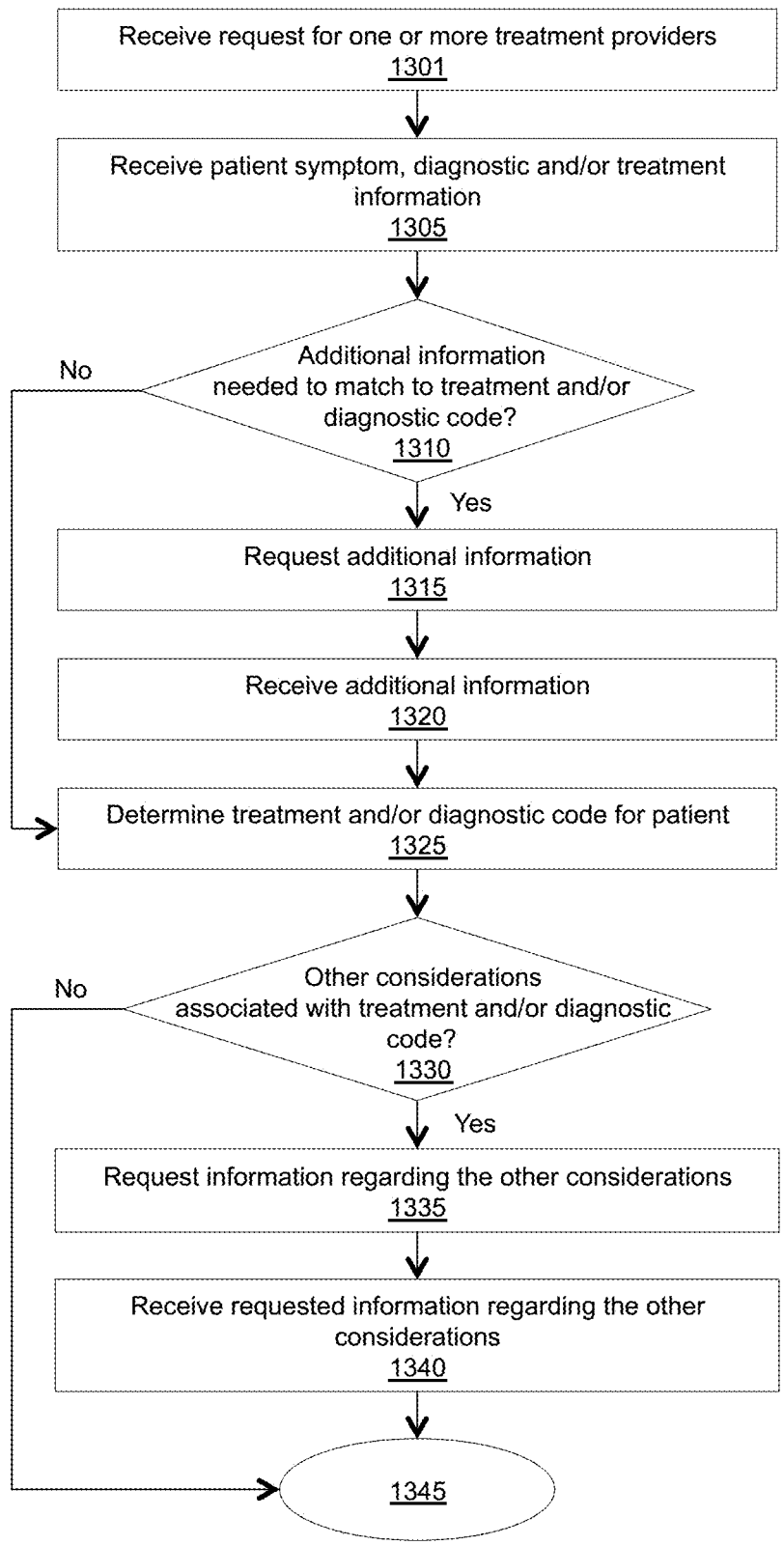
FIGS. 13A and 13B provide flowcharts of an exemplary process for determining one or more treatment providers for a patient, in accordance with some embodiments of the present invention.
Figure 13B:
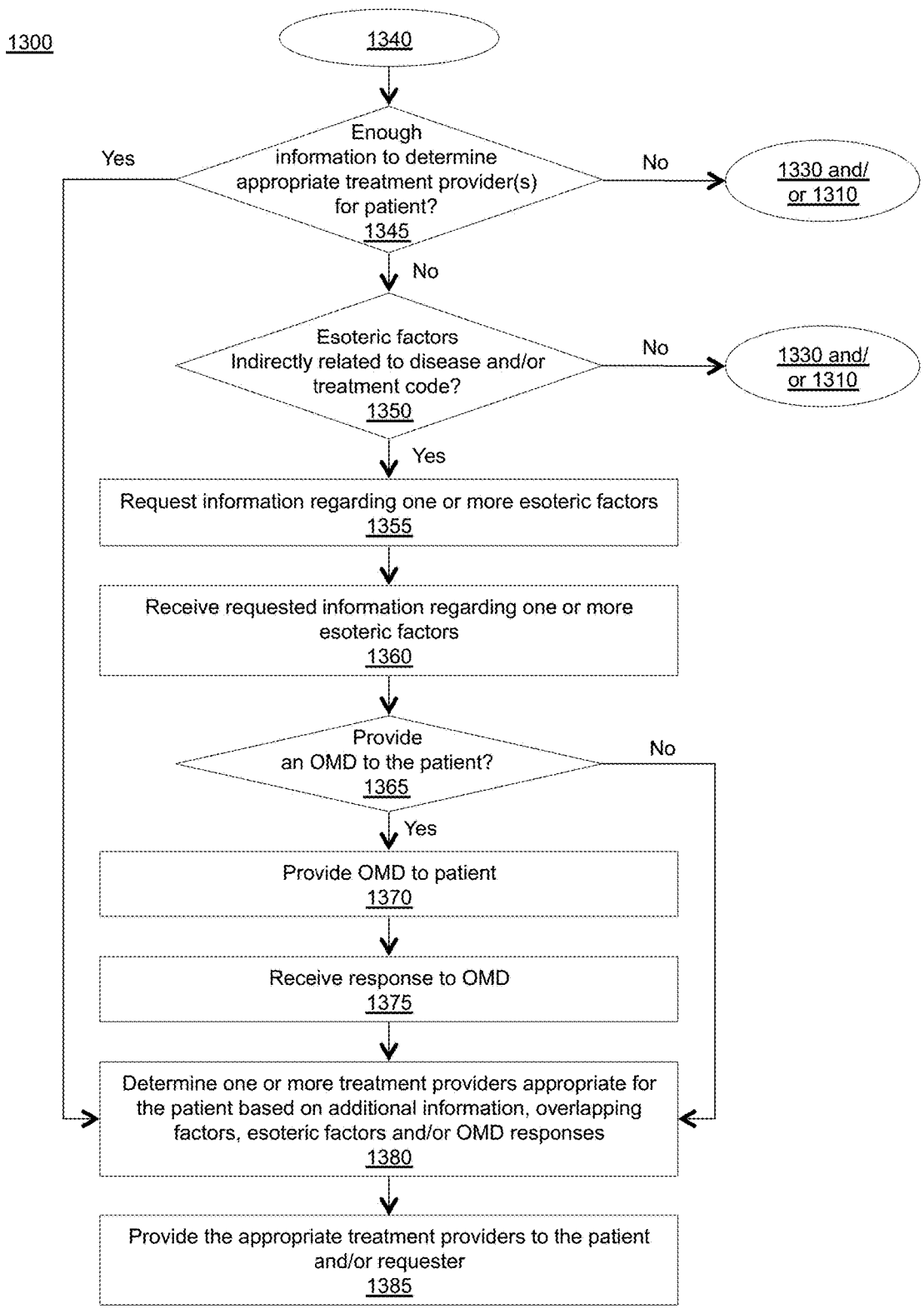

FIGS. 13A and 13B provide flowcharts of an exemplary process 1300 for determining one or more treatment providers for a patient. Process 1300 begins in FIG. 13A and then continues in FIG. 13B. Process 1300 may be executed by, for example, any of the systems, system components, and/or combination of system components disclosed herein.

Initially, in step 1301, a request for one or more treatment providers may be received from a requester. Following such request, various information may be received (described below in steps 1305, 1320, 1340, 1360 and 1375), and such information may be used to select one or more treatment providers from a list of treatment providers for provision to the requester. Exemplary requesters include, but are not limited to, patients, treatment providers, and/or patient caregivers. In some instances, the request received in step 1301 may be received via a patient's wellness account.

In step 1305, patient symptom, diagnostic, and/or treatment information may be received by, for example, reporting module 122 from, for example, treatment provider device 124, patient device 128, and/or treatment facility computer system 134. In some instances, the information may be received from, for example, a patient, a caregiver, and/or a treatment provider (collectively referred to herein as the "requester") when he or she is attempting to gain information about one or more treatment providers that may be appropriate for treating a particular condition or diagnosis for the patient or for performing a particular treatment. In some instances, the information received in step 1305 may include one or more preferences of a requester for a treatment provider. Exemplary preferences include location, area of specialization, board certification status, minimum treatment effectiveness scores, years of experience, treatment provider gender, and/or hospital admission privileges for a treatment provider. In some instances, the symptom, diagnostic and/or treatment information received in step 1305 may be associated with an account of the requester and/or patient that may supply, for example, a medical history for the patient as well as other information about the patient (e.g., preferences, age, lifestyle, etc.). In some instances, the requester and/or patient wellness account may be able to access and/or extract information from the patient's EMR as may be stored in, for example, patient EMR database 130 and/or otherwise associated with the patient's wellness account.

Next, in step 1310, it may be determined whether additional information is needed to match the patient symptom, diagnostic, and/or treatment information received in step 1305 with a treatment and/or diagnostic code, such as, but not limited to a CPT code. For example, if a requester enters non-specific diagnostic and/or treatment information in step 1305, it may be difficult to ascertain the relevant treatment and/or diagnostic code. Consider, for example, receiving symptom, diagnostic, and/or treatment information that indicates the patient has a sore leg. Execution of process 1300 will need more information to determine one or more appropriate treatment providers for a "sore leg" because this symptom may have many causes and many appropriate treatments.

When additional information regarding the symptom, diagnosis, and/or treatment information is needed, it may be requested (step 1315) and the requested information may be received in step 1320. Exemplary methods of requesting more information include, but are not limited to, asking the requester one or more questions about the patient's symptoms, diagnosis and/or treatment information. In some instances, these questions may be targeted, or focused, using information received in step 1305 and/or historical information about the patient that may be accessed, for example, via the patient and/or requester account. The questions may take any format (e.g., multiple choice, true/false, sliding scale, etc.) and, in some instances, may be used to gauge the severity of the patient symptom or diagnosis. On some occasions, the request for additional information may be provided to the requester via an interface (e.g., visual and/or audio) on his or her device (e.g., patient device 128 and/or treatment provider device 124). In some embodiments, a patient may be provided with a picture of an affected area of the body (e.g., a leg) and asked to point to a location on the picture the pain where is most severe.

When additional information is not needed in step 1310 or when the additional information is received in step 1320, a treatment and/or diagnostic code matching the received information may be determined (step 1325). In some instances, step 1325 may be performed by directly and/or indirectly using the medical literature to assist with the classification of the received information as pertaining to one or more treatment and/or diagnostic codes. On some occasions, step 1325 may be performed via execution (in whole or in part) of one or more processes described herein such as process 300 and/or 400.

In step 1330, it may be determined whether there are other considerations that overlap and/or interact with a medical condition associated with the determined treatment diagnostic code. For example, certain treatment and/or diagnostic codes may be associated with one or more other considerations as may be indicated and/or stored in other consideration database 132. For example, a diagnostic code associated with hypertension may be associated in, for example, other consideration database 132, with factors such as weight, diet, whether or not the patient smokes, etc. In another example, a diagnostic code associated with a form of cancer may be associated with factors that are side effects (e.g., nausea, weight loss, insomnia, etc.) of known treatments for the form of cancer the patient has symptoms of and/or has been diagnosed with. In a further example, a diagnostic code that is associated with pregnancy may be associated with factors such as age, weight, previous pregnancies, diabetes, hypertension, prior miscarriages, etc. In some embodiments, execution of step 1330 may be included directly and/or indirectly using the medical literature to assist with determining one or more factors overlapping with and/or pertaining to one or more treatment and/or diagnostic codes. In some instances, other considerations and/or factors that may interact with a medical condition associated with the determined treatment diagnostic code may include different aspects of a treatment that may have been, or may need to be, performed.

In step 1335, information regarding the one or more other considerations determined in step 1330 may be requested from the patient and/or requester. Exemplary methods of requesting more information include, but are not limited to, asking the requester one or more questions about the patient's symptoms, diagnosis and/or treatment information via an interface displayed on the patient's patient device, such as patient device 128. In some instances, these questions may be targeted, or focused, using information received in step 1305, step 1320, and/or historical information about the patient that may be accessed, for example, via the patient's EMR and/or patient wellness account. The questions may take any format (e.g., multiple choice, true/false, sliding scale, etc.) and, in some instances, may be used to gauge the severity of the patient symptom or diagnosis. On some occasions, the request for additional information may be provided to the requester via an interface (e.g., visual and/or audio) on his or her device (e.g., patient device 128 and/or treatment provider device 124). In some embodiments, a patient's and/or requester's answer to a question may trigger the request for still more information. For example, if smoking is determined to be an other consideration for a treatment and/or diagnostic code, the patient and/or requester may be asked whether he or she smokes and, upon receiving the information that the patient does smoke, one or more follow up questions (e.g., how many cigarettes per day, how many years has he or she been a smoker, etc.) may be asked via execution of step 1335. In another example, if the treatment code determined in step 1325 is cardiothoracic surgery, then a number of other considerations, or sub-treatments factor into the "cardiothoracic surgery" treatment, such as anesthesia, wound care, post operative care, medication, etc. and the information requested in step 1335 may relate to one or more of these factors or sub-factors.

In step 1340, the requested additional information may be received. When there are no other considerations in step 1330 and/or when the additional information is received in step 1340, it may be determined whether enough information regarding the patient has been received to determine one or more treatment providers that are appropriate for the patient (step 1345, which is shown in FIG. 13B). When enough information has been received, process 1300 advances to step 1380, which will be discussed below. When insufficient information has been received (step 1345), step 1330 and/or 1310 may be repeated to determine if there are additional other considerations associated with the treatment and/or diagnostic code that may be relevant and then steps 1335-1345 may be repeated as well. Additionally, or alternatively, when insufficient information has been received in step 1345, it may be determined if one or more esoteric factors are known to be indirectly related to the disease and/or treatment code (step 1350). Execution of step 1350 may be performed by directly and/or indirectly using the medical literature to assist with the classification of the received information as pertaining to one or more treatment and/or diagnostic codes. Esoteric factors include factors that do not contribute directly to the patient's diagnosis and/or treatment but may, in some way, affect his or her health. Exemplary esoteric factors include region of the country where a patient lives or works, a patient's race or ethnicity, a patient's socio-economic status, and so on. In some instances, when no esoteric factors are known, process 1300 may repeat step(s) 1310 and/or 1330.

When there are one or more esoteric factors that relate to the disease and/or treatment code, information regarding the esoteric factors may be requested (step 1355). Exemplary methods of requesting more information include, but are not limited to, asking the requester one or more questions about the patient's symptoms, diagnosis and/or treatment information. In some instances, these questions may be targeted, or focused, using information received in step 1305, step 1325, step 1340, and/or historical information about the patient that may be accessed via, for example, the requester and/or the patient's wellness account. The questions may take any format (e.g., multiple choice, true/false, sliding scale, etc.) and, in some instances, may be used to gauge the severity of the patient symptom or diagnosis. On some occasions, the request for additional information may be provided to the requester via an interface (e.g., visual and/or audio) on his or her device (e.g., patient device 128 and/or treatment provider device 124). In some embodiments, a patient's and/or requester's answer to a question may trigger the request for still more information. For example, if an esoteric factor for a particular treatment and/or diagnostic code is exposure to lead then, the request for additional information may ask the patient and/or requester whether the patient lives in a house that is more than 50 years old, whether the patient lives in a house that has old paint, and/or whether the patient lives in an area that is known to have lead in the water supply.

Optionally, in some instances, execution of process 1300 may include determining whether or not to provide an OMD to a patient (step 1365). When step 1365 is performed, selection of the OMD to provide to the patient may be based upon, for example, some, or all, of the information received in process 1300. In some instances, selection of the OMD to provide to the patient may include execution of some, or all, of processes 300 and/or 400. When an OMD is to be provided to a patient, it may be provided in step 1370 and a response to the OMD may be received in step 1375. Responses to the OMD may be analyzed and/or scored via execution of, for example, process 300 and/or 400.

When enough information to determine one or more appropriate treatment provider(s) has been received (step 1345), when an OMD is not to be provided to the patient and/or requester, and/or following step 1375, one or more appropriate treatment providers for the patient may be determined (step 1380). The determination of step 1380 may include, for example, using the information received via process 1300 to determine one or more treatment providers related to the information received. The effectiveness scores for the treatment providers may be determined using, for example, process(es) 400 and/or 600. In some instances, the determination of step 1380 may include selecting a number of treatment providers with the highest effectiveness scores related to the information received. In some instances, a geo-location of the treatment provider may be factored into the selection of the number of treatment providers.

In step 1385, the treatment providers (e.g., the name, contact information, location thereof) determined in step 1380 may be provided to the patient and/or requester. The indication may be provided as, for example, a list of appropriate treatment providers along with the treatment provider's effectiveness scores for the patient's treatment and/or diagnostic code, other considerations, esoteric factors, and/or OMD information. Additionally, or alternatively, the appropriate treatment providers may be provided to the patient and/or requester via icons arranged on a map, similar to the treatment provider interface depicted in FIGS. 19A-19C.

Figure 14A:
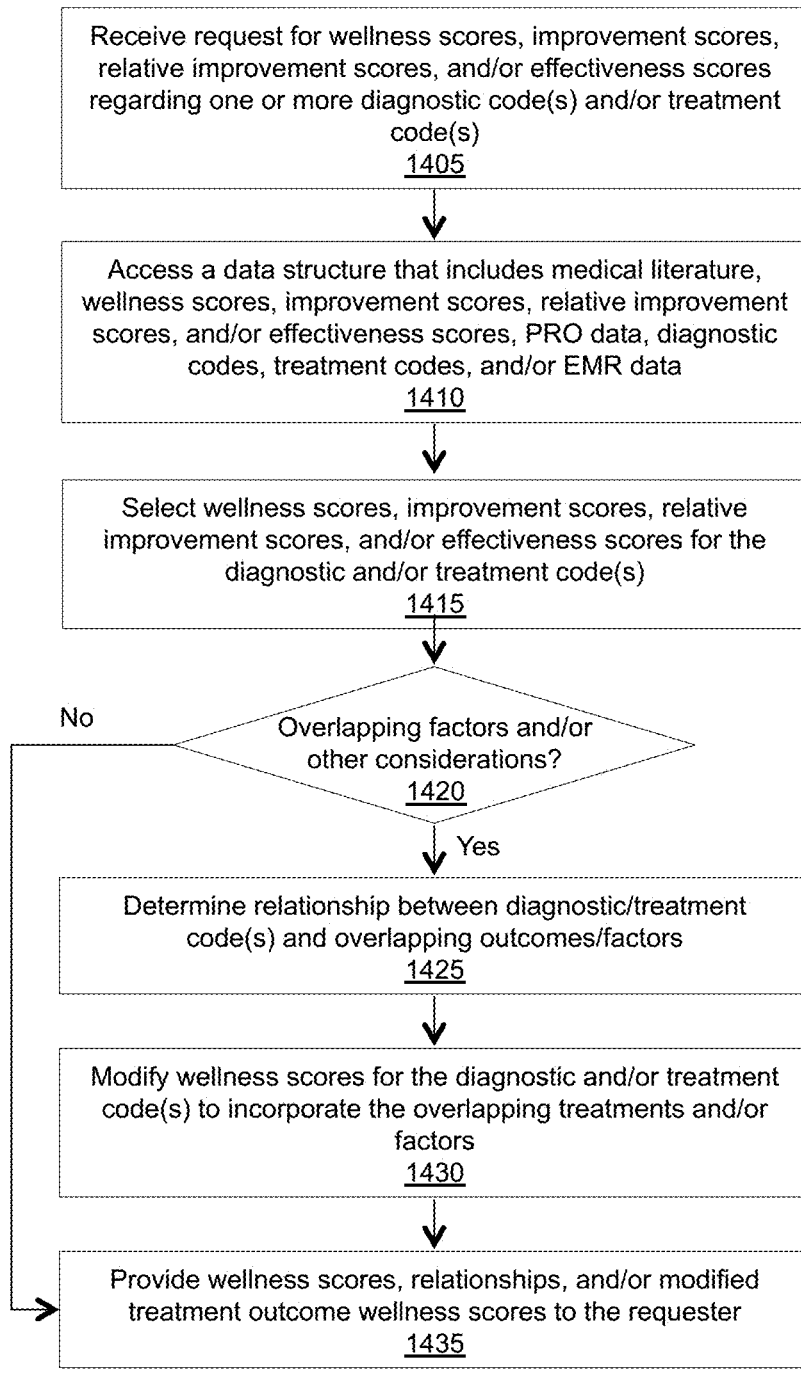
FIG. 14A provides a flowchart of exemplary process for conducting a medical inquiry and/or designing a medical study and receiving study data related thereto, in accordance with some embodiments of the present invention.

FIG. 14 provides a flowchart of exemplary process 1400 for conducting a medical inquiry and/or designing a medical study and receiving study data related thereto. Process 1400 may be performed by, for example, any of the systems, system components, and/or combination of system components discussed herein.

In step 1405, a request for wellness scores (e.g., pre-treatment and/or post-treatment), improvement scores, relative improvement scores, and/or effectiveness scores regarding one or more factors directly or indirectly relating to one or more diagnostic code(s) and/or treatment code(s) may be received. The query may be received from a user, who may be, for example, a treatment provider, a treatment facility administrator, and/or a patient using one or more of, for example, treatment provider device 124, and patient device 128. The query may be received by, for example, reporting module 122. The query received in step 1405 may also include one or more criteria not related to a diagnostic and/or treatment code such as the location of a treatment provider, demographic information for the patients, the presence of preexisting conditions for a patient, pharmaceuticals used in conjunction with a treatment and/or diagnostic code, and so on. At times, the query of step 1405 may include information from a patient's EMR and/or hypothetical patient characteristics. When the query includes information from the patient's EMR, that information may, at times, be indirectly (i.e., automatically) entered into or added onto the query. For example, if a treatment provider is looking for information regarding an array of treatment options for a particular patient's diagnosis, the treatment provider may be able to enter his or her query directly through and/or by adding a link to the patient's EMR so that the treatment provider does not have to enter all of the patient's characteristics into the query. In this way, a treatment provider may easily and effectively search for treatment options for a patient that may be personalized to that patient's medical condition or state of health.

In step 1410, a data structure that stores medical literature, OMDs, wellness scores, improvement scores, relative improvement scores, effectiveness scores, diagnostic codes, treatment codes, and/or EMR data may be accessed. The accessed data structure may include one or more of the medical-condition-specific registry of information, treatment-specific registry of information, disease-specific registry of information, medical-condition-specific registry of information, diagnosis-specific registry of information, treatment-facility-specific registry of information, and/or treatment-provider-specific registry of information.

In some embodiments, some, or all, of the data that is accessed may be and/or may have been stripped of patient-identifying information and may, therefore, be anonymized. Exemplary data structures that may be accessed in step 1410 include medical literature database 204, OMD database 108, OMD response database 110, score database 120, treatment and/or diagnostic code database 202 and patient EMR database 130.

Next, wellness scores, improvement scores, relative improvement scores, and/or effectiveness scores provided by the accessing of step 410 may be selected responsively to the received request (step 1415). A table of an exemplary range of post-treatment wellness scores for patients who are treated with a treatment having a treatment code corresponding to knee replacement surgery is provided by Table 1, below. More specifically, Table 1 provides a grid of post-treatment wellness scores as the correspond to a primary factor knee replacement implant type (implant A, implant B, or implant C) and a secondary factor (none, drug A, drug B, drug C, technique A, technique B, technique C, associated procedure A, associated procedure B, and associated procedure C).

It is important to note that the flowcharts provided in the attached figures (as well as the discussion thereof) indicate ordered steps for various processes. However, in some instances, the steps do not need to be performed in the order provided. Thus, the order in which steps are listed may not, in some instances, limit the scope of the invention.

In some embodiments, the present invention may provide a portal for treatment providers and/or treatment facilities to view, monitor, edit, and/or modify some, or all, of, for example, the patient-entered information and/or determinations made herein. For example, a treatment provider may access information and/or determinations regarding their patients as described herein and may be enabled to filter, or otherwise organize the data, by, for example, treatment type, treatment outcome scores, contributing factors, patient demographic information, etc. In some instances, this information may be used to generate clinically relevant information that may be used to, for example, generate a publication and/or medical literature.

It is important to note that effectiveness scores provided by the systems and processes described herein are nearly absent of human bias. This is because the effectiveness scores are objectively determined by an entity other than the treatment provider or scientist conducting the treatments or underlying research used to determine the effectiveness scores. Stated differently, bias typically enters the medical literature because doctors and scientists that sponsor clinical trials and FDA studies gather, analyze, and publish the results, which can lead to bias because the doctor or scientist has control of both the data and the analysis of the data. The systems and processes described herein automatically generate the clinical data without involvement of a clinician and, in some instances, make the clinical data and effectiveness scores available to the public for the first time ever.

The effectiveness scores generated by the systems and processes described herein may be used to select the best treatments for patients and may be used to assist treatment providers in providing better treatments. Consider, for example, a treatment provider who has an effectiveness score of 58 for rotator cuff repair, but wants to improve his or her score. He or she may consult a study published by another treatment provider with an effectiveness score of 98 that is based on data generated by the systems and processes described herein and 1) actually believe the data because it is unbiased, and 2) be motivated to change to the technique that the other treatment provider performs (because these other treatment providers are being judged based on their result in an unbiased manner).

TABLE 1

Post-Treatment Wellness Scores for Primary and Secondary Treatments Relating to a Knee Replacement Treatment

| | Secondary Treatment | | |
| --- | --- | --- | --- |
| | Primary Treatment: Implant A | Primary Treatment: Implant B | Primary Treatment: Implant C |
| None | 68 | 85 | 82 |
| Drug A | 68 | 95 | 80 |
| Drug B | 82 | 85 | 82 |
| Drug C | 100 | 90 | 94 |
| Technique A | 68 | 100 | 69 |
| Technique B | 88 | 98 | 100 |
| Technique C | 100 | 90 | 97 |
| Associated Procedure A | 90 | 85 | 78 |
| Associated Procedure B | 88 | 97 | 86 |
| Associated Procedure C | 65 | 95 | 90 |

The data in Table 1 may be used to make determinations regarding the effect of various secondary treatments on the three primary treatments, which correspond to the use of implant A, implant B, and implant C during a knee replacement treatment. For example, Table 1 may be used to determine that treatment with implant A, when performed without administration of a drug has a post-treatment wellness score of 68, which may be unacceptably low. However, use of drug C along with implant A may raise the post-treatment wellness for implant A to 100, which may be considered an ideal outcome, or cure.

Table 1 may be further used to determine that use of implant A with a secondary treatment of technique C produces a post-treatment wellness score of 100, use of implant B with a secondary treatment of technique A produces a post-treatment wellness score of 100, and use of implant C with a secondary treatment of technique B produces a post-treatment wellness score of 100. Thus, a treatment provider and/or treatment facility may choose which technique to use when performing a knee replacement with implant A, implant B, and implant C.

In this way, treatment providers, treatment administrators, treatment facilities can use the data provided in a table like Table 1 to make decisions regarding which primary and secondary treatments may be most effective for a particular treatment. The data provided by a table like Table 1 may also be adjusted to factor in, for example, EMR data of the patient (e.g., age, gender, pre-existing conditions), cost of treatment, patient preference, insurance company preference, and/or treatment provider preference. In some instances, the data in Table 1 may assume that the pre-treatment wellness scores (i.e., prior to treatment) for the patients are all identical, or substantially similar, thereby allowing for the difference in post-treatment wellness scores to be attributable to the secondary treatment.

In some embodiments, a table like Table 1 may be generated using improvement scores instead of wellness scores via, for example, analysis of and/or correlation of improvement scores for patients with a particular diagnosis, or have undergone a particular primary treatment, secondary treatment, combination of primary and secondary treatments, and/or combination of primary and a plurality of secondary treatments.

In some embodiments, a table like Table 1 generated using wellness and/or improvement scores may be generating via the use of one or more correlation algorithms that correlate, for example, wellness and/or improvement scores for patients (who may have various characteristics) with various primary treatments, secondary treatments, combinations of primary and secondary treatments and/or combinations of primary and a plurality of secondary treatments. The correlation algorithm(s) may make use of, for example, identifiers and/or tags associated with, for example, patients under consideration, wellness scores, improvement scores, primary treatments, secondary treatments, combinations of primary and secondary treatments and/or combinations of primary and a plurality of secondary treatments. In some instances, the correlation algorithm may form correlations between, for example, a treatment facility's entire EMR record and the outcome of every treatment.

A table like Table 1 may be used by, for example, a treatment provider and/or academic to see how treatments relate to one another and, possibly, determine optimum (e.g., a score of 100) treatments and/or combinations of treatments for patients who are associated with a particular diagnosis. In one example, consider a diagnosis of lung cancer where the standard of care is administration of 10 different chemotherapeutic agents to all patients with this diagnosis. Analysis of how other treatments these cancer patients are getting (e.g., for high blood pressure, diabetes, etc.) effect the wellness and/or improvement scores of the patients with the lung cancer diagnosis may lead to unexpected findings regarding positive and/or negative interactions between the 10 different chemotherapeutic agents and the other treatments for diagnoses not related to the cancer.

Optionally, in step 1420 a determination may be made as to whether there are overlapping, other considerations, or secondary treatment outcomes and/or factors that may affect an outcome for the primary factor. If so, one or more relationships between the overlapping or secondary factor outcomes may be determined (step 1425). In some circumstances, the overlapping factors and/or other considerations may be known to be associated with the treatment and/or diagnostic code(s) associated with the request of step 1405 and, in other circumstances, the overlapping factors and/or other considerations may be entered by the requester as part of, and/or subsequent to receipt of, the request of step 1405. When there are no overlapping outcomes or factors, process 1400 may advance to step 1435, which will be discussed below.

In some embodiments, the information of a table like Table 1 may be analyzed and/or cross-correlated with overlapping factors and/or other considerations in order to, for example, determine one or more relationships between, for example, two or more of the implants, drugs, techniques, and/or associated procedures (via, for example, step 1425) and the overlapping factors and/or other considerations. For example, an overlapping factor may be the administration of vitamin B12 along with implants A, B, and C in order to determine an effect thereof and step 1425 may determine that patients who received implant A, drug B, and vitamin B12 had post-treatment wellness scores that were 5 points higher than without vitamin B12. In some circumstances, the determination of step 1425 may be performed automatically and, in other circumstances, the analysis may be performed by an individual or group of individuals (e.g., treatment providers).

In step 1430, the wellness scores, improvement scores, relative improvement scores, and/or effectiveness scores selected in step 1415 may be modified to incorporate the overlapping treatments and/or factors and/or the relationship therebetween and, in step 1435, the wellness scores, relationships, and/or modified wellness scores may be provided to the requester. Exemplary modifications include recalculation of a wellness score or a determination of wellness score that includes footnotes or other notations that incorporate the overlapping treatments and/or factors.

Process 700 and/or 1400 may be executed in order to determine and provide, for example, wellness scores, improvement scores, relative improvement scores, and/or effectiveness scores, relationships between treatment codes and diagnosis codes, relationships between two or more treatment codes, and so on. In this way, the output of process 1400 may be personalized to a particular person, set of patient characteristics, set of esoteric factors, and/or set of circumstances. In the example of a patient, a request for wellness scores may be specific, or personalized to a particular patient's medical condition and/or factors that may contribute to a treatment outcome. For example, if a patient has been diagnosed with breast cancer, the request received in steps 1405 may request post-treatment wellness scores, improvement scores, relative improvement scores, and/or effectiveness scores for a breast cancer diagnosis and/or one or more treatments for breast cancer. The request may be very specific and may indicate, for example, the particular type of breast cancer the patient has, what stage the cancer is in, information about the cancer's genome, where the cancer has metastasized to, and so on. Wellness scores, improvement scores, relative improvement scores, and/or effectiveness scores associated with the diagnosis and/or treatment may then be determined and provided to the requester. In some instances, the wellness scores, improvement scores, relative improvement scores, and/or effectiveness scores may be for theoretical treatments that may, or may not, be performed on the patient. For example, a treatment provider may run various scenarios with different treatment information to determine which treatment has the highest post-treatment wellness score or improvement score for the patient's diagnosis and/or treatment code.

In some instances, process 1400 may also be used to determine wellness scores for addressing the side effects of a treatment. To continue with the above example, process 1400 may be used to determine post-treatment wellness scores, improvement scores, relative improvement scores, and/or effectiveness scores for various treatments to combat the side effects of cancer treatment. In another example, process 1400 may be used to determine post-treatment wellness scores, improvement scores, relative improvement scores, and/or effectiveness scores for post-treatment activity such as physical therapy, ice application, or medication usage following a treatment for an orthopedic surgery.

For embodiments that incorporate determining whether there is an overlapping treatment and/or factor (i.e., the answer for step 1420 is yes), overlapping treatments and/or factors for the patient's treatment and/or diagnosis may be provided. Exemplary overlapping outcomes include treatments, other than the treatment indicated in the request of steps 1405, that the patient is undergoing or considering undergoing. Exemplary other considerations include a patient's age, gender, weight, comorbidities, etc. Continuing the breast cancer example above, process 1400 may be used to determine post-treatment wellness scores, improvement scores, relative improvement scores, and/or effectiveness scores when two or more treatments (e.g., chemotherapy and radiation) are combined.

In some instances, process 1400 may be executed in order to generate a body of information and wellness scores that may be useful in conducting a clinical (or scientific) analysis of treatment outcomes in a manner consistent with academic research. For example, an individual may request wellness scores that incorporate a variety of different factors and/or overlapping treatments or sets of different factors and/or overlapping treatments and may use responses to these requests to draw conclusions about treatment efficacy in a manner similar to the way traditional clinical trials are conducted. The results provided by execution of process 1400 may then be analyzed by one or more study authors and these results and the analysis may be converted into a publication that becomes part of the medical literature.

Figure 14B:
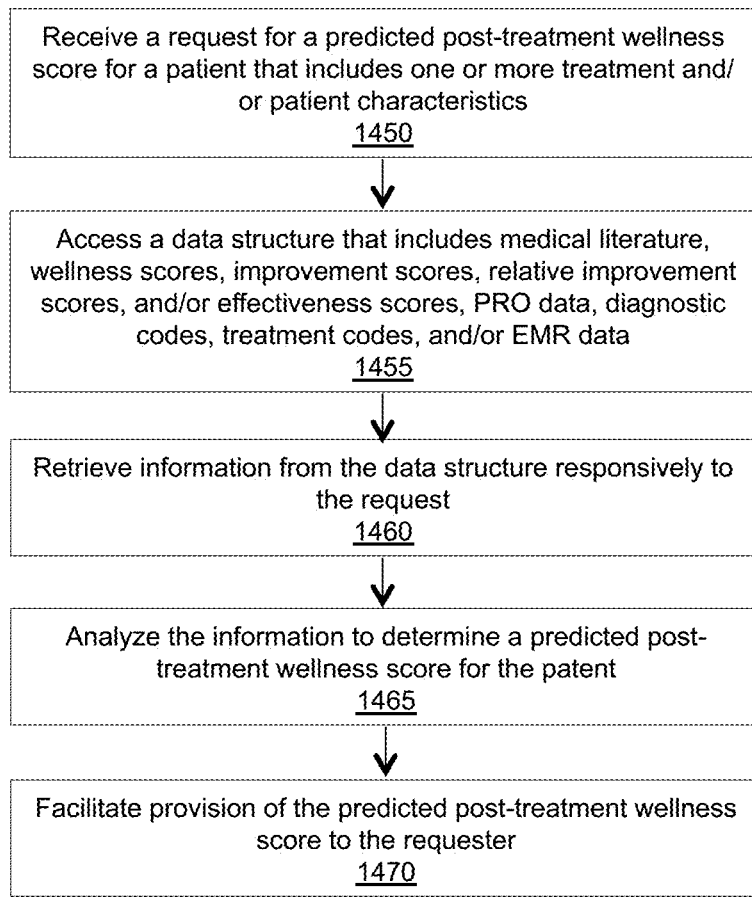
FIG. 14B provides a flowchart of exemplary process for predicting a post-treatment wellness score for a patient, in accordance with some embodiments of the present invention.

FIG. 14B provides a flowchart of exemplary process 1401 for predicting a post-treatment wellness score for a patient. Process 1401 may be executed by, for example, any of the systems and/or system components disclosed herein.

In step 1450, a request for a predicted post-treatment wellness score for a treatment a patient has undergone or is expected to undergo may be received. In many cases, the request may include information about/characteristics of the patient such as, age, gender, height, weight, race, comorbidities, previously administered treatments, medications consumed by the patient and so on. At times, this patient information may concern one or more other considerations as discussed above with regard to process 1300 and FIG. 13. This patient information may be directly added to the request via, for example, a fillable form and/or may be extracted from the patient's EMR via, for example, an automatic extraction process. In some cases, the request of step 1450 may be received via a patient's wellness account when, for example, the patient is interacting with his or her wellness account.

Next, in step 1455, a data structure that stores medical literature, OMDs, wellness scores, improvement scores, relative improvement scores, effectiveness scores, diagnostic codes, treatment codes, and/or EMR data may be accessed. The accessed data structure may also include one or more of the medical-condition-specific registry of information, treatment-specific registry of information, disease-specific registry of information, medical-condition-specific registry of information, diagnosis-specific registry of information, treatment-facility-specific registry of information, and/or treatment-provider-specific registry of information in order to retrieve information responsive to and/or matching the request (step 1460). The retrieved information may include, for example, previously determined post-treatment wellness scores of other patients who underwent the same, or a similar, treatment as the patient has undergone or scheduled to undergo. In some instances, the retrieved information may be specific to and/or relevant for one or more of the patient characteristics associated with the request. For example, if the patient for whom the request is made is a 65-year old woman with osteoporosis who is 50 pounds overweight and the treatment the patient is scheduled to receive is a knee replacement then, information relating to female patients with who have undergone knee surgery, are within the age range of 60-70 years of age, and who have osteoporosis may be retrieved from the data structure in step 1460.

The retrieved information may be analyzed to determine a predicted post-treatment wellness score for the patient (step 1465). This analysis may include weighting or other statistical means to determine how relevant the pre-determined post-treatment wellness scores are to the patient and/or which characteristics of the patient are more likely to be determinative to his or her recovery. In some instances, the analysis of step 1465 may be performed using other factors and/or scoring procedures used to determine the pre-calculated post-treatment wellness scores as discussed above with regard to processes 1000 and/or 1300 and FIGS. 10 and 13, respectively. Continuing with the example above, if it is known that the 65-year old patient scheduled for the knee replacement is also allergic to pollen and wears glasses, the analysis of step 1465 may not include this information as it has minimal relevance to how well the patient is expected to recover from knee replacement surgery.

On some occasions, execution of step 1460 may include analysis of one or more pre-treatment and/or post-treatment responses received from the patient via, for example, process 1000. Additionally, or alternatively, execution of step 1460 may include analysis of one or more pre-treatment wellness scores and/or post-treatment wellness scores determined for the patient via, for example, process 1000.

In some instances, execution of step 1465 may include determining a plurality, or series, of predicted post-treatment wellness scores that may be spread out over time (e.g., every month, quarter, year, etc.) so that a patient may see long-range predictions of his or her post-treatment wellness scores. In some circumstances, the series of predicted post-treatment wellness scores may be dynamically updated as time goes by and the patient provides more information regarding his or her post-treatment recovery.

In step 1470, provision of the predicted post-treatment wellness score(s) to the requestor and/or patient may be facilitated. An exemplary interface that displays predicted post-treatment wellness scores is provided by FIGS. 17H and 18C, which provide an updated wellness tracker interface 1802 that shows a predicted post-treatment wellness score 1845 for a patient 3 months in the future.

Figure 14C:
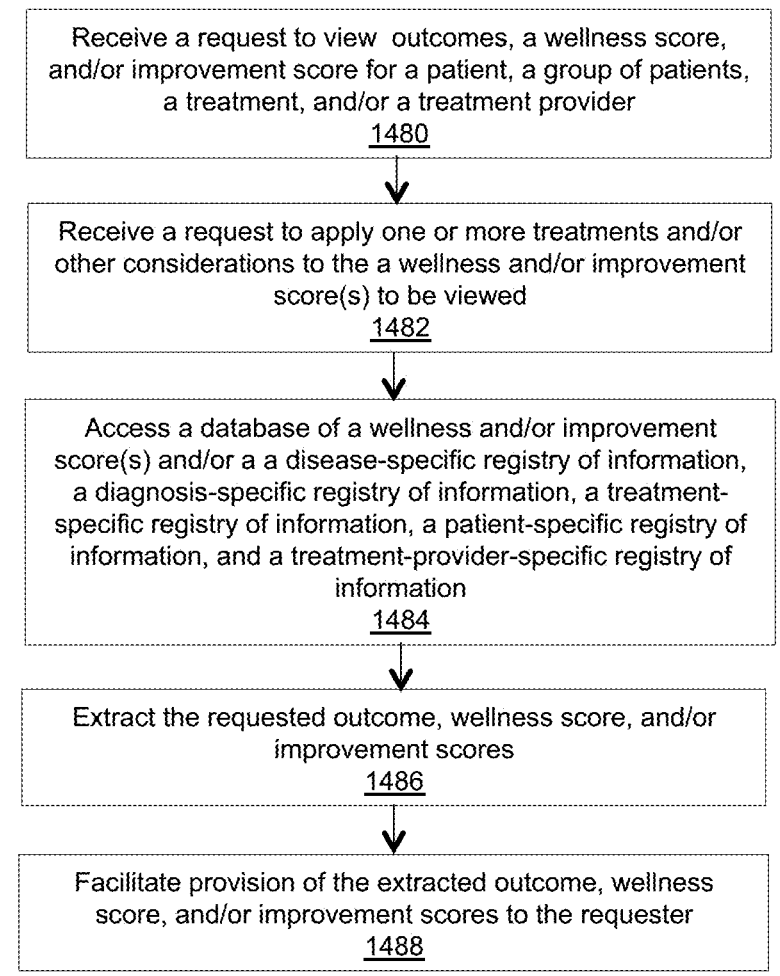
FIG. 14C provides a flowchart of exemplary process for obtaining wellness scores and/or improvement scores for a patient or a group of patients, in accordance with some embodiments of the present invention.

FIG. 14C provides a flowchart of exemplary process 1402 for obtaining wellness scores and/or improvement scores for a patient or a group of patients. Process 1402 may be executed by, for example, system 100 and/or a component or combination of components thereof.

In step 1480, a request to view an outcome, a wellness (e.g., pre-treatment and/or post treatment) score and/or an improvement score associated with a patient, a group of patients, a treatment, a treatment provider may be received. The request may be received from, for example, a treatment provider or a treatment administrator. At times, the request may include a time period over which the requester would like to see wellness and/or improvement scores. For example, the request may be a request to view a patient's wellness over a 1, 5, or 10 year period. Additionally, or alternatively, the request may include a request to view wellness and/or improvement scores for patients associated with one or more diseases, medical conditions, treatments and, optionally, in step 1482, may further include a request to view wellness and/or improvement scores associated with one or more treatments or other considerations. In some embodiments, the request may further include a request to view raw wellness and/or improvement scores and/or adjusted or normalized wellness and/or improvement scores provided on a normalized scale.

In step 1484, a database of a wellness and/or improvement score(s) and/or a disease-specific registry of information, a diagnosis-specific registry of information, a treatment-specific registry of information, a patient-specific registry of information, and a treatment-provider-specific registry of information such as score database 120 may be accessed and/or queried to extract the requested wellness and/or improvement scores (step 1486). Then, provision of the extracted outcome(s), wellness score(s), and/or improvement score(s) to the requester may be facilitated (step 1488). In some instances, execution of step 1488 may include preparing a report that includes, for example, a table, chart, or graph.

FIGS. 24A-24E provide exemplary interfaces by which a request may be received from requester and extracted outcomes, wellness scores, and/or improvement scores may be provided to the requester. More specifically, FIG. 24A provides an exemplary interface 2401 by which a requester may enter some information and/or criteria for the request. More specifically, interface 2401 includes a patient identifier text box 2406A into which a requester may enter, for example, a patient's name, an anomyzed identifier associated with the patient, a date of birth, and/or a health insurance identifier. Interface 2401 also includes a treatment provider identifier text box 2405B into which a requester may enter, for example, a name of a treatment provider or group of treatment providers. Interface 2401 further includes a patient characteristic text box 2405C into which a requester may enter, for example, a name of a treatment provider or group of treatment providers In some embodiments, a requester may enter multiple patient identifiers, multiple treatment providers, and/or multiple patient characteristics separated by, for example, a comma or semicolon into patient identifier text box 2406A, treatment provider identifier text box 2405B, and patient characteristics text box 2405C.

Interface 2401 also includes a number of check boxes 2410 for further clarifying the scope of the request/inquiry. More specifically, interface 2401 includes a multiple patients check box 2410A, an outcomes check box 2410B, a wellness scores check box 2410C, and an improvement scores check box 2401D. Selection of multiple patients check box 2410A may enable a requester to request information regarding multiple patients by, for example, causing display of another interface (not shown) by which a requester may enter a plurality of patient identifiers. Selection of outcomes check box 2410B may add a request to view outcomes for the identified patient(s)/treatment provider(s) the request received in step 1480. Likewise, selection of wellness scores check box 2410C and improvement scores check box 2401D may add a request to view wellness scores and/or improvement scores, respectively, for the identified patient(s)/treatment provider(s) associated with the request received in step 1480.

FIG. 24B provides an exemplary diagnosis/medical condition selection interface 2402, which provides a global health selection button 2415 as well as an array of disease/diagnosis-specific selection buttons 2420. Array 2420 may include any number of disease/diagnosis-specific selection buttons 2425. Exemplary disease/diagnosis-specific selection buttons 2425 include disease/diagnosis-specific selection buttons for atrial fibrillation 2425A, anxiety 2425B, arthritis 2425C, asthma 2425D, back pain 2425E, BPH 2425F, chronic pain 2425G, CHF 2425H, COPD 2425I, CAD 2425J, depression 2425K, eczema 2425L, fatigue 2425M, gout 2425N, headache/migraines 2425O, heartburn/GERD 2425P, inflammatory bowel 2425Q, and osteoporosis 2425R. Selection of global health selection button 2415 and/or one or more disease/diagnosis-specific selection buttons 2425 may add the associated criteria to the request (step 1480). Interface 2403 may also provide a list 2417 of one or more exemplary options that enable a requester to add criteria relating to how the user would like to see the requested scores/information to his or her request. The exemplary options included in list 2417 enable a requester to request viewing wellness scores as raw scores (i.e. scored according to the scale provided by the scoring procedure used to score responses to an OMD underlying and/or used to generate the wellness and/or improvement score), as an adjusted score (e.g., adjusted to be on a scale from 1-100), and/or as an improvement score.

Interface 2402 also provides a requester with a list 2418 of options to select a time period over which to extract outcomes, wellness, and/or improvement scores. For example, list 2418 provides a requester with an option to select a report period (e.g., day, month, year-to-date, decade, etc.) as well as an option to set a start and stop date within which to extract outcomes, wellness, and/or improvement scores for provision to the requester.

In one example, a requester selects CAD disease/diagnosis-specific selection button 2425J from array 2420 to specify that the requester would like to see outcomes/scores related to CAD for a specific patient (in this case, Karen Smith) and also selects the option to extract/view improvement scores (as opposed to outcomes or wellness scores) for CAD from list 2417. Following this selection, a treatment selection interface like treatment selection interface 2403 of FIG. 24C may be provided to the requester. Treatment selection interface 2403 provides the requester with a list 2430 of treatment options that he or she may select so as to further refine the scope of the improvement scores returned in response to the request (step 1482). List 2430 includes a treatment option button for treatment A 2430A, treatment B 2430B, treatment C 2430C, treatment D 2430D, treatment E 2430E, treatment F 2430F, and treatment G 2430G. It will be understood by those of skill in the art that although the treatment selection buttons of interface 2403 may be used to select any kind of treatment (e.g., medication, physical therapy, etc.) or dosage/frequency of treatment. Furthermore, a treatment selection interface like treatment selection interface 2403 may provide selection options for a frequency or prescribed amount of treatment. In the case of medication, this may be a dosage amount and/or frequency of dosage. For other treatments (e.g., group therapy, physical therapy) a set of frequency options may include weekly, bi-weekly, daily, etc.

Upon selecting a treatment selection button (in this case, treatment selection button 2430D for treatment D), process 1402 may advance to accessing a database (step 1484) to extract the requested set of improvement scores for a particular patient (Karen Smith) over the time frame established via entry of information into list 2418 (in this case, nine months). Then, an improvement score interface, like improvement score interface 2404 of FIG. 24D, may be provided to the requester (step 1488). Improvement score interface 2404 provides a graph 2440 of improvement scores determined for the selected patient (Karen Smith) over a nine-month time frame from January 2016 through September 2016 along with a trend line 2445 showing the average change in improvement score (in this case approximately 0.667 or 67%) over the nine-month time period. Viewing the improvement scores of the patient over time in this manner allows the requester to see data regarding how the patient's condition (in this case, CAD) has improved (or deteriorated) in response to receiving a treatment (in this case, treatment D) over time. A treatment provider or other requester may use this information to determine the overall effect of the selected treatment on the patient's disease or symptoms of the disease.

Figure 24E:
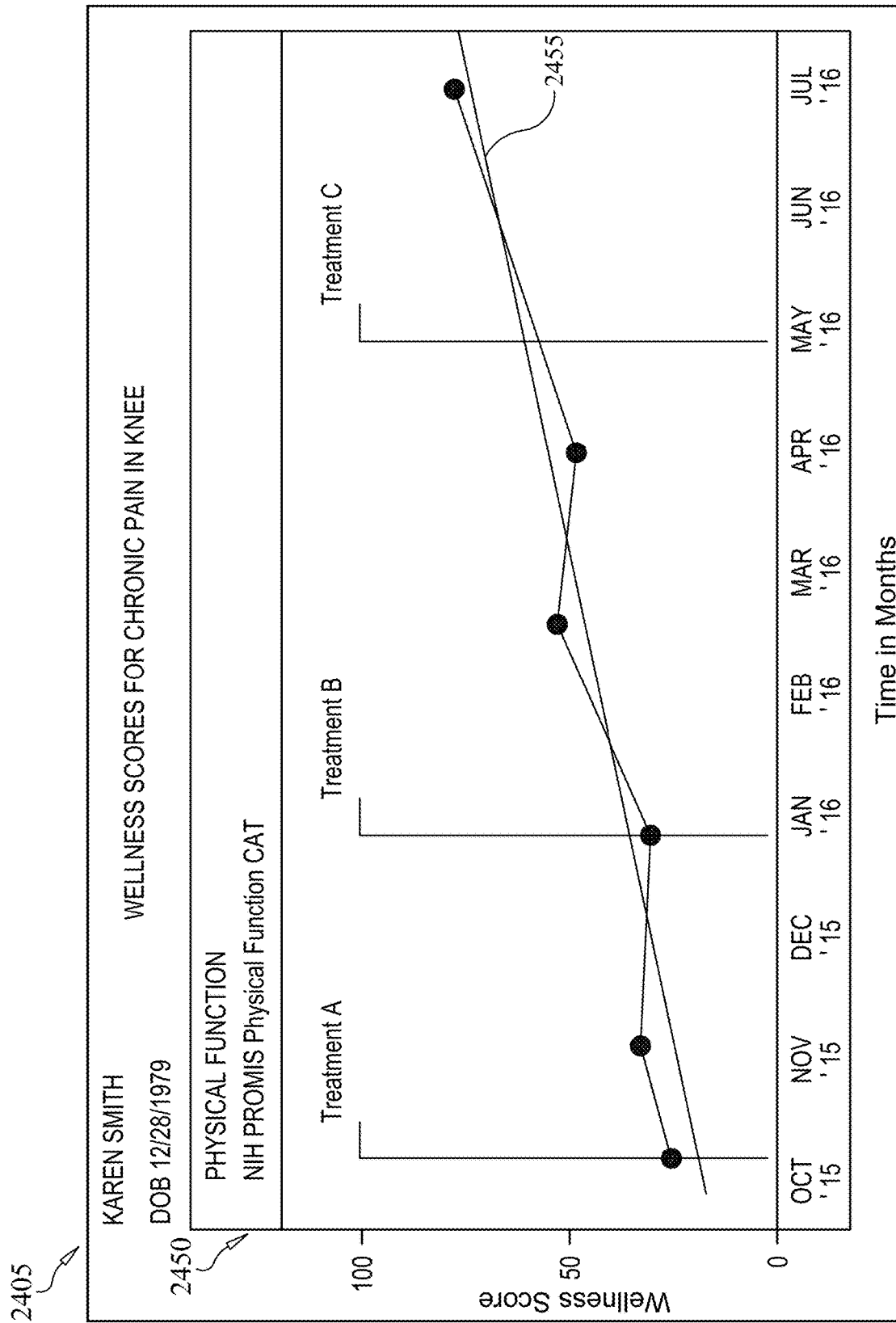

FIG. 24E provides an exemplary wellness score interface 2405 for patient Karen Smith provided to a requester in response to receiving a request for wellness scores over a ten-month time frame (i.e., October 2015 through July 2016) in relation to the disease/symptom chronic pain associated with the patient's knee (via selection of the disease/diagnosis-specific selection button 2425G for chronic pain from list 2420) and administration of treatments A, B, and C (via selection of the treatment option buttons for treatment A 2430A, treatment B 2430B, treatment C 2430C) on the patient within the selected 10-month time frame. Exemplary wellness score interface 2405 includes a graph 2450 that provides wellness score values determined in October 2015, November 2015, January 2016, late February 2016, April 2016, and July 2016 as well as a trend line 2455 that shows the average change in wellness scores over the ten-month time frame.

In some instances, a requester may desire to have information regarding two different diagnoses for a patient or group of patients provided to them in a single report so that they may simultaneously assess how the wellness and/or improvement scores for the patient or the group of patients are progressing with time. For example, a requester may wish to view (via, for example, graph or table) how the wellness scores for a patient diagnosed with anxiety and depression have changed over a 1-year time period. To generate such a report, the requester may enter the patient name into interface 2401, select the disease/diagnosis-specific selection buttons for anxiety 2425B and depression 2425K, and enter a 1-year time period into list 2418. Then, for example, a graph showing the wellness scores for the patient with regard to the patient's anxiety wellness and depression wellness may be provided on the same graph so that, for example, trends, similarities, and/or differences between the patient's anxiety wellness and depression wellness may be observed. The requester may, in some instances, also wish to see information regarding the patient's overall, or global health, and may add this information to the graph via selection of global health selection button 2415.

In another example, a requester may request information regarding a patient's overall, or global health, via selection of global health selection button 2415 and the patient's headache/migraines wellness via selection of the disease/diagnosis-specific selection buttons for headache/migraines 2425O when receiving a treatment A (via selection of treatment option buttons for treatment A 2430A) for the treatment of the headaches/migraines to be simultaneously displayed on a single report as, for example, a graph so as to, for example, monitor the effect of treatment A on the patient's global wellness and/or headache/migraine wellness scores so as to, for example, determine whether side effects of treatment A are substantially impacting the patient's global wellness.

In a further example, a requester may request information regarding improvement scores for a particular diagnosis for a plurality of patients who are diagnosed with the same medical condition and treated with a variety of treatments so as to, for example, determine the best treatment for the diagnosis. This may be accomplished by, for example, selecting multiple patients checkbox 2410A, selecting improvement scores from list 2417, selecting a time period from list 2418, selecting a diagnosis of interest (e.g., atrial fibrillation via selection of the disease/diagnosis-specific selection buttons for atrial fibrillation 2425A), and then selecting a plurality of treatments of interest (e.g., treatments A, C, and D via selection of treatment option buttons for treatment A 2430A, 2430C, and 2430D, respectively). Optionally, the requester may also enter one or more patient characteristics (e.g., age, gender, etc.) A report showing the wellness scores for the plurality of patients who have been diagnosed with atrial fibrillation (and share the optionally entered patient characteristics) and have received treatments A, C, and D over the requested time period may then be provided.

In yet another example, a requester may desire to receive wellness and/or improvement scores for patients who have received a combination of treatments. This may be accomplished by, for example, selecting multiple patients checkbox 2410A, selecting wellness scores from list 2417, selecting a time period from list 2418, selecting a diagnosis of interest (e.g., atrial fibrillation via selection of the disease/diagnosis-specific selection buttons for atrial fibrillation 2425A), and then selecting a plurality of combined primary and secondary treatments of interest (e.g., a combination of primary treatment A and secondary treatment B; a combination of primary treatment A and secondary treatment C, and a combination of primary treatment D and secondary treatment B via selection of a combination of treatment option buttons for 2430A, 2430B, 2430C, and 2430D, respectively). Optionally, the requester may also enter one or more patient characteristics (e.g., age, gender, etc.) A report showing the wellness scores for the plurality of patients who have been diagnosed with atrial fibrillation (and share the optionally entered patient characteristics) and have received the combination of treatments over the requested time period may then be provided. In addition, the requester may also request wellness scores for the diagnosis with just the primary treatment holding all other request criteria the same. In this way, the requester may see the effect of secondary treatments on the primary treatment and see whether any secondary treatments are advantageous to combine with a primary treatment.

Figure 15A:
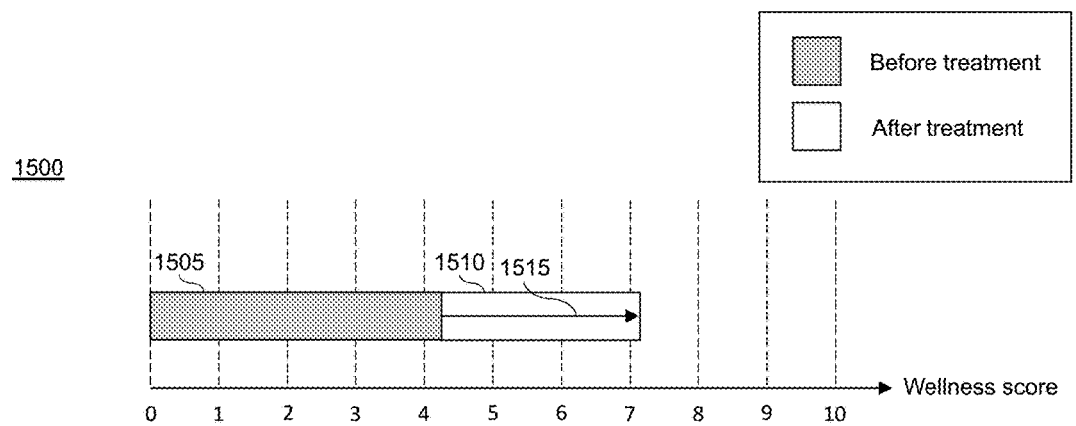
FIGS. 15A-15C provide exemplary bar-chart representations of wellness scores, in accordance with some embodiments of the present invention.
Figure 15B:
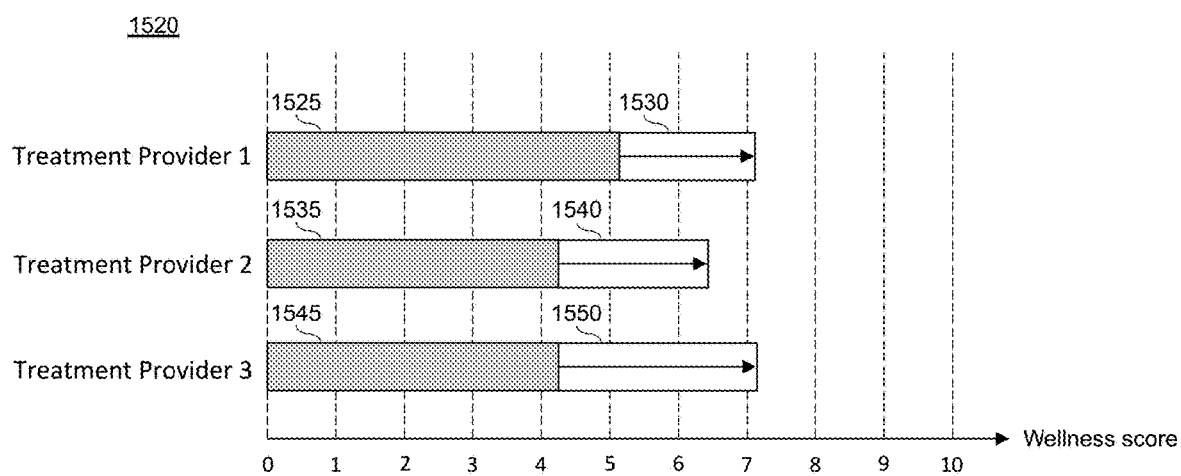
Figure 15C:
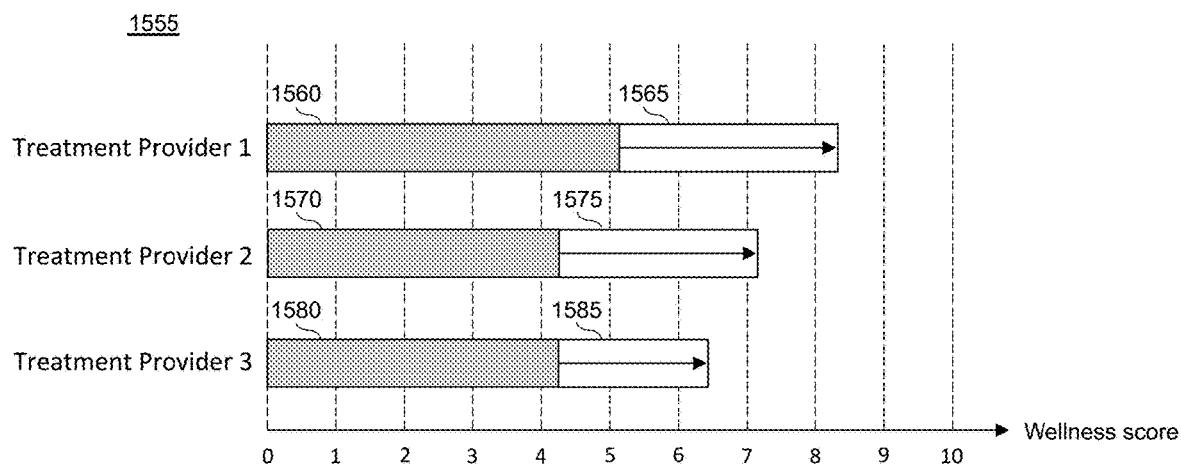

FIGS. 15A-15C provide exemplary bar-chart representations of wellness scores for a particular patient or a group of patients associated with a particular treatment provider in the form of bar charts 1500, 1520, and 1555, respectively. The wellness scores of charts 1500, 1520, and 1555 of FIGS. 15A-15C, respectively, are scaled on an exemplary numerical scale ranging from 0-10), with a score of 1 indicating a low or poor score and 10 indicating a high, or excellent, score. It will be appreciated that other scales (e.g., 0-20, 0-100, poor-satisfactory-excellent) may be used for representing a wellness score without deviating from the scope of the invention. Also, while a linear scale is used for bar charts 1500, 1520, and 1555 it is understood that a nonlinear scale (e.g., exponential or logarithmic scale) may be used instead.

FIG. 15A provides a bar chart 1500 representing a pre-treatment wellness score, a post-treatment wellness score and an improvement score for an exemplary patient. The pre-treatment wellness score, post-treatment wellness score and improvement score may be determined via execution of, for example, some or all of processes 300, 400, 500, 600, 700, 800, 900, 1000, and/or 1100.

In some instances, the patient's pre-treatment wellness score may correspond with a state of health for a patient generally and/or with regard to a particular medical condition with which the patient has been diagnosed. For the purposes of the example FIG. 15A, the patient's pre-treatment wellness score 1505 is determined to be 4.3, and is displayed as a pre-treatment wellness score bar 1505 in a bar chart 1500.

An indicator of the patient's change in wellness (i.e., an improvement score) following treatment (or how much the patient's condition has improved/declined following treatment) may be shown as an improvement bar 1510 and/or an improvement arrow 1515 (or both). In the example of FIG. 15A, the patient's wellness score following a treatment was 7.2, and the improvement in the patient's wellness score was 2.9, as depicted in the improvement bar 1510 and improvement arrow 1515.

In some instances, a patient's health may not improve after receiving a treatment, and could remain unchanged or worsen (e.g., there may be unforeseen complications resulting from the treatment). Therefore, any discussion of a "patient's improvement" may more generally be recast as a patient's health progression (i.e., "improvement bar" may be called a "health progression bar", etc.).

Another measure of a patient's improvement after a treatment may be a measure of relative improvement (i.e., relative to a maximum possible improvement score), also called a relative improvement score or an improvement percentage. In mathematical notation, the relative improvement score may be calculated as follows:

$$\text{relative improvement score} = \text{improvement score} / \text{maximum improvement score} * 100\% \quad \text{(Equation 2)}$$

This relative improvement score may be represented as a number and/or a percentage. Yet another way to determine a relative improvement score is as follows:

$$\text{Wellness Score at time 2} - \text{Wellness Score at time 1} / \text{Maximum Wellness Score} - \text{Wellness Score at time 1} * 100\% \quad \text{(Equation 3)}$$

For example, suppose a patient is being treated for an ACL injury. The patient's pre-treatment wellness score, using a particular OMD, prior to knee surgery is determined to be 12. Three months following knee surgery, the patient's post-treatment wellness score (using the particular OMD) is determined to be 36. Further, suppose that the maximum wellness score for the particular OMD is 47. Based on the mathematical equations presented above, the relative improvement score of the patient may be calculated $$36 - 12 / 47 - 12 * 100\% = 68\%.$$

Figure 18B:
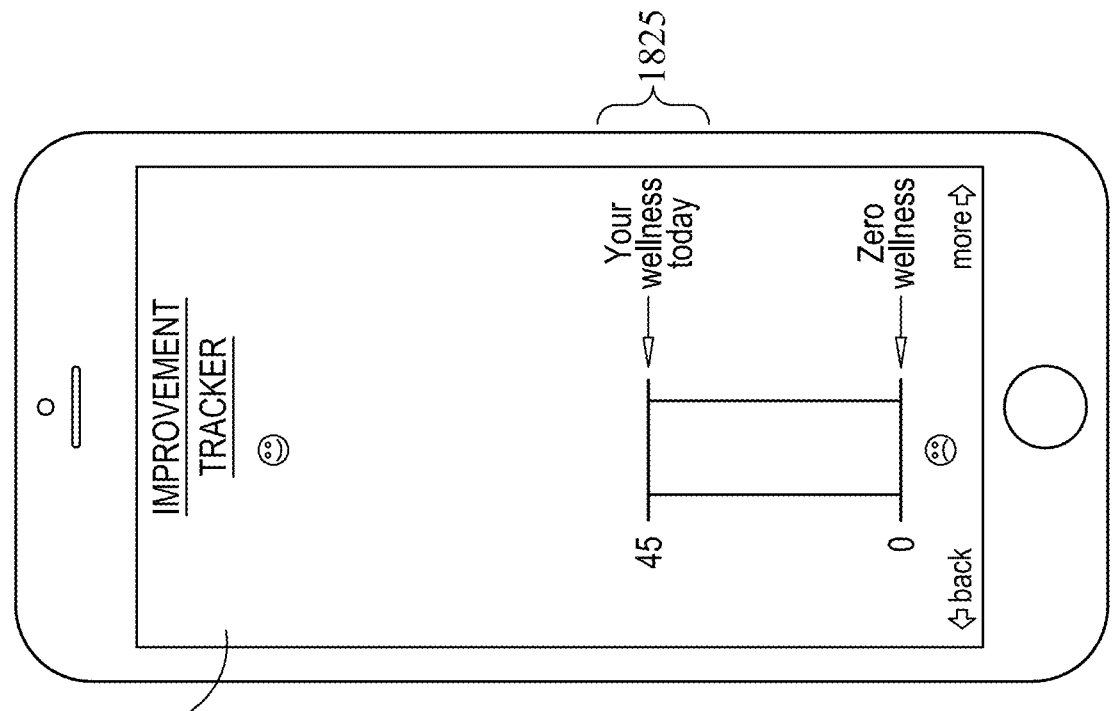
FIGS. 18A-18N provide screenshots of various user interfaces by which a patient may be provided with information about his or her health and/or wellness, in accordance with some embodiments of the present invention.
Figure 18A:
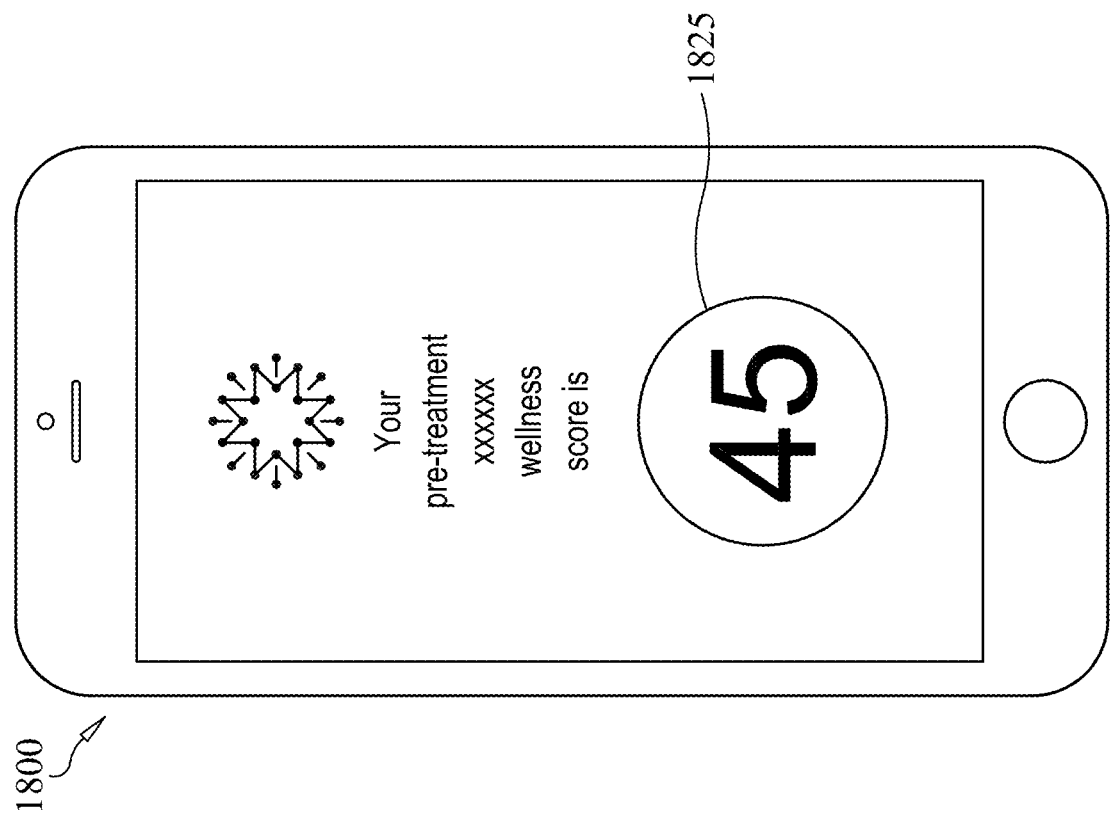
Figure 18D:
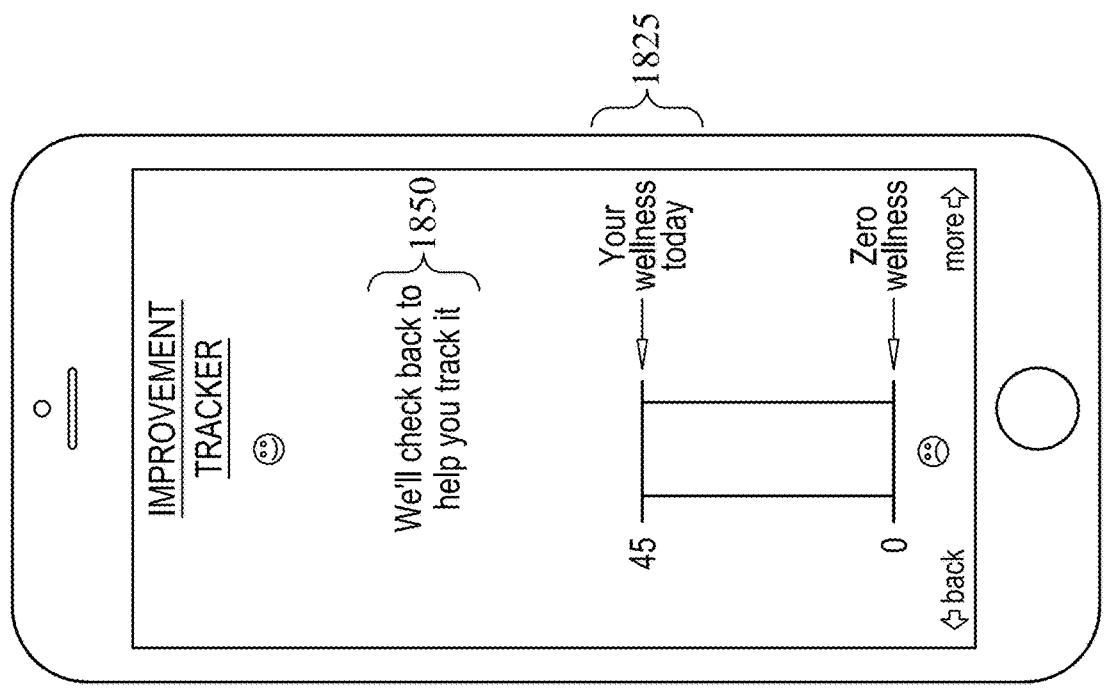
Figure 18C:
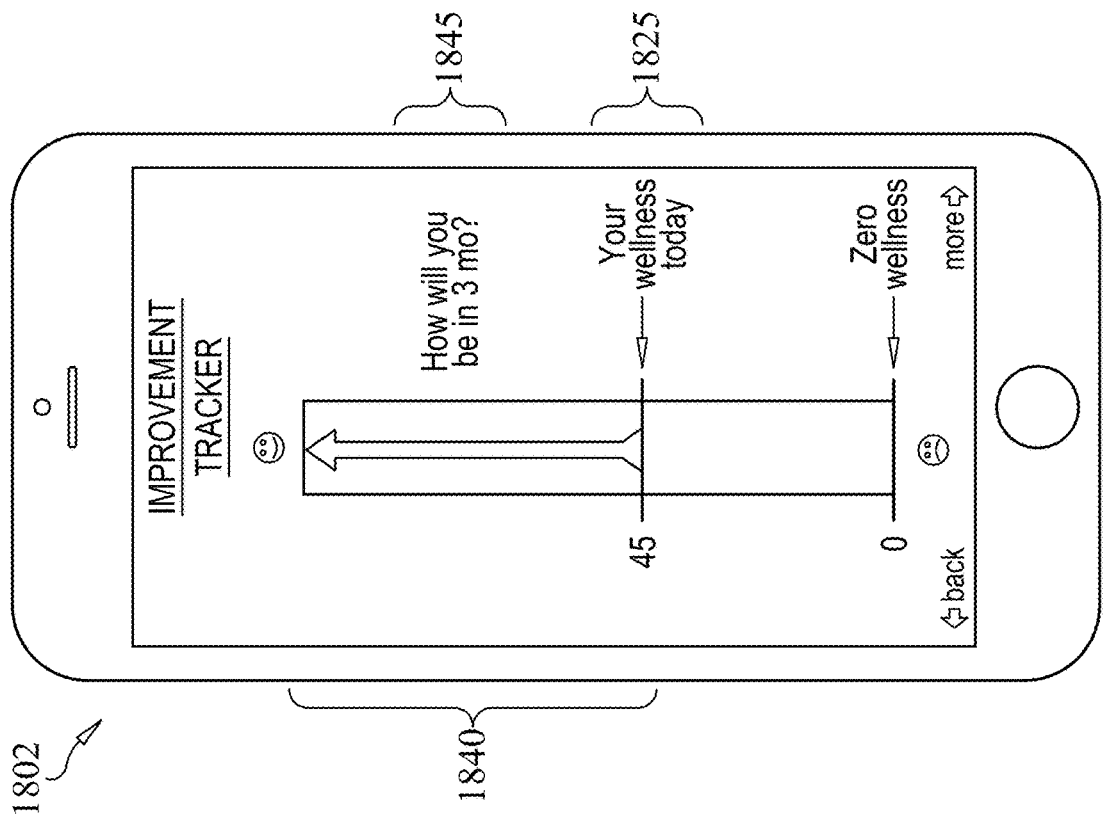
Figure 18F:
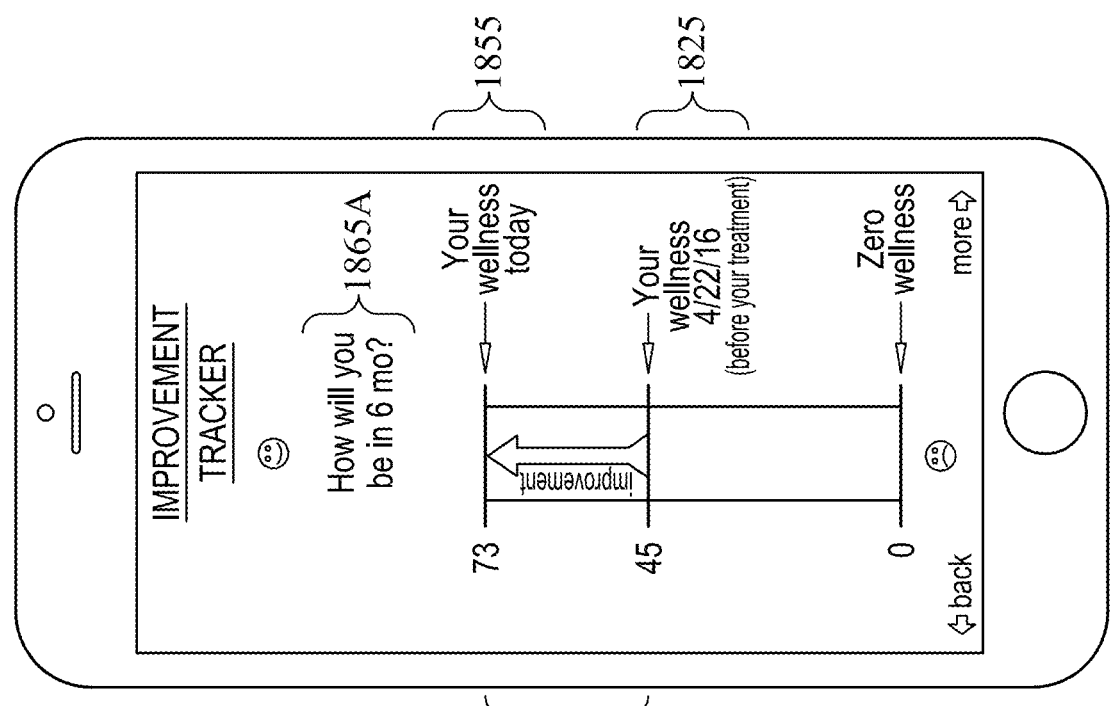
Figure 18E:
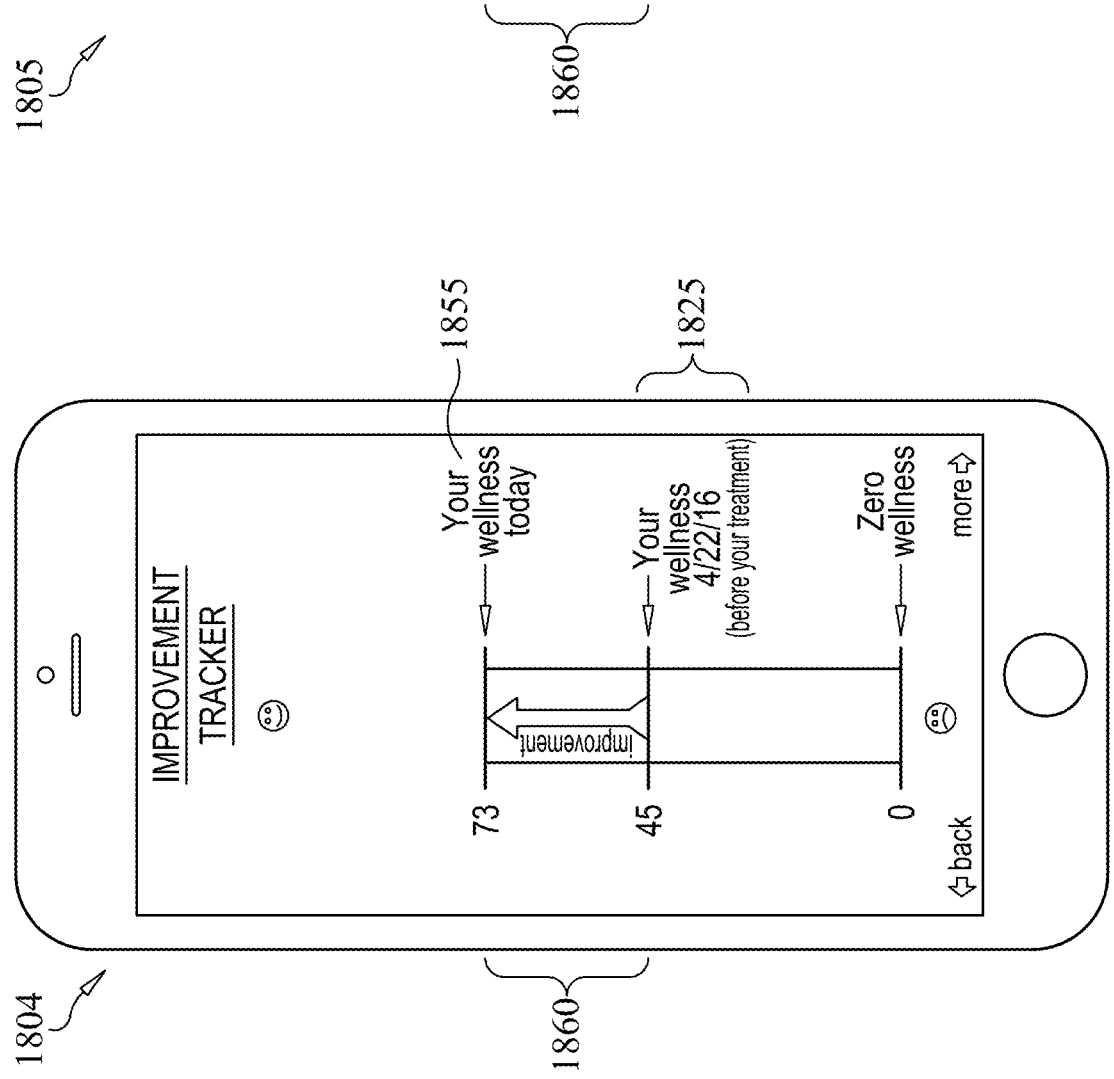
Figure 18H:
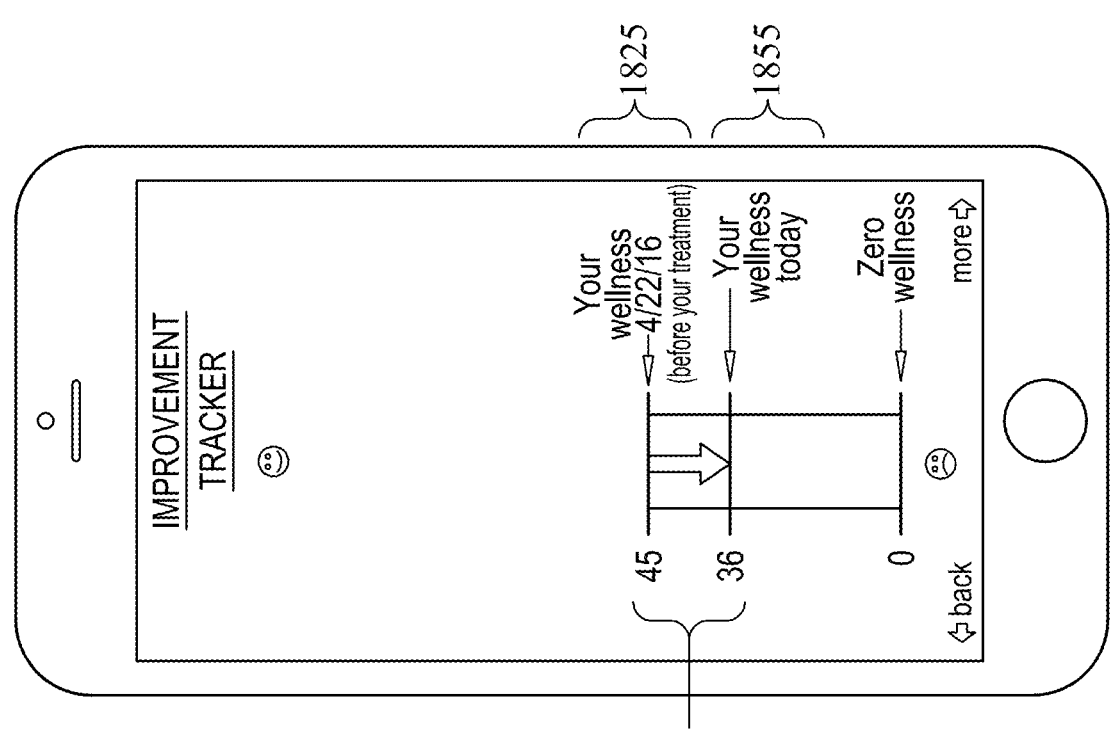
Figure 18G:
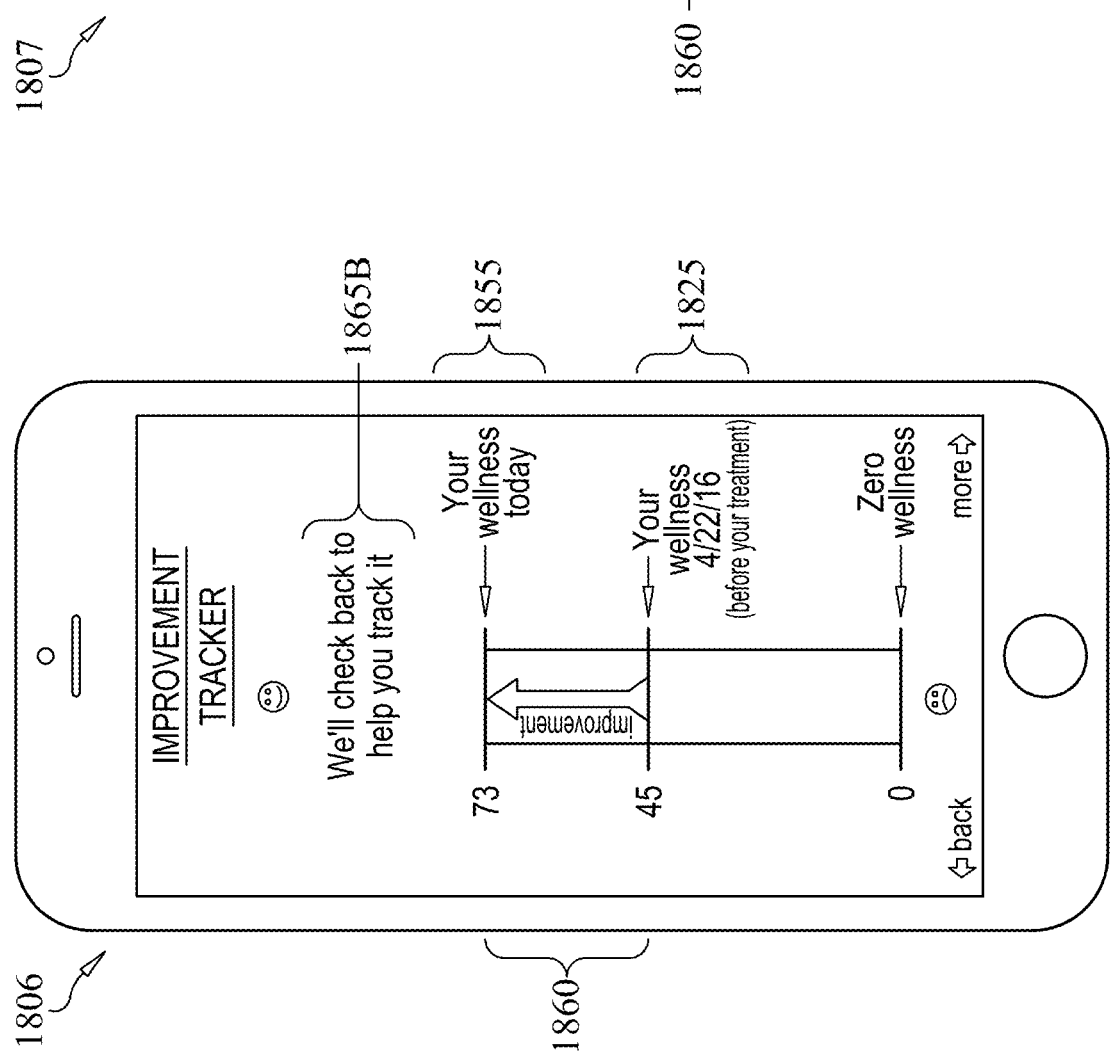
Figure 18J:
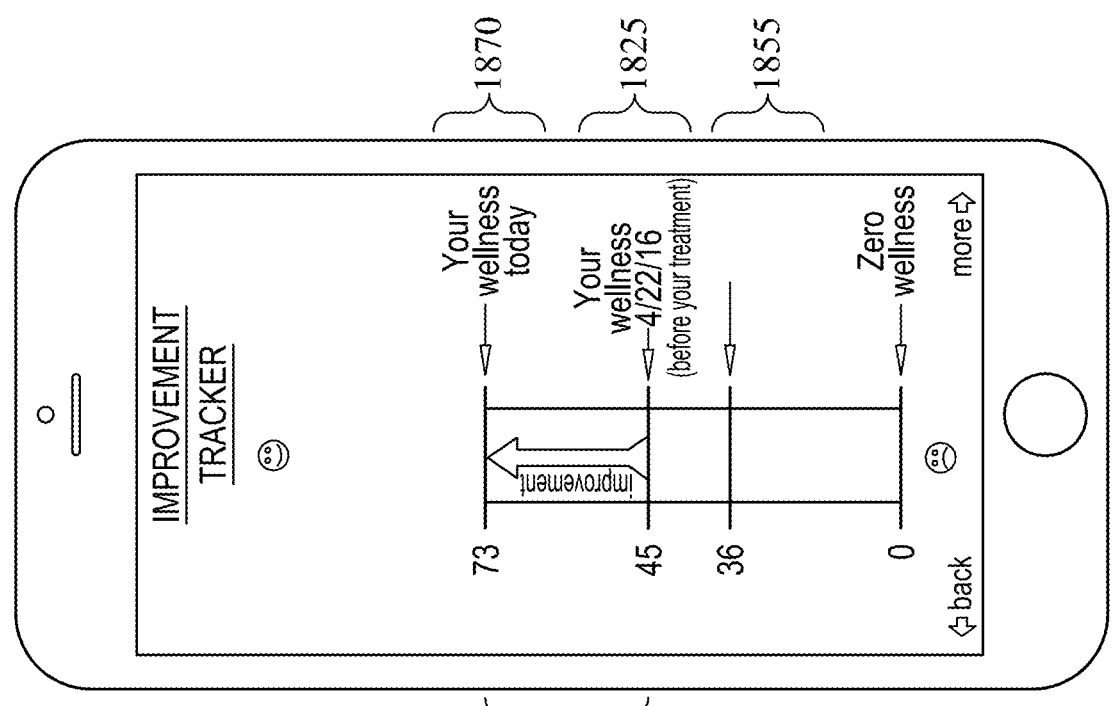
Figure 18I:
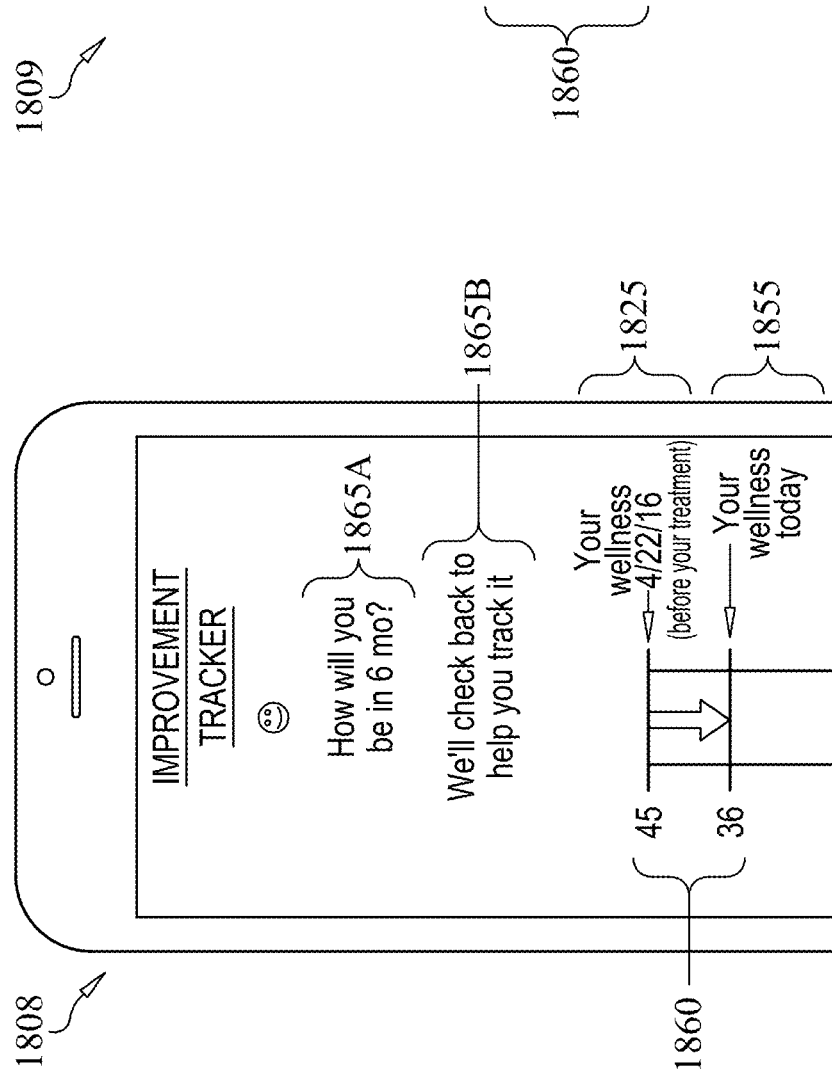
Figure 18L:
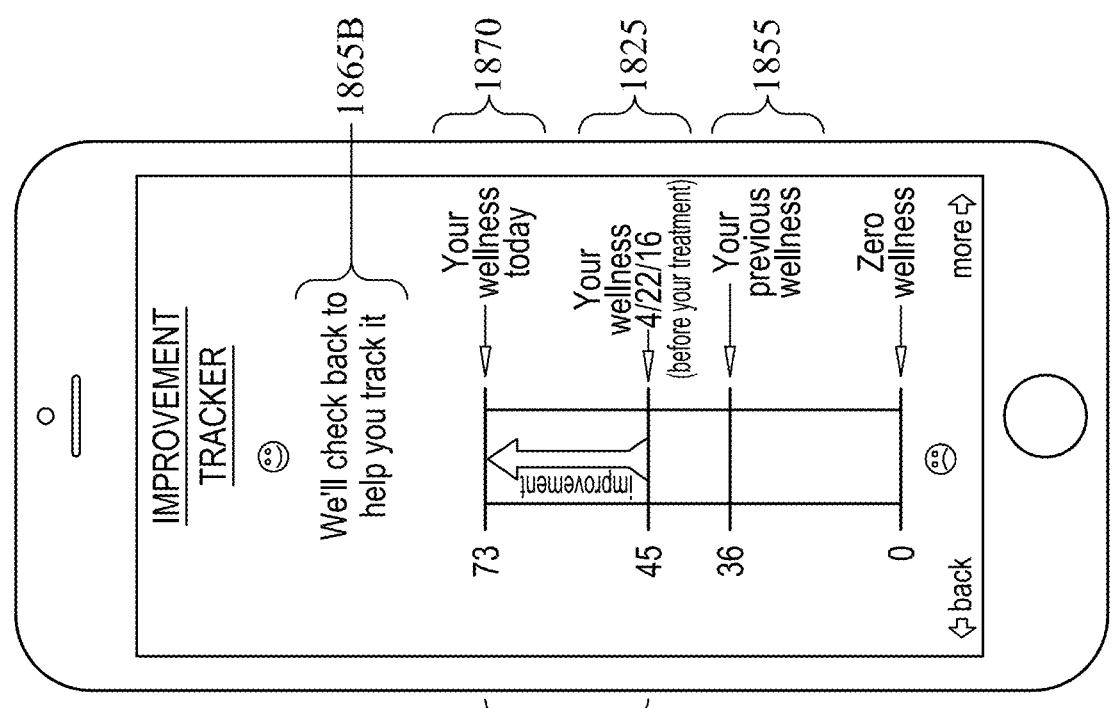
Figure 18K:
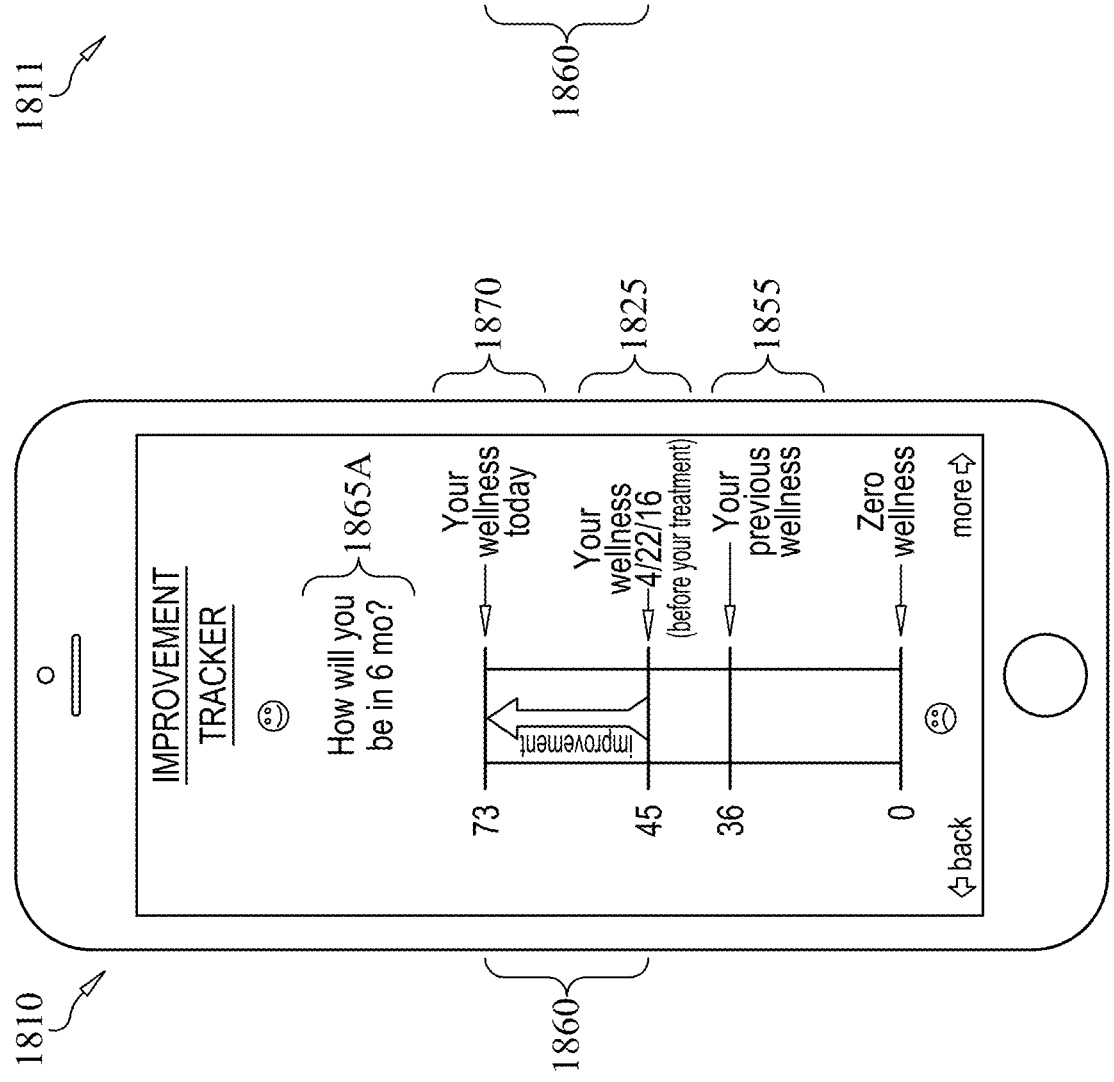
Figure 18N:
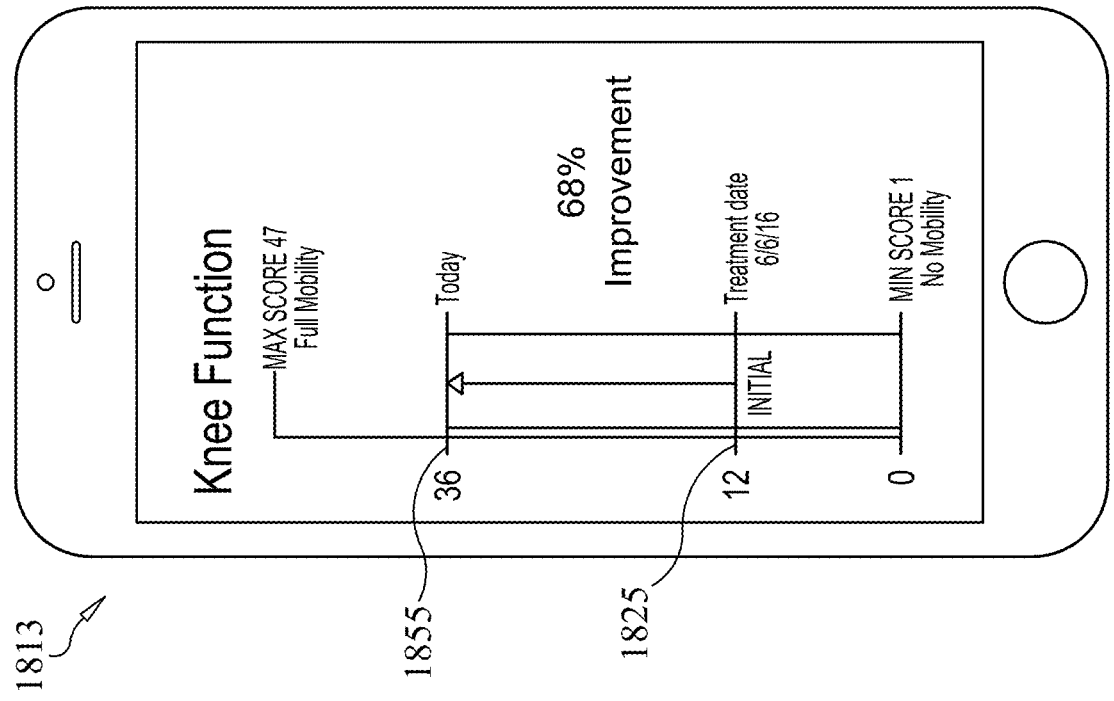

Such an example is presented in a graphical form in the user interface 1813 depicted in FIG. 18N.

A motivation for the measure of relative improvement is that the improvement following a treatment is expected to vary based on a number of factors. For example, a younger patient may be expected to have a greater degree of improvement as compared to an older patient. As another example, a patient with a more severe injury (e.g., a bone fracture) is expected to have a lower degree of improvement as compared to a patient with a less severe injury (e.g., muscle tear).

As an approximation, a treatment effectiveness score for a patient's recovery from a treatment may be set equal to the relative improvement score. Such relationship is only an approximation because there could be many factors to a patient's improving (or declining) health that may not be a result of the treatment and/or the quality of the treatment provider or treatment facility. For instance, a patient's health may improve solely due to the body's innate ability to heal itself (e.g., spontaneous healing). As another example, a patient's health may decline (i.e., treatment recovery may not show an improvement) due to aging, stress from a failed marriage, poor diet, or another reason unrelated to a treatment. In some cases, it is expected that a relative improvement score that is calculated soon after a treatment is performed is a more reliable indicator of the treatment effectiveness than a relative improvement score that is calculated years (or even decades) after a treatment, since the immediate calculation of a relative improvement score can temporally exclude many factors unrelated to the treatment. However, in other cases, it may be true that a relative improvement score that is calculated several months or years after a treatment may be a more reliable indicator of treatment effectiveness than a relative improvement score that is calculated immediately after a treatment, as some treatments may take several months or longer before becoming effective (e.g., medication to treat depression or other mental health issues).

FIG. 15B depicts a bar chart 1520, which compares effectiveness scores for three treatment providers; treatment provider 1, treatment provider 2, and treatment provider 3. In contrast to FIG. 15A, the baseline bars 1525, 1535 and 1545 in FIG. 15B do not depict the pre-treatment wellness scores for individual patients, but rather depict the average pre-treatment wellness scores for three pools of patients that were treated by treatment providers 1, 2 and 3, respectively. Often times the patients within three pools will share at least some common characteristics (e.g., middle aged, female, non-smoking, diabetics, etc.) so that statistically significant differences in the effectiveness scores for the treatment providers may be established. It is noted that the three pools of patients are typically disjoint sets of patients, but it is possible for one patient to have been treated by two or more of treatment providers 1, 2 and 3. Similarly, the improvement bars 1530, 1540 and 1550 do not represent the improvement in wellness scores for individual patients following a certain treatment (e.g., rotator cuff surgery), but rather the average improvement (i.e., change) in wellness scores for the three pools of patients that were treated by treatment providers 1, 2 and 3, respectively. In some circumstances, the treatments provided to the patients of the three patient pools may be the same or very similar (e.g., associated with the same or similar treatment and/or diagnostic codes).

The average pre-treatment wellness scores for the two pools of patients treated by treatment providers 2 and 3 are identical (i.e., 4.3), allowing a comparison between the treatment effectiveness of treatment providers 2 and 3. In the instant example, the average improvement in wellness scores for the pool of patients treated by treatment provider 2 was 2.2, whereas the average improvement in wellness scores for the pool of patients treated by treatment provider 2 was 2.9, indicating that treatment provider 3 is potentially more effective at performing a certain treatment (e.g., rotator cuff surgery) than treatment provider 2 for certain types of patients (i.e., those that share the same characteristics as the pool of patients).

Of the three treatment providers, the average improvement in wellness scores for treatment provider 1 was the lowest at 2.0. Such average improvement in wellness scores for treatment provider 1 may not, however, indicate that treatment provider 1 is any less effective at performing a given treatment (e.g., rotator cuff surgery) than treatment providers 2 and 3. Rather, treatment provider 1 had a pool of patients with a higher average pre-treatment wellness score than treatment providers 2 and 3 (e.g., a healthier group of patients), so it possible that the average improvement average improvement in wellness scores for treatment provider 1 was lower simply due to treatment provider 1 treating a group of patients who were on average healthier before the treatment. It could be the case that if treatment provider 1 instead treated the group of patients that were treated by treatment provider 2, treatment provider 1 could achieve the same (or better) average effectiveness score as treatment provider 2. Therefore, it may be helpful for the average pre-treatment wellness scores between two treatment providers to be the same (or at least similar) before making a comparison between the effectiveness of two treatment providers.

It is further noted that in the case of a treatment that involves a group of treatment providers (as is common for surgery or cancer treatment), the type of comparison of the effectiveness scores provided by bar chart 1520 may between the groups of treatment providers or between treatment providers within a group. However, if a more detailed comparison of a particular treatment provider outside of his or her group (e.g., a comparison of three surgeons) is desired, it may be necessary to collect and/or analyze more data before making any inferences or conclusions regarding the relative effectiveness of the three surgeons. For example, data may need to be collected regarding factors that may impact the effectiveness of the surgery other than the skill of the surgeon (e.g., the availability and relative skill of support staff present for each of the surgeons when performing the surgery, the type of equipment available to perform the surgery, etc.) so that meaningful comparisons between the three surgeons may be made.

FIG. 15C illustrates that the patient pool (or the subset of patients being analyzed) could alter the results of the bar chart. Assume that the three treatment providers represented in the bar chart 1555 of FIG. 15C are identical to the three treatment providers represented in the bar chart 1520 of FIG. 15B. Further assume that the patient pools are different between the bar charts. For instance, suppose the patient pool represented in bar chart 1555 include females who are middle-aged, non-smokers, and diabetic, whereas the patient pool represented in bar chart 1520 include females who are middle-aged, smokers, and diabetic. In the example of FIGS. 15B and 15C, all the bars depicted in bar chart 1555 are identical to the bars depicted in bar chart 1520 (i.e., bar 1560 is identical to bar 1525, bar 1570 is identical to bar 1535, and bar 1580 is identical to bar 1545) however, improvement bars 1565, 1575, and 1585 are different from improvement bars 1530, 1540, and 1550. Assuming that the patient pools of bar chart 1520 have a first set of characteristics (e.g., age, gender, comorbidities) and the patient pools of bar chart 1550 have a second set of characteristics, a comparison of bar chart 1520 with 1555 may serve to indicate which treatment provider is better at providing a treatment to a patient with the first set of characteristics as opposed to the second set of characteristics. For example, improvement bars 1565, 1575, and 1585 may indicate that treatment provider 1 is more effective (highest value for the improvement bar) at treating patients with a second set of characteristics and treatment provider 3 is more effective at treating patients with the first set of characteristics.

Figure 16A:
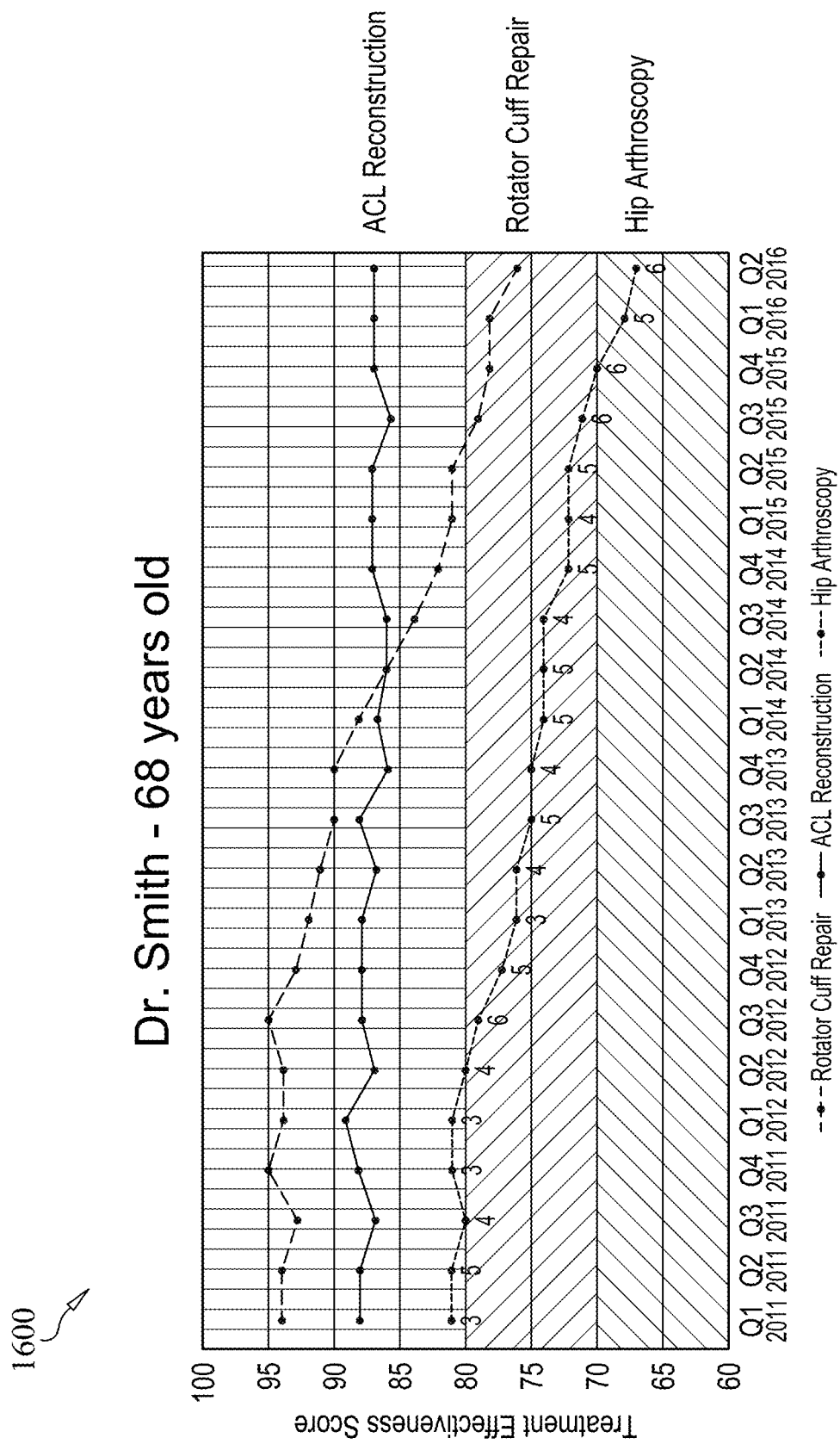
FIGS. 16A and 16B provide graphs that visually display treatment effectiveness scores along the Y-axis as a function of time along the X-axis, in accordance with some embodiments of the present invention.
Figure 16B:
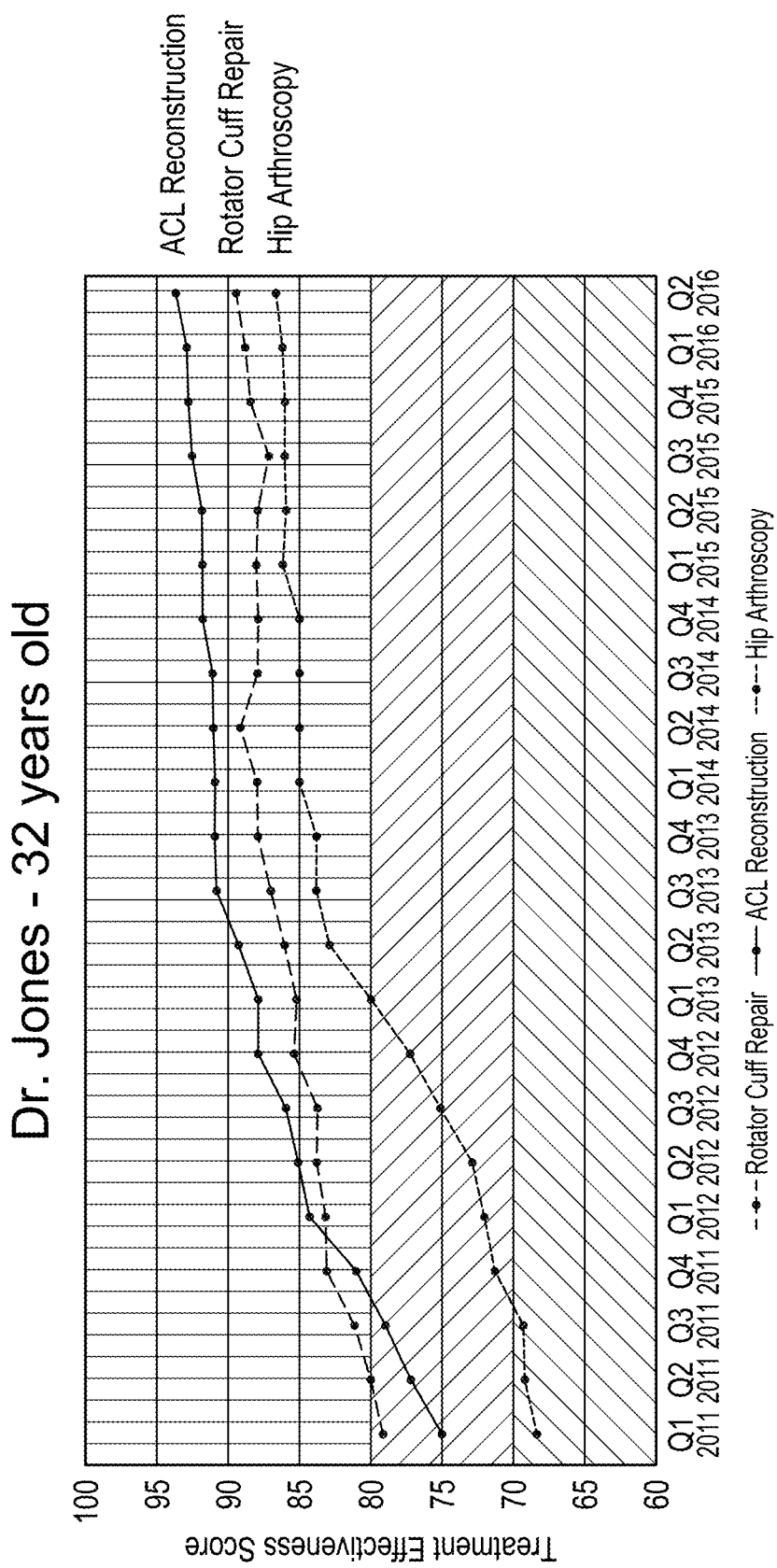

FIGS. 16A and 16B provide graphs 1600 and 1601, respectively, that visually display treatment effectiveness scores on a scale (e.g., between 60 and 100) along the Y-axis as a function of time along the X-axis. The Y-axis may be broken down into one or more ranges of values (e.g., 60-70, 70-80 and 80-100) according to, for example, treatment facility or treatment provider preference. The ranges may be set up by, for example, a treatment facility, in order to assist in determinations of treatment provider/doctor competency and/or quality of patient care. For instance, a treatment effectiveness score range of 60-70, 70-80, and 80-100 may indicate an unsatisfactory level of patient care, satisfactory level of patient care and an excellent level of patient care, respectively. The information displayed in FIGS. 16A and 16B may be used to establish, for example, relative treatment provider quality which may, in turn, be used to establish work assignments or privileges for particular treatments. For example, doctors associated with a treatment effectiveness score range of 80-100 for a particular treatment may be assigned to perform that particular treatment on more patients, while doctors associated with a treatment effectiveness score range of 60-70 for a particular treatment may be reassigned to perform an alternative treatment for which they have higher treatment effectiveness scores. When a treatment effectiveness score falls below a certain threshold (e.g., 75) and/or shows a downward decline, this may trigger an intervention by a treatment facility according to treatment facility rules and guidelines. Interventions may be as simple as a quick conversation to determine a reason for the downward trend or as severe as a revocation of privileges to perform the treatment at the treatment facility.

Graphs, such as graphs 1600 and 1601, may be used to, for example, track doctor performance for various treatments over time. Graphs similar to graphs 1600 and 1601 may be used to track any effectiveness score related to a treatment, diagnosis, and/or treatment outcome over time using system 100. For example, graphs similar to 1600 and 1601 may be generated that are treatment specific so that treatment effectiveness scores for various treatments or procedures associated with a diagnosis may be tracked over time. This information may be used to assess, for example, which treatments work best over time or when/how a change to a treatment procedure affects the treatment effectiveness score for the procedure.

Returning to FIG. 16A, graph 1600 provides treatment effectiveness scores for ACL reconstruction surgery, rotator cuff repair surgery, and hip arthroscopy as performed by a first treatment provider, in this case Dr. Smith, from the first quarter of 2011 to the second quarter of 2016 with the first range being between 60 and 70, the second range being between 70 and 80, and the third range being between 80 and 100. The graph 1600 demonstrates that Dr. Smith's treatment effectiveness scores for rotator cuff repair surgery and hip arthroscopy treatments have declined over time while Dr. Smith's effectiveness scores for ACL reconstruction treatments have remained relatively constant over time. These trends may indicate to, for example, hospital administration and/or insurance companies that Dr. Smith's declining treatment effectiveness scores are a cause for concern and that an investigation is warranted to determine the reasons why the treatment effectiveness scores for Dr. Smith's rotator cuff repair surgery and hip arthroscopy treatments have declined over time.

In some instances, such as when a treatment effectiveness score for a doctor's treatments falls below a predetermined number (e.g., 60), the doctor's privileges to perform the treatment at the treatment facility may be revoked (e.g., the doctor's card key may be de-activated, the doctor's name may be removed from the hospital directory, etc.). For instance, because Dr. Smith's treatment effectiveness scores for hip arthroscopy have been scored at 70 or below for three consecutive quarters (Q4 2015-Q2 2016), treatment facility administrative staff may decide to revoke Dr. Smith's privileges for performing hip arthroscopy treatments according to, for example, a policy of the treatment facility.

In some instances, while declining treatment effectiveness scores could indicate a declining quality of care, this is not always so, as there could be other factors that could cause declining treatment effectiveness scores, other than a declining quality of care. For instance, declining treatment effectiveness scores could be due to a mutation of a virus or bacteria. For instance, an antibiotic resistant strain of bacteria could develop, leading to patients recovering at a slower pace or not recovering at all. As another example, a downturn in the economy could cause patients to experience a greater degree of stress, leading to a slower pace of recovery for patients. It should be evident that declining treatment effectiveness scores exhibited in these scenarios might have nothing to do with a declining quality of care. Nevertheless, declining treatment effectiveness scores still might be a useful statistical indicator that prompts an investigation into a root cause of the declining scores, whether due to a declining quality of patient care or other factor.

Graph 1601 of FIG. 16B provides treatment effectiveness scores for ACL reconstruction surgery, rotator cuff repair surgery, and hip arthroscopy as performed by a second treatment provider, in this case Dr. Jones, from the first quarter of 2011 to the second quarter of 2016 with the first range being between 60 and 70, the second range being between 70 and 80, and the third being between 80 and 100. Graph 1601 may demonstrate that Dr. Jones' treatment effectiveness scores for all three treatments have increased over time in a manner consistent with a surgeon who skills are improving.

It is, however, noted that treatment effectiveness scores may not definitively be correlated with a treatment provider's skill, as there could be numerous factors that could cause increasing treatment effectiveness scores, other than a treatment provider's skill. For example, a hospital might receive a large grant from the government that allows the hospital to purchase state of the art equipment, build new patient rooms, etc., which contribute to increasing treatment effectiveness scores. As another example, new cancer treatments may be developed which increase the cancer remission rate of patients. In such case, it may be debatable whether the improved treatment effectiveness is due to the skill of the treatment provider or due to the new cancer treatments. Nevertheless, increasing treatment effectiveness scores still might be a useful statistical indicator that prompts an analysis of the skill of a doctor.

In some instances, treatment effectiveness scores for treatments and/or treatment providers may be monitored and an automated or semi-automated notification process (e.g., performed by a software daemon) may be set up for a treatment facility and/or treatment provider with the purpose of notifying the treatment facility and/or treatment provider that treatment effectiveness scores for treatments and/or treatment providers have fallen below a certain threshold. In this way, a treatment facility administrator may monitor the treatment effectiveness scores for the doctors with privileges to perform treatments at the treatment facility (at which the administrator is employed) as a background process.

FIGS. 18A-18N provide screenshots of various user interfaces 1800-1813 by which a patient may be provided with information about his or her health and/or wellness. The information gathered from and/or provided to a patient via interfaces 1800-1813 may be generated, processed, analyzed, and/or stored in accordance with one or more processes described herein. In most instances, the information provided to a patient via the interfaces 1800-1813 of FIGS. 18A-18N will be associated with the patient's wellness account as established/provided via execution of one or more of process(es) 800, 900, 1000, and/or 1100.

Some of interfaces 1800-1813 refer to an xxxxxx wellness, whereby the "xxxxxx" is a placeholder for a particular type of wellness relevant to the patient and/or the subject of a patient's wellness account. For example, if the patient is undergoing treatment for breast cancer, the "xxxxxx" placeholder may be changed to "breast wellness." Likewise, if the patient is undergoing treatment for a torn rotator cuff, the "xxxxxx" placeholder may be changed to "rotator cuff wellness" or "shoulder wellness." In some instances, the "xxxxxx" placeholder may indicate a patient's name or user name.

Often times, interfaces 1800-1813 will relate to one particular condition, diagnosis, or treatment for a patient but this need not always be the case. For example, a patient's wellness account may be set up and/or modified according to, for example, process 800 and/or 900 to monitor multiple conditions for which the patient is being treated. For example, the wellness indicators may provide an indication of the patient's wellness with regard to multiple conditions, diagnoses, and/or treatments. In some circumstances, the wellness information may be determined relative to a plurality of discrete conditions, diagnoses, and/or treatments and, in other circumstances, the wellness information may be determined by aggregating the plurality of determinations and/or determining an overall wellness that factors in one or more of the conditions, diagnoses, and/or treatments relevant to the patient.

FIG. 18A provides an initial interface 1800 that shows a patient his or her wellness score 1825 prior to the patient undergoing a treatment (i.e., a pre-treatment wellness score) along with a message providing information regarding the wellness score (i.e., "your pre-treatment xxxxxx wellness score is"). In the example of FIG. 18A, the patient's pre-treatment wellness score is 45. This score may be determined via execution of, for example, process 1000 and/or 1100 as discussed above with regard to FIGS. 10 and 11, respectively. For example, the wellness score 1825 provided by initial interface 1800 may be analogous to the indication of the patient's wellness provided to the patient via execution of step 1035 or 1075 and/or a state of recovery and/or wellness provided to the patient via execution of step 1135.

FIG. 18B shows a preliminary improvement tracker interface 1801 that provides a patient with an indicator of his or her wellness today 1825 (e.g., pre-treatment wellness score) as shown on a bar graph that also provides an indicator of a zero wellness score. The wellness score of preliminary improvement tracker interface 1801 is determined in a manner similar to the determination of the wellness score of initial interface 1800. FIG. 18B also provides a message, or heading ("improvement tracker"), 1830 that serves to indicate what the information on interface 1801 relates to.

FIG. 18C provides an updated improvement tracker interface 1802 that shows a projection (or prediction) 1840 of the patient's wellness within a given time period (shown as an improvement arrow), in this case, within three months along with a message 1845 regarding the projection 1840. The projection of the patient's wellness may be determined via execution of process 1401 and/or use of a baseline and/or modified recovery vector as discussed above with regard to processes 700, 900, 1100, and shown in FIGS. 7, 9, and 11, respectively. For example, the patient may be undergoing treatment for a knee replacement and the pre-treatment wellness score of 45 may indicate that he or she has limited mobility and substantial knee pain. The projection of the patient's wellness may be determined based on how much it is expected that the patient's mobility will improve and pain will decrease using a baseline recovery vector for knee replacements and/or a modified baseline recovery vector for knee replacements that is modified according to, for example, one or more other considerations related to the patient. For example, the modified baseline recovery vector for knee replacements may incorporate one or more other considerations stemming from, for example, the patient's medical condition, age, gender, weight and/or the treatment itself (e.g., type of replacement used, complexity of the surgery, etc.). In some instances, the contributing factors may also incorporate post-treatment activity such as physical therapy and medication. Additionally, or alternatively, execution of some, or all, of process(es) 700, 900, and/or 1100 may be used to determine and/or assist with a determination of a projection of the patient's wellness and/or wellness score.

FIG. 18D shows an interface 1803 similar to that of interface 1801, with the additional message 1850 (i.e., "We'll check back to help you track it") indicating a next step in the wellness account and/or wellness measurement process.

FIG. 18E shows an improvement interface 1804 that provides a bar graph with an indication of a patient's first post-treatment wellness score (i.e., current wellness, or wellness today) 1855, which has a score of 73 (i.e., wellness today), in relation to the patient's wellness at a previous time 1825 (i.e., pre-treatment wellness) (which has a score of 45) and provides an improvement arrow 1860 to demonstrate how much the patient's wellness has improved. Determination of the patient's "wellness today" may be made via execution of, for example, process 1100, 1200, 1400. For example, the patient's wellness account may indicate that one or more particular OMDs are to be provided to a patient (e.g., execution of step 1020 and/or 1045) and, the received response to the OMD may be compared with a baseline recovery vector and/or modified baseline recovery vector associated with the patient wellness account to determine the patient's "wellness today."

FIG. 18F shows an interface 1805 similar to that of interface 1804 with the exception that interface 1805 provides a message 1865A to the patient indicating when the patient's wellness score will be calculated again (i.e., "How will you be in 6 mo.?"). FIG. 18G shows an interface 1806 similar to that of interface 1804 with the exception that interface 1806 provides an encouraging message 1865B to the patient (i.e., "We'll check back to help you track it"). The differing messages of interfaces 1805 and 1806 may provide an indication of, for example, a patient wellness account configuration preference for the types of messages to be delivered.

FIG. 18H shows an interface 1807 that provides an indication of a patient's current wellness, when the patient has not improved over a given time period, in the form of a bar graph. In the example of interface 1807, the patient's wellness score has dropped from the pre-treatment wellness score 1825 value of 45 to a first post-treatment wellness score 1855 value of 36 and, as such, the improvement arrow 1860 for interface 1807 is pointing downward (i.e., indicating that the wellness score has decreased relative to the pre-treatment wellness score). FIG. 18I shows an interface 1808 similar to that of interface 1807 with the exception that interface 1808 provides a message 1865A to the patient indicating when the patient's wellness score will be calculated again (i.e., "How will you be in 6 mo.?") and an encouraging message 1865B to the patient (i.e., "We'll check back to help you track it").

FIG. 18J shows an interface 1809 that provides an indication of a patient's second wellness score 1870 (i.e., current wellness score at a second check in point of the wellness protocol) associated with the patient's wellness account. Interface 1809 provides a bar graph showing that the patient's second post-treatment wellness score is 73 and also shows how the patient has improved from their pre-treatment wellness score 1825 of 45 in the form of improvement arrow 1860.

FIG. 18K shows an interface 1810 similar to that of interface 1809 with the exception that interface 1810 provides message 1865A to the patient indicating when the patient's wellness score will be calculated again (i.e., "How will you be in 6 mo.?"). FIG. 18L shows an interface 1811 similar to that of interface 1809 with the exception that interface 1811 provides encouraging message 1865B to the patient (i.e., "We'll check back to help you track it").

Figure 18M:
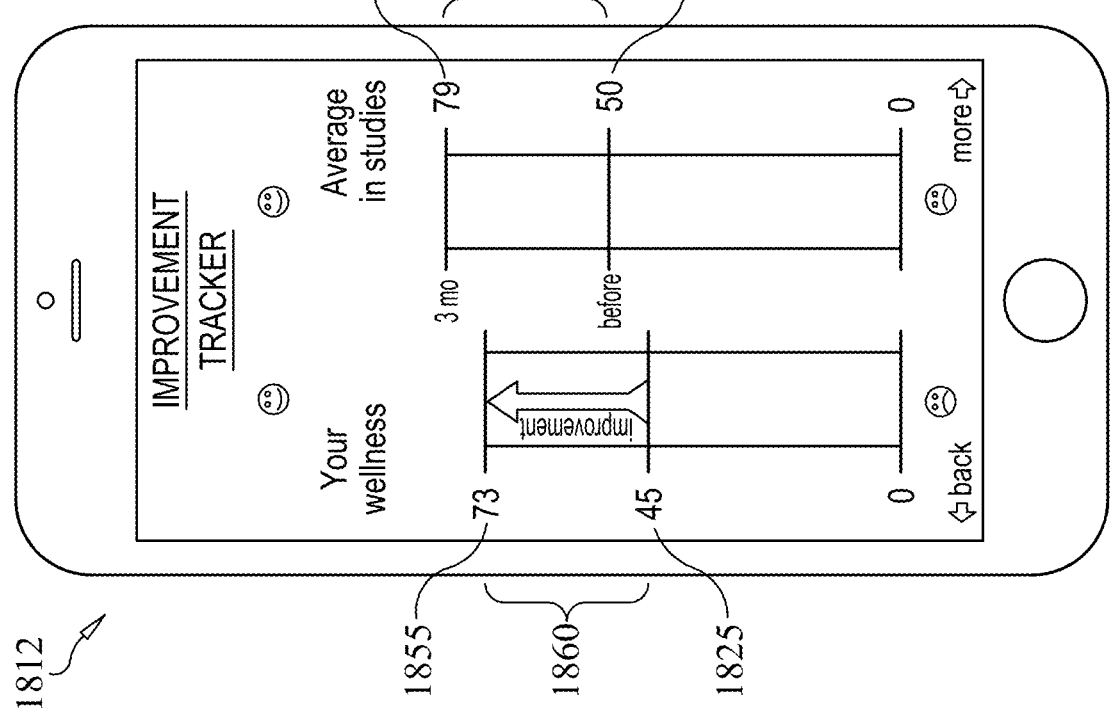

FIG. 18M shows an interface 1812 that provides an indication of a patient's current wellness as compared to a baseline and/or modified wellness vector (i.e., average in studies) for the treatment in the form of two side-by-side bar graphs. The bar graph showing the baseline and/or modified wellness vector provides an average pre-treatment wellness score 1870 of 50, a first post-treatment wellness score 1875 of 79, and an improvement in the wellness score 1880 with a value of 29.

FIG. 18N shows an interface 1813 that provides a patient's wellness scores regarding his/her "knee function". As depicted in the bar chart of interface 1813, the patient's pre-treatment wellness score is 12, and the patient's first post-wellness score is 36. The minimum wellness score of 1 is also depicted (corresponding to no mobility of the knee) and the maximum wellness score of 47 is also depicted (corresponding to full mobility of the knee, wherein the maximum value of "47" is established by the OMD used to determine the wellness score), which provide reference points for the patient's wellness scores. The improvement in the patient's wellness score is 36−12=24, and the improvement score relative to the maximum possible improvement score is 68%, calculated as ((36−12)/(47−12))*100%.

Although not shown in interfaces 1800-1813, a patient's wellness account may separately monitor different aspects of a treatment recovery process and/or separately monitor different treatments and/or diagnosis relevant to the patient wellness account. For example, a patient's wellness account may separately monitor several indicators of a patient's recovery from a treatment simultaneously using, for example, responses to one or more OMDs. Indicators of the patient's wellness with regard to each of these indicators may then be provided to the patient via, for example, interfaces like interfaces 1800-1813.

Figure 19A:
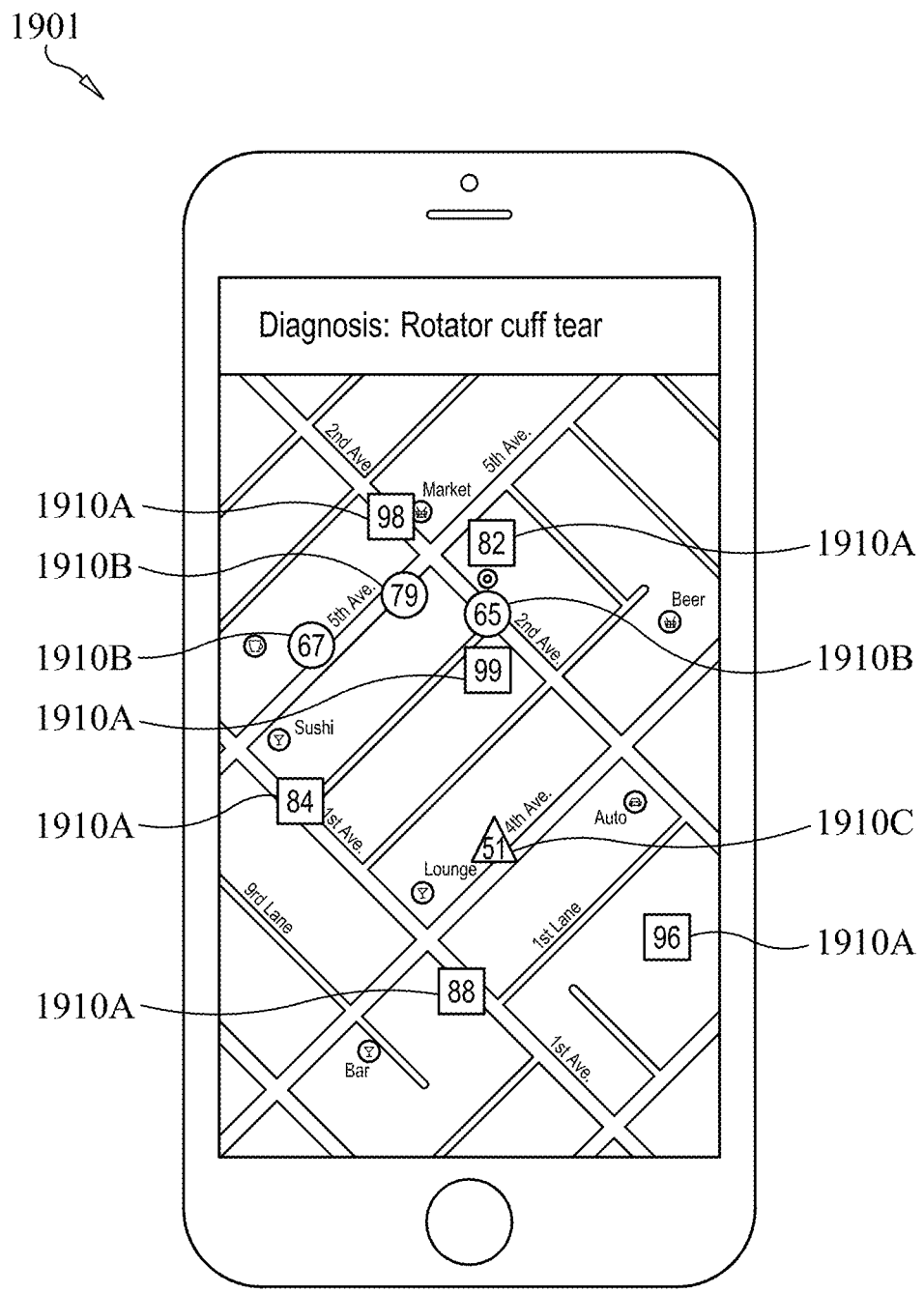
FIGS. 19A-19C provide a series of interfaces responsive to a request for a treatment provider, in accordance with some embodiments of the present invention.
Figure 19B:
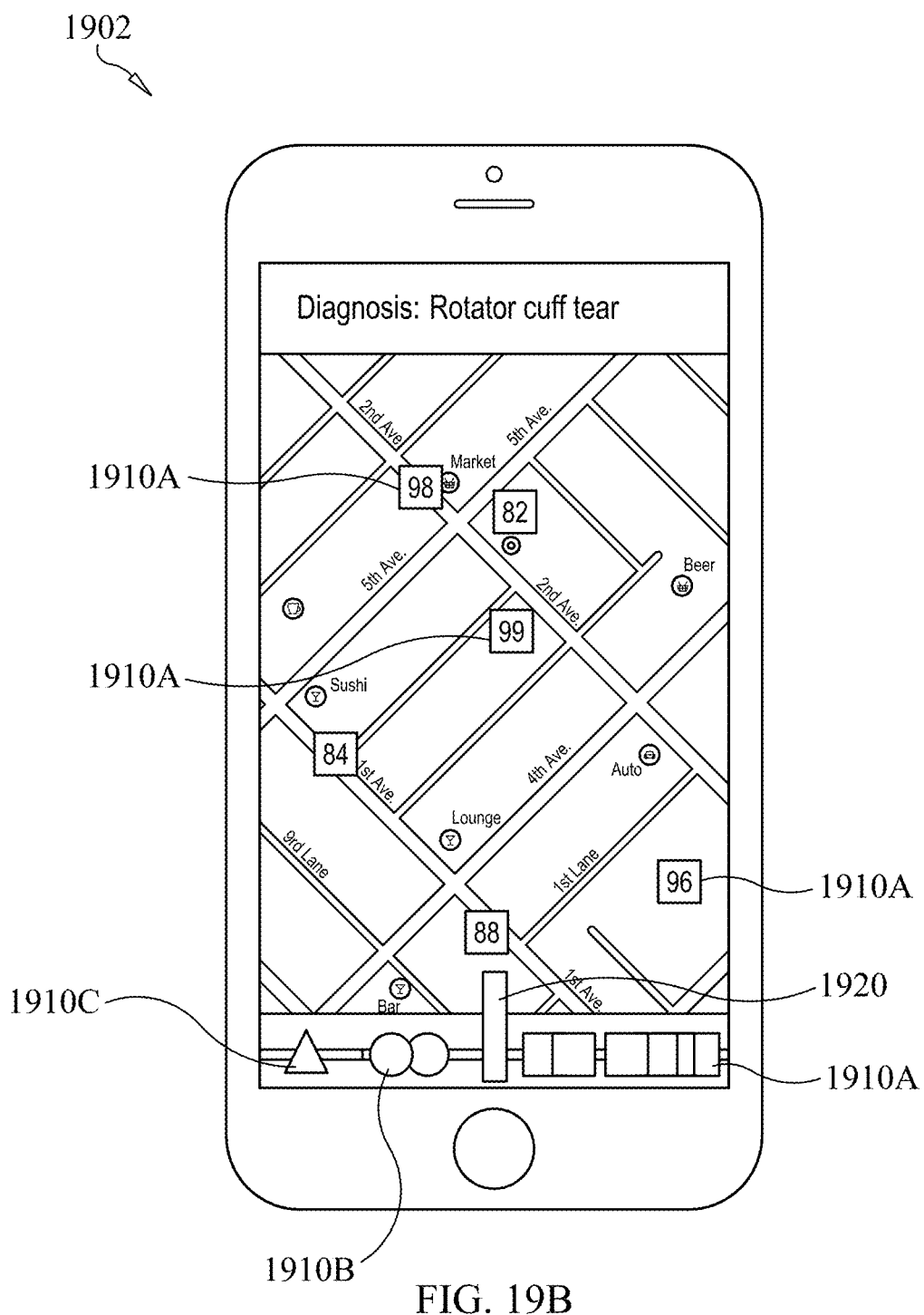
Figure 19C:

FIGS. 19A-19C provide a series of interfaces responsive to a request (executed in, or example, step 1301, discussed above with regard to FIG. 13) for a treatment provider who provides treatments for a diagnosis of a rotator cuff tear and who is located in the New York, N.Y. geographical area.

FIG. 19A provides an exemplary treatment provider interface 1901 overlaid on a map of the requested geographical area. As can be seen in FIG. 19A, interface 1901 provides a plurality of icons 1910 that display an effectiveness score for each of a plurality of treatment providers who are trained to treat patients with a rotator cuff tear diagnosis and/or are trained to provide a rotator cuff repair treatment within a geographical area. The icons 1910 of interface 1901 may be depicted with a plurality of contrasting characteristics (e.g., contrasting in terms of shape, color, texture, etc.) so that icons depicted with a first characteristic represent treatment providers with a first range of effectiveness scores, icons depicted with a second characteristic represent treatment providers with a second range of effectiveness scores, and so on. In a preferred embodiment, the ranges of effectiveness scores are non-overlapping ranges. In the example of FIG. 19A, square icons 1910A represent treatment providers with effective scores of 80 or above, circular icons 1910B represent treatment providers with effectiveness scores within the range of 60-79, while triangular icons 1910C represent treatment providers with effectiveness scores below 59. In this way, the patient can easily determine the respective locations of the treatment providers, as well as the treatment providers with the highest effectiveness scores for his or her particular diagnosis or requested treatment.

FIG. 19B provides an alternative treatment provider map interface 1902 with a slider bar 1920 positioned at the bottom of the interface. The slider bar 1920 allows the patient to selectively display treatment providers with an effectiveness score above a certain threshold. In the example of FIG. 19C, the slider bar 1920 is set to a position which results in only the treatment providers with an effectiveness score above 80 to be displayed. Further, icons 1925 are depicted on (or over) the slider bar at positions representative of their associated effectiveness scores, allowing the patient to easily see a distribution of the treatment providers' effectiveness scores (i.e., whether there are many treatment providers with high effectiveness scores, whether there are many treatment providers with low effectiveness scores, etc.).

A patient may access further information regarding any of the treatment providers displayed on the interface by selecting the respective icon (on the interface 1901 and/or 1902) that represents the treatment provider. The further information regarding the treatment provider may be presented to the patient via a treatment provider interface, such as the treatment provider interface 1903 shown in FIG. 19C. Treatment provider interface 1903 may provide, for example, address and other contact information of the treatment provider, as well as one or more ways for the patient to schedule an appointment with the treatment provider. Treatment provider interface 1903 may also provide billing information (e.g., an estimate of how much the selected procedure will cost) and/or health insurance information (e.g., which health insurances are accepted by the treatment provider). Such further information in addition to the effectiveness scores discussed above may allow a patient to make a more informed decision when selecting a treatment provider.

Figure 25:
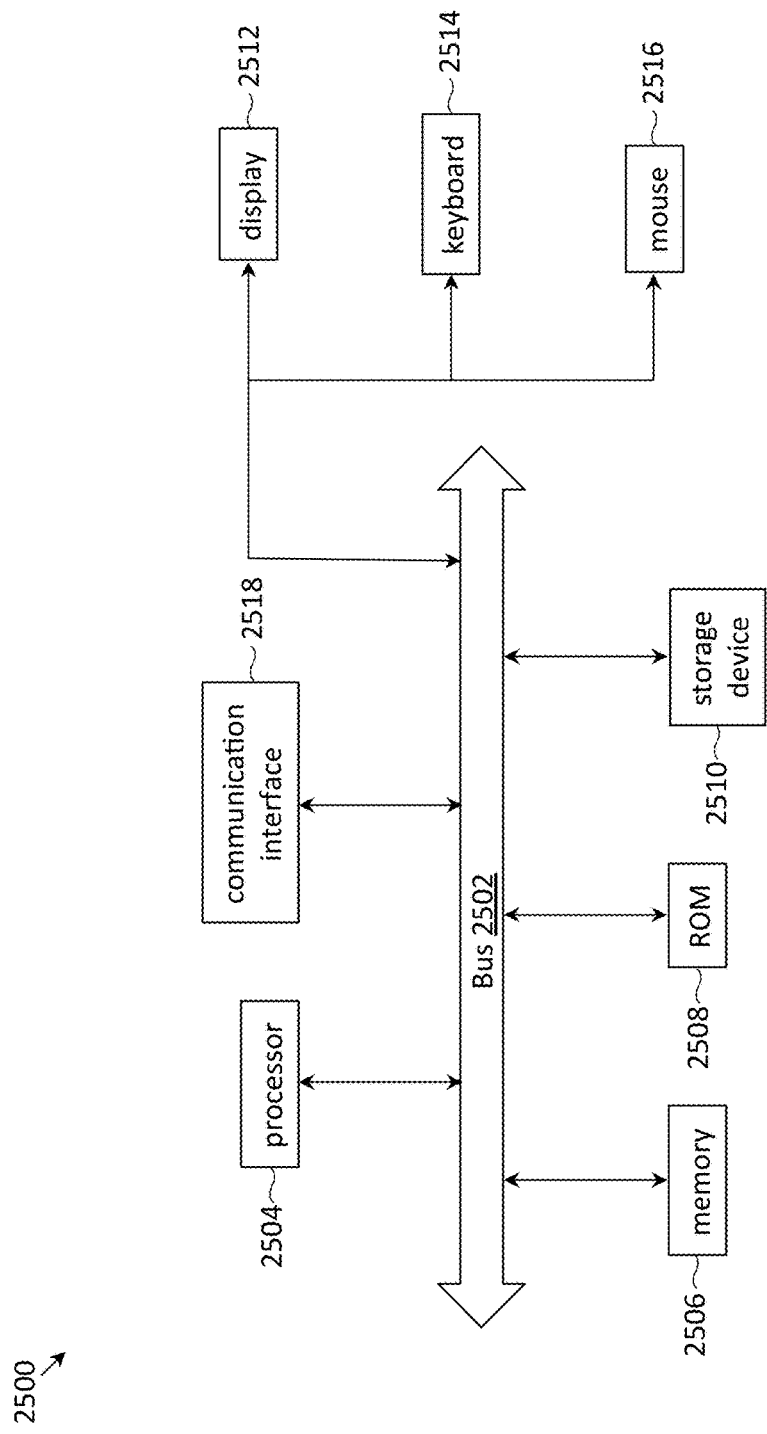
FIG. 25 depicts components of a computer system in which computer readable instructions instantiating the methods of the present invention may be stored and executed in accordance with some embodiments of the present invention.

FIG. 25 depicts components of a computer system 2500 in which computer readable instructions instantiating the methods of the present invention may be stored and executed. As is apparent from the foregoing discussion, aspects of the present invention involve the use of various computer systems and computer readable storage media having computer-readable instructions stored thereon. FIG. 25 provides an example of a system 2500 that may be representative of any of the computing systems (e.g., server 102, treatment provider device 124, patent device 128, HIPAA compliance server 126, treatment facility computer system 134, etc.) discussed herein. Examples of system 2500 may include a smartphone, a desktop, a laptop, a mainframe computer, an embedded system, etc. Note, not all of the various computer systems have all of the features of system 2500. For example, certain ones of the computer systems discussed above may not include a display inasmuch as the display function may be provided by a client computer communicatively coupled to the computer system or a display function may be unnecessary. Such details are not critical to the present invention.

System 2500 includes a bus 2502 or other communication mechanism for communicating information, and a processor 2504 coupled with the bus 2502 for processing information. Computer system 2500 also includes a main memory 2506, such as a random access memory (RAM) or other dynamic storage device, coupled to the bus 2502 for storing information and instructions to be executed by processor 2504. Main memory 2506 also may be used for storing temporary variables or other intermediate information during execution of instructions to be executed by processor 2504. Computer system 2500 further includes a read only memory (ROM) 2508 or other static storage device coupled to the bus 2502 for storing static information and instructions for the processor 2504. A storage device 2510, for example a hard disk, flash memory-based storage medium, or other storage medium from which processor 2504 can read, is provided and coupled to the bus 2502 for storing information and instructions (e.g., operating systems, applications programs and the like).

Computer system 2500 may be coupled via the bus 2502 to a display 2512, such as a flat panel display, for displaying information to a computer user. An input device 2514, such as a keyboard including alphanumeric and other keys, may be coupled to the bus 2502 for communicating information and command selections to the processor 2504. Another type of user input device is cursor control device 2516, such as a mouse, a track pad, or similar input device for communicating direction information and command selections to processor 2504 and for controlling cursor movement on the display 2512. Other user interface devices, such as microphones, speakers, etc. are not shown in detail but may be involved with the receipt of user input and/or presentation of output.

The processes referred to herein may be implemented by processor 2504 executing appropriate sequences of computer-readable instructions contained in main memory 2506. Such instructions may be read into main memory 2506 from another computer-readable medium, such as storage device 2510, and execution of the sequences of instructions contained in the main memory 2506 causes the processor 2504 to perform the associated actions. In alternative embodiments, hard-wired circuitry or firmware-controlled processing units may be used in place of or in combination with processor 2504 and its associated computer software instructions to implement the invention. The computer-readable instructions may be rendered in any computer language.

In general, all of the above process descriptions are meant to encompass any series of logical steps performed in a sequence to accomplish a given purpose, which is the hallmark of any computer-executable application. Unless specifically stated otherwise, it should be appreciated that throughout the description of the present invention, use of terms such as "processing", "computing", "calculating", "determining", "displaying", "receiving", "transmitting" or the like, refer to the action and processes of an appropriately programmed computer system, such as computer system 2500 or similar electronic computing device, that manipulates and transforms data represented as physical (electronic) quantities within its registers and memories into other data similarly represented as physical quantities within its memories or registers or other such information storage, transmission or display devices.

Computer system 2500 also includes a communication interface 2518 coupled to the bus 2502. Communication interface 2518 may provide a two-way data communication channel with a computer network, which provides connectivity to and among the various computer systems discussed above. For example, communication interface 2518 may be a local area network (LAN) card to provide a data communication connection to a compatible LAN, which itself is communicatively coupled to the Internet through one or more Internet service provider networks. The precise details of such communication paths are not critical to the present invention. What is important is that computer system 2500 can send and receive messages and data through the communication interface 2518 and in that way communicate with hosts accessible via the Internet. It is noted that the components of system 2500 may be located in a single device or located in a plurality of physically and/or geographically distributed devices.

Thus, methods and systems for determining a pre-treatment wellness score a post-treatment wellness score, an improvement score, and/or an effectiveness score with regard to a medical treatment have been described. It is to be understood that the above-description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

We claim:

1. A computer-implemented method comprising:
    receiving, by a server, an indication that a medical treatment has been scheduled for a patient from a medical treatment scheduler communicatively coupled to the server over a communication network, the indication being encoded with a medical treatment code, an identity of the patient that is mapped to an anonymous identifier used to anonymize identifying information of the patient, the patient being associated with an electronic medical record (EMR) stored in an EMR database, the anonymous identifier being known to both the server and the EMR database, the EMR database being a device that is physically separate from the server and the medical treatment scheduler being a device that is physically separate from the EMR database and the server;
    determining, by the server, a plurality of medical questionnaires associated with the medical treatment code responsively to the received indication that the medical treatment has been scheduled;
    querying, by the server, a database of medical questionnaires for the plurality of medical questionnaires specific to the medical treatment code over the communication network, each of the medical questionnaires being associated with a scoring procedure;
    receiving, by the server, the plurality of medical questionnaires specific to the medical treatment code from the database of medical questionnaires responsively to the querying of the database of medical questionnaires;
    querying, by the server, the EMR database using the anonymous identifier mapped to the identity of the patient over the communication network for one or more characteristics of the patient;
    receiving, by the server, the queried for one or more characteristics of the patient from the EMR database responsively to the querying of the EMR database;
    determining, by the server, which specific medical questionnaire of the plurality of medical questionnaires to provide to the patient using the one or more characteristics of the patient;
    combining, by the server, the anonymous identifier mapped to the identity of the patient to data representing the specific medical questionnaire;
    communicating, by the server, a combination of the data representing the specific medical questionnaire and the anonymous identifier mapped to the identity of the patient to a patient device physically separate from and communicatively coupled to the server over the communication network, the patient device including a processor configured to display the specific medical questionnaire to the patient, receive a set of responses to the specific medical questionnaire from the patient, and communicate the received set of responses and the anonymous identifier mapped to the identity of the patient to the server;
    receiving, by the server, a set of responses to the specific medical questionnaire and the anonymous identifier mapped to the identity of the patient from the patient device over the communication network;
    determining, by the server, a wellness score for the patient by applying the scoring procedure for the specific medical questionnaire to the set of responses; and
    communicating, by the server, anonymized data representing the wellness score to the patient device over the communication network, the patient device being configured to display the wellness score to the patient.

2. The computer-implemented method of claim 1, wherein the wellness score is a raw wellness score provided on a scale determined by the scoring procedure, the method further comprising:
    adjusting, by the server, the raw wellness score to be on a normalized scale, thereby generating an adjusted wellness score, wherein facilitating provision of the wellness score to the patient includes facilitating provision of the adjusted wellness score to the patient.

3. The computer-implemented method of claim 1, wherein the medical questionnaire is provided to the patient as a first questionnaire, the method further comprising:
    providing, by the server, a second medical questionnaire to the patient device, the second medical questionnaire being different from the first medical questionnaire and associated with a second scoring procedure for scoring responses to the second medical questionnaire, wherein the second scoring procedure and a second identifier of the second medical questionnaire are stored in a scoring-procedure database and the second identifier of the second medical questionnaire is used to retrieve the second scoring procedure from the scoring-procedure database;
    wherein the set of responses includes responses to the first medical questionnaire and the second medical questionnaire, the method further comprising:
        associating, by the server, each of the responses in the set of responses responsive the first questionnaire into a first set of responses;
        retrieving, by the server, the first scoring procedure from the scoring-procedure database using an identifier of the first medical questionnaire;
        determining, by the server, a first wellness score by applying the first scoring procedure to the first set of responses;
        associating, by the server, each of the responses in the set of responses responsive the second questionnaire into a second set of responses;
        retrieving, by the server, the second scoring procedure from the scoring-procedure database using the identifier of the second medical questionnaire;
        determining, by the server, a second wellness score by applying the second scoring procedure to the second set of responses;
        facilitating, by the server, provision of the first and second wellness scores to the patient.

4. The computer-implemented method of claim 1, wherein facilitating provision of the wellness score to the patient further comprises:
  determining, by the server, whether the medical questionnaire is associated with alternate terminology for a name of the medical questionnaire;
  providing, by the server, the alternate terminology to the patient along with the wellness score responsively to a determination that the medical questionnaire is associated with alternate terminology.

5. The computer-implemented method of claim 1, further comprising:
  receiving, by the server, an indication of at least one of a diagnosis and a treatment associated with the patient prior to facilitating provision of the medical questionnaire to the patient;
  selecting, by the server, the medical questionnaire for provision to the patient responsively to the indication.

6. The computer-implemented method of claim 1, wherein facilitating provision of the wellness score to the patient further comprises:
  receiving, by the server, an indication of at least one of a diagnosis and a treatment associated with the patient prior to facilitating provision of the wellness score to the patient;
  determining, by the server, whether the at least one diagnosis and treatment are associated with alternate terminology for a name of the least one diagnosis and treatment; and
  providing, by the server, the alternate terminology to the patient along with the wellness score responsively to a determination that the least one diagnosis and treatment is associated with alternate terminology.

7. The computer-implemented method of claim 1, wherein facilitating provision of the wellness score to the patient further comprises:
  providing, by the server, the patient with a numerical wellness score; and
  depicting, by the server, a location for the numerical wellness score within a graphically represented wellness score progress chart, a location of the numerical wellness score on the graphically represented wellness score progress chart being associated with a magnitude of the numerical wellness score.

8. The computer-implemented method of claim 1, wherein facilitating provision of the wellness score to the patient further comprises:
  providing, by the server, the patient with a numerical wellness score;
  depicting, by the server, a location for the numerical wellness score within a graphically represented wellness score progress chart, a location of the numerical wellness score on the graphically represented wellness score progress chart being associated with a magnitude of the numerical wellness score; and
  depicting, by the server, a location for a maximum numerical wellness score on the graphically represented wellness score progress chart such that a relative distance between the location of the numerical wellness score and the location of the maximum numerical wellness score indicates how close the numerical wellness score is to a maximum wellness score.

9. The computer-implemented method of claim 1, further comprising:
  communicating, by the server, the wellness score to a treatment facility computer system for storage in an electronic medical record (EMR) database in communication with the treatment facility computer system.

10. The computer-implemented method of claim 1, further comprising:
  communicating, by the server, the wellness score to a treatment facility computer system for storage in a treatment facility electronic medical record (EMR) database in communication with the treatment facility computer system, wherein patient-identifying information associated with the wellness score is removed from the wellness score prior to communication of the wellness score to the treatment facility computer system.

11. The computer-implemented method of claim 1, wherein the medical questionnaire is provided to each of a plurality of patients, responses to the medical questionnaire are received from at least one of the plurality of patients, and a wellness score is determined for at least one of the plurality of patients, the method further comprising:
  creating, by the server, at least one of a disease-specific registry of information, a diagnosis-specific registry of information, a treatment-specific registry of information, a patient-specific registry of information, and a treatment-provider-specific registry of information using at least one of the responses to the medical questionnaire received from the at least one of the plurality of patients and the wellness scores determined for the at least one of the patients; and
  storing, by the server, the at least one disease-specific registry of information, diagnosis-specific registry of information, treatment-specific registry of information, patient-specific registry of information, and treatment-provider-specific registry of information in a database.

12. The computer-implemented method of claim 1, wherein the medical questionnaire is provided to each of a plurality of patients, responses to the medical questionnaire are received from at least one of the plurality of patients, and a wellness score is determined for at least one of the plurality of patients, the method further comprising:
  creating, by the server, at least one of a disease-specific registry of information, a diagnosis-specific registry of information, a treatment-specific registry of information, a patient-specific registry of information, and a treatment-provider-specific registry of information using at least one of the responses to the medical questionnaire received from the at least one of the plurality of patients and the wellness scores determined for the at least one of the patients;
  storing, by the server, the at least one disease-specific registry of information, diagnosis-specific registry of information, treatment-specific registry of information, patient-specific registry of information, and treatment-provider-specific registry of information in a database; and
  removing, by the server, all patient-identifying information from the received responses to the medical questionnaire and the determined wellness scores prior to creation of the least one disease-specific registry of information, diagnosis-specific registry of information, treatment-specific registry of information, patient-specific registry of information, and treatment-provider-specific registry of information so that no patient-identifying information is stored in the least one of one disease-specific registry of information, diagnosis-specific registry of information, treatment-specific registry of information, patient-specific registry of information, and treatment-provider-specific registry of information.

13. The computer-implemented method of claim 1, further comprising:
 determining, by the server, whether the wellness score falls below a minimum threshold;
 generating, by the server, a notification that indicates the wellness score is below the minimum threshold; and
 facilitating, by the server, provision of the notification to a treatment provider.

14. The computer-implemented method of claim 1, further comprising:
 determining, by the server, whether the wellness score falls below a minimum threshold;
 generating, by the server, a notification that indicates the wellness score is below the minimum threshold, wherein the notification includes contact information of the patient; and
 facilitating, by the server, provision of the notification to a treatment provider.

15. The computer-implemented method of claim 1, further comprising:
 determining, by the server, whether the wellness score falls below a first minimum threshold;
 upon determining that the wellness score does fall below the first minimum threshold, determining, by the server, whether the wellness score falls below a second minimum threshold;
 upon determining that the wellness score does fall below the second minimum threshold, generating, by the server, a notification that indicates the wellness score is below the second minimum threshold; and
 facilitating, by the server, provision of the notification to a treatment provider.

16. The computer-implemented method of claim 1, further comprising:
 facilitating, by the server, a subsequent provision of the medical questionnaire to the patient;
 receiving, by the server, a subsequent set of responses to the medical questionnaire from the patient;
 retrieving, by the server, the scoring procedure from the scoring-procedure database using an identifier of the medical questionnaire;
 determining, by the server, a subsequent wellness score by applying the scoring procedure to the subsequent set of responses; and
 facilitating, by the server, provision of the subsequent wellness score to the patient.

17. The computer-implemented method of claim 1, further comprising:
 facilitating, by the server, a subsequent provision of the medical questionnaire to the patient;
 receiving, by the server, a subsequent set of responses to the medical questionnaire from the patient;
 retrieving, by the server, the scoring procedure from the scoring-procedure database using an identifier of the medical questionnaire;
 determining, by the server, a subsequent wellness score by applying the scoring procedure to the subsequent set of responses;
 facilitating, by the server, provision of the subsequent wellness score to the patient;
 determining, by the server, an improvement score using the wellness score and the subsequent wellness score; and
 facilitating, by the server, provision of the improvement score to the patient.

18. The computer-implemented method of claim 1, further comprising:
 facilitating, by the server, a subsequent provision of the medical questionnaire to the patient;
 receiving, by the server, a subsequent set of responses to the medical questionnaire from the patient;
 retrieving, by the server, the scoring procedure from the scoring-procedure database using an identifier of the medical questionnaire;
 determining, by the server, a subsequent wellness score by applying the scoring procedure to the subsequent set of responses;
 facilitating, by the server, provision of the subsequent wellness score to the patient;
 determining, by the server, an improvement score using the wellness score and the subsequent wellness score;
 facilitating, by the server, provision of the improvement score to the patient;
 determining, by the server, whether the improvement score falls below a minimum threshold;
 generating, by the server, a notification that indicates the improvement score is below the minimum threshold responsively to a determination that the improvement score is below the minimum threshold; and
 facilitating, by the server, provision of the notification to a treatment provider.

19. The computer-implemented method of claim 1, further comprising:
 facilitating, by the server, a subsequent provision of the medical questionnaire to the patient;
 receiving, by the server, a subsequent set of responses to the medical questionnaire from the patient;
 retrieving, by the server, the scoring procedure from the scoring-procedure database using an identifier of the medical questionnaire;
 determining, by the server, a subsequent wellness score by applying the scoring procedure to the subsequent set of responses;
 facilitating, by the server, provision of the subsequent wellness score to the patient;
 determining, by the server, an improvement score using the wellness score and the subsequent wellness score;
 facilitating, by the server, provision of the improvement score to the patient;
 determining, by the server, whether the improvement score falls below a minimum threshold;
 generating, by the server, a notification that indicates the improvement score is below the minimum threshold responsively to a determination that the improvement score is below the minimum threshold, wherein the notification includes contact information of the patient; and
 facilitating, by the server, provision of the notification to a treatment provider.

20. The computer-implemented method of claim 1, wherein facilitating provision of the wellness score to the patient does not involve an action from a treatment provider, doctor, nurse, researcher, clinician or treatment facility administrator.

21. The computer-implemented method of claim 1, further comprising:
 facilitating, by the server, provision of at least one of the set of responses and the wellness score to at least one of a treatment provider for the patient and a treatment administrator.

22. The computer-implemented method of claim 1, wherein the medical questionnaire is at least one of a medical symptom questionnaire, a disease-specific medical symptom questionnaire, a global medical symptom questionnaire, and a patient reported outcome questionnaire.

23. The computer-implemented method of claim 1, further comprising:
    accessing, by the server, an electronic medical record of the patient;
    extracting, by the server, information about the patient from the accessed electronic medical record; and
    correlating, by the server, the extracted information with the wellness score.

24. The computer-implemented method of claim 1, further comprising:
    upon an expiration of a predetermined time period measured from at least one of a time at which the patient received a treatment and a time at which the set of responses was received from the patient, facilitating, by the server, an additional provision of the medical questionnaire to the patient;
    receiving, by the server, an additional set of responses to the medical questionnaire from the patient;
    determining, by the server, an additional wellness score by applying the scoring procedure to the additional set of responses; and
    facilitating, by the server, provision of the additional wellness score to the patient.

25. The computer-implemented method of claim 1, further comprising repeatedly facilitating the provision of the medical questionnaire to the patient at a plurality of time points.

26. The computer-implemented method of claim 1, further comprising:
    determining, by the server, a predicted wellness score for the patient.

27. A computer-implemented method comprising:
    receiving, by a server, an indication that a medical treatment has been performed for a patient from an external medical treatment scheduler communicatively coupled to the server over a communication network, the indication being encoded with a medical treatment code and including an anonymous identifier for the patient mapped to an identity of the patient, the patient being associated with an electronic medical record (EMR) stored in an EMR database, the anonymous identifier being known to both the server and the EMR database, the EMR database being a device that is physically separate from the server and the medical treatment scheduler being a device that is physically separate from the EMR database and the server;
    determining, by the server, a plurality of medical questionnaires associated with the medical treatment code responsively to the received indication that the medical treatment has been performed;
    querying, by the server, a database of medical questionnaires for the plurality of medical questionnaires specific to the medical treatment code, each of the medical questionnaires being associated with a scoring procedure;
    receiving, by the server, the plurality of medical questionnaires specific to the medical treatment code responsively to the query from the database of medical questionnaires;
    querying, by the server, the EMR database using the anonymous identifier mapped to the identity of the patient over the communication network for one or more characteristics of the patient;
    receiving, by the server, the queried for one or more characteristics of the patient from the EMR database responsively to the querying of the EMR database;
    determining, by the server, which specific medical questionnaire of the plurality of medical questionnaires to provide to the patient using the one or more characteristics of the patient;
    combining, by the server, the anonymous identifier mapped to the identity of the patient to data representing the specific medical questionnaire;
    communicating, by the server, a post-treatment provision of the medical questionnaire to a patient device that includes a processor configured to display the medical questionnaire to the patient and receive responses to the medical questionnaire from the patient;
    communicating, by the server, a combination of the data representing the specific medical questionnaire and the anonymous identifier mapped to the identity of the patient to a patient device physically separate from and communicatively coupled to the server over the communication network following provision of the treatment to the patient, the patient device including a processor configured to display the specific medical questionnaire to the patient, receive a set of responses to the specific medical questionnaire from the patient, and communicate the received set of responses and the anonymous identifier mapped to the identity of the patient to the server;
    receiving, by the server, a post-treatment set of responses to the specific medical questionnaire and the anonymous identifier mapped to the identity of the patient from the patient device over the communication network;
    determining, by the server, a post-treatment wellness score for the patient by applying the scoring procedure for the specific medical questionnaire to the post-treatment set of responses; and
    communicating, by the server, anonymized data representing the post-treatment wellness score to the patient device over the communication network, the patient device being configured to display the wellness score to the patient.

28. The computer-implemented method of claim 27, further comprising repeatedly facilitating the post-treatment provision of the medical questionnaire to the patient at a plurality of time points after the patient receives the treatment.

29. A computer-implemented method comprising:
    for each of a plurality of patients:
    receiving, by a server, an indication that a medical treatment for treating a medical condition has been scheduled for a patient from a medical treatment scheduler communicatively coupled to the server over a communication network, the indication being encoded with a medical treatment code, an identity of the patient being mapped to an anonymous identifier used to anonymize identifying information of the patient, and the patient being associated with an electronic medical record (EMR) stored in an EMR database, the anonymous identifier being known to both the server and the EMR database, the EMR database being a device that is physically separate from the server and the medical treatment scheduler being a device that is physically separate from the EMR database and the server;
    determining, by the server, a plurality of medical questionnaires associated with the medical treatment code responsively to the received indication that the medical treatment has been scheduled;

querying, by the server, a database of medical questionnaires for the plurality of medical questionnaires specific to the medical treatment code over the communication network, each of the medical questionnaires being associated with a scoring procedure;

receiving, by the server, the plurality of medical questionnaires specific to the medical treatment code responsively to the query from the database of medical questionnaires;

querying, by the server, the EMR database using the anonymous identifier mapped to the identity of the patient over the communication network for one or more characteristics of the patient;

receiving, by the server, the queried for one or more characteristics of the patient from the EMR database responsively to the querying of the EMR database;

determining, by the server, which specific medical questionnaire of the plurality of medical questionnaires to provide to the patient using the one or more characteristics of the patient;

combining, by the server, the anonymous identifier mapped to the identity of the patient to data representing the specific medical questionnaire;

communicating, by the server, a combination of the data representing the specific medical questionnaire and the anonymous identifier mapped to the identity of the patient to a patient device physically separate from and communicatively coupled to the server over the communication network, the patient device including a processor configured to display the specific medical questionnaire to the patient, receive a set of responses to the specific medical questionnaire from the patient, and communicate the received set of responses and the anonymous identifier mapped to the identity of the patient to the server;

receiving, by the server, a set of responses to the specific medical questionnaire and the anonymous identifier mapped to the identity of the patient from the patient device over the communication network;

determining, by the server, a wellness score for the patient's medical condition by applying the scoring procedure for the specific medical questionnaire to the set of responses;

storing, by the server, the received set of responses, the wellness score for the patient's medical condition, and an association between the received set of responses and the wellness score for the patient in a database; and creating, by the server, a medical-condition-specific registry of information by associating at least one of the received set of responses and the determined wellness score with the treatment.

30. The computer-implemented method of claim 29, further comprising:
receiving, by the server, one or more patient characteristics for at least one of the patients of the plurality of patients, the creating of the medical-condition-specific registry further including mapping the received patient characteristics to the medical condition.

31. The computer-implemented method of claim 29, further comprising:
for each of the patients, accessing, by the server, an electronic medical record of the patient; and
for at least one of the patients, extracting, by the server, one or more patient characteristics from the electronic medical record of the patient, the creating of the medical-condition-specific registry further including mapping the extracted one or more patient characteristics to the medical condition.

32. The computer-implemented method of claim 29, further comprising repeatedly facilitating the provision of the medical questionnaire to the patient at a plurality of time points after the patient receives a treatment.

33. The computer-implemented method of claim 1, wherein completion of the medical questionnaire is required prior to commencement of the medical treatment, the method further comprising:
authorizing, by the server, commencement of the scheduled medical treatment responsively to receipt of the set of responses.

34. The computer-implemented method of claim 1, further comprising:
automatically adding the wellness score to the patient's EMR using the anonymous identifier mapped to the patient.

* * * * *